United States Patent
Hoekstra et al.

(10) Patent No.: US 9,556,143 B2
(45) Date of Patent: Jan. 31, 2017

(54) METALLOENZYME INHIBITOR COMPOUNDS

(71) Applicant: Viamet Pharmaceuticals, Inc., Durham, NC (US)

(72) Inventors: William J. Hoekstra, Durham, NC (US); Stephen W. Rafferty, Lake Worth, FL (US); Christopher M. Yates, Raleigh, NC (US); Robert J. Schotzinger, Raleigh, NC (US); Michael R. Loso, Carmel, IN (US); Michael T. Sullenberger, Westfield, IN (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 14/557,117

(22) Filed: Dec. 1, 2014

(65) Prior Publication Data

US 2015/0099750 A1  Apr. 9, 2015

Related U.S. Application Data

(62) Division of application No. 13/527,402, filed on Jun. 19, 2012, now Pat. No. 8,901,121.

(60) Provisional application No. 61/498,571, filed on Jun. 19, 2011, provisional application No. 61/505,949, filed on Jul. 8, 2011, provisional application No. 61/611,880, filed on Mar. 16, 2012.

(51) Int. Cl.

| A01N 43/84 | (2006.01) |
|---|---|
| A01N 43/653 | (2006.01) |
| A01N 43/78 | (2006.01) |
| A01N 43/76 | (2006.01) |
| A01N 43/713 | (2006.01) |
| A01N 43/647 | (2006.01) |
| C07D 401/06 | (2006.01) |
| C07D 409/14 | (2006.01) |
| C07D 413/06 | (2006.01) |
| C07D 417/06 | (2006.01) |
| C07D 405/06 | (2006.01) |
| C07D 401/14 | (2006.01) |
| A01N 43/54 | (2006.01) |
| A01N 43/56 | (2006.01) |

(52) U.S. Cl.
CPC ............. *C07D 401/06* (2013.01); *A01N 43/54* (2013.01); *A01N 43/56* (2013.01); *A01N 43/647* (2013.01); *A01N 43/653* (2013.01); *A01N 43/713* (2013.01); *A01N 43/76* (2013.01); *A01N 43/78* (2013.01); *A01N 43/84* (2013.01); *C07D 401/14* (2013.01); *C07D 405/06* (2013.01); *C07D 409/14* (2013.01); *C07D 413/06* (2013.01); *C07D 417/06* (2013.01)

(58) Field of Classification Search
CPC ...... A01N 43/84; A01N 43/653; A01N 43/78; A01N 43/76; A01N 43/713; A01N 43/56; A01N 43/647; A01N 43/54; C07D 401/06; C07D 409/14; C07D 413/06; C07D 417/06; C07D 405/06; C07D 401/14
See application file for complete search history.

(56) References Cited

U.S. PATENT DOCUMENTS

| 4,690,942 | A | 9/1987 | Frick et al. |
|---|---|---|---|
| 5,206,364 | A | 4/1993 | Dickinson et al. |
| 5,364,938 | A | 11/1994 | Dickinson et al. |
| 5,541,203 | A | 7/1996 | Bell et al. |
| 5,981,560 | A | 11/1999 | Bell et al. |
| 6,015,825 | A * | 1/2000 | Bell ............... A61K 47/48969 514/383 |
| 8,236,962 | B2 | 8/2012 | Hoekstra et al. |
| 8,748,461 | B2 | 6/2014 | Hoekstra et al. |
| 8,796,001 | B2 | 8/2014 | Hoekstra et al. |
| 8,809,378 | B2 | 8/2014 | Hoekstra et al. |
| 8,901,121 | B2 | 12/2014 | Hoekstra et al. |
| 9,221,791 | B2 | 12/2015 | Hoekstra et al. |
| 2006/0058397 | A1 | 3/2006 | Salmon et al. |
| 2009/0048309 | A1 | 2/2009 | Yang et al. |
| 2012/0329788 | A1 | 12/2012 | Hoekstra et al. |
| 2012/0329802 | A1 | 12/2012 | Hoekstra et al. |
| 2013/0005729 | A1 | 1/2013 | Hoekstra et al. |
| 2013/0005752 | A1 | 1/2013 | Hoekstra et al. |
| 2013/0012503 | A1 | 1/2013 | Hoekstra et al. |
| 2014/0349973 | A1 | 11/2014 | Hoekstra et al. |
| 2015/0004666 | A1 | 1/2015 | Hoekstra et al. |
| 2015/0246898 | A1* | 9/2015 | Gustafson ............ C07D 401/06 514/252.03 |

FOREIGN PATENT DOCUMENTS

| CN | 1189162 A | 7/1998 |
|---|---|---|
| EP | 0 357 241 A1 | 3/1990 |
| EP | 0 796 858 A1 | 9/1997 |
| JP | 59-137470 A | 8/1984 |
| JP | 59-163374 A | 9/1984 |
| JP | 59-196867 A | 11/1984 |
| JP | 60-222464 A | 11/1985 |
| JP | 61-215390 A | 9/1986 |
| JP | 02-104583 A | 4/1990 |
| JP | 07-502022 A | 3/1995 |

(Continued)

OTHER PUBLICATIONS

Partial Supplementary Search Report mailed Apr. 20, 2015 in connection with EP 12802388.4.

(Continued)

*Primary Examiner* — Alexander R Pagano
*Assistant Examiner* — Ebenezer O Sackey
(74) *Attorney, Agent, or Firm* — Wolf, Greenfield & Sacks, P.C.

(57) ABSTRACT

The instant invention describes compounds having metalloenzyme modulating activity, and methods of treating diseases, disorders or symptoms thereof mediated by such metalloenzymes.

20 Claims, No Drawings

(56) References Cited

FOREIGN PATENT DOCUMENTS

| | | |
|---|---|---|
| JP | 08-020578 A | 1/1996 |
| JP | 10-007663 A | 1/1998 |
| JP | 10-506652 A | 6/1998 |
| JP | 2000-344744 A | 12/2000 |
| JP | 2010-510248 A | 4/2010 |
| JP | 2014-516091 A | 7/2014 |
| JP | 2014-518219 A | 7/2014 |
| WO | WO-9701552 A1 | 1/1997 |
| WO | WO 2006/096949 A2 | 9/2006 |
| WO | WO 2008/124131 A1 | 10/2008 |
| WO | WO 2011/133875 A2 | 10/2011 |
| WO | WO 2011/134911 A2 | 11/2011 |
| WO | WO 2012/177603 A2 | 12/2012 |
| WO | WO 2012/177608 A1 | 12/2012 |
| WO | WO 2012/177635 A1 | 12/2012 |
| WO | WO 2012/177638 A1 | 12/2012 |
| WO | WO 2012/177725 A1 | 12/2012 |
| WO | WO 2012/177728 A1 | 12/2012 |

OTHER PUBLICATIONS

Extended European Search Report mailed Sep. 2, 2015 in connection with EP 12802388.4.
Extended European Search Report mailed Aug. 26, 2015 in connection with EP 12801966.8.
Partial Supplementary Search Report mailed Apr. 20, 2015 in connection with EP 12801966.8.
Eto, Hiromichi et al., New Antifungal 1,2,4-Triazoles with Difluoro (heteroaryl) methyl Moiety, Chem. Pharm. Bull. 2000, vol. 48, No. 7, pp. 982-990.
Dickinson, Roger P. et al; Novel Antifungal 2-Aryl-1-(1H-1,2,4-triazol-1-YL)butan-2-ol derivatives with high activity against Aspergillus Fumigatus, Bioorganic & Medicinal Chemistry Letter, 1996, vol. 6, No. 16, pp. 2031-2036.
International Search Report of PCT Appln. No. PCT/US2012/043094.
I.J. Holb, Timing of First and Final Sprays Against Apple Scab Combined With Leaf Removal and Pruning in Organic Apple Production; 27 Crop Protection 814-822 (2008).
R.D. Kelley et al., Evaluation of Two Triazole Fungicides for Postinfection Control of Apple Scab; 71 Phytopathology, 737-742 (1981).
L.M. Abell et al., Target-Site Directed Herbicide Design in Pest Control with Enhanced Environmental Safety; ACS Sympoisium Series: American Chemical Society, S. Duke, et al., eds, 1993).
S.C. Knight et al., Rationale and Perspectives on the Development of Fungicides; Annual Review of Phytopathology 35, 349-372, 357 (1997).
W.T. Ruegg et al., Herbicide Research and Development: Challenges and Opportunities; 47(4), 271-275, 271 (2006).
International Search Report of PCT/US2012/043101.
Baya, Mounir et al., "Fungicidal activity of β-thujaplicin analogues"; 57 Pest Management Science 833-838, 836 (2001).
Nishimura, Masahiro et al; Cell-associated collagenolytic activity by *Candida albicans*; 153 Mycopathologia, 125-128 (2001).

* cited by examiner

METALLOENZYME INHIBITOR COMPOUNDS

CROSS-REFERENCE TO RELATED APPLICATIONS

The present application is a Divisional patent application of Ser. No. 13/527,402, file Jun. 19, 2012, now issued U.S. Pat. No. 8,901,121, issued on Dec. 2, 2014, which claims priority benefit under 35 U. S. C. §119(e) of U.S. Provisional Patent Application Ser. No. 61/498,571, filed Jun. 19, 2011; U.S. Provisional Patent Application Ser. No. 61/505,949, filed Jul. 8, 2011; and U.S. Provisional Patent Application Ser. No. 61/611,880, filed Mar. 16, 2012. The disclosures of these applications are incorporated herein by reference.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as cytochrome P450 2C9 (CYP2C9), CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

Fungicides are compounds, of natural or synthetic origin, which act to protect and cure plants against damage caused by agriculturally relevant fungi. Generally, no single fungicide is useful in all situations. Consequently, research is ongoing to produce fungicides that may have better performance, are easier to use, and cost less.

The present disclosure relates to compounds of Formula I, shown below, and their derivatives and their use as fungicides. The compounds of the present disclosure may offer protection against ascomycetes, basidiomycetes, deuteromycetes and oomycetes.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

A method of controlling a pathogen-induced disease in a plant that is at risk of being diseased from the pathogen comprising contacting one of the plant and an area adjacent to the plant with a composition of Formula I, or salt, solvate, hydrate or prodrug thereof, wherein:

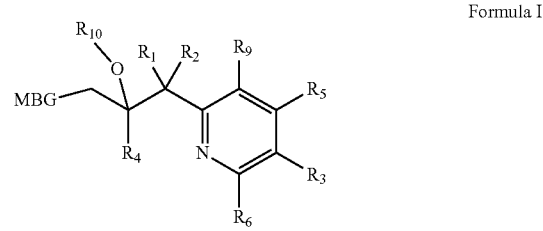

Formula I

MBG is optionally substituted tetrazolyl, optionally substituted triazolyl, optionally substituted oxazolyl, optionally substituted pyrimidinyl, optionally substituted thiazolyl, or optionally substituted pyrazolyl;

$R_1$ is H, halo, alkyl, or haloalkyl;

$R_2$ is H, halo, alkyl, or haloalkyl;

$R_3$ is independently H, alkyl, alkenyl, cycloalkyl, heteroaryl, hydroxyalkyl, cyano, haloalkyl, halo, —C(O)aryl, —CH(OH)(aryl), —CH$_2$(aryl), —CH$_2$(heteroaryl), —CF$_2$(aryl), —CF$_2$(heteroaryl), —CH$_2$O(aryl), —CH$_2$O(heteroaryl), —CH$_2$S(O)$_x$(aryl), and cyclic amino, wherein each of the alkyl, alkenyl, cycloalkyl, heteroaryl, hydroxyalkyl, haloalkyl, —C(O)aryl, —CH(OH)(aryl), —CH$_2$(aryl), —CH$_2$(heteroaryl), —CF$_2$(aryl), CF$_2$(heteroaryl), —CH$_2$O (aryl), —CH$_2$O(heteroaryl), —CH$_2$S(O)$_x$(aryl), and cyclic amino may be optionally substituted with 1, 2 or 3 independent $R_7$;

R$_4$ is aryl, heteroaryl, alkyl, or cycloalkyl, each optionally substituted with 0, 1, 2 or 3 independent R$_8$;

R$_5$ is independently H, halo, alkyl, alkoxy, cyano, haloalkyl, haloalkoxy, halothioalkyl, thioalkyl, SF$_3$, SF$_6$, SCN, SO$_2$R$_{11}$, cycloalkyl, —C(O)alkyl, —C(O)OH, —C(O)Oalkyl;

R$_6$ is independently H, halo, alkyl, alkoxy, cyano, haloalkyl, haloalkoxy, halothioalkyl, thioalkyl, SF$_3$, SF$_6$, SCN, SO$_2$R$_{11}$, cycloalkyl, —C(O)alkyl, —C(O)OH, —C(O)Oalkyl;

each R$_7$ is independently cyano, cycloalkyl, haloalkyl, hydroxy, alkoxy, aryl, aryloxy, heteroaryloxy, halo, haloalkoxy, —C(O)alkyl, —C(O)OH, —C(O)Oalkyl;

each R$_8$ is independently cyano, haloalkyl, hydroxy, alkoxy, halo, or haloalkoxy;

R$_9$ is H, halo, or haloalkyl;

R$_{10}$ is H, alkyl, —Si(R$_{12}$)$_3$, —P(O)(OH)$_2$, —CH$_2$—O—P(O)(OH)$_2$, or —C(O)alkyl optionally substituted with amino;

R$_{11}$ is independently alkyl, aryl, substituted aryl, heteroaryl or substituted heteroaryl;

R$_{12}$ is independently alkyl or aryl;

x is independently 0, 1, or 2.

One aspect is a compound of Formula I, or salt, solvate, hydrate or prodrug thereof, wherein:

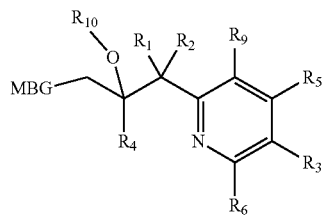

Formula I

MBG is optionally substituted tetrazolyl, optionally substituted triazolyl, optionally substituted oxazolyl, optionally substituted pyrimidinyl, optionally substituted thiazolyl, or optionally substituted pyrazolyl;

R$_1$ is halo;

R$_2$ is halo;

R$_3$ is independently H, alkyl, alkenyl, heteroaryl, cyano, haloalkyl, halo, each of which may be optionally substituted with 1, 2 or 3 independent R$_7$;

R$_4$ is aryl optionally substituted with 0, 1, 2 or 3 independent R$_8$;

R$_5$ is independently H, halo, alkyl, alkoxy, cyano, haloalkyl, haloalkoxy;

R$_6$ is independently H, alkyl, alkoxy, cyano, haloalkyl, haloalkoxy; and each R$_7$ is independently cyano, haloalkyl, hydroxy, alkoxy, halo, haloalkoxy, —C(O)alkyl, —C(O)OH, —C(O)Oalkyl;

each R$_8$ is independently cyano, haloalkyl, hydroxy, alkoxy, halo, or haloalkoxy;

R$_9$ is H, halo, or haloalkyl;

In other aspects, the compound is any of the formulae herein:

wherein MBG is tetrazolyl, triazolyl, oxazolyl, pyrimidinyl, thiazolyl, or pyrazolyl, each optionally substituted with 1, 2 or 3 independent R$_7$;

wherein MBG is 1H-tetrazol-1-yl, 1H-1,2,4-triazol-1-yl, pyrimidin-5-yl, 1H-pyrazol-3-yl, 1H-pyrazol-3-yl, 1H-pyrazol-4-yl, 2H-tetrazol-2-yl, oxazol-5-yl, or thiazol-5-yl, each optionally substituted with 1, 2 or 3 independent R$_7$;

wherein MBG is 1H-tetrazol-1-yl, or 2H-tetrazol-2-yl;

wherein MBG is 1H-pyrazol-3-yl, 1H-pyrazol-3-yl, or 1H-pyrazol-4-yl;

wherein R$_1$ is fluoro;

wherein R$_2$ is fluoro;

wherein R$_1$ and R$_2$ are fluoro;

wherein R$_4$ is phenyl optionally substituted with 0, 1, 2 or 3 independent R$_8$;

wherein R$_4$ is phenyl optionally substituted with 0, 1, 2 or 3 independent halo;

wherein R$_4$ is phenyl optionally substituted with 0, 1, 2 or 3 independent fluoro;

wherein R$_4$ is 2,4-difluorophenyl;

wherein R$_5$ is halo;

wherein R$_3$ is heteroaryl optionally substituted with 1, 2 or 3 independent R$_7$;

wherein R$_3$ is pyridyl, pyrimidinyl, thienyl, or triazolyl, each optionally substituted with 1, 2 or 3 independent R$_7$;

wherein R$_3$ is 3-pyridyl, 4-pyrimidinyl, 2-thienyl, or 2H-1,2,3-triazolyl, each optionally substituted with 1, 2 or 3 independent R$_7$;

wherein R$_3$ is cycloalkyl optionally substituted with 1, 2 or 3 independent R$_7$;

wherein R$_3$ is alkyl substituted with 1, 2 or 3 independent R$_7$;

wherein R$_3$ is alkenyl substituted with 1, 2 or 3 independent R$_7$;

wherein R$_3$ is alkenyl substituted with 1, 2 or 3 independent R$_7$;

wherein R$_3$ is —C(O)aryl optionally substituted with 1, 2 or 3 independent R$_7$;

wherein R$_3$ is alkyl substituted with haloalkyl;

wherein:
R$_1$ is fluoro;
R$_2$ is fluoro;
R$_4$ is 2,4-difluorophenyl; and
R$_3$ is cycloalkyl optionally substituted with 1, 2 or 3 independent R$_7$;

wherein:
R$_1$ is fluoro;
R$_2$ is fluoro;
R$_4$ is 2,4-difluorophenyl; and
R$_3$ is alkyl substituted with 1, 2 or 3 independent R$_7$;

wherein:
R$_1$ is fluoro;
R$_2$ is fluoro;
R$_4$ is 2,4-difluorophenyl; and
R$_3$ is pyridyl, pyrimidinyl, thienyl, or triazolyl, each optionally substituted with 1, 2 or 3 independent R$_7$;

wherein:
R$_1$ is fluoro;
R$_2$ is fluoro;
R$_4$ is 2,4-difluorophenyl; and
R$_3$ is —C(O)aryl optionally substituted with 1, 2 or 3 independent R;

wherein:
R$_1$ is fluoro;
R$_2$ is fluoro;
R$_4$ is 2,4-difluorophenyl; and
R$_3$ is alkenyl substituted with 1, 2 or 3 independent R$_7$; or
wherein R$_3$ is halo.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi-cation interactions, pi-anion interactions, dipole-dipole interactions, ion-dipole interactions. In one aspect, the compound is identified as having a bonding interaction with the metal via the 1-tetrazolyl moiety; in another aspect, the compound is identified as having a bonding interaction with the metal via the N2 of the 1-tetrazolyl moiety; in another aspect, the compound is identified as having a bonding interaction with the metal via the N3 of the 1-tetrazolyl moiety; in another aspect, the compound is identified as having a bonding interaction with the metal via the N4 of the 1-tetrazolyl moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson, John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of Formula I (and pharmaceutically and agriculturally acceptable salts, solvates, or hydrates thereof)

1-(5-Bromopyridin-2-yl)-2-(2,4-difluorophenyl)-1,1-difluoro-3-(1H-tetrazol-1-yl)propan-2-ol (1);

2-(2,4-Difluorophenyl)-1,1-difluoro-1-(pyridin-2-yl)-3-(1H-tetrazol-1-yl)propan-2-ol (2);

(E)-3-(6-(2-(2,4-Difluorophenyl)-1,1-difluoro-2-hydroxy-3-(1H-tetrazol-1-yl)propyl)pyridin-3-yl)acrylonitrile (3);

(E)-Ethyl 3-(6-(2-(2,4-difluorophenyl)-1,1-difluoro-2-hydroxy-3-(1H-tetrazol-1-yl)propyl)pyridin-3-yl)acrylate (4);

Ethyl 3-(6-(2-(2,4-difluorophenyl)-1,1-difluoro-2-hydroxy-3-(1H-tetrazol-1-yl)propyl)pyridin-3-yl)propanoate (5);

(E)-2-(2,4-Difluorophenyl)-1,1-difluoro-3-(1H-tetrazol-1-yl)-1-(5-(3-(2,2,2-trifluoroethoxy)prop-1-en-1-yl)pyridin-2-yl)propan-2-ol (6);

(E)-4-(6-(2-(2,4-Difluorophenyl)-1,1-difluoro-2-hydroxy-3-(1H-tetrazol-1-yl)propyl)pyridin-3-yl)but-3-en-2-one (7);

4-(6-(2-(2,4-Difluorophenyl)-1,1-difluoro-2-hydroxy-3-(1H-tetrazol-1-yl)propyl)pyridin-3-yl)butan-2-one (8);

1-(5-(2H-1,2,3-Triazol-2-yl)pyridin-2-yl)-2-(2,4-difluorophenyl)-1,1-difluoro-3-(1H-tetrazol-1-yl)propan-2-ol (9);

2-(2,4-Difluorophenyl)-1,1-difluoro-1-(5-fluoropyridin-2-yl)-3-(1H-tetrazol-1-yl)propan-2-ol (10);

2-(4-Chloro-2-fluorophenyl)-1,1-difluoro-1-(pyridin-2-yl)-3-(1H-tetrazol-1-yl)propan-2-ol (11);

1-(5-Chloropyridin-2-yl)-2-(2,4-difluorophenyl)-1,1-difluoro-3-(1H-tetrazol-1-yl)propan-2-ol (12);

2-(2,4-Difluorophenyl)-1,1-difluoro-1-(4-fluoropyridin-2-yl)-3-(1H-tetrazol-1-yl)propan-2-ol (13);

1-(4-Chloropyridin-2-yl)-2-(2,4-difluorophenyl)-1,1-difluoro-3-(1H-tetrazol-1-yl)propan-2-ol (14);

2-(2,4-Difluorophenyl)-1,1-difluoro-1-(5-(5-fluoropyrimidin-4-yl)pyridin-2-yl)-3-(1H-tetrazol-1-yl)propan-2-ol (15);

2-(2,5-Difluorophenyl)-1,1-difluoro-1-(4-fluoropyridin-2-yl)-3-(1H-tetrazol-1-yl)propan-2-ol (16);

2-(2,4-Difluorophenyl)-1,1-difluoro-3-(1H-tetrazol-1-yl)-1-(5-(2,2,2-trifluoroethyl)pyridin-2-yl)propan-2-ol (17);

1-(5-Cyclopropylpyridin-2-yl)-2-(2,4-difluorophenyl)-1,1-difluoro-3-(1H-tetrazol-1-yl)propan-2-ol (18);

2-(2,4-Difluorophenyl)-1,1-difluoro-3-(1H-tetrazol-1-yl)-1-(5-(trifluoromethyl)pyridin-2-yl)propan-2-ol (19);

1-(6-Bromopyridin-2-yl)-2-(2,4-difluorophenyl)-1,1-difluoro-3-(1H-tetrazol-1-yl)propan-2-ol (20);

1-(5-Bromopyridin-2-yl)-2-(2,5-difluorophenyl)-1,1-difluoro-3-(1H-tetrazol-1-yl)propan-2-ol (21);

1-(5-Bromopyridin-2-yl)-2-(4-chloro-2-fluorophenyl)-1,1-difluoro-3-(1H-tetrazol-1-yl)propan-2-ol (22);

1-(5-Bromopyridin-2-yl)-1,1-fluoro-2-(2-fluoro-4-(trifluoromethyl)phenyl)-3-(1H-tetrazol-1-yl)propan-2-ol (23);

1-(4-Bromopyridin-2-yl)-2-(2,4-difluorophenyl)-1,1-difluoro-3-(1H-tetrazol-1-yl)propan-2-ol (24);

2-(2,4-Difluorophenyl)-1,1-difluoro-1-(5-methylpyridin-2-yl)-3-(1H-tetrazol-1-yl)propan-2-ol (25);

2-(4-Chloro-2-fluorophenyl)-1-(5-chloropyridin-2-yl)-1,1-difluoro-3-(1H-tetrazol-1-yl)propan-2-ol (26);

2-(4-Cloro-2-fluorophenyl)-1,1-difluoro-1-(5-fluoropyridin-2-yl)-3-(1H-tetrazol-1-yl)propan-2-ol (27);

1-(5-(2H-1,2,3-Triazol-2-yl)pyridin-2-yl)-2-(4-chloro-2-fluorophenyl)-1,1-difluoro-3-(1H-tetrazol-1-yl)propan-2-ol (28);

1-(5-Chloropyridin-2-yl)-2-(2,4-difluorophenyl)-1,1-difluoro-3-(1H-1,2,4-triazol-1-yl)propan-2-ol (29);

1-(6'-Chloro-[3,3'-bipyridin]-6-yl)-2-(2,4-difluorophenyl)-1,1-difluoro-3-(1H-tetrazol-1-yl)propan-2-ol (30); 2-(2,4-Difluorophenyl)-1,1-difluoro-1-(6'-fluoro-[3,3'-bipyridin]-6-yl)-3-(1H-tetrazol-1-yl)propan-2-ol (31);

2-(2,4-Difluorophenyl)-1,1-difluoro-1-(5-(5-methoxythiophen-2-yl)pyridin-2-yl)-3-(1H-tetrazol-1-yl)propan-2-ol (32);

1-(5-(5-(Difluoromethyl)thiophen-2-yl)pyridin-2-yl)-2-(2,4-difluorophenyl)-1,1-difluoro-3-(1H-tetrazol-1-yl)propan-2-ol (33);

2-(2,4-Difluorophenyl)-1,1-difluoro-3-(1H-tetrazol-1-yl)-1-(5-(5-(trifluoromethyl)thiophen-2-yl)pyridin-2-yl)propan-2-ol (34);

2-(2,4-Difluorophenyl)-1,1-difluoro-3-(1H-tetrazol-1-yl)-1-(6'-(trifluoromethyl)-[3,3'-bipyridin]-6-yl)propan-2-ol (35);

1-(5-(5-Bromothiazol-2-yl)pyridin-2-yl)-2-(2,4-difluorophenyl)-1,1-difluoro-3-(1H-tetrazol-1-yl)propan-2-ol (36);

2-(2,4-Difluorophenyl)-1,1-difluoro-1-(5-(2-methoxypyrimidin-5-yl)pyridin-2-yl)-3-(1H-tetrazol-1-yl)propan-2-ol (37);

2-(2,4-Difluorophenyl)-1,1-difluoro-3-(1H-tetrazol-1-yl)-1-(5-(thiazol-2-yl)pyridin-2-yl)propan-2-ol (38);

2-(4-Chloro-2-fluorophenyl)-1,1-difluoro-3-(1H-tetrazol-1-yl)-1-(5-(2,2,2-trifluoroethyl)pyridin-2-yl)propan-2-ol (39);

2-(4-Chloro-2-fluorophenyl)-1-(5-cyclopropylpyridin-2-yl)-1,1-difluoro-3-(1H-tetrazol-1-yl)propan-2-ol (40);

Methyl 2-((6-(2-(2,4-difluorophenyl)-1,1-difluoro-2-hydroxy-3-(1H-tetrazol-1-yl)propyl)pyridin-3-yl)thio)acetate (41);

(E)-1-(5-(3-(1H-Tetrazol-1-yl)prop-1-en-1-yl)pyridin-2-yl)-2-(2,4-difluorophenyl)-1,1-difluoro-3-(1H-tetrazol-1-yl)propan-2-ol (42);

(E)-3-(6-(2-(2,4-Difluorophenyl)-1,1-difluoro-2-hydroxy-3-(1H-tetrazol-1-yl)propyl)pyridin-3-yl)prop-2-en-1-ol (43);

3-(6-(2-(2,4-Difluorophenyl)-1,1-difluoro-2-hydroxy-3-(1H-tetrazol-1-yl)propyl)pyridin-3-yl)propan-1-ol (44);

2-(2,4-Difluorophenyl)-1,1-difluoro-3-(1H-tetrazol-1-yl)-1-(5-(3-(2,2,2-trifluoroethoxy)propyl)pyridin-2-yl)propan-2-ol (45);

(E)-4-(6-(2-(2,4-Difluorophenyl)-1,1-difluoro-2-hydroxy-3-(1H-tetrazol-1-yl)propyl)pyridin-3-yl)but-3-en-2-ol (46);

4-(6-(2-(2,4-Difluorophenyl)-1,1-difluoro-2-hydroxy-3-(1H-tetrazol-1-yl)propyl)pyridin-3-yl)butan-2-ol (47);

(E)-2-(2,4-Difluorophenyl)-1,1-difluoro-1-(5-(3-methoxyprop-1-en-1-yl)pyridin-2-yl)-3-(1H-tetrazol-1-yl)propan-2-ol (48);

(Z)-2-(2,4-Difluorophenyl)-1,1-difluoro-1-(5-(3-methoxyprop-1-en-1-yl)pyridin-2-yl)-3-(1H-tetrazol-1-yl)propan-2-ol (49);

2-(2,4-Difluorophenyl)-1,1-difluoro-1-(5-(3-methoxypropyl)pyridin-2-yl)-3-(1H-tetrazol-1-yl)propan-2-ol (50);

(E)-2-(2,4-Difluorophenyl)-1-(5-(3-ethoxyprop-1-en-1-yl)pyridin-2-yl)-1,1-difluoro-3-(1H-tetrazol-1-yl)propan-2-ol (51);

(Z)-2-(2,4-Difluorophenyl)-1-(5-(3-ethoxyprop-1-en-1-yl)pyridin-2-yl)-1,1-difluoro-3-(1H-tetrazol-1-yl)propan-2-ol (52);

2-(2,4-Difluorophenyl)-1-(5-(3-ethoxypropyl)pyridin-2-yl)-1,1-difluoro-3-(1H-tetrazol-1-yl)propan-2-ol (53);

(E)-2-(2,4-Difluorophenyl)-1,1-difluoro-1-(5-(3-isopropoxyprop-1-en-1-yl)pyridin-2-yl)-3-(1H-tetrazol-1-yl)propan-2-ol (54);

2-(2,4-Difluorophenyl)-1,1-difluoro-1-(5-(3-isopropoxypropyl)pyridin-2-yl)-3-(1H-tetrazol-1-yl)propan-2-ol (55);

1-(5-(2-Chloropyrimidin-5-yl)pyridin-2-yl)-2-(2,4-difluorophenyl)-1,1-difluoro-3-(1H-tetrazol-1-yl)propan-2-ol (56);

2-(2,4-Difluorophenyl)-1,1-difluoro-3-(1H-tetrazol-1-yl)-1-(5-(2,2,2-trifluoro-1-hydroxyethyl)pyridin-2-yl)propan-2-ol (57);

2-(5-Bromopyridin-2-yl)-1-(2,4-difluorophenyl)-2,2-difluoro-1-(pyrimidin-5-yl)ethanol (58);

1-(5-(Cyclopropylmethyl)pyridin-2-yl)-2-(2,4-difluorophenyl)-1,1-difluoro-3-(1H-tetrazol-1-yl)propan-2-ol (59);

7-(4-Chloro-fluorophenyl)-1-(5-(cyclopropylmethyl)pyridin-2-yl)-1,1-difluoro-3-(1H-tetrazol-1-yl)propan-2-ol (60);

1-(5-Allylpyridin-2-yl)-2-(2,4-difluorophenyl)-1,1-difluoro-3-(1H-tetrazol-1-yl)propan-2-ol (61);

1-(5-Bromopyridin-2-yl)-2-(2,4-difluorophenyl)-1,1-difluoro-3-(1H-pyrazol-3-yl)propan-2-ol (62);

1-(5-(2H-1,2,3-Triazol-2-yl)pyridin-2-yl)-2-(2,4-difluorophenyl)-1,1-difluoro-3-(1H-pyrazol-3-yl)propan-2-ol (63);

1-(5-(1H-1,2,3-Triazol-1-yl)pyridin-2-yl)-2-(2,4-difluorophenyl)-1,1-difluoro-3-(1H-pyrazol-3-yl)propan-2-ol (64);

2-(2,4-Difluorophenyl)-1,1-difluoro-3-(1H-pyrazol-4-yl)-1-(pyridin-2-yl)propan-2-ol (65);

(6-(2-(2,4-Difluorophenyl)-1,1-difluoro-2-hydroxy-3-(1H-tetrazol-1-yl)propyl)pyridin-3-yl)(4-(trifluoromethyl)phenyl)methanone (66);

(4-Chlorophenyl)(6-(2-(2,4-difluorophenyl)-1,1-difluoro-2-hydroxy-3-(1H-tetrazol-1-yl)propyl)pyridin-3-yl)methanone (67);

(6-(2-(2,4-Difluorophenyl)-1,1-difluoro-2-hydroxy-3-(1H-tetrazol-1-yl)propyl)pyridin-3-yl)(4-(2,2,2-trifluoroethoxy)phenyl)methanone (68);

(6-(2-(2,4-Difluorophenyl)-1,1-difluoro-2-hydroxy-3-(1H-tetrazol-1-yl)propyl)pyridin-3-yl)(4-fluorophenyl)methanone (69);

(3,4-Difluorophenyl)(6-(2-(2,4-difluorophenyl)-1,1-difluoro-2-hydroxy-3-(1H-tetrazol-1-yl)propyl)pyridin-3-yl)methanone (70);

(4-Chloro-3-fluorophenyl)(6-(2-(2,4-difluorophenyl)-1,1-difluoro-2-hydroxy-3-(1H-tetrazol-1-yl)propyl)pyridin-3-yl)methanone (71);

2-(2,4-Difluorophenyl)-1,1-difluoro-1-(5-(hydroxy(4-(trifluoromethyl)phenyl)methyl)pyridin-2-yl)-3-(1H-tetrazol-1-yl)propan-2-ol (72);

2-(2,4-Difluorophenyl)-1,1-difluoro-3-(1H-tetrazol-1-yl)-1-(5-(4-(trifluoromethyl)benzyl)pyridin-2-yl)propan-2-ol (73);

1-(5-((4-Chlorophenyl)difluoromethyl)pyridin-2-yl)-2-(2,4-difluorophenyl)-1,1-difluoro-3-(1H-tetrazol-1-yl)propan-2-ol (74);

1-(5-Benzylpyridin-2-yl)-2-(2,4-difluorophenyl)-1,1-difluoro-3-(1H-tetrazol-1-yl)propan-2-ol (75);

2-(2,4-Difluorophenyl)-1,1-difluoro-3-(1H-tetrazol-1-yl)-1-(5-(4-(trifluoromethoxy)benzyl)pyridin-2-yl)propan-2-ol (76);

1-(5-(4-Chlorobenzyl)pyridin-2-yl)-2-(2,4-difluorophenyl)-1,1-difluoro-3-(1H-tetrazol-1-yl)propan-2-ol (77);

1-(5-(5-Bromothiophen-2-yl)pyridin-2-yl)-2-(2,4-difluorophenyl)-1,1-difluoro-3-(1H-tetrazol-1-yl)propan-2-ol (78);

4-((6-(2-(2,4-Difluorophenyl)-1,1-difluoro-2-hydroxy-3-(1H-tetrazol-1-yl)propyl)pyridin-3-yl)methoxy)benzonitrile (79);

4-((6-(2-(2,4-Difluorophenyl)-1,1-difluoro-2-hydroxy-3-(2H-tetrazol-2-yl)propyl)pyridin-3-yl)methoxy)benzonitrile (80);

2-(2,4-Difluorophenyl)-1,1-difluoro-1-(5-morpholinopyridin-2-yl)-3-(1H-tetrazol-1-yl)propan-2-ol (81);

2-(2,4-Difluorophenyl)-1,1-difluoro-1-(5-(piperidin-1-yl)pyridin-2-yl)-3-(1H-tetrazol-1-yl)propan-2-ol (82);

1-(5-Bromopyridin-2-yl)-2-(2,4-difluorophenyl)-1,1-difluoro-3-(oxazol-5-yl)propan-2-ol (83);

3-(5-Bromopyridin-2-yl)-2-(2,4-difluorophenyl)-3-fluoro-1-(1H-tetrazol-1-yl)butan-2-ol (84);

3-(5-Bromopyridin-2-yl)-2-(2,4-difluorophenyl)-3-fluoro-1-(1H-tetrazol-1-yl)butan-2-ol (85);

2-(2,4-Difluorophenyl)-1,1-difluoro-1-(pyridin-2-yl)-3-(thiazol-5-yl)propan-2-ol (86);

1-(5-(5-Chlorothiophen-2-yl) pyridin-2-yl)-2-(2,4-difluorophenyl)-1,1-difluoro-3-(1H-tetrazol-1-yl) propan-2-ol (87);

4-((6-(2-(2,4-difluorophenyl)-1,1-difluoro-2-hydroxy-3-(1H-tetrazol-1-yl)propyl)pyridin-3-yl)methoxy)-3-fluorobenzonitrile (88);

3-((6-(2-(2,4-difluorophenyl)-1,1-difluoro-2-hydroxy-3-(1H-tetrazol-1-yl)propyl)pyridin-3-yl)methoxy)-2-fluorobenzonitrile (89);

4-(((6-(2-(2,4-difluorophenyl)-1,1-difluoro-2-hydroxy-3-(1H-tetrazol-1-yl)propyl)pyridin-3-yl)methyl)thio)-3-fluorobenzonitrile (90);

2-(2,4-difluorophenyl)-1,1-difluoro-1-(5-(isopropoxymethyl)pyridin-2-yl)-3-(1H-tetrazol-1-yl)propan-2-ol (91); or 1-(5-((difluoromethoxy)methyl)pyridin-2-yl)-2-(2,4-difluorophenyl)-1,1-difluoro-3-(1H-tetrazol-1-yl)propan-2-ol (92).

1-(5-chloro-[2,3'-bipyridin]-6'-yl)-2-(2,4-difluorophenyl)-1,1-difluoro-3-(1H-tetrazol-1-yl)propan-2-ol (93).

2-(2,4-Difluorophenyl)-1,1-difluoro-3-(1H-tetrazol-1-yl)-1-(5-(trifluoromethyl)-[2,3'-bipyridin]-6'-yl)propan-2-ol (94).

6'-(2-(2,4-difluorophenyl)-1,1-difluoro-2-hydroxy-3-(1H-tetrazol-1-yl)propyl)-[2,3'-bipyridin]-5-carbonitrile (95).

1-([3,4'-bipyridin]-6-yl)-2-(2,4-difluorophenyl)-1,1-difluoro-3-(1H-tetrazol-1-yl)propan-2-ol (96).

1-(5-(((6-chloropyridin-3-yl)methyl)pyridin-2-yl)-2-(2,4-difluorophenyl)-1,1-difluoro-3-(1H-tetrazol-1-yl)propan-2-ol (97).

6-((6-(2-(2,4-difluorophenyl)-1,1-difluoro-2-hydroxy-3-(1H-tetrazol-1-yl)propyl)pyridin-3-yl)methoxy)nicotinonitrile (98).

2-(2,4-difluorophenyl)-1,1-difluoro-3-(1H-tetrazol-1-yl)-1-(5-(((5-(trifluoromethyl)pyridin-2-yl)oxy)methyl)pyridin-2-yl)propan-2-ol (99).

1-(5-(((3-chloro-5-(trifluoromethyl)pyridin-2-yl)oxy)methyl)pyridin-2-yl)-2-(2,4-difluorophenyl)-1,1-difluoro-3-(1H-tetrazol-1-yl)propan-2-ol (100).

1-(5-(difluoro(4-fluorophenyl)methyl)pyridin-2-yl)-2-(2,4-difluorophenyl)-1,1-difluoro-3-(1H-tetrazol-1-yl)propan-2-ol (101).

1-(5-(difluoro(4-(trifluoromethyl)phenyl)methyl)pyridin-2-yl)-2-(2,4-difluorophenyl)-1,1-difluoro-3-(1H-tetrazol-1-yl)propan-2-ol (102).

4-((6-(2-(2,4-difluorophenyl)-1,1-difluoro-2-hydroxy-3-(1H-tetrazol-1-yl)propyl)pyridin-3-yl)difluoromethyl)benzonitrile (103).

In another aspect, the invention provides an agricultural composition comprising the compound of Formula I and an agriculturally acceptable carrier.

In other aspects, the invention provides a compound of any of the formulae herein, wherein the compound inhibits (or is identified to inhibit) lanosterol demethylase (CYP51).

In other aspects, the invention provides a compound of any of the formulae herein, wherein the compound is identified as having an activity range against a target organism (e.g., *C. albicans* minimum inhibitory concentration (MIC) <0.25 micrograms per milliliter (μg/mL)); *S. tritici* minimum inhibitory concentration (MIC)<0.5 micrograms per milliliter (μg/mL); e.g., *P. triticina* minimum inhibitory concentration (MIC)<0.5 micrograms per milliliter (μg/mL).

In another aspect, the invention provides a pharmaceutical composition comprising the compound of any the formulae herein (e.g., Formula I) and a pharmaceutically acceptable carrier.

In other aspects, the invention provides a method of modulating metalloenzyme activity in a subject, comprising contacting the subject with a compound of any the formulae herein (e.g., Formula I), in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound of any the formulae herein (e.g., Formula I) or pharmaceutical composition thereof.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound of any the formulae herein (e.g., Formula I) or pharmaceutical composition thereof, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound of any the formulae herein (e.g., Formula I), or pharmaceutical composition thereof, such that metalloenzyme activity in said subject is modulated (e.g., down regulated, inhibited).

The methods herein include those wherein the disease or disorder is mediated by any of 4-hydroxyphenyl pyruvate dioxygenase, 5-lipoxygenase, adenosine deaminase, alcohol dehydrogenase, aminopeptidase N, angiotensin converting enzyme, aromatase (CYP19), calcineurin, carbamoyl phosphate synthetase, carbonic anhydrase family, catechol-O-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase 111, phosphodiesteraseIV, phosphodiesteraseV, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is mediated by any of 1-deoxy-D-xylulose-5-phosphate reductoisomerase (DXR), 17-alpha hydroxylase (CYP17), aldosterone synthase (CYP11B2), aminopeptidase P, anthrax lethal factor, arginase, beta-lactamase, cytochrome P450 2A6, D-Ala D-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesteraseVII, relaxase, retinoic acid hydroxylase (CYP26), TNF-alpha converting enzyme (TACE), UDP-(3-O—(R-3-hydroxymyristoyl))-N-acetylglucosamine deacetylase (LpxC), vascular adhesion protein-1 (VAP-1), or vitamin D hydroxylase (CYP24).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic fungal infection, skin structure fungal infection, mucosal fungal infection, or onychomycosis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another aspect of the invention is a composition comprising a compound of a formulae herein (e.g., Formula I) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically or agriculturally effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 micrograms per kilogram (µg/kg) to about 200 milligrams per kilogram (mg/kg), preferably about 0.01 mg/kg to about 200 mg/kg, more preferably about 0.015 mg/kg to about 30 mg/kg of body weight. In other embodiments, the therapeutically effect amount may range from about 1.0 picomolar (pM) to about 10 micromolar (µM). The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between about 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al (1977) "Pharmaceutical Salts", J. Pharm. Sci. 66:1-19) The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of a metalloenzyme, as compared to the activity of a metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used throughout this specification, the term 'R' refers to the group consisting of $C_{1-8}$ alkyl, $C_{3-8}$ alkenyl or $C_{3-8}$ alkynyl, unless stated otherwise.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "haloalkyl" refers to an alkyl radical that is substituted by one or more halo substituents. Examples of haloalkyl groups include fluoromethyl difluoromethyl, trifluoromethyl, bromomethyl, chloromethyl, and 2,2,2-trifluoroethyl.

The term "alkoxy" refers to an —OR substituent radical.

As used herein, the term "halogen", "hal" or "halo" means —F, —Cl, —Br or —I.

The term "haloalkoxy" refers to an —OR substituent where R is fully or partially substituted with Cl, F, I or Br or any combination thereof. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remaining ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxyalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jähnisch, K et al., *Angew. Chem. Int. Ed. Engl.* 2004, 43, 406; and references therein). Additional reaction schemes and protocols may be determined by the skilled artisan by use of commercially available structure-searchable database software, for instance, SciFinder® (Chemical Abstracts Service (CAS®) division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms; in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

In another aspect, the invention provides a method of synthesizing a compound of formula I (or any of the formulae herein) as described herein. Another embodiment is a method of making a compound of any of the formulae herein using any one, or combination of, reactions delineated herein. The method can include the use of one or more intermediates or chemical reagents delineated herein.

Methods of Treatment

In one aspect, the invention provides a method of modulating the metalloenzyme activity of a cell in a subject, comprising contacting the subject with a compound of Formula I, in an amount and under conditions sufficient to modulate metalloenzyme activity.

In one embodiment, the modulation is inhibition.

In another aspect, the invention provides a method of treating a subject suffering from or susceptible to a metalloenzyme-mediated disorder or disease, comprising administering to the subject an effective amount of a compound or pharmaceutical or agricultural composition of Formula I.

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical or agricultural composition of Formula I, such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is prostate cancer, breast cancer, inflammatory bowel disease, psoriasis, systemic fungal infection, skin structure fungal infection, mucosal fungal infection, and onychomycosis.

In certain embodiments, the subject is a mammal, preferably a primate or human.

In another embodiment, the invention provides a method as described above, wherein the effective amount of the compound of Formula I is as described above.

In another embodiment, the invention provides a method as described above, wherein the compound of Formula I is administered intravenously, intramuscularly, subcutaneously, intracerebroventricularly, orally or topically.

In other embodiments, the invention provides a method as described above, wherein the compound of Formula I is administered alone or in combination with one or more other therapeutics. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of Formula I and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of Formula I, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *J. Pharm. Sci.* 1997, 66, 1-19). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intracerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar, alginic acids; pyrogen-free water; isotonic saline; and phosphate buffer solution; skim milk powder, as well as other non-toxic compatible substances used in pharmaceutical formulations such as Vitamin C, estrogen and Echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making, levigating, emulsifying, encapsulating, entrapping or lyophilization processes. The compositions can be formulated in a conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen-free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/mL); benzalkonium chloride (0.1-0.2 mg/mL); polysorbate 80 (TWEEN® 80; 0.5-5 mg/mL); carboxymethylcellulose sodium or microcrystalline cellulose (1-15 mg/mL); phenylethanol (1-4 mg/mL); and dextrose (20-50 mg/mL). The pH of the final suspension can be adjusted to range from about pH 5 to pH 7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay, such as the in vitro fungal MIC or minimal fungicidal concentration MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, 12th edition, McGraw-Hill Professional, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

Compounds of Formula I may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Compounds of Formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Suitable salts include those derived from alkali or alkaline earth metals and those derived from ammonia and amines. Preferred cations include sodium, potassium, magnesium, and aminium cations of the formula:

$R^{13}R^{14}R^{15}R^{16}N^+$ wherein $R^{13}$, $R^{14}$, $R^{15}$ and $R^{16}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{13}$, $R^{14}$, $R^{15}$ and $R^{16}$ are sterically compatible. Additionally, any two of $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula I because they are water-soluble and lend themselves to the preparation of desirable aqueous based herbicidal compositions.

The compounds and compositions herein can be used in methods of modulating metalloenzyme activity in a microorganism on a plant comprising contacting a compound herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

One aspect is a method of treating or preventing a fungal disease or disorder in or on a plant comprising contacting a compound (or composition) of any of the formulae herein with the plant. Another aspect is a method of treating or preventing fungi growth in or on a plant comprising contacting a compound (or composition) of any of the formulae herein with the plant. Another aspect is a method of inhibiting microorganisms in or on a plant comprising contacting a compound (or composition) of any of the formulae herein with the plant.

The compounds and compositions herein may be used in methods of preventing or controlling pathogen induced diseases on a plant comprising contacting a compound herein with the plant (e.g., seed, seedling, grass, weed, grain) or an area adjacent to the plant. The compounds and compositions herein may be used to treat a plant, field or other agricultural area by administering the compound or composition (e.g., contacting, applying, spraying, atomizing, dusting, etc.) to the subject plant, field or other agricultural area. The administration may be either pre- or post-emergence. The administration may be either as a treatment or preventative regimen. As such, the compounds, compositions and agricultural uses herein include lawn, turf, ornamental vegetation, home and garden, farming, range and pasture applications. The pathogen may be any on a plant and include those delineated herein.

One embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants.

The compounds herein can be used alone or in combination with other agriculturally active agents. The use of the compounds or compositions (and the compositions) herein can further comprise an additional active agent such as an azole fungicide selected from epoxiconazole, tebuconazole, fluquinconazole, flutriafol, metconazole, myclobutanil, cycproconazole, prothioconazole and propiconazole.

The use of the compounds or compositions (and the compositions) herein can further comprise an additional active agent such as an azole fungicide selected from the group trifloxystrobin, pyraclostrobin, orysastrobin, fluoxastrobin and azoxystrobin.

Preferably, the compounds of the present disclosure are applied in the form of a formulation, comprising one or more of the compounds of Formula I with an agriculturally or phytologically acceptable carrier. The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The present disclosure contemplates all vehicles by which one or more of the compounds may be formulated for delivery and use as a fungicide. Typically, formulations are applied as aqueous suspensions or emulsions. Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water, such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid, it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rapeseed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodium carboxymethylcellulose, ethyl cellulose, hydroxypropyl methyl cellulose, and mixtures thereof.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer, polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, I-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin; diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemetonmethyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vemolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

The compositions of Formula I may be effective against pathogen induced diseases where the plant fungal pathogen belonging to at least one genera selected from *Blumeria, Podosphaera, Sphaerotheca, Uncinula, Erysiphe, Puccinia, Phakopsora, Gymnosporangiumn, Hemileia, Uromyces, Alternaria, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminthosporium. Stagonospora, Exserohilum*, and *Pyricularia*. Pathogens such as *Venturia inaequalis, Septoria tritici, Cercospora beticola, Cercospora arachidicola, Colletotrichum lagenarium, Puccinia graminis* f. sp. *tritici, Puccinia recondita tritici, Uncinula necator, Blumeria graminis*, and *Mycosphaerella fijiensis* may be controlled by compositions of Formula I. Additionally, the compositions of Formula I may be effective in preventing or controlling diseases including apple scab, speckled leaf blotch of wheat, leaf spot of sugarbeets, leaf spot of peanut, cucumber anthracnose, wheat leaf rust, grape powdery mildew, wheat powdery mildew, and black sigatoka.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound of any the formulae herein (e.g., Formula I); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder, precautions; warnings; description of research studies; and/or references. The instructions may be printed directly on the container (when present), or as a label applied to the container, or as a separate sheet, pamphlet, card, or folder supplied in or with the container.

The compounds of the present disclosure may be effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Azole Targets

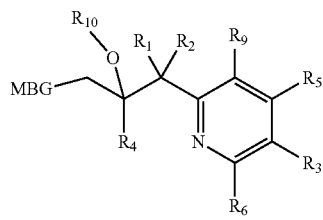

Formula I

Syntheses of azole targets (compounds of Formula I) may be accomplished using the example synthesis that is shown below (Scheme 1). The 2-pyridine example below (Formula I in Scheme 2), may be prepared starting from functionalized halo-aromatic starting materials. For the purpose of this example, $R_4$ is a halogenated benzene moiety. The bromo-intermediates (C) may be treated with olefins or nucleophiles to introduce an $R_3$ moiety (M=metal or counter-ion; Schemes 1 and 2). For Heck couplings, $R_3$-M is the combination of a palladium (Pd) catalyst with the olefin. Typically, M is potassium, lithium, or magnesium. Additionally, bromo-intermediates (C) may be converted to the corresponding boronic acids (using n-butyllithium (n-BuLi) and trimethyl borate ($B(OCH_3)_3$)) and then coupled using Suzuki cross-coupling methodology with bromo-aromatic reagents ($R_3$—Br). The functionalized compound (D) can then be treated with the azoles to obtain compounds of Formula 1.

Scheme 1

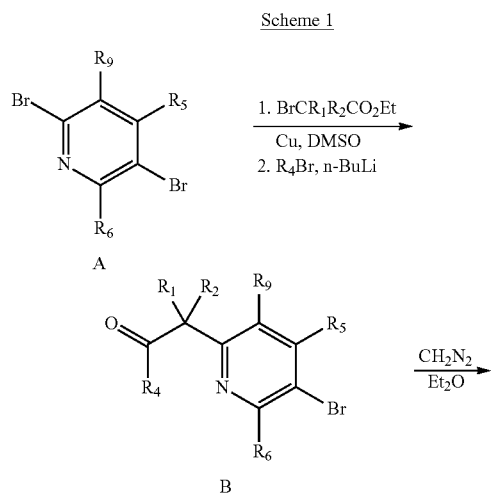

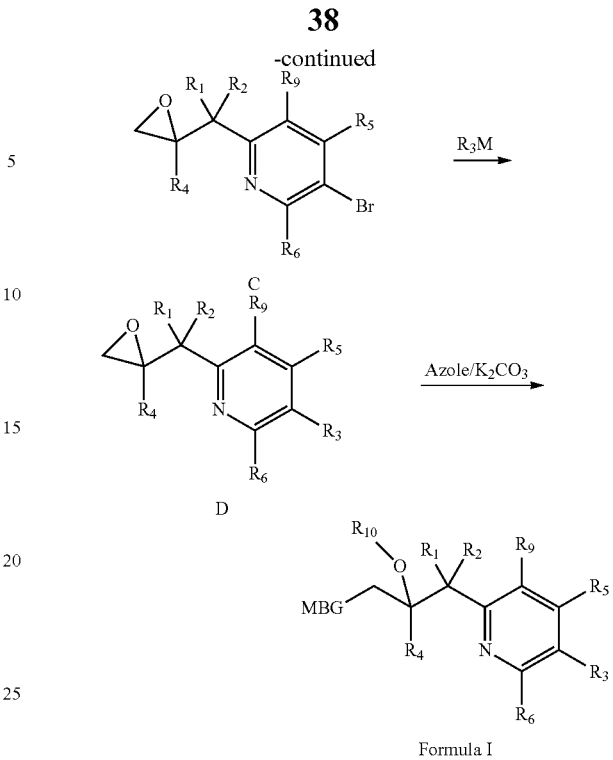

Formula I

The example synthesis commences with condensation of 2,5-dibromopyridine with copper-activated ethyl 2-bromo-2,2-difluoroacetate followed by condensation of the incipient ethyl ester product with lithiated 1-bromo-2,4-difluorobenzene to furnish ketone E (Scheme 2). The ketone is epoxidized with diazomethane to afford F. The 1-tetrazole product 1 is obtained by opening the epoxide F with tetrazole in the presence of potassium carbonate.

Scheme 2

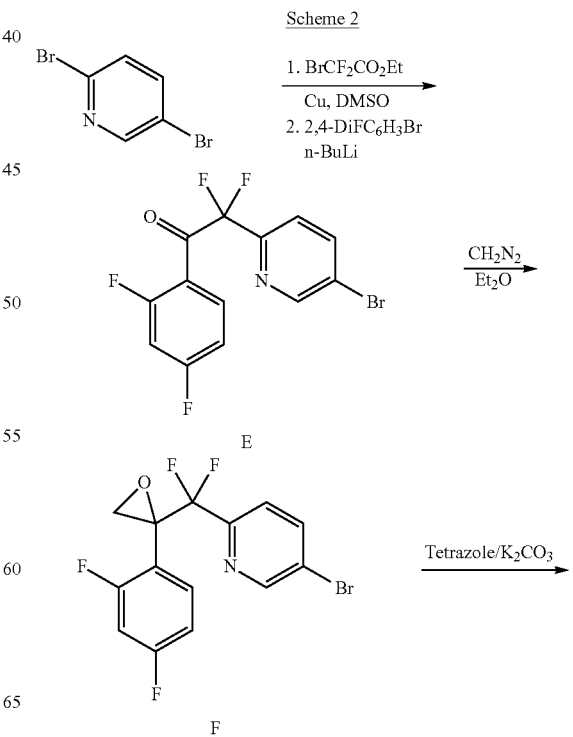

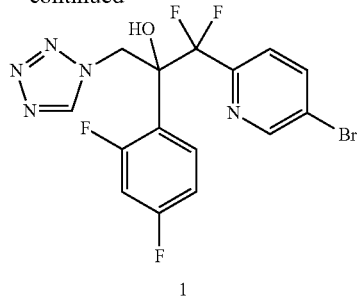

1

Synthesis of 2-(5-bromopyridin-2-yl)-1-(2,4-difluorophenyl)-2,2-difluoroethanone (E)

To a suspension of copper powder (2.68 grams (g), 42.2 millimoles (mmol)) in dimethyl sulfoxide (DMSO; 35 mL) was added ethyl 2-bromo-2,2-difluoroacetate (2.70 milliliters (mL), 21.10 mmol), and the mixture was stirred for 1 hour (h) at room temperature (RT). 2,5-Dibromopyridine (2.50 g, 10.55 mmol) was then added and stirring was continued for 15 h at RT. The reaction was quenched with aqueous (aq) ammonium chloride ($NH_4Cl$), and the mixture was extracted with dichloromethane ($CH_2C_2$; 3×25 mL). The combined organic layers were washed with water, washed with brine, dried over anhydrous sodium sulfate ($Na_2SO_4$), and concentrated under reduced pressure to afford crude product mixture. Purification by column chromatography (eluting with EtOAc-hexane) afforded the ethyl ester intermediate (2.40 g, 8.57 mmol, 81%) as a pale yellow oil. $^1$H NMR (500 MHz, $CDCl_3$): δ 8.71 (s, 1H), 8.00 (d, J=9.0 Hz, 1H), 7.64 (d, J=9.0 Hz, 1H), 4.42-4.35 (m, 2H), 1.39-1.31 (m, 3H).

To a stirred solution of 1-bromo-2,4-difluorobenzene (1.65 g, 8.57 mmol) in diethyl ether ($Et_2O$; 10 mL) was added n-BuLi (2.3 Molar (M) in hexane; 3.70 mL, 8.57 mmol) at −70° C. followed by of the above ester (2.40 g, 8.57 mmol) in $Et_2O$ (5 mL) after 15 minutes (min). The reaction mixture was stirred for 1 h at −70° C., then warmed to RT and stirred for another 2 h. The reaction was quenched with aq $NH_4Cl$ solution and extracted with ethyl acetate (EtOAc; 3×20 mL). The combined organic layers were washed with water, washed with brine, dried over anhydrous $Na_2SO_4$, and concentrated under reduced pressure. The crude compound was purified by column chromatography (eluting with EtOAc/hexane) to afford ketone E (1.30 g, 3.73 mmol, 43%) as yellow liquid. $^1$H NMR (500 MHz, $CDCl_3$): δ 8.62 (s, 1H), 8.08-8.04 (m, 2H), 7.74-7.70 (m, 1K), 7.05-6.95 (m, 1H), 6.88-6.78 (m, 1H). MS (ESI): m/z 347, 349 [($M^+$+1)+2].

Synthesis of 5-bromo-2-((2-(2,4-difluorophenyl)oxiran-2-yl)difluoromethyl)pyridine (F)

To a stirred solution of ketone E (1.30 g, 3.73 mmol) in $Et_2O$ (300 mL) was added freshly prepared diazomethane at 0° C. The reaction mixture was warmed to RT and stirred for 2 h. The volatiles were removed under reduced pressure to afford a crude product mixture. Column chromatography (eluting with EtOAc-hexane) afforded oxirane F (800 mg, 2.20 mmol, 59%) as light yellow solid. $^1$H NMR (500 MHz, $CDCl_3$): δ 8.72 (s, 1H), 7.89 (d, J=9.0 Hz, 1H), 7.39-7.35 (m, 2H), 6.86-6.83 (m, 1H), 6.77-6.74 (m, 1H), 3.44 (s, 1K), 2.98 (s, 1H). MS (ESI): m/z 362, 364 [($M^+$+1)+2].

Example 1

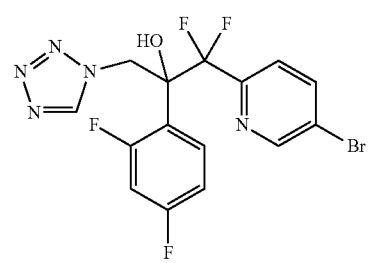 [SMILES: OC(Cn1cnnn1)(c1ccc(F)cc1F)C(F)(F)c1ccc(Br)cn1]

1-(5-Bromopyridin-2-yl)-2-(2,4-difluorophenyl)-1,1-difluoro-3-(1H-tetrazol-1-yl)propan-2-ol (1)

To a stirred solution of tetrazole (248 milligrams (mg), 3.54 mmol) in N,N-dimethylformamide (DMF; 10 milliliters (mL)) was added potassium carbonate ($K_2CO_3$) (244 mg, 3.54 mmol) followed by epoxide F (1.28 grams (g), 3.54 mmol). The reaction mixture was stirred for 3 h at 60° C. The volatiles were removed under reduced pressure. The residue was taken into EtOAc and washed with brine, washed with water, and dried over anhydrous $Na_2SO_4$. Purification by column chromatography (eluting with EtOAc/hexane) afforded compound 1 (350 mg, 0.81 mmol, 23%) as a pale yellow powder. $^1$H NMR (500 MHz, $CDCl_3$): δ 8.74 (s, 1H), 8.62 (s, 1H), 7.94 (d, J=7.50 Hz, 1H), 7.46 (d, J=9.0 Hz, 1H), 7.31-7.26 (m, 1H), 6.88 (s, 1H), 6.78-6.74 (m, 1H), 6.70-6.67 (m, 1H), 5.60 (d, J=14.50 Hz, 1H), 5.11 (d, J=14.50 Hz, 1H). MS (ESI): m/z 432, 434 [$M^+$+2]. HPLC: 95.65%.

Compounds 19-27 in Table 1 were prepared using the same conditions as compound 1. (See Table 1 for starting materials.)

Example 2

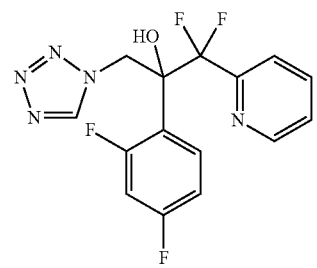 [SMILES: OC(Cn1cnnn1)(c1ccc(F)cc1F)C(F)(F)c1ccccn1]

2-(2,4-Difluorophenyl)-1,1-difluoro-1-(pyridin-2-yl)-3-(1H-tetrazol-1-yl)propan-2-ol (2)

To a stirred solution of tetrazole (49 mg, 0.7 mmol) in DMF (5 mL) was added $K_2CO_3$ (49 mg, 0.35 mol) followed by the analogous epoxide (prepared starting from 2-bromopyridine using the synthesis shown in Scheme 2; 200 mg, 0.7 mmol). The reaction mixture was stirred for 4 h at 65° C. The volatiles were removed under reduced pressure and extracted with EtOAc (2×20 mL). The organic layer was washed with water, washed with brine, and dried over anhydrous Na₂SO₄. The crude compound was purified by column chromatography (eluting with EtOAc/hexane) to afford compound 2 (30 mg, 0.09 mmol, 12%) as white solid. ¹H NMR (500 MHz, CDCl₃): δ 8.75 (s, 1H), 8.55 (d, J=4.0 Hz, 1H), 7.84-7.82 (m, 1H), 7.75 (s, 1H), 7.59 (d, J=7.50 Hz, 1H), 7.45-7.43 (m, 1H), 7.34-7.26 (m, 1H), 6.78-6.76 (m, 1H), 6.67-6.64 (m, 1H), 5.58 (d, J=13.50 Hz, 1H), 5.12 (d, J=13.50 Hz, 1H). HPLC: 95.42%. MS (ESI): m/z 354 [M⁺+1].

Chiral Preparative high-Performance Liquid Chromatography (HPLC) Separation of Enantiomers of 2

The enantiomers of 2 were separated by preparative HPLC using a CHIRALPAK® AD-H column (250×20 mm, 5μ; mobile phase (A) 0.1% trifluoroacetic acid (TFA) in n-hexane-(B) isopropyl alcohol (IPA) (A:B=93:7) and flow rate 15 mL/min) to obtain 2-(−) as off-white solid.

Analytical Data:

Chiral HPLC: 99.69% ee, $R_f$=36.90 min (CHIRALPAK® AD-H, 250×4.6 mm, 5μ; mobile phase (A) 0.1% TFA in n-hexane-(B) IPA (A:B=93:7); flow rate 1.00 mL/min). Optical rotation $[\alpha]_D^{25}$: −13.68° (c=0.1% in methyl alcohol (CH₃OH)). ¹H NMR (500 MHz, CDCl₃): δ 8.76 (s, 1H), 8.54 (s, 1H), 7.83 (t, J=7.0 Hz, 1H), 7.64 (s, 1H), 7.59 (d, J=8.0 Hz, 1H), 7.46-7.43 (m, 1H), 7.35-7.30 (m, 1H), 6.78-6.74 (m, 1H), 6.66-6.63 (m, 1H), 5.59 (d, J=14.5 Hz, 1H), 5.12 (d, J=14.5 Hz, 1H). MS (ESI): m/z 354 [M+H]⁺. HPLC: 98.1%.

Example 3

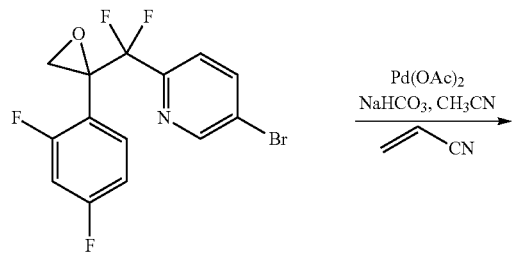

(E)-3-(6-(2-(2,4-Difluorophenyl)-1,1-difluoro-2-hydroxy-3-(1H-tetrazol-1-yl)propyl)pyridin-3-yl)acrylonitrile (3)

To a stirred solution of F (1.0 g, 2.76 mmol) in DMF (10 mL) were added acrylonitrile (0.52 g, 9.9 mmol), a catalytic amount of tetrabutylammonium bromide (TBAB), and sodium bicarbonate (NaHCO₃; 0.27 g, 3.32 mmol) at RT under nitrogen (N₂) atmosphere. After the mixture was purged with argon for a period of 30 min, palladium(II) acetate (Pd(OAc)₂; 0.18 g, 0.82 mmol) was added. The temperature was elevated to 110° C. and stirring was continued for 4 h. After complete consumption of starting material, the reaction mixture was cooled, the volatiles were evaporated under reduced pressure and the obtained residue was dissolved in EtOAc (250 mL). The organic layer was washed with water (2×50 mL), brine (50 mL) and dried over anhydrous Na₂SO₄. After filtering off the solid, the solvent was evaporated under reduced pressure to give crude compound. The crude material was purified by column chromatography (eluting with EtOAc/hexane) to afford G (0.19 g, 0.56 mmol, 20%) as a thick syrup. ¹H NMR (200 MHz, CDCl₃): δ 8.72 (s, 1H), 7.84 (d, J=8.0 Hz, 1H), 7.56-7.32 (m, 3H), 6.88-6.69 (m, 2H), 6.05 (d, J=16.8 Hz, 1H), 3.46 (d, J=5.2 Hz, 1H), 3.00 (d, J=5.2 Hz, 1H).

To a stirred solution of G (170 mg, 0.5 mmol) in DMF (10 mL) were added 1H-tetrazole (124 mg, 1.77 mmol) and K₂CO₃ (35 mg, 0.25 mmol) at RT under N₂ atmosphere. The reaction mixture was stirred for 22 h at 65° C. The volatiles were evaporated under reduced pressure and the resulting residue was dissolved in EtOAc (150 mL). The organic layer was washed with water (2×75 mL) and brine (50 mL), dried over anhydrous Na₂SO₄ and evaporated under reduced pressure. The crude material was purified by column chromatography (eluting with EtOAc/hexane) to afford 3 (30 mg, 0.074 mmol, 14%) as a solid. ¹H NMR (500 MHz, CDCl₃): δ 8.73 (s, 1H), 8.58 (s, 1H), 7.88 (d, J=6.5 Hz, 1H), 7.64 (d, J=7.5 Hz, 1H), 7.39 (d, J=16.5 Hz, 1H), 7.35-7.30 (m, 1H), 6.95 (br s, 1H), 6.79-6.73 (m, 1H), 6.68 (t, J=8.5 Hz, 1H), 6.04 (d, J=16.5 Hz, 1H), 5.53 (d, J=14.0 Hz, 1H), 5.18 (d, J=14.0 Hz, 1H). MS (ESI): m/z 405 [M⁺+1]. HPLC: 99.3%.

Example 4

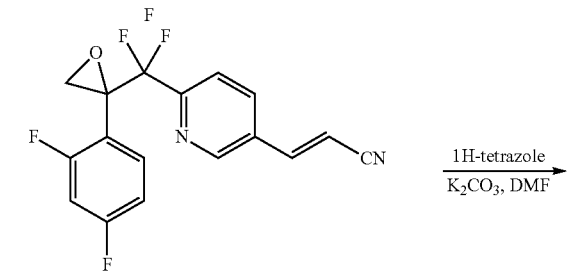

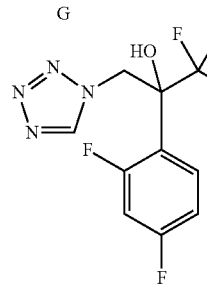

3

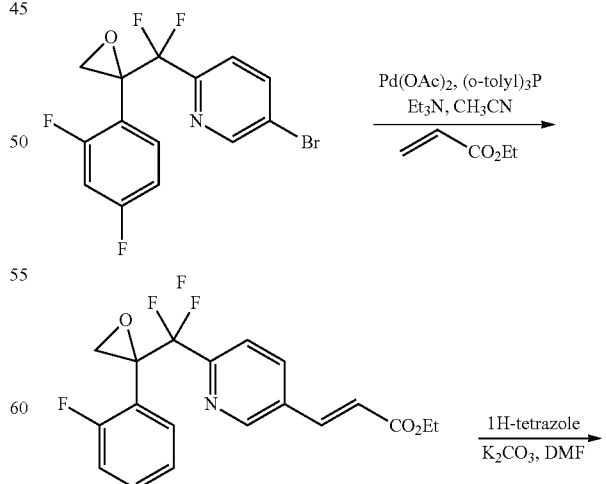

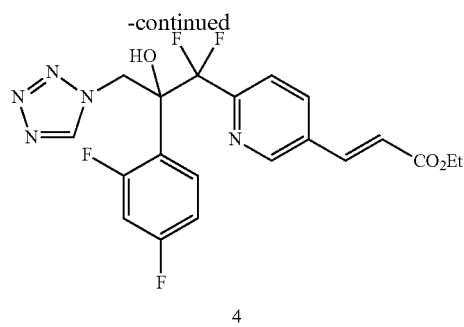

4

(E)-Ethyl 3-(6-(2-(2,4-difluorophenyl)-1,1-difluoro-2-hydroxy-3-(1H-tetrazol-1-yl)propyl)pyridin-3-yl)acrylate (4)

To a stirred solution of F (0.5 g, 1.38 mmol) in acetonitrile (CH$_3$CN; 2 mL) were added triethylamine (Et$_3$N; 0.37 g, 3.6 mmol) and tri-o-tolylphosphine (0.13 g, 0.42 mmol), followed by ethyl acrylate (0.49 g, 4.8 mmol) at RT under N$_2$ atmosphere. After purging with argon for a period of 30 min, Pd(OAc)$_2$ (68 mg, 0.30 mmol) was added to the reaction mixture. Then gradually the temperature was elevated to 90° C. and stirring was continued for 16-18 h. After complete consumption of starting material (by thin layer chromatography (TLC)), the reaction mixture was cooled to RT and diluted with water (50 mL). The aqueous layer was extracted with Et$_2$O (3×50 mL); the combined organic phases were washed with water (2×25 mL) and brine (25 mL) and dried over anhydrous Na$_2$SO$_4$. After filtration and evaporation, the crude material was purified by column chromatography (eluting with EtOAc/hexane) to afford coupled product H (0.14 g, 0.070 mmol, 26.9%) as a yellow color semi-solid. $^1$H NMR (200 MHz, CDCl$_3$): δ 8.77 (s, 1H), 7.87 (d, J=8.0 Hz, 1H), 7.70 (d, J=16.0 Hz, 1H), 7.50 (d, J=8.0 Hz, 1H), 7.45-7.30 (m, 1H), 6.90-6.55 (m, 2H), 6.55 (d, J=16.0 Hz, 1H), 4.30 (q, J=7.2 Hz, 2H), 3.46 (d, J=5.0 Hz, 1H), 2.97-2.98 (m, 1H), 1.35 (t, J=7.4 Hz, 3H). MS(ESI): m/z 382 [M$^+$+1].

To a stirred solution of H (1.25 g, 3.2 mmol) in DMF (5 mL) were added 1H-tetrazole (0.34 g, 4.8 mmol) and K$_2$CO$_3$ (0.9 g, 6.5 mmol) at RT under N$_2$ atmosphere. The reaction mixture was slowly heated to 65° C. and stirring was continued for 10 h. The reaction mixture was cooled to RT, diluted with water (40 mL), and the aqueous layer was extracted with Et$_2$O (2×100 mL). The combined organic phases were washed with water (2×25 mL) and brine (25 mL), dried over anhydrous Na$_2$SO$_4$ and concentrated under reduced pressure. The crude material was purified by column chromatography (eluting with EtOAc/hexane) to afford 4 (0.2 g, 0.044 mmol, 13.6%) as an off-white solid. $^1$H NMR (200 MHz, CDCl$_3$): δ 8.76 (s, 1H), 8.64 (s, 1H), 7.94 (dd, J=8.2, 2.2 Hz, 1H), 7.68-7.59 (m, 2H), 7.40-7.28 (m, 2H), 6.81-6.61 (m, 2H), 6.55 (d, J=16.2 Hz, 1H), 5.60 (d, J=14.5 Hz, 1H), 5.15 (d, J=14.5 Hz, 1H), 4.30 (q, J=7.2 Hz, 2H), 1.35 (t, J=7.4 Hz, 3H). MS (ESI): m/z 452 [M$^+$+1].

Example 5

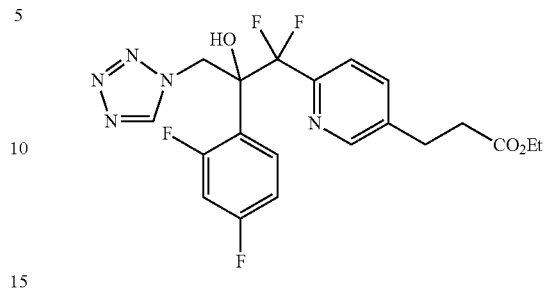

Ethyl 3-(6-(2-(2,4-difluorophenyl)-1,1-difluoro-2-hydroxy-3-(1H-tetrazol-1-yl)propyl)pyridin-3-yl)propanoate (5)

To a solution of 4 (20 mg, 0.04 mmol) in ethyl alcohol (EtOH; 5 mL) was added 10% palladium on carbon (Pd/C; 2 mg) under N$_2$ atmosphere, and the reaction mixture was stirred under hydrogen atmosphere (balloon pressure) at RT for 3 h. The reaction mixture was filtered through a pad of Celite®, the Celite® bed was washed thoroughly with EtOH (2×5 mL), and the obtained filtrate was concentrated under vacuum. The crude material was purified by column chromatography (eluting with EtOAc/hexane) to afford 5 (10 mg, 0.02 mmol, 50%) as an off-white solid. $^1$H NMR (500 MHz, CDCl$_3$): δ 8.75 (s, 1H), 8.40 (s, 1H), 7.67 (d, J=7.5 Hz, 1H), 7.50 (d, J=8.5 Hz, 1H), 7.36-7.31 (m, 1H), 6.77 (app t, 1H), 6.65 (app t, 1H), 5.56 (d, J=14.5 Hz, 1H), 5.10 (d, J=14.5 Hz, 1H), 4.12 (q, J=7.5 Hz, 2H), 2.98 (t, J=7.0 Hz, 2H), 2.64 (t, J=7.0 Hz, 2H), 1.23 (t, J=7.4 Hz, 3H). MS (ESI): m/z 454 [M$^+$+1]. HPLC: 97.4%.

Example 6

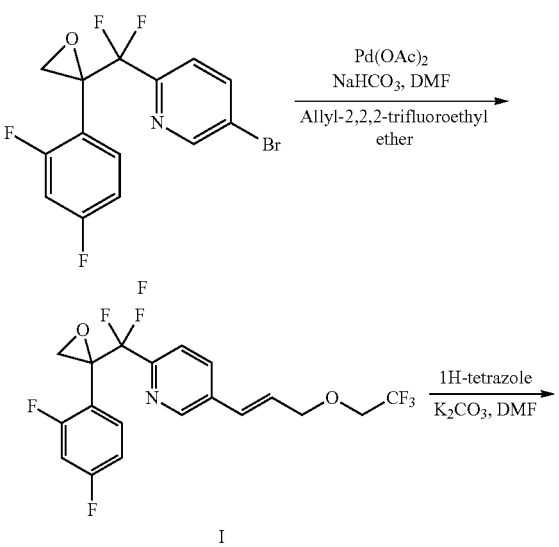

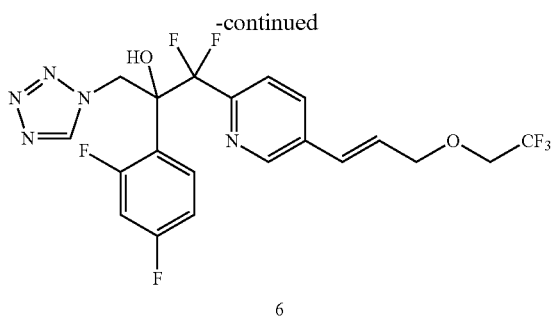

6

(E)-2-(2,4-Difluorophenyl)-1,1-difluoro-3-(1H-tetrazol-1-yl)-1-(5-3-(2,2,2-trifluoroethoxy)prop-1-enyl)pyridin-2-yl) propan-2-ol (6)

To a stirred solution of F (1.0 g, 2.76 mmol) in DMF (10 mL) were added allyl-2,2,2-trifluoro-ethyl ether (1.4 g, 9.9 mmol), a catalytic amount of TBAB and NaHCO$_3$ (0.3 g, 3.58 mmol) at RT under N$_2$ atmosphere. After purging with argon for a period of 30 min, Pd(OAc)$_2$ (0.18 g, 0.83 mmol) was added to the reaction mixture. Then gradually the temperature was elevated to 100° C. and stirring was continued for 3 h. The reaction mixture was cooled to RT, diluted with EtOAc (150 mL), and filtered through a pad of Celite®. The filtrate was washed with water (2×50 mL) and brine (50 mL) and dried over anhydrous Na$_2$SO$_4$. After filtering off the solid, the solvent was evaporated under reduced pressure to give I (0.48 g, crude) as a thick syrup. The crude compound was used in the next step without further purification.

To a stirred solution of K (0.39 g, crude) in DMF (10 mL) were added 1H-tetrazole (0.22 g, 3.2 mmol) and K$_2$CO$_3$ (0.23 g, 1.66 mmol) at RT under N$_2$ atmosphere. The reaction mixture was stirred for 16 h at 65° C. The reaction mixture was cooled to RT and diluted with EtOAc (150 mL). The organic layer was washed with water (2×75 mL) and brine (50 mL), dried over anhydrous Na$_2$SO$_4$, filtered, and evaporated under reduced pressure. The crude material was purified by column chromatography (eluting with EtOAc/hexane) to afford 6 (0.26 g, 0.52 mmol, 57%) as a solid. $^1$H NMR (500 MHz, CDCl$_3$): δ 8.74 (s, 1H), 8.51 (s, 1H), 7.80 (dd, J=8.0, 2.0 Hz, 1H), 7.57 (s, 1H), 7.54 (d, J=8.0 Hz, 1H), 7.35-7.30 (m, 1H), 6.77-6.73 (m, 1H), 6.67-6.63 (m, 2H), 6.43-6.37 (m, 1H), 5.58 (d, J=14.0 Hz, 1H), 5.11 (d, J=14.0 Hz, 1H), 4.35 (app d, 2H), 3.92-3.87 (m, 2H). MS (ESI): m/z 492 [M$^+$+1]. HPLC: 99.6%.

Example 7

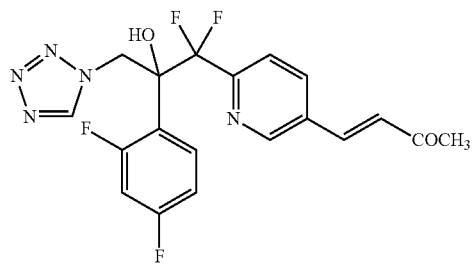 [SMILES: CC(=O)/C=C/c1ccc(C(F)(F)C(O)(Cn2cnnn2)c2ccc(F)cc2F)nc1]

(Z)-4-(6-(2-(2,4-Difluorophenyl)-1,1-difluoro-2-hydroxy-3-(1H-tetrazol-1-yl)propyl)pyridin-3-yl)but-3-en-2-one (7)

To a stirred solution of F (1.0 g, 2.76 mmol) in CH$_3$CN (10 mL) were added Et$_3$N (1.0 mL, 7.4 mmol) and tri-o-tolylphosphine (0.26 g, 0.88 mmol) followed by methyl vinyl ketone (0.8 mL, 8.2 mmol) at RT under N$_2$ atmosphere. After purging with argon for a period of 30 min, Pd(OAc)$_2$ (136 mg, 0.67 mmol) was added to the reaction mixture. Then gradually the temperature was raised to 90° C., and stirring was continued for 16-18 h. After complete consumption of starting precursor (by TLC), the reaction mixture was cooled to RT and filtered through a pad of Celite®. The filtrate was concentrated; the residue was diluted with water (50 mL). The aqueous layer was extracted with Et$_2$O (3×50 mL); the combined organic phases were washed with water (2×25 mL) and brine (25 mL) and dried over anhydrous Na$_2$SO$_4$. After filtration and evaporation, the crude material was purified by column chromatography (eluting with EtOAc/hexane) to afford the coupled product (0.4 g, 1.1 mmol, 41%) as a yellow colored semi-solid. $^1$H NMR (500 MHz, CDCl$_3$): δ 8.78 (s, 1H), 7.90 (d, J=8.0 Hz, 1H), 7.52-7.48 (m, 2H), 7.40-7.36 (m, 1H), 6.85-6.79 (m, 2H), 6.76-6.71 (m, 1H), 3.46 (d, J=5.5 Hz, 1H), 2.98 (d, J=4.5 Hz, 1H), 2.41 (s, 3H). MS (ESI): m/z 352 [M$^+$+1].

To a stirred solution of coupled product (0.42 g, 1.16 mmol) in DMF (5 mL) were added 1H-tetrazole (81 mg, 1.16 mmol) and K$_2$CO$_3$ (80 mg, 0.58 mmol) at RT under N$_2$ atmosphere. The reaction mixture was slowly heated to reflux temperature and stirring was continued for 3-4 h. The progress of the reaction was monitored by TLC. The volatiles were evaporated under reduced pressure; the resulting residue was diluted with water (25 mL). The aqueous layer was extracted with EtOAc (3×20 mL); the combined organic phases were washed with water (25 mL) and brine (25 mL) and dried over anhydrous Na$_2$SO$_4$. After filtration and evaporation, the crude material was purified by column chromatography (eluting with EtOAc/hexane) to afford 7 (14.6 mg, 0.034 mmol, 3%) as a semi-solid. $^1$H NMR (500 MHz, CDCl$_3$): δ 8.74 (s, 1H), 8.64 (s, 1H), 7.95 (d, J=6.5 Hz, 1H), 7.61 (d, J=8.5 Hz, 1H), 7.45 (dd, J=16.5, 4.5 Hz, 1H), 7.35-7.30 (m, 2H), 6.82-6.74 (m, 2H), 6.68-6.65 (m, 1H), 5.55 (d, J=15.0 Hz, 1H), 5.16 (d, J=15.0 Hz, 1H), 2.40 (s, 3H). MS (ESI): m/z 422 [M$^+$+1].

Example 8

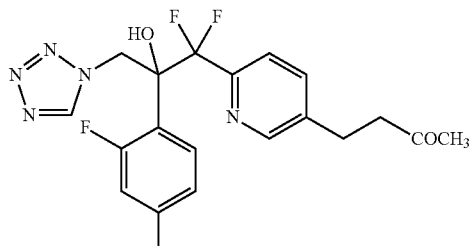

4-(6-(2-(2,4-Difluorophenyl)-1,1-difluoro-2-hydroxy-3-(1H-tetrazol-1-yl)propyl)pyridin-3-yl)butan-2-one (8)

To a solution of 7 (30 mg, 0.071 mmol) in CH$_3$OH (10 mL) was added 10% Pd/C (10 mg) under N$_2$ atmosphere and the reaction mixture was stirred under hydrogen atmosphere at RT for 30 min. The reaction mixture was filtered through a pad of Celite®, the Celite® bed was washed thoroughly with EtOAc (3×10 mL) and then the filtrate was concentrated under vacuum. The crude material was purified by column chromatography (eluting with EtOAc/hexane) to afford 8 (16 mg, 0.037 mmol, 53%) as a colorless semi-solid. $^1$H NMR (500 MHz, DMSO-d$_6$): δ 9.11 (s, 1H), 8.45 (s, 1H), 7.74 (d, J=8.0 Hz, 1H), 7.34 (d, J=8.0 Hz, 1H), 7.24-7.21 (m, 2H), 7.17-7.12 (m, 1H), 6.89-6.85 (m, 1H), 5.61 (d, J=14.5 Hz, 1H), 5.06 (d, J=14.5 Hz, 1H), 2.81 (br s, 4H), 2.08 (s, 3H). MS (ESI): m/z 424 [M$^+$+1]. HPLC: 95.3%.

Example 9

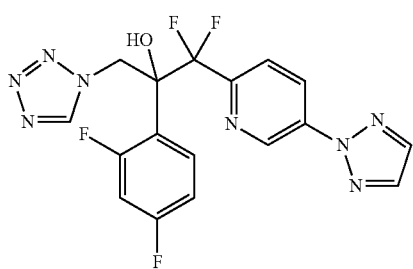 [SMILES: OC(Cn1cnnn1)(c1ccc(F)cc1F)C(F)(F)c1ccc(-n2nccn2)cn1]

1-(5-(2H-1,2,3-Triazol-2-yl)pyridin-2-yl)-2-(2,4-difluorophenyl)-1,1-difluoro-3-(1H-tetrazol-1-yl)propan-2-ol (9)

To a stirred solution of 1H-1,2,3-triazole (410 mg, 5.93 mmol) were added copper (Cu) powder (93 mg, 1.45 mmol), K$_2$CO$_3$ (160 mg, 1.15 mmol) and 1 (300 mg, 0.694 mmol) under N$_2$ atmosphere. The reaction mixture was gradually heated to 140° C. and stirred for 4 h. The reaction mixture was cooled to 100° C., quenched with ethylenediaminetetraacetic acid (EDTA) sodium (Na) salt solution, and made basic with sodium carbonate (Na$_2$CO$_3$) solution. The aqueous layer was extracted with CH$_2$Cl$_2$ (3×50 mL); the combined organic phases were washed with brine, dried over anhydrous Na$_2$SO$_4$ and evaporated under reduced pressure. The crude material was purified by silica gel column chromatography (eluting with 45% EtOAc/hexane) to afford 9 (0.12 g, 0.297 mmol, 42%) as a solid. $^1$H NMR (500 MHz, CDCl$_3$): δ 9.33 (s, 1H), 8.77 (s, 1H), 8.47 (dd, J=8.5, 2.0 Hz, 1H), 7.90 (s, 2H), 7.70 (d, J=9.0 Hz, 1H), 7.34-7.29 (m, 1H), 6.78-6.73 (m, 1H), 6.67-6.64 (m, 1H), 5.64 (d, J=14.0 Hz, 1H), 5.14 (d, J=14.0 Hz, 1H). MS (ESI): m/z 420.9 [M$^+$+1]. HPLC: 99.9%.

Compound 28 in Table 1 was prepared using the same conditions as compound 9. (See Table 1 for starting material.)

Example 10

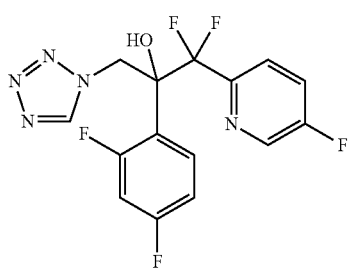 [SMILES: OC(Cn1cnnn1)(c1ccc(F)cc1F)C(F)(F)c1ccc(F)cn1]

2-(2,4-Difluorophenyl)-1,1-difluoro-1-(5-fluoropyridin-2-yl)-3-(1H-tetrazol-1-yl)propan-2-ol (10)

Compound 10 was prepared in a similar manner to compound 1. To a stirred solution of ethyl 2-bromo-2,2-difluoroacetate (2.18 mL, 17.0 mmol) in DMSO (18 mL) was added copper powder (2.16 g, 34.0 mmol) at RT under N$_2$ atmosphere. After being stirred for 2 h at RT, 2-bromo-5-fluoropyridine (1.50 g, 8.52 mmol) was then added, and stirring was continued for 3 h at RT. The progress of the reaction was monitored by TLC. The reaction was quenched with aqueous NH$_4$Cl and extracted with CH$_2$Cl$_2$ (3×50 mL). The combined organic layers were washed with water and brine, dried over anhydrous Na$_2$SO$_4$ and concentrated under reduced pressure to afford crude product mixture. Purification by column chromatography (eluting with EtOAc/hexane) afforded the ester (1.40 g, 6.3 mmol, 77%) as a pale yellow oil. $^1$H NMR (500 MHz, CDCl$_3$): δ 8.50 (s, 1H), 7.78 (dd, J=9.0, 4.0 Hz, 1H), 7.60-7.51 (m, 1H), 4.42-4.32 (m, 2H), 1.39-1.31 (m, 3H). MS (ESI): m/z 220 [M$^+$+1].

To a stirred solution of 1-bromo-2,4-difluorobenzene (1.32 g, 6.84 mmol) in Et$_2$O (15 mL) was added n-BuLi (2.5 M in hexane; 2.7 mL, 6.8 mmol) at −70° C. under N$_2$ atmosphere. After being stirred for 15 min at the same temperature, the ester (1.50 g, 6.84 mmol) in Et$_2$O (5 mL) was added to reaction mixture at −70° C. The reaction mixture was stirred for 1 h at −70° C., warmed to RT and stirred for another 2 h. The progress of the reaction was monitored by TLC. The reaction was quenched with aqueous NH$_4$Cl solution and extracted with EtOAc (3×50 mL). The combined organic layers were washed with water and brine, dried over anhydrous Na$_2$SO$_4$ and concentrated under reduced pressure. The crude compound was purified by column chromatography (eluting with EtOAc/hexane) to afford the ketone (0.69 g, 2.4 mmol, 35%) as a colorless syrup. $^1$H NMR (200 MHz, CDCl$_3$): δ 8.42 (s, 1H), 8.12-8.00 (m, 1H), 7.90-7.83 (m, 1H), 7.66-7.56 (m, 1H), 7.08-6.90 (m, 1H), 6.89-6.70 (m, 1H). MS (ESI): m/z 288 [M$^+$+1].

To a stirred solution of ketone (0.69 g, 2.4 mmol) in Et$_2$O (50 mL) was added freshly prepared diazomethane [Nitrosyl methyl urea (NMU; 1.8 g) in 10% potassium hydroxide (KOH; 300 mL)] at 0° C. and then the mixture was warmed to RT. After stirring at RT for 2 h, the solvent was evaporated under reduced pressure to afford the crude product. The crude product was purified by column chromatography (eluting with a 5-7% EtOAc/hexane gradient) to afford the epoxide (0.49 g, 1.62 mmol, 67.7%) as a colorless semi-solid. $^1$H NMR (200 MHz, CDCl$_3$): δ 8.51 (s, 1H), 7.56-7.30 (m, 3H), 6.89-6.67 (m, 2H), 3.44 (d, J=5.2 Hz, 1H), 3.00-2.96 (m, 1H). MS (ESI): m/z 302 [M$^+$+1].

To a stirred solution of epoxide (0.49 g, 1.62 mmol) in DMF (10 mL) was added 1H-tetrazole (0.11 g, 1.62 mmol) followed by K$_2$CO$_3$ (0.11 g, 0.81 mmol) at RT under inert atmosphere. The reaction mixture was stirred for 4 h at 75° C. The volatiles were removed under reduced pressure and obtained residue was diluted with EtOAc (50 mL). The organic layer was washed with water, brine and dried over anhydrous Na$_2$SO$_4$. After filtering off solid, the solvent was evaporated under reduced pressure to give crude compound. The crude compound was purified by column chromatography (eluting with EtOAc/hexane) to afford 10 (0.18 g, 0.48 mmol, 29.8%) as white solid. $^1$H NMR (500 MHz, CDCl$_3$): δ 8.73 (s, 1H), 8.41 (s, 1H), 7.63-7.58 (m, 1H), 7.54-7.50 (m, 1H), 7.32-7.27 (m, 1H), 6.90 (s, 1H), 6.80-6.71 (m, 1H), 6.70-6.65 (m, 1H), 5.58 (d, J=14.0 Hz, 1H), 5.12 (d, J=14.0 Hz, 1H). MS (ESI): m/z 372 [M$^+$+1]. HPLC: 98.6%.

Chiral Preparative HPLC Separation of Enantiomers of 10

The (+) and (−) enantiomers of 10 were separated by chiral preparative HPLC using a CHIRALPAK® AD H column (250×4.6 mm, 5μ; mobile phase A) 0.1% TFA in n-hexane-B) EtOH (A:B=80:20) and flow rate 1.00 mL/min). The diluent was EtOH:hexane (20:80).

Optical Rotation:

(−)-enantiomer $[\alpha]_D$-29.7° (c=1 w/v % in CH$_2$Cl$_2$); (+)-enantiomer $[\alpha]_D$+29.4° (c=1 w/v % in CH$_2$Cl$_2$).

Example 11

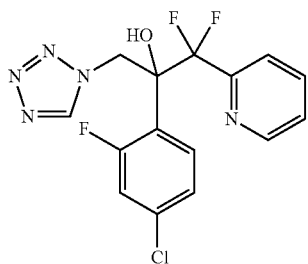 [SMILES: OC(Cn1cnnn1)(c1ccc(Cl)cc1F)C(F)(F)c1ccccn1]

2-(4-Chloro-2-fluorophenyl)-1,1-difluoro-1-(pyridin-2-yl)-3-(1H-tetrazol-1-yl)propan-2-ol (11)

Compound 11 was synthesized employing the same conditions as compound 1 using 2-bromopyridine and 1-bromo-4-chloro-2-fluorobenzene.

Intermediate 1-(4-chloro-2-fluorophenyl)-2,2-difluoro-2-(pyridin-2-yl)ethanone

Yield: 49%. $^1$H NMR (200 MHz, CDCl$_3$): δ 8.58 (d, J=4.4 Hz, 1H), 8.01-7.80 (m, 3H), 7.43 (t, J=5.6 Hz, 1H), 7.28-7.07 (m, 2H). MS (ESI): m/z 286 [M$^+$+1].

Intermediate 2-((2-(4-chloro-2-fluorophenyl)oxiran-2-yl)difluoromethyl)pyridine

Yield: 34%. $^1$H NMR (500 MHz, CDCl$_3$): δ 8.67 (d, J=4.0 Hz, 1H), 7.75 (t, J=8.0 Hz, 1H), 7.48 (d, J=7.5 Hz, 1H), 7.39-7.31 (m, 2H), 7.10-7.08 (m, 1H), 7.02 (dd, J=9.5, 2.0 Hz, 1H), 3.46 (d, J=5.0 Hz, 1H), 2.97 (d, J=5.0 Hz, 1H). MS (ESI): m/z 300 [M$^+$+1].

2-(4-Chloro-2-fluorophenyl)-1,1-difluoro-1-(pyridin-2-yl)-3-(1H-tetrazol-1-yl)propan-2-ol (11)

Yield: 32% (0.023 g). $^1$H NMR (200 MHz, CDCl$_3$): δ 8.76 (s, 1H), 8.54 (d, J=4.4 Hz, 1H), 7.88-7.80 (m, 2H), 7.59 (d, J=7.6 Hz, 1H), 7.45 (t, J=7.8 Hz, 1H), 7.32-7.24 (m, 1H), 7.04 (dd, J=11.6, 1.8 Hz, 1H), 6.90 (dd, J=8.8, 1.8 Hz, 1H), 5.59 (d, J=14.2 Hz, 1H), 5.11 (d, J=14.2 Hz, 1H). MS (ESI): m/z 370 [M$^+$+1]. HPLC: 99.4%.

Example 12

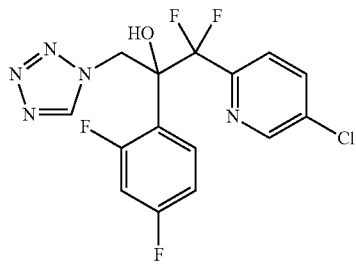 [SMILES: OC(Cn1cnnn1)(c1ccc(F)cc1F)C(F)(F)c1ccc(Cl)cn1]

1-(5-Chloropyridin-2-yl)-2-(2,4-difluorophenyl)-1,1-difluoro-3-(1H-tetrazol-1-yl)propan-2-ol (12)

Compound 12 was synthesized using the same conditions as compound 1.

Intermediate ethyl 2-(5-chloropyridin-2-yl)-2,2-difluoroacetate

Yield: 32.7%. $^1$H NMR (200 MHz, CDCl$_3$): δ 8.61 (s, 1H), 7.85 (dd, J=8.4, 2.6 Hz, 1H), 7.70 (d, J=8.4 Hz, 1H), 4.37 (q, J=7.0 Hz, 2H), 1.33 (t, J=7.0 Hz, 3H).

Intermediate 2-(5-chloropyridin-2-yl)-(2,4-difluorophenyl)-2,2-difluoroethanone

Yield: 51.8%. $^1$H NMR (200 MHz, CDCl$_3$): δ 8.51 (s, 1H), 8.10-8.00 (m, 1H), 7.91-7.75 (m, 2H), 7.03-6.95 (m, 1H), 6.90-6.70 (m, 1H).

Intermediate 5-chloro-2-((2-(2,4-difluorophenyl)oxiran-2-yl)difluoromethyl)pyridine The uncharacterized, crude product was taken ahead to the next step without further purification.

1-(5-Chloropyridin-2-yl)-2-(2,4-difluorophenyl)-1,1-difluoro-3-(1H-tetrazol-1-yl)propan-2-ol (12)

Yield: 41% (0.021 g). $^1$H NMR (500 MHz, CDCl$_3$): δ 8.79 (s, 1H), 8.54 (s, 1H), 7.83-7.74 (m, 1H), 7.54 (d, J=5.5 Hz, 1H), 7.39-7.22 (m, 1H), 6.91 (s, 1H), 6.81-6.62 (m, 2H), 5.62 (d, J=15.0 Hz, 1H), 5.15 (d, J=15.0 Hz, 1H). MS (ESI): m/z 388 [M$^+$+1]. HPLC: 99.1%.

Compound 29 in Table 1 was prepared using the same conditions as compound 12. (See Table 1 for starting material.)

Example 13

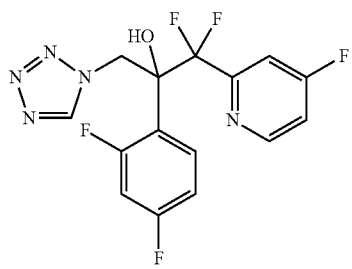 [SMILES: OC(Cn1cnnn1)(c1ccc(F)cc1F)C(F)(F)c1cc(F)ccn1]

2-(2,4-Difluorophenyl)-1,1-difluoro-1-(4-fluoropyridin-2-yl)-3-(1H-tetrazol-1-yl)propan-2-ol (13)

To a suspension of copper powder (0.72 g, 11.4 mmol) in DMSO (10 mL) was added ethyl 2-bromo-2,2-difluoroacetate (0.73 mL, 5.7 mmol), and the mixture was stirred for 1 h at RT. 2-bromo-4-fluoropyridine (0.5 g, 2.85 mmol) was then added, and stirring was continued for 15 h at RT. The progress of the reaction was monitored by TLC. The reaction was quenched with aqueous NH$_4$Cl (15 mL) and extracted with CH$_2$Cl$_2$ (3×15 mL). The combined organic layers were washed with water and brine, dried over anhydrous Na$_2$SO$_4$ and concentrated under reduced pressure to afford a crude product. Column chromatography (eluting with EtOAc/hexane) gave the ester (0.37 g, 1.68 mmol, 59%) as a light yellow liquid. $^1$H NMR (500 MHz, CDCl$_3$): δ 8.50 (s, 1H), 7.78 (dd, J=9.0, 4.5 Hz, 1H), 7.58-7.54 (m, 1H), 4.41-4.34 (m, 2H), 1.39-1.31 (m, 3H). MS (ESI): m/z 220 [M$^+$+1].

To a stirred solution of the 1-bromo-2,4-difluorobenzene (0.19 mL, 1.68 mmol) in Et$_2$O (10 mL) was added n-BuLi (2.5 M in hexane; 0.67 mL, 1.68 mmol) at −70° C., and the mixture was stirred for 20 min. A solution of the ester (0.37 g, 1.68 mmol) in Et$_2$O (10 mL) was added drop-wise, and the mixture was stirred for 1 h at −70° C. The temperature was raised gradually to ambient temperature and the mixture was stirred for another 3 h. The reaction mixture was quenched with aqueous NH$_4$Cl and extracted with EtOAc (3×20 mL). The combined organic layers were washed with water and brine, dried over anhydrous Na$_2$SO$_4$ and concentrated under reduced pressure. Purification by column chromatography (eluting with EtOAc/hexane) afforded the ketone (0.2 g, 0.69 mmol, 41%) as a yellow liquid. $^1$H NMR (500 MHz, CDCl$_3$): δ 8.41 (s, 1H), 8.05 (app q, 1H), 7.85 (dd, J=9.0, 4.5 Hz, 1H), 7.62-7.58 (m, 1H), 7.01-6.97 (m, 1H), 6.84-6.79 (m, 1H). MS (ESI): m/z 288 [M$^+$+1].

Diazomethane was prepared as follows: To the cold solution of 10% aqueous KOH (50 mL) and ether (30 mL) was added nitrosomethyl urea (2 g) portion-wise and the mixture was stirred for 1 h. The ether layer was separated. To a stirred solution of ketone (0.2 g, 0.69 mmol) in Et$_2$O (25 mL) was added freshly prepared diazomethane at 0° C. and the mixture was warmed to RT. After stirring for 3 h at RT, the solvent was evaporated under reduced pressure to afford a crude product. The crude product was purified by column chromatography (eluting with EtOAc/hexane) to afford the epoxide (0.12 g, 0.41 mmol, 59%) as a liquid. $^1$H NMR (500 MHz, CDCl$_3$): δ 8.51 (s, 1H), 7.52-7.43 (m, 2H), 7.39-7.35 (m, 1H), 6.86-6.81 (m, 1H), 6.76-6.71 (m, 1H), 3.43 (d, J=5.0 Hz, 1H), 2.97 (app s, 1H).

To a stirred solution of the above epoxide (0.12 g, 0.41 mmol) in DMF (5 mL) was added K$_2$CO$_3$ (29 mg, 0.20 mmol) followed by 1H-tetrazole (29 mg, 0.41 mmol) at RT under inert atmosphere. The reaction mixture was stirred for 5 h at 80° C. The volatiles were removed under reduced pressure and the obtained residue was dissolved in EtOAc (30 mL). The organic layer was washed with water and brine, dried over anhydrous Na$_2$SO$_4$ and concentrated under reduced pressure. Purification by column chromatography (eluting with EtOAc/hexane) afforded compound 13 (50 mg, 0.13 mmol, 32%) as a semi-solid. $^1$H NMR (500 MHz, CDCl$_3$): δ 8.73 (s, 1H), 8.41 (s, 1H), 7.61 (dd, J=9.0, 4.5 Hz, 1H), 7.54-7.50 (m, 1H), 7.50-7.27 (m, 1H), 6.90 (s, 1H), 6.78-6.73 (m, 1H), 6.69-6.65 (m, 1H), 5.58 (d, J=14.5 Hz, 1H), 5.13 (d, J=14.5 Hz, 1H). MS (ESI): m/z 372 [M$^+$+1]. HPLC: 97.1%.

Chiral Preparative HPLC Separation of Enantiomers of 13:

The enantiomers of 13 (180 mg, 0.48 mmol) were separated by preparative HPLC using a CHIRALPAK® AD-H column (250×20 mm, 5μ); with mobile phase (A) 0.1% TFA in n-hexane-(B) EtOH (A:B=90:10) and flow rate 15 mL/min) to obtain 13-(−) (60.0 mg, 0.16 mmol, 33%) as an off-white solid.

Analytical Data:

Chiral HPLC: 97.4% ee R=9.429 min (CHIRALPAK® AD-H, 250×4.6 mm, 5μ; mobile phase (A) n-hexane (B) EtOH (A:B=80:20); flow rate 1.00 mL/min). Optical rotation [α]$_D^{24}$: −20.36° (c=0.1% in CH$_3$OH). $^1$H NMR (500 MHz, CDCl$_3$): δ 8.73 (s, 1H), 8.41 (d, J=2.5 Hz, 1H), 7.62-7.59 (m, 1H), 7.54-7.50 (m, 1H), 7.32-7.27 (m, 1H), 6.90 (s, 1H), 6.78-6.73 (m, 1H), 6.69-6.65 (m, 1H), 5.58 (d, J=14.5 Hz, 1H), 5.13 (d, J=14.5 Hz, 1H). MS (ESI): m/z 372 [M+H]$^+$. HPLC: 98.7%.

Example 14

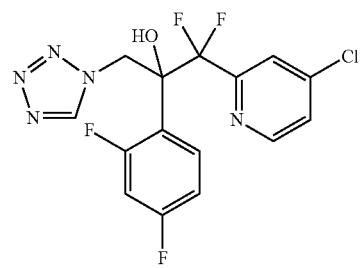 [SMILES: OC(Cn1cnnn1)(c1ccc(F)cc1F)C(F)(F)c1cc(Cl)ccn1]

1-(4-Chloropyridin-2-yl)-2-(2,4-difluorophenyl)-1,1-difluoro-3-(1H-tetrazol-1-yl)propan-2-ol (14)

Compound 14 was synthesized using the same conditions as compound 13.

Intermediate ethyl 2-(4-chloropyridin-2-yl)-2,2-difluoroacetate

Yield: 33%. $^1$H NMR (500 MHz, CDCl$_3$): δ 8.57 (d, J=5.2 Hz, 1H), 7.84 (s, 1H), 7.43 (dd, J=6.4, 2.2 Hz, 1H), 4.37 (q, J=7.0 Hz, 2H), 1.36 (t, J=7.0 Hz, 3H).

Intermediate 2-(4-chloropyridin-2-yl)-1-(2,4-difluorophenyl)-2,2-difluoroethanone Yield: 58%. $^1$H NMR (200 MHz, CDCl$_3$): δ 8.47 (d, J=5.2 Hz, 1H), 8.12-8.01 (m, 1H), 7.84 (s, 1H), 7.43 (dd, J=5.4, 1.8 Hz, 1H), 7.05-6.96 (m, 1H), 6.87-6.77 (m, 1H).

Intermediate 4-chloro-2-((2-(2,4-difluorophenyl)oxiran-2-yl)difluoromethyl)pyridine Yield: 48%. $^1$H NMR (500 MHz, CDCl$_3$): δ 8.57 (d, J=5.0 Hz, 1H), 7.51 (s, 1H), 7.40-7.36 (m, 2H), 6.87-6.84 (m, 1H), 6.83-6.74 (m, 1H), 3.45 (d, J=5.0 Hz, 1H), 2.98 (br s, 1H).

1-(4-Chloropyridin-2-yl)-2-(2,4-difluorophenyl)-1,1-difluoro-3-(1H-tetrazol-1-yl)propan-2-ol (14)

Yield: 30% (0.028 g). $^1$H NMR (500 MHz, CDCl$_3$): δ 8.73 (s, 1H), 8.44 (d, J=5.5 Hz, 1H), 7.60 (s, 1H), 7.44 (dd, J=5.5, 1.5 Hz, 1H), 7.35-7.30 (m, 1H), 6.80-6.75 (m, 1H), 6.70-6.66 (m, 1H), 5.57 (d, J=14.5 Hz, 1H), 5.12 (d, J=14.5 Hz, 1H). MS (ESI): m/z 388 [M$^+$+1]. HPLC: 99.2%.

Example 15

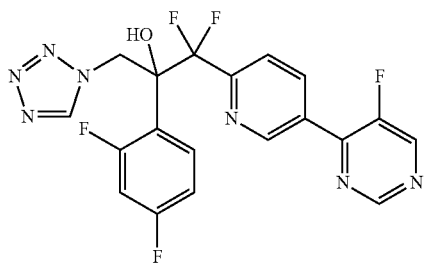 [SMILES: OC(Cn1cnnn1)(c1ccc(F)cc1F)C(F)(F)c1ccc(-c2ncncc2F)cn1]

2-(2,4-Difluorophenyl)-1,1-difluoro-1-(5-(5-fluoro-pyrimidin-4-yl)pyridin-2-yl)-3-(1H-tetrazol-1-yl)propan-2-ol (15)

To a stirred solution of F (2 g, 5.52 mmol) in anhydrous Et$_2$O (100 mL) was added n-BuLi (1.6 M in hexane; 7 mL, 11.04 mmol) at −78° C. under an inert atmosphere. After being stirred for 45 min at −78° C., trimethyl borate (1.25 mL, 11.04 mmol) was added to the reaction mixture, and stirring was continued for an additional 10 min at −78° C. and then for 1 h at RT. Progress of the reaction was monitored by TLC. The reaction was quenched with a solution of acetic acid (AcOH) in water at 0° C. and then stirred for another 30 min. The reaction mixture was made basic with 2 Normal (N) sodium hydroxide (NaOH; pH∼12) and washed with Et$_2$O (2×50 mL). The aqueous layer was made acidic with 2 N HCl (pH∼6) and extracted with CH$_2$C$_2$ (3×50 mL). The combined organic layers were washed with water and brine, dried over anhydrous Na$_2$SO$_4$ and concentrated under reduced pressure to afford the corresponding 5-pyridyl-boronic acid (1.6 g, 4.89 mmol, 88%) as a solid. $^1$H NMR (200 MHz, CDCl$_3$): δ 8.21 (s, 1H), 7.42-7.38 (m, 2H), 7.25-7.18 (m, 1H), 6.88-6.64 (m, 2H), 3.42 (d, J=5.2 Hz, 1H), 2.98 (br s, 1H).

To a stirred solution of this boronic acid (0.2 g, 0.61 mmol) and 4-bromo-5-fluoropyrimidine (0.054 g, 0.30 mmol) in 1,4-dioxane (10 mL) were added K$_2$CO$_3$ (0.084 g, 0.61 mmol) and tetrakis(triphenylphosphine) palladium(0) (Pd(PPh$_3$)$_4$; 0.035 g, 0.03 mmol) at RT under an inert atmosphere. The resulting mixture was stirred at 100° C. for 5 h. Progress of the reaction was monitored by TLC. The reaction was allowed to cool to RT, diluted with water and extracted with EtOAc (3×50 mL). The combined organic phases were washed with water and brine, dried over anhydrous Na$_2$SO$_4$ and concentrated in vacuo. The crude material was purified by silica gel column chromatography (eluting with EtOAc/hexane) to afford coupled product (0.14 g, 0.36 mmol, 60%). $^1$H NMR (500 MHz, CDCl$_3$): δ 9.42 (s, 1H), 9.15 (s, 1H), 8.74 (d, J=3.0 Hz, 1H), 8.53 (dd, J=8.0, 2.0 Hz, 1H), 7.66-7.63 (m, 1H), 7.43-7.39 (m, 1H), 6.86-6.83 (m, 1H), 6.77-6.73 (m, 1H), 3.51-3.48 (m, 1H), 3.01 (brs, 1H). MS (ESI): m/z 380 [M$^+$+1].

To a stirred solution of coupled product (0.14 g, 0.36 mmol) in DMF (3 mL) was added 1H-tetrazole (0.031 g, 0.44 mmol) followed by K$_2$CO$_3$ (0.025 g, 0.18 mmol) at RT under inert atmosphere. The reaction mixture was stirred at 70° C. for 16 h. The reaction mixture was cooled to RT, diluted with water (5 mL) and extracted with EtOAc (2×20 mL). The organic layer was washed with water and brine and dried over anhydrous Na$_2$SO$_4$. After filtering off the solid, the solvent was evaporated under reduced pressure to give crude compound. Silica gel column chromatography (eluting with EtOAc/hexane) afforded 15 (0.025 g, 0.05 mmol, 15%) as a solid. $^1$H NMR (500 MHz, CDCl$_3$): δ 9.32 (s, 1H), 9.15 (s, 1H), 8.77 (s, 2H), 8.61 (dd, J=8.5, 2.0 Hz, 1H), 7.75 (d, J=8.5 Hz, 1H), 7.37-7.30 (m, 2H), 6.79-6.75 (m, 1H), 6.68-6.64 (m, 1H), 5.61 (d, J=14.0 Hz, 1H), 5.17 (d, J=14.0 Hz, 1H). MS (ESI): m/z 450 [M$^+$+1]. HPLC: 94.47%.

Compounds 30-38 and 93-96 in Table 1 were prepared using the same conditions as compound 15. (See Table 1 for starting materials.)

Chiral Preparative HPLC Separation of Enantiomers of 30:

The enantiomers of 30 (300 mg, 0.64 mmol) were separated by preparative HPLC using a CHIRALPAK® IA column (250×20 mm, 5µ) with mobile phase (A) n-hexane-(B) IPA (A:B=80:20) and flow rate 15 mL/min to obtain 30-(+) (60 mg, 0.13 mmol) as an off-white solid.

Analytical Data:

Chiral HPLC: 99.42% ee, R$_t$=13.98 min (CHIRALPAK® IB column, 250×4.6 mm, 5µ; mobile phase (A) n-hexane-(B) EtOH (A:B=75:25); flow rate: 1.00 mL/min). Optical rotation [α]$_D^{24}$: +18.56° (c=0.1% in CH$_3$OH). $^1$H NMR (500 MHz, CDCl$_3$): δ 8.75 (s, 1H), 8.70 (s, 1H), 8.60 (d, J=2.0 Hz, 1H), 7.99 (d, J=8.0 Hz, 1H), 7.84 (dd, J=8.0, 2.0 Hz, 1H), 7.72 (d, J=8.0 Hz, 1H), 7.49 (d, J=8.0 Hz, 1H), 7.47-7.38 (m, 1H), 7.33 (s, 1H), 6.81-6.76 (m, 1H), 6.72-6.69 (m, 1H), 5.55 (d, J=14.5 Hz, 1H), 5.19 (d, J=14.5 Hz, 1H). MS (ESI): m/z 465 [M+H]$^+$. HPLC: 99.1%.

Chiral Preparative HPLC Separation of Enantiomers of 31:

The enantiomers of 31 (315 mg, 0.70 mmol) were separated by preparative HPLC using a CHIRALPAK® IC column (250×20 mm, 5µ) with mobile phase (A) n-hexane-(B) EtOH (A:B=80:20) and flow rate 15 mL/min to obtain 31-(+) (90 mg, 0.20 mmol) as an off-white solid.

Analytical Data:

Chiral HPLC: 100% ee, R$_t$=15.22 min (CHIRALPAK® IC column, 250×4.6 mm, 5µ; mobile phase (A) n-hexane-(B) EtOH (A:B=80:20); flow rate: 1.00 mL/min). Optical rotation [α]$_D^{25}$: +13.96° (c=0.1% in CH$_3$OH). $^1$H NMR (500 MHz, CDCl$_3$): δ 8.76 (s, 1H), 8.70 (s, 1H), 8.44 (d, J=2.0 Hz, 1H), 7.99-7.97 (m, 2H), 7.72 (d, J=8.5 Hz, 1H), 7.44-7.38 (m, 2H), 7.11 (dd, J=8.5, 2.0 Hz, 1H), 6.82-6.77 (m, 1H), 6.73-6.69 (m, 1H), 5.55 (d, J=14.5 Hz, 1H), 5.20 (d, J=14.5 Hz, 1H) MS (ESI): m/z 449 [M+H]$^+$. HPLC: 95.1%.

Example 16

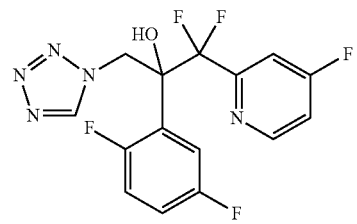 [SMILES: OC(Cn1cnnn1)(c1cc(F)ccc1F)C(F)(F)c1cc(F)ccn1]

2-(2,5-Difluorophenyl)-1,1-difluoro-1-(4-fluoropyridin-2-yl)-3-(1H-tetrazol-1-yl)propan-2-ol (16)

Compound 16 was prepared using 2,5-difluoro-bromobenzene while employing the conditions to prepare 13:

0.021 g as a glass. $^1$H NMR (500 MHz, CDCl$_3$): δ 8.74 (s, 1H), 8.41 (s, 1H), 7.64-7.62 (m, 1H), 7.55-7.51 (m, 1H), 7.07-7.03 (m, 1H), 7.01-6.97 (m, 1H), 6.96-6.90 (m, 2H), 5.58 (d, J=14.5 Hz, 1H), 5.15 (d, J=14.5 Hz, 1H). MS (ESI): m/z 372 [M$^+$+I]. HPLC: 96.3%.

Example 17

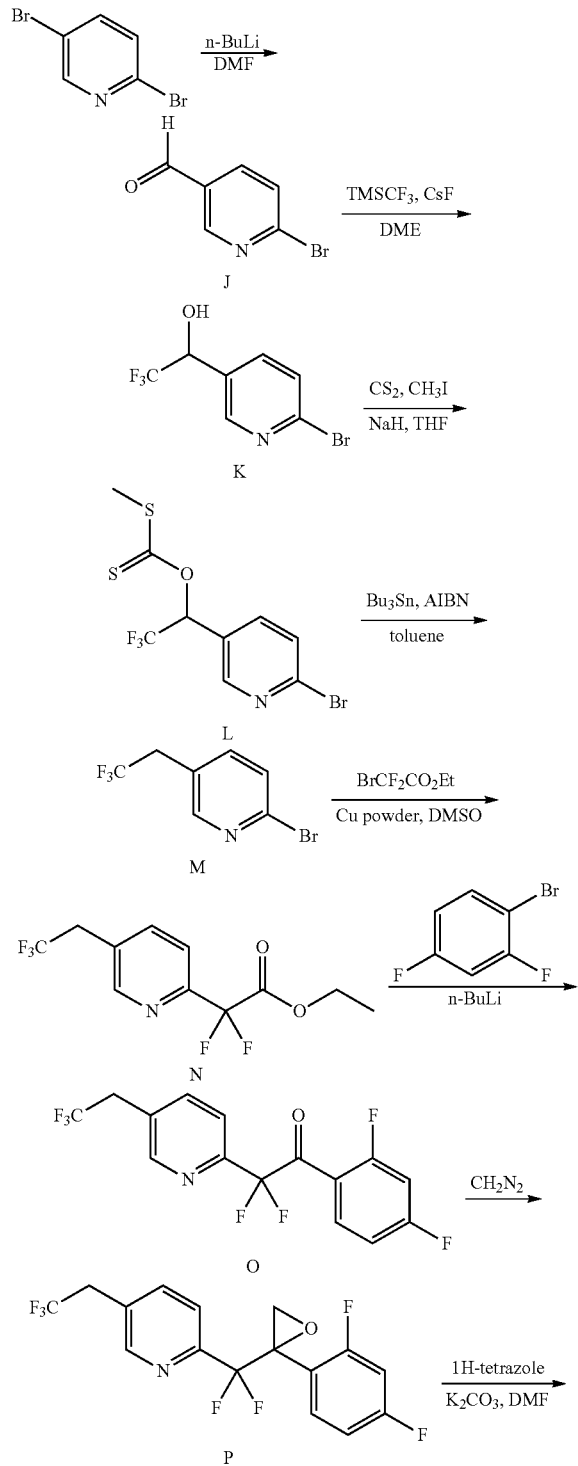

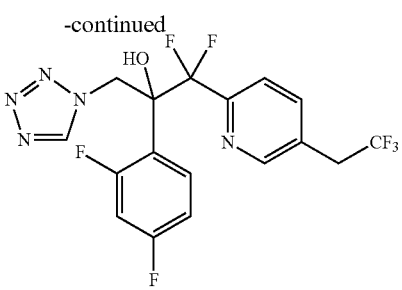

2-(2,4-Difluorophenyl)-1,1-difluoro-3-(1H-tetrazol-1-yl)-1-(5-(2,2,2-trifluoroethyl)pyridin-2-yl)propan-2-ol (17)

To a stirred solution of 2,5-dibromopyridine (20 g, 84.1 mmol) in dry ether (400 mL) was added n-BuLi (1.6 M solution in hexane; 62.98 mL, 100.77 mmol) slowly at −78° C. After being stirred for 45 min, DMF (12.28 g, 168.2 mmol) was added to the reaction mixture at −78° C., and the stirring was continued for another 2 h. After consumption of the starting material (by TLC), the reaction was quenched with saturated (satd) NH$_4$Cl solution and extracted with EtOAc (4×500 mL). The combined organic extracts were dried over anhydrous Na$_2$SO$_4$ and concentrated under reduced pressure to obtain the crude material. Purification by silica gel column chromatography (eluting with 15% EtOAc/hexane) afforded aldehyde J (7.0 g, 37.8 mmol, 45%) as a yellow solid. $^1$H NMR (500 MHz, CDCl$_3$): δ 10.09 (s, 1H), 8.83 (d, J=2.0 Hz, 1H), 8.02 (dd, J=8.0, 2.0 Hz, 1H), 7.68 (d, J=8.0 Hz, 1H). MS (ESI): m/z 186 [M$^+$].

To a stirred solution of aldehyde J (1.0 g, 5.40 mmol) in 1,2-dimethoxyethane (DME; 10 mL) was added trimethyl(trifluoromethyl)silane (TMSCF$_3$; 1.3 mL, 8.10 mmol) followed by cesium fluoride (CsF; 821 mg, 5.40 mmol) slowly at 0° C. under inert atmosphere. The resulting solution was stirred for 12 h at RT; progress of the reaction was monitored by TLC. After consumption of the starting material, the reaction mixture was quenched with 1 N hydrochloric acid (HCl; 5.0 mL), stirred for 30 min and then extracted with EtOAc (2×150 mL). The combined organic extracts were washed with water and satd NaHCO$_3$ solution, dried over anhydrous Na$_2$SO$_4$ and concentrated under reduced pressure to obtain the crude material. Purification by silica gel column chromatography (eluting with 20% EtOAc/hexane) afforded compound K (0.6 g, 2.34 mmol, 43%) as a yellow solid. $^1$H NMR (500 MHz, CDCl$_3$): δ 8.44 (d, J=2.0 Hz, 1H), 7.73 (dd, J=8.5, 2.0 Hz, 1H), 7.56 (d, J=8.5 Hz, 1H), 5.09-5.06 (m, 1H), 3.27 (br s, 1H). MS (ESI): m/z 258 [M$^+$+2]. HPLC: 97.05%.

To a stirred solution of compound K (5.0 g, 19.53 mmol) in dry THF (60 mL) was added sodium hydride (NaH; 935 mg, 39.06 mmol) portionwise at 0° C. under inert atmosphere. After being stirred for 1 h, carbon disulfide (CS$_2$; 2.35 mL, 39.06 mmol) was added to the reaction mixture dropwise, and the mixture was stirred for 1 h at 0° C. To the resulting reaction mixture iodomethane (CH$_3$I; 2.43 mL, 39.06 mmol) was added at 0° C., and then the mixture was stirred for 2 h at RT. After consumption of the starting material (by TLC), the reaction mixture was quenched with ice-cold water and extracted with CH$_2$Cl$_2$ (2×100 mL). The combined organic extracts were dried over anhydrous Na$_2$SO$_4$ and concentrated under reduced pressure to afford dithionate L (7.0 g) that was used in the next step without any further purification. ¹H NMR (400 MHz, CDCl₃): δ 8.47 (d, J=2.4 Hz, 1H), 7.65 (dd, J=8.0, 2.4 Hz, 1H), 7.56 (d, J=8.0 Hz, 1H), 6.88 (q, J=6.8 Hz, 1H), 2.61 (s, 3H). MS (ESI): m/z 348 [M⁺+2].

To a stirred solution of compound L (7.0 g, crude) in dry toluene (40 mL) was added tributyltin stannane (Bu₃SnH; 10.5 mL, 30.34 mmol) followed by 2,2'-azobis(isobutyronitrile) (AIBN; 728 mg, 3.03 mmol) at RT under inert atmosphere. The reaction mixture was gradually heated up to 90° C. and stirred for 2 h. After consumption of the starting material (by TLC), the volatiles were removed under reduced pressure to obtain the crude material. Purification by silica gel column chromatography (eluting with 8% EtOAc/Hexane) afforded compound M (3.0 g, 12.5 mmol, 61%) as a pale-yellow liquid. This material contained a small amount of tin impurity and was used in the next step without any further purification. ¹H NMR (400 MHz, CDCl₃): δ 8.31 (s, 1H), 7.51 (s, 2H), 3.36 (q, J=10.4 Hz, 2H). MS (ESI): m/z 240 [M⁺].

To a stirred suspension of copper powder (3.17 g, 50 mmol) in DMSO (30 mL) was added ethyl 2-bromo-2,2-difluoroacetate (5.07 g, 25 mmol) and the mixture was stirred for 1 h at RT. To the resulting reaction mixture compound M (3.0 g, 12.5 mmol) was added, and the mixture was stirred for 12 h at RT. After completion of reaction (by TLC), the reaction mixture was quenched with satd NH₄Cl solution and extracted with EtOAc (2×50 mL). The combined organic extracts were dried over anhydrous Na₂SO₄, filtered and concentrated under reduced pressure to obtain the crude material. Purification by silica gel column chromatography (eluting with 8% EtOAc/Hexane) afforded ester N (2.5 g, 8.83 mmol, 70%) as a pale-yellow liquid. ¹H NMR (400 MHz, CDCl₃): δ8.58 (s, 1H), 7.83 (dd, J=8.0, 1.6 Hz, 1H), 7.75 (d, J=8.0 Hz, 1H), 4.37 (q, J=7.2 Hz, 2H), 3.46 (q, J=10.4 Hz, 2H), 1.36 (t, J=7.2 Hz, 3H). MS (ESI): m/z 284.2 [M⁺+1].

To a stirred solution of I-bromo-2,4-difluorobenzene (818 mg, 4.24 mmol) in dry ether (15 mL) was added n-BuLi (1.6 M solution in hexane; 2.65 mL, 4.24 mmol) at –78° C. under inert atmosphere. After being stirred for 45 min, a solution of ester N (1.0 g, 3.53 mmol) in ether (5 mL) was added to the reaction mixture and stirring was continued for another 1 h at –78° C. After completion of the reaction (by TLC), the reaction mixture was quenched with satd NH₄Cl solution and extracted with CH₂Cl₂ (2×150 mL). The combined organic extracts were dried over anhydrous Na₂SO₄ and concentrated under reduced pressure to afford ketone O (1.5 g) as brownish crude liquid. This crude material was used in the next step without any purification. ¹H NMR (500 MHz, CDCl₃): δ 8.51 (s, 1H), 8.10-8.05 (m, 1H), 7.88-7.83 (m, 2H), 7.01-6.98 (m, 1H), 6.84-6.80 (m, 1H), 3.46 (q, J=10.5 Hz, 2H).

To a stirred solution of ketone O (0.9 g, crude) in ether (100 mL) was added freshly prepared diazomethane [prepared by dissolving NMU (2.64 g, 25.64 mmol) in a 1:1 mixture of 10% KOH solution (100 mL) and ether (100 mL) at 0° C. followed by separation and drying of the organic layer using KOH pellets] at 0° C., and the mixture was stirred for 30 min. The resulting reaction mixture was stirred for 12 h at RT; progress of the reaction was monitored by TLC. After completion of the reaction, the reaction mixture was concentrated under reduced pressure to obtain a crude product. Purification by silica gel column chromatography (eluting with 10% EtOAc/hexane) afforded the epoxide P (0.3 g, 0.82 mmol) as a brownish liquid. ¹H NMR (400 MHz, CDCl₃): δ 8.59 (s, 1H), 7.72 (d, J=8.4 Hz, 1H), 7.49 (d, J=8.4 Hz, 1H), 7.40-7.34 (m, 1H), 6.85-6.80 (m, 1H), 6.76-6.70 (m, 1H), 3.48-3.40 (m, 3H), 2.97 (d, J=4.8 Hz, 1H). MS (ESI): m/z 366 [M⁺+1].

To a stirred solution of epoxide P (0.3 g, 0.82 mmol) in dry DMF (8 mL) was added 1H-tetrazole (113.4 mg, 1.23 mmol) followed by K₂CO₃ (113.4 mg, 0.82 mmol) at RT under inert atmosphere. The reaction mixture was then stirred for 14 h at 65° C. After completion of the reaction (by TLC), the reaction mixture was quenched with ice-cold water and extracted with EtOAc (2×100 mL). The combined organic extracts were dried over Na₂SO₄ and concentrated under reduced pressure to obtain the crude material. Purification by silica gel column chromatography (eluting with 50% EtOAc/hexane) afforded 17 (0.18 g, 0.41 mmol, 50%) as a brownish liquid. ¹H NMR (500 MHz, CDCl₃): δ 8.75 (s, 1H), 8.48 (s, 1H), 7.79 (d, J=8.5 Hz, 1H), 7.60 (d, J=8.5 Hz, 1H), 7.34-7.30 (m, 2H), 6.78-6.74 (m, 1H), 6.68-6.65 (m, 1H), 5.57 (d, J=14.5 Hz, 1H), 5.13 (d, J=14.5 Hz, 1H), 3.45 (q, J=10.5 Hz, 2H). MS (ESI): m/z 434 [M⁺–1]. HPLC: 98.09%.

Compound 39 in Table 1 was prepared using the same conditions as compound 17. (See Table 1 for starting material.)

Example 18

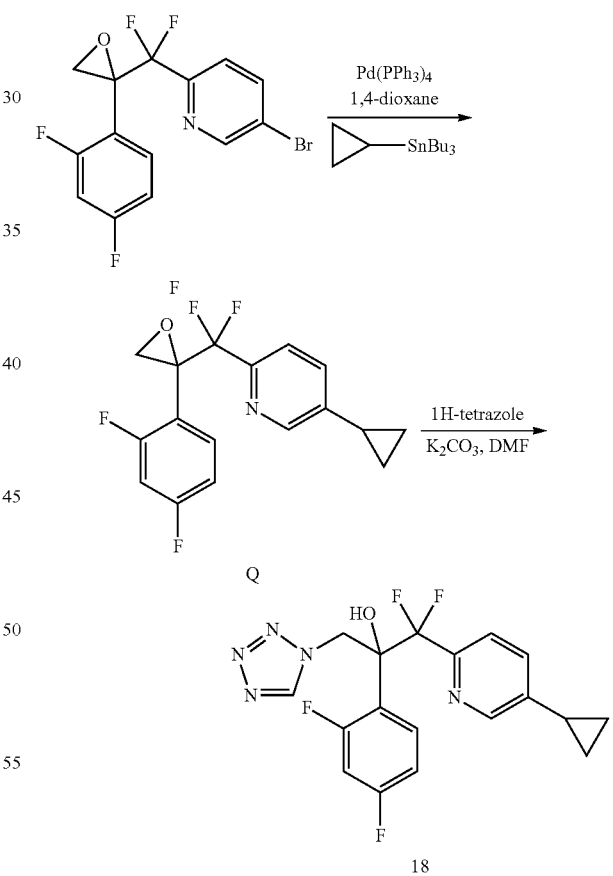

1-(5-Cyclopropylpyridin-2-yl)-2-(2,4-difluorophenyl)-1,1-difluoro-3-(1H-tetrazol-1-yl)propan-2-ol (18)

A stirred solution of 5-bromo-2-((2-(2,4-difluorophenyl)oxiran-2-yl)difluoromethyl)pyridine (F; 0.4 g, 1.1 mmol)

and tributyl(cyclopropyl)stannane (1.8 g, 5.5 mmol) in 1,4-dioxane (15 mL) was degassed by purging with inert gas for 10 min at RT. To the resulting reaction mixture was added Pd(PPh$_3$)$_4$ (64 mg, 0.055 mmol), and the mixture was degassed for another 10 min at RT. The reaction mixture was then stirred for 3 h at reflux. After complete consumption of the starting material (by TLC), the reaction mixture was cooled to RT, filtered through a pad of Celite® and the filtrate was concentrated under reduced pressure to obtain the crude material. Purification by silica gel column chromatography (eluting with 10% EtOAc/hexane) afforded compound Q (0.35 g, 1.08 mmol, 87%) as a colorless liquid. This material contained some tin impurities and was used in the next step without further purification. $^1$H NMR (500 MHz, CDCl$_3$): δ 8.45 (s, 1H), 7.40-7.29 (m, 3H), 6.84-6.80 (m, 1H), 6.76-6.72 (m, 1H), 3.49 (d, J=6.0 Hz, 1H), 3.42 (d, J=6.0 Hz, 1H), 1.95-1.91 (m, 1H), 1.11-1.07 (m, 2H), 0.77-0.74 (m, 2H).

To a stirred solution of compound Q (0.35 g, 1.09 mmol) in DMF (6 mL) was added K$_2$CO$_3$ (0.15 g, 1.09 mmol) followed by 1H-tetrazole (115 mg, 1.64 mmol) at RT under an inert atmosphere. The resulting reaction mixture was gradually heated up to 65° C. and stirred for 18 h. The reaction mixture was cooled to RT, diluted with water and extracted with EtOAc (2×50 mL). The combined organic layer was washed with brine, dried over anhydrous Na$_2$SO$_4$ and concentrated under reduced pressure to obtain the crude material. Purification by silica gel column chromatography (eluting with 40% EtOAc/hexane) afforded 18 (0.1 g, 0.25 mmol, 23%) as a colorless semi-solid. $^1$H NMR (500 MHz, CDCl$_3$): δ 8.74 (s, 1H), 8.31 (s, 1H), 7.92 (br s, 1H), 7.46 (d, J=8.5 Hz, 1H), 7.39-7.32 (m, 2H), 6.77-6.73 (m, 1H), 6.68-6.64 (m, 1H), 5.58 (d, J=14.0 Hz, 1H), 5.06 (d, J=14.0 Hz, 1H), 1.94-1.90 (m, 1H), 1.15-1.11 (m, 2H), 0.78-0.77 (m, 2H). MS (ESI): m/z 394.7 [M$^+$+1]. HPLC: 99.59%.

Compound 40 in Table 1 was prepared using the same conditions as compound 18. (See Table 1 for starting material.)

Example 19

Preparation of Intermediates

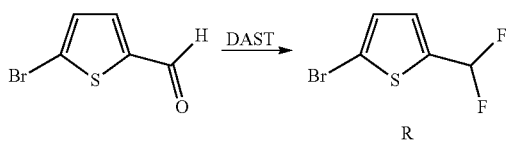

2-Bromo-5-(difluoromethyl)thiophene (R)

To a stirred solution of 5-bromothiophene-2-carboxaldehyde (1.5 g, 7.8 mmol) in CH$_2$C$_{12}$ (10 mL) was added diethylaminosulfur trifluoride (DAST; 3.0 mL, 22.7 mmol) at 0° C. under inert atmosphere. The reaction mixture was stirred at RT for 16 h, quenched with ice-cold water (100 mL) and extracted with CH$_2$Cl$_2$ (3×75 mL). The combined organic extracts were washed with water (50 mL) and brine (50 mL), dried over anhydrous Na$_2$SO$_4$ and concentrated under reduced pressure to obtain the crude material. Purification by silica gel column chromatography (eluting with 2% EtOAc/hexanes) afforded compound R (1.0 g, 4.6 mmol, 62%) as a brown syrup. $^1$H NMR (500 MHz, CDCl$_3$): δ 7.04-7.01 (m, 2H), 6.73 (t, J$_{F-H}$=56.0 Hz, 1H).

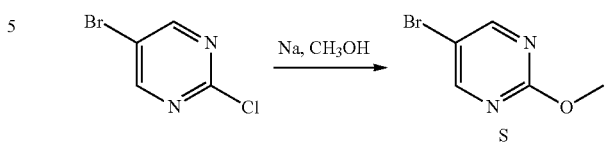

5-Bromo-2-methoxypyrimidine (S)

Sodium metal (74 mg, 3.10 mmol) was added in portions to CH$_3$OH (25 mL) at 0° C. and the mixture was stirred for 30 min at RT. 5-Bromo-2-chloropyrimidine (500 mg, 2.58 mmol) was added to the above mixture at 0° C., and the resulting reaction mixture was gradually heated to reflux temperature and stirred for 2 h. After complete consumption of the starting material (by TLC), the volatiles were concentrated under reduced pressure; the residue was quenched with ice-cold water (50 mL) and extracted with EtOAc (2×50 mL). The combined organic extracts were washed with water (50 mL) and brine (50 mL), dried over anhydrous Na$_2$SO$_4$ and concentrated under reduced pressure to obtain the crude S (400 mg). The crude material was used directly in the next step without any further purification.

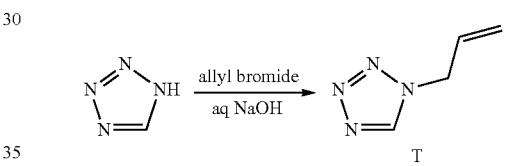

1-Ally-1H-tetrazole (T)

A stirred solution of 1H-tetrazole (5.0 g, 71.47 mmol) in water (10 mL) was cooled to 15° C., and then aq NaOH (4.8 g, 107.13 mmol) followed by allyl bromide (9.2 mL, 107.13 mmol) were added. The resulting reaction mixture was gradually heated up to 60° C. and stirred for 16 h; progress of the reaction was monitored by TLC. The reaction mixture was cooled to RT and concentrated under reduced pressure. The residue was diluted with acetone and the precipitate was filtered through a pad of Celite® and washed with acetone. The filtrate was concentrated under reduced pressure to obtain the crude T (3.69 g) as a pale yellow syrup.

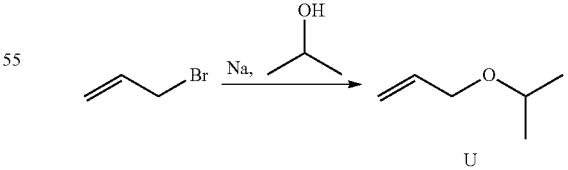

3-Isopropoxyprop-1-ene (U)

Sodium metal (4.21 g, 0.18 mol) was added in portions to isopropyl alcohol (10 g, 0.16 mol) at 0° C., and the mixture was heated to reflux temperature for 2 h. The volatiles were concentrated under reduced pressure to obtain the sodium isopropoxide. The solid sodium isopropoxide was taken up in dry CH$_2$Cl$_2$ (30 mL) and cooled to 10° C.; allyl bromide (13.6 mL, 0.18 mol) was added at 10° C.; and the reaction mixture was stirred at RT for 16 h. After complete consumption of starting material (by TLC), the reaction mixture was diluted with CH$_2$Cl$_2$ (200 mL), washed with water (100 mL) and brine (100 mL), dried over anhydrous Na$_2$SO$_4$ and concentrated under atmospheric pressure to obtain the crude U (6.6 g) as a colorless liquid. $^1$H NMR (500 MHz, CDCl$_3$): δ 5.95-5.88 (m, 1H), 5.27 (dd, J=17.5 Hz, 1H), 5.14 (dd, J=10.5, 1.5 Hz, 1H), 3.98-3.96 (m, 2H), 3.65-3.60 (m, 1H), 1.17 (d, J=6.0 Hz, 6H).

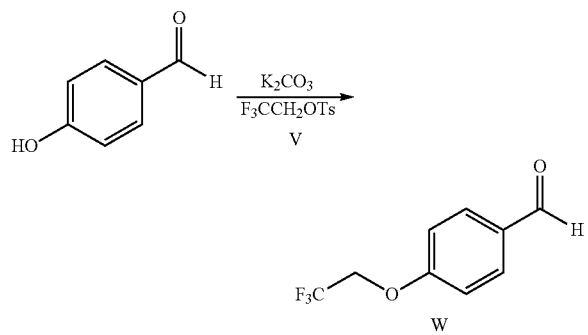

4-(2,2,2-Trifluoroethoxy)benzaldehyde (W)

To a stirred solution of 2,2,2-trifluoroethanol (10.0 g, 100 mmol) in CH$_2$Cl$_2$ (100 mL) were added Et$_3$N (27.8 mL, 200 mmol), p-toluenesulfonyl chloride (19.1 g, 100 mmol) and a catalytic amount of 4-dimethylaminopyridine (DMAP; 10 mg) at 0° C. under inert atmosphere. The reaction mixture was allowed to warm to RT, and stirring was continued for another 5 h. The reaction mixture was diluted with H$_2$O (100 mL) and extracted with CH$_2$Cl$_2$ (3×200 mL). The combined organic extracts were washed with H$_2$O (50 mL) and brine (50 mL), dried over anhydrous Na$_2$SO$_4$ and concentrated under reduced pressure to afford compound V (25.0 g, 98.42 mmol, crude) as a semi-solid. $^1$H NMR (200 MHz, CDCl$_3$): δ 7.81 (d, J=8.0 Hz, 2H), 7.38 (d, J=8.0 Hz, 2H), 4.35 (q, J=8.0 Hz, 2H), 2.47 (s, 3H). MS(ESI): m/z 256 [M+2]$^+$.

To a stirred solution of 4-hydroxybenzaldehyde (1.0 g, 8.19 mmol) in DMF (10 mL) was added K$_2$CO$_3$ (3.39 g, 24.59 mmol) followed by compound V (2.48 g, 8.19 mmol) at RT under inert atmosphere. The resulting reaction mixture was gradually heated up to 110° C. and stirred for 16 h. The reaction mixture was cooled to RT, quenched with ice-cold water (100 mL) and extracted with EtOAc (3×100 mL). The combined organic extracts were washed with water (100 mL) and brine (100 mL), dried over anhydrous Na$_2$SO$_4$ and concentrated under reduced pressure to obtain the crude material. Purification by silica gel column chromatography (eluting with 5% EtOAc/hexane) afforded compound W (1.5 g, 7.35 mmol, 89%) as a pale yellow syrup. $^1$H NMR (200 MHz, CDCl$_3$): δ 9.93 (s, 1H), 7.90 (d, J=9.0 Hz, 2H), 7.06 (d, J=9.0 Hz, 2H), 4.44 (q, J=8.0 Hz, 2H).

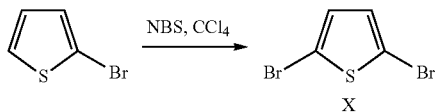

2,5-Dibromothiophene (X)

To a stirred solution of 2-bromothiophene (500 mg, 3.00 mmol) in carbon tetrachloride (CCl$_4$; 10 mL) was added N-bromosuccinimide (NBS; 801 mg, 4.50 mmol) followed by perchloric acid (3 mg, 0.03 mmol), and the mixture was stirred at RT for 48 h (while being monitored by TLC). The reaction mixture was filtered through a pad of Celite® and the Celite® cake was washed with CCl$_4$ (2×50 mL). The filtrate was concentrated under reduced pressure to afford crude compound X (900 mg) which was used in the next reaction without further purification. $^1$H NMR (500 MHz, CDCl$_3$): δ 6.84 (s, 2H).

Example 20

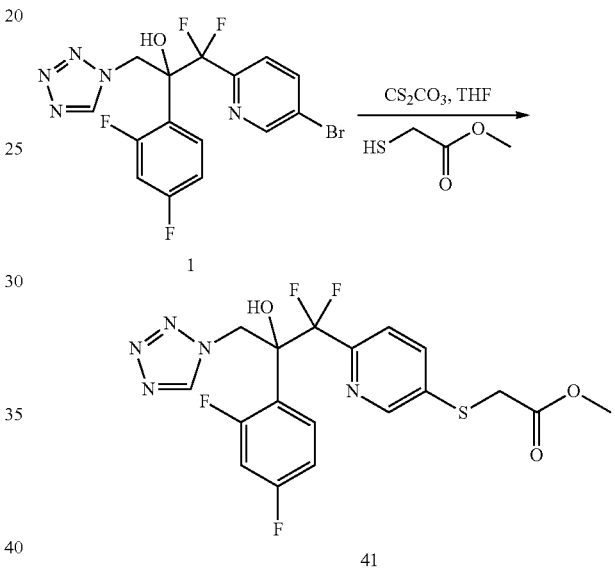

Methyl-2-(6-(2-(2,4-difluorophenyl)-1,1-difluoro-2-hydroxy-3-(1H-tetrazol-1-yl) propyl)pyridin-3-yl) thio)acetate (41)

To a stirred solution of methyl 2-mercaptoacetate (206 mg, 2.31 mmol) in THF (10 mL) was added cesium carbonate (Cs$_2$CO$_3$; 752 mg, 2.31 mmol) followed by compound 1 (200 mg, 0.46 mmol) at RT under inert atmosphere. The resulting reaction mixture was heated to 65° C. and stirred for 48 h. After complete consumption of the starting material (by TLC), the reaction mixture was diluted with EtOAc (100 mL). The organic layer was washed with satd NaHCO$_3$ solution (50 mL), water (50 mL) and brine (50 mL), dried over anhydrous Na$_2$SO$_4$ and concentrated under reduced pressure to obtain the crude material. Purification by silica gel column chromatography (eluting with 45% EtOAc/hexanes) afforded 41 (30 mg, 0.06 mmol, 14%). $^1$H NMR (500 MHz, CDCl$_3$): δ 8.75 (s, 1H), 8.50 (s, 1H), 7.80 (d, J=8.0 Hz, 1H), 7.47 (d, J=8.0 Hz, 1H), 7.34-7.27 (m, 2H), 6.78-6.73 (m, 1H), 6.69-6.66 (m, 1H), 5.58 (d, J=14.0 Hz, 1H), 5.10 (d, J=14.0 Hz, 1H), 3.74 (s, 2H), 3.70 (s, 3H). MS (ESI): m/z 458 [M+H]$^+$. HPLC: 93%.

Example 21

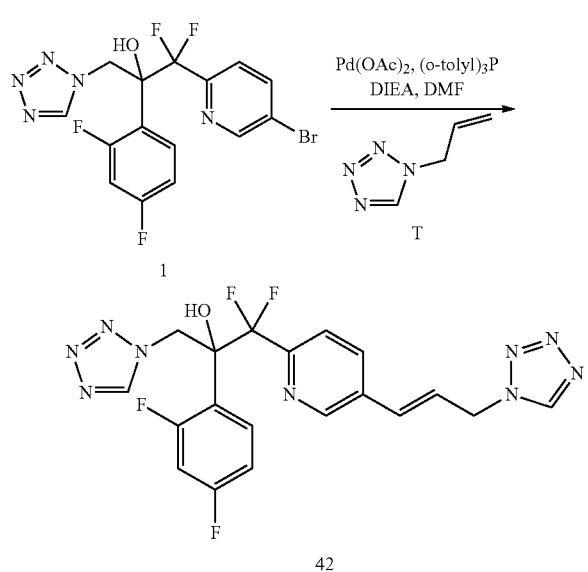

(E)-1-(5-(3-(1H-Tetrazol-1-yl)prop-1-en-1-yl)pyridin-2-yl)-2-(2,4-difluorophenyl)-1,1-difluoro-3-(1H-tetrazol-1-yl)propan-2-ol (42)

To a stirred solution of compound 1 (200 mg, 0.46 mmol) in DMF (2 mL) were added compound T (161 mg, 1.47 mmol), tri-o-tolylphosphine (447 mg, 0.14 mmol), Pd(OAc)$_2$ (22.7 mg, 0.10 mmol) and N,N-diethylisopropylamine (DIEA; 179 mg, 1.38 mmol) at RT, and the mixture was purged with inert gas for 15 min. The resulting reaction mixture was stirred at 110° C. under microwave heating for 15 min; progress of the reaction was monitored by TLC. The reaction mixture was cooled to RT, diluted with water (50 mL) and extracted with EtOAc (2×50 mL). The combined organic extracts were washed with water (50 mL) and brine (50 mL), dried over anhydrous Na$_2$SO$_4$ and concentrated under reduced pressure to obtain the crude material. Purification by silica gel column chromatography (eluting with 75% EtOAc/hexanes) afforded 42 (30 mg, 0.06 mmol, 14.3%). $^1$H NMR (500 MHz, CDCl$_3$): δ 8.73 (s, 1H), 8.67 (s, 1H), 8.49 (s, 1H), 7.80 (d, J=8.0 Hz, 1H), 7.57 (d, J=8.0 Hz, 1H), 7.37-7.31 (m, 2H), 6.78-6.68 (m, 1H), 6.67-6.64 (m, 1H), 6.61 (s, OH), 6.53-6.48 (m, 1H), 5.52 (d, J=14.5 Hz, 1H), 5.27 (d, J=6.0 Hz, 2H), 5.16 (d, J=14.5 Hz, 1H). MS (ESI): m/z 462 [M+H]$^+$. HPLC: 94.2%.

Example 22

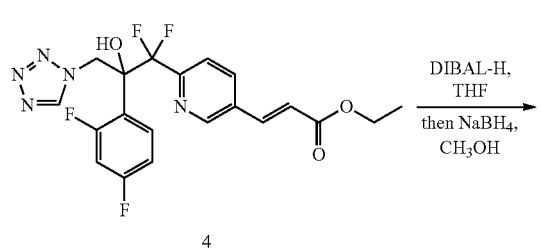

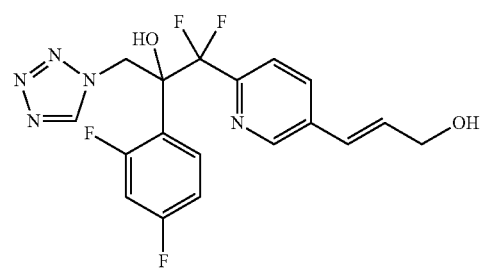

(E)-3-(2-(2,4-Difluorophenyl)-1,1-difluoro-2-hydroxy-3-(1H-tetrazol-1-yl)propyl)pyridin-3-yl)prop-2-en-1-ol (43)

To a stirred solution of (E)-ethyl 3-(6-(2-(2,4-difluorophenyl)-1,1-difluoro-2-hydroxy-3-(1H-tetrazol-1-yl)propyl)pyridin-3-yl)acrylate (4; 150 mg, 0.332 mmol) in dry CH$_2$Cl$_2$ (5 mL) was added diisobutylaluminum hydride (DIBAL-H, 1.6 M in toluene; 0.42 mL, 0.66 mmol) at −78° C. and maintained for 2 h under inert atmosphere. After completion of reaction (by TLC), the reaction was quenched with CH$_3$OH (2 mL) and the obtained heterogeneous mixture was then filtered through a pad of Celite®. The filtrate was concentrated under reduced pressure to obtain the residue. The residue was dissolved in CH$_3$OH (4 mL), and the mixture was stirred at 0° C. under inert atmosphere. Sodium borohydride (NaBH$_4$; 18.9 mg, 0.499 mmol) was added to the stirring solution, and the mixture was maintained at the same temperature for 30 min. The reaction mixture was quenched with satd NH$_4$Cl solution (5 mL) and extracted with EtOAc (3×20 mL). The organic extracts were washed with water (20 mL) and brine (20 mL), dried over anhydrous Na$_2$SO$_4$ and then concentrated in vacuo. Purification by silica gel column chromatography (eluting with 65-75% EtOAc/hexanes) yielded 43 (80 mg, 0.19 mmol, 58%). $^1$H NMR (500 MHz, CDCl$_3$): δ 8.75 (s, 1H), 8.51 (s, 1H), 7.79 (dd, J=8.5, 2.0 Hz, 1H), 7.52 (d, J=8.5 Hz, 1H), 7.36-7.31 (m, 1H), 6.78-6.74 (m, 1H), 6.68 (br s, OH), 6.67-6.63 (m, 2H), 6.54-6.49 (m, 1H), 5.58 (d, J=14.5 Hz, 1H), 5.11 (d, J=14.5 Hz, 1H), 4.41-4.39 (m, 2H), 3.45 (br s, OH). MS (ESI): m/z 410 [M+H]$^+$. HPLC: 99%.

Example 23

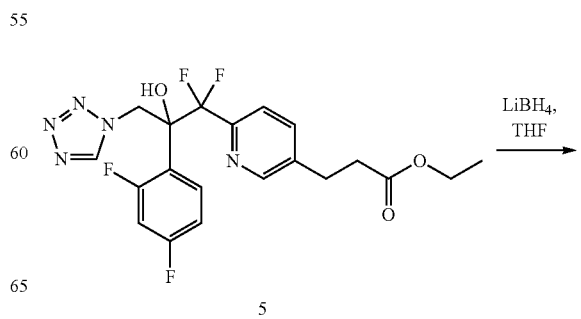

-continued

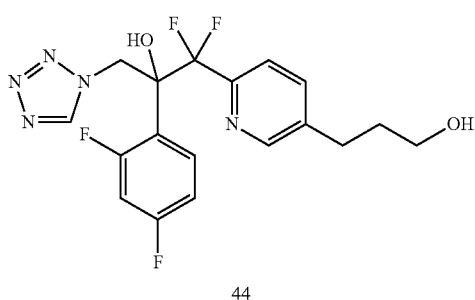

44

3-(6-(2-(2,4-Difluorophenyl)-1,1-difluoro-2-hydroxy-3-(1H-tetrazol-1-yl)propyl)pyridin-3-yl)propan-1-ol (44)

To a stirred solution of ethyl 3-(6-(2-(2,4-difluorophenyl)-1,1-difluoro-2-hydroxy-3-(1H-tetrazol-1-yl)propyl)pyridin-3-yl)propanoate (44; 200 mg, 0.44 mmol) in dry THF (5 mL) were added lithium chloride (LiCl; 37.5 mg, 0.88 mmol) and NaBH$_4$ (33.5 mg, 0.88 mmol) at 0° C., and the mixture was maintained at 0° C. to RT under inert atmosphere for 20 h. After consumption of the starting material (monitored by TLC), the reaction was quenched with ice-cold water and extracted with EtOAc (3×25 mL). The organic extracts were washed with water (20 mL) and brine (20 mL), dried over anhydrous Na$_2$SO$_4$ and then concentrated in vacuo. Purification by silica gel column chromatography (65-75% EtOAc/hexanes) yielded 44 (23 mg, 0.056 mmol, 12%). $^1$H NMR (500 MHz, CDCl$_3$): δ 8.75 (s, 1H), 8.36 (s, 1H), 7.67 (d, J=8.0 Hz, 1H), 7.51 (d, J=8.0 Hz, 1H), 7.42-7.37 (m, 1H), 6.79-6.74 (m, 1H), 6.70-6.66 (m, 1H), 5.50 (d, J=14.5 Hz, 1H), 5.14 (d, J=14.5 Hz, 1H), 3.67 (t, J=6.0 Hz, 2H), 2.78 (t, J=7.0 Hz, 2H), 1.91-1.85 (m, 2H). MS (ESI): m/z 412 [M+H]$^+$. HPLC: 98%.

Example 24

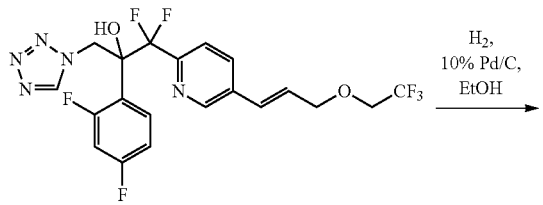

6

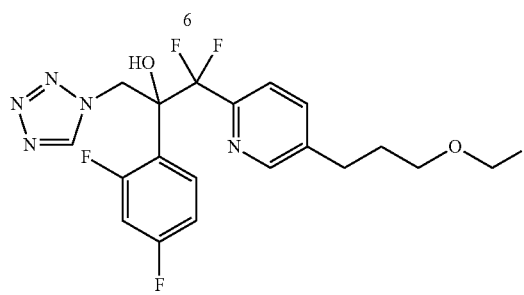

45

2-(2,4-Difluorophenyl)-1,1-difluoro-3-(1H-tetrazol-1-yl)-1-(5-(3-(2,2,2-trifluoroethoxy)propyl)pyridin-2-yl)propan-2-ol (45)

To a stirred solution of (E)-2-(2,4-difluorophenyl)-1,1-difluoro-3-(1H-tetrazol-1-yl)-1-(5-(3-(2,2,2-trifluoroethoxy)prop-1-enyl)pyridin-2-yl)propan-2-ol (6; 140 mg, 0.28 mmol) in EtOH (10 mL) was added 10% Pd/C (14 mg), and the mixture was stirred under hydrogen atmosphere for 2 h. After consumption of the starting material (by TLC), the reaction mixture was filtered through a pad of Celite® and the Celite® cake was washed thoroughly with EtOAc (3×20 mL). The filtrate was concentrated under reduced pressure to obtain the crude material. Purification by silica gel column chromatography (eluting with 30% EtOAc/hexanes) afforded 45 (105 mg, 0.21 mmol, 75%) as a white solid. $^1$H NMR (500 MHz, CDCl$_3$): δ 8.74 (s, 1H), 8.34 (s, 1H), 7.84 (s, 1H), 7.64 (d, J=6.5 Hz, 1H), 7.52 (d, J=8.0 Hz, 1H), 7.40-7.36 (m, 1H), 6.78-6.74 (m, 1H), 6.69-6.65 (m, 1H), 5.52 (d, J=14.0 Hz, 1H), 5.12 (d, J=14.0 Hz, 1H), 3.81 (q, J=8.0 Hz, 2H), 3.59 (t, J=6.0 Hz, 2H), 2.78 (t, J=8.0 Hz, 2H), 1.95-1.90 (m, 2H). MS (ESI): m/z 494 (M+H)$^+$. HPLC: 96%

Example 25

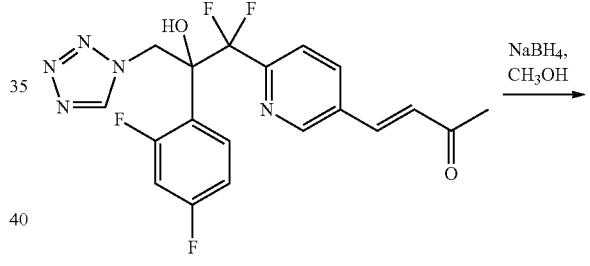

7

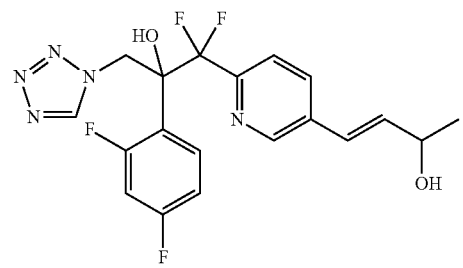

46

(E)-4-(6-(2-(2,4-Difluorophenyl)-1,1-difluoro-2-hydroxy-3-(1H-tetrazol-1-yl)propyl)pyridin-3-yl)but-3-en-2-ol (46)

To a stirred solution of (E)-4-(6-(2-(2,4-difluorophenyl)-1,1-difluoro-2-hydroxy-3-(1H-tetrazol-1-yl)propyl)pyridin-3-yl)but-3-en-2-one (7; 450 mg, 1.069 mmol) in CH$_3$OH (20 mL) was added NaBH$_4$ (216 mg, 3.20 mmol) at 0° C. under inert atmosphere. The reaction mixture was allowed to warm to RT and maintained for 1 h. After consumption of starting material (monitored by TLC), the reaction mixture was quenched with satd NH₄Cl solution (5 mL) and then concentrated under reduced pressure. The residue was diluted with water (10 mL) and extracted with EtOAc (3×25 mL). The combined organic extracts were washed with water (25 mL) and brine (25 mL), dried over anhydrous Na₂SO₄ and concentrated under reduced pressure. The crude material was purified by silica gel column chromatography to afford 46 (230 mg, 0.54 mmol, 50%) as a viscous liquid. ¹H NMR (500 MHz, CDCl₃): δ 8.78 (s, 1H), 8.50 (s, 1H), 7.79 (d, J=8.2 Hz, 1H), 7.52 (d, J=8.2 Hz, 1H), 7.35-7.31 (m, 1H), 6.81-6.74 (m, 1H), 6.68-6.64 (m, 1H), 6.59 (d, J=16.5 Hz, 1H), 6.43 (dd, J=16.5, 5.5 Hz, 1H), 5.60 (d, J=14.5 Hz, 1H), 5.12 (d, J=14.5 Hz, 1H), 4.59-4.56 (m, 1H), 1.76 (br s, OH), 1.40 (d, J=7.0 Hz, 3H). MS (ESI): m/z 424 [M+H]⁺. HPLC: 98%.

Example 26

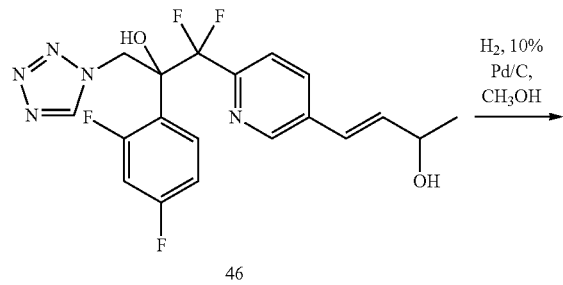

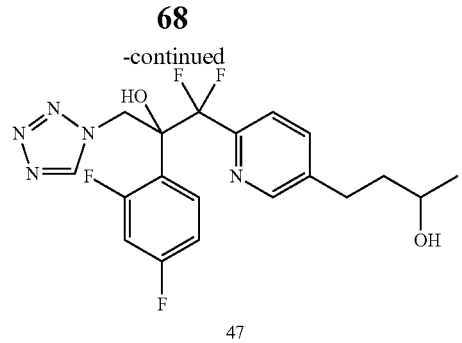

47

4-(6-(2-(2,4-Difluorophenyl)-1,1-difluoro-2-hydroxy-3-(1H-tetrazol-1-yl)propyl)pyridin-3-yl)butan-2-ol (47)

To a solution of (E)-4-(6-(2-(2,4-difluorophenyl)-1,1-difluoro-2-hydroxy-3-(1H-tetrazol-1-yl)propyl)pyridin-3-yl)but-3-en-2-ol (46; 150 mg, 0.35 mmol) in CH₃OH (10 mL) was added 10% Pd/C (10 mg), and the mixture was stirred under hydrogen atmosphere for 30 min. The reaction mixture was filtered through a pad of Celite®, the Celite® cake was washed with EtOAc (3×20 mL) and the filtrate was concentrated under reduced pressure. Purification by silica gel column chromatography (eluting with EtOAc/hexane) afforded 47 (77 mg, 0.18 mmol, 51%) as a viscous liquid. ¹H NMR (500 MHz, CDCl₃): δ 8.78 (s, 1H), 8.39-8.38 (m, 1H), 7.68-7.65 (m, 1H), 7.53-7.51 (m, 1H), 7.43-7.36 (m, 1H), 6.80-6.68 (m, 1H), 6.66-6.62 (m, 1H), 5.47-5.45 (m, 1H), 5.18-5.12 (m, 1H), 3.82-3.79 (m, 1H), 2.84-2.81 (m, 1H), 2.79-2.76 (m, 1H), 1.80-1.76 (m, 2H), 1.23 (d, J=7.0 Hz, 3H). MS (ESI): m/z 426 [M+H]⁺. HPLC: 98%.

Example 27

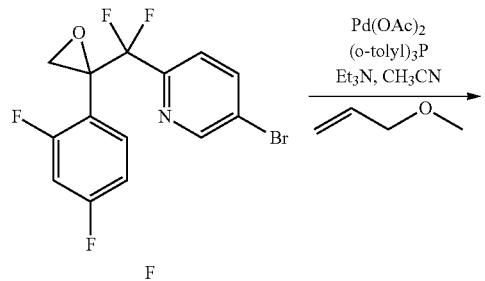

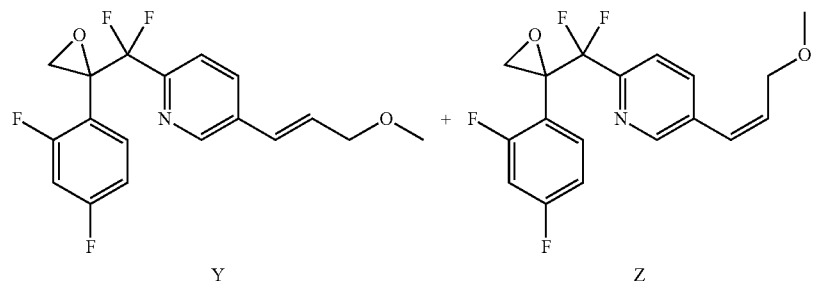

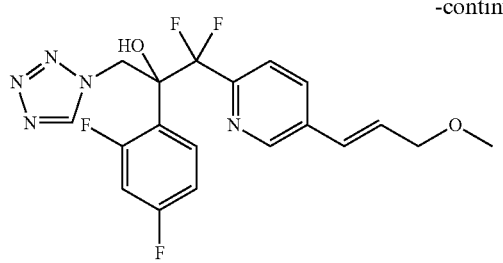
48

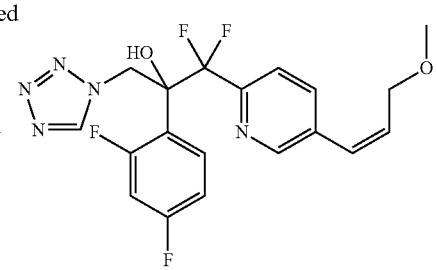
49

(E)-2-(2,4-Difluorophenyl)-1,1-difluoro-1-(5-(3-methoxyprop-1-en-1-yl)pyridin-2-yl)-3-(1H-tetrazol-1-yl)propan-2-ol (48) and (Z)-2-(2,4-difluorophenyl)-1,1-difluoro-1-(5-(3-methoxyprop-1-en-1-yl)pyridin-2-yl)-3-(1H-tetrazol-1-yl)propan-2-ol (49)

A mixture of compound F (200 mg, 0.55 mmol), Et$_3$N (141 mg, 1.4 mmol), tri-o-tolylphosphine (53 mg, 0.17 mmol), allyl methyl ether (143 mg, 1.98 mmol) and Pd(OAc)$_2$ (37 mg, 0.16 mmol) in CH$_3$CN (20 mL) was degassed and backfilled with argon for 20 min. The reaction mixture was heated to 90° C. and stirred for 18 h. After consumption of the starting material (by TLC), the reaction mixture was allowed to cool to RT; the reaction mixture was filtered through a pad of Celite® and the Celite® cake was washed with EtOAc (3×50 mL). The filtrate was concentrated under reduced pressure to obtain the crude material. Purification by silica gel column chromatography afforded compound Z (25 mg, 0.045 mmol, 8%) (eluent: 1% CH$_3$OH/CH$_2$C$_2$) as a thick syrup and compound Y (20 mg, 0.036 mmol, 6%) (eluent: 2% CH$_3$OH/CH$_2$Cl$_2$) as a colorless thick syrup. Compound Y: $^1$H NMR (500 MHz, CDCl$_3$): δ 8.64 (s, 1H), 7.73 (d, J=8.0 Hz, 1H), 7.41 (d, J=8.0 Hz, 1H), 7.39-7.34 (m, 1H), 6.84-6.81 (m, 1H), 6.75-6.71 (m, 1H), 6.64 (d, J=16.5 Hz, 1H), 6.45-6.40 (m, 1H), 4.13 (d, J=5.0 Hz, 2H), 3.45 (d, J=5.0 Hz, 1H), 3.43 (s, 3H), 2.97 (d, J=5.0 Hz, 1H). MS (ESI): m/z 354 [M+H]$^+$. Compound Z: $^1$H NMR (500 MHz, CDCl$_3$): δ 8.51 (s, 1H), 7.56 (dd, J=8.0, 2.0 Hz, 1H), 7.40-7.35 (m, 2H), 6.84-6.80 (m, 1H), 6.76-6.71 (m, 1H), 6.06 (d, J=6.0 Hz, 1H), 4.53-4.49 (m, 2H), 3.64 (s, 3H), 3.45-3.42 (m, 2H), 2.95 (m, 1H). MS (ESI): m/z 354 [M+H]$^+$.

To a stirred solution of compound Y (140 mg, 0.39 mmol) in DMF (7 mL) was added 1H-tetrazole (14 mg, 0.39 mmol) followed by K$_2$CO$_3$ (28 mg, 0.20 mmol) at RT under inert atmosphere. The resulting reaction mixture was gradually heated up to 65° C. and stirred for 5 h. After consumption of the starting material (by TLC), the reaction mixture was cooled to RT, diluted with water (25 mL) and extracted with EtOAc (2×25 mL). The combined organic extracts were washed with water (25 mL) and brine (25 mL), dried over anhydrous Na$_2$SO$_4$ and concentrated under reduced pressure to obtain the crude material. Purification by silica gel column chromatography (eluting with 4% CH$_3$OH/CH$_2$Cl$_2$) afforded 48 (86 mg, 0.20 mmol, 52%) as a semi-solid. $^1$H NMR (500 MHz, CDCl$_3$): δ 8.74 (s, 1H), 8.50 (s, 1H), 7.77 (dd, J=8.5, 2.0 Hz, 1H), 7.65 (br s, OH), 7.51 (d, J=8.5 Hz, 1H), 7.34-7.29 (m, 1H), 6.77-6.72 (m, 1H), 6.66-6.65 (m, 1H), 6.61 (d, J=16.5 Hz, 1H), 6.45-6.41 (m, 1H), 5.59 (d, J=14.0 Hz, 1H), 5.08 (d, J=14.0 Hz, 1H), 4.12 (d, J=5.0 Hz, 2H), 3.42 (s, 3H). MS (ESI): m/z 424 [M+H]$^+$. HPLC: 90%.

To a stirred solution of compound Z (186 mg, 0.53 mmol) in DMF (10 mL) was added 1H-tetrazole (36 mg, 0.53 mmol) followed by K$_2$CO$_3$ (36 mg, 0.26 mmol) at RT under inert atmosphere. The resulting reaction mixture was gradually heated up to 65° C. and stirred for 5 h. After consumption of the starting material (by TLC), the reaction mixture was cooled to RT, diluted with water (30 mL) and extracted with EtOAc (2×25 mL). The combined organic extracts were washed with water (25 mL) and brine (25 mL), dried over anhydrous Na$_2$SO$_4$ and concentrated under reduced pressure to obtain the crude material. Purification by silica gel column chromatography (eluting with 4% CH$_3$OH/CH$_2$Cl$_2$) afforded 49 (86 mg, 0.20 mmol, 38%) as a semi-solid. $^1$H NMR (500 MHz, CDCl$_3$): δ 8.74 (s, 1H), 8.38 (s, 1H), 7.98 (s, OH), 7.65 (dd, J=8.0, 2.0 Hz, 1H), 7.48 (d, J=8.0 Hz, 1H), 7.37-7.32 (m, 1H), 6.77-6.72 (m, 1H), 6.67-6.63 (m, 1H), 6.08 (dd, J=6.0, 2.0 Hz, 1H), 5.58 (d, J=14.0 Hz, 1H), 5.04 (d, J=14.0 Hz, 1H), 4.51-4.47 (m, 1H), 3.64 (s, 3H), 3.42 (d, J=7.5 Hz, 2H). MS (ESI): m/z 424 [M+H]$^+$. HPLC: 98%.

Example 28

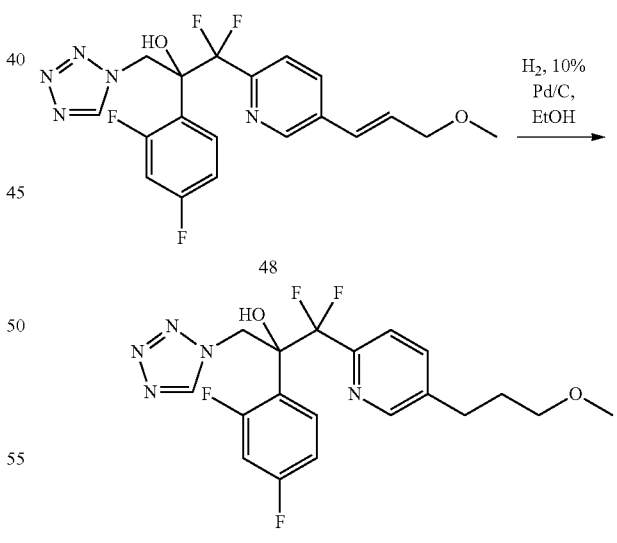

2-(2,4-Difluorophenyl)-1,1-difluoro-1-(5-(3-methoxypropyl)pyridin-2-yl)-3-(1H-tetrazol-1-yl)propan-2-ol (50)

To a stirred solution of (E)-2-(2,4-difluorophenyl)-1,1-difluoro-1-(5-(3-methoxyprop-1-en-1-yl)pyridin-2-yl)-3-

(1H-tetrazol-1-yl)propan-2-ol (48; 80 mg, 0.18 mmol) in EtOH (10 mL) was added 10% Pd/C (8 mg), and the mixture was stirred under hydrogen atmosphere for 1 h. The reaction mixture was filtered through a pad of Celite®, the Celite® cake was washed thoroughly with EtOAc (3×30 mL) and then the filtrate was concentrated under reduced pressure to obtain the crude material. Purification by silica gel column chromatography (eluting with 45-50% EtOAc/hexanes) afforded 50 (65 mg, 0.14 mmol, 77%) as a semi-solid. $^1$H NMR (500 MHz, CDCl$_3$): δ 8.74 (s, 1H), 8.36 (s, 1H), 7.87 (s, 1H), 7.64 (d, J=8.0 Hz, 1H), 7.50 (d, J=8.0 Hz, 1H), 7.38-7.33 (m, 1H), 6.77-6.73 (m, 1H), 6.67-6.63 (m, 1H), 5.56 (d, J=14.5 Hz, 1H), 5.09 (d, J=14.5 Hz, 1H), 3.37-3.34 (m, 2H), 3.33 (s, 3H), 2.75 (t, J=7.0 Hz, 2H), 1.90-1.85 (m, 2H). MS (ESI): m/z 426 (M+H)$^+$. HPLC: 97%.

Example 29

(93 mg, 0.41 mmol) in CH$_3$CN (50 mL) was degassed and backfilled with argon for 20 min. The reaction mixture was heated to 90° C. and stirred for 16 h. After consumption of the starting material (by TLC), the reaction mixture was allowed to cool to RT; the reaction mixture was filtered through a pad of Celite® and the Celite® cake was washed with EtOAc (3×50 mL). The filtrate was concentrated under reduced pressure to obtain the crude material. Purification by silica gel column chromatography to afford compound AB (250 mg, 0.44 mmol, 50%) (eluent: 10% EtOAc/hexanes) as a thick syrup and compound AA (90 mg, 0.16 mmol, 18%) (eluent: 12% EtOAc/hexanes) as a thick syrup. Compound AA: $^1$H NMR (500 MHz, CDCl$_3$): δ 8.63 (s, 1H), 7.73 (d, J=8.5 Hz, 1H), 7.41 (d, J=8.5 Hz, 1H), 7.38-7.34 (m, 1H), 6.83-6.80 (m, 1H), 6.75-6.71 (m, 1H), 6.64 (d, J=16.0 Hz, 1H), 6.47-6.42 (m, 1H), 4.17 (d, J=5.0 Hz, 2H), 3.58 (q, J=7.0 Hz, 2H), 3.45 (d, J=5.0 Hz, 1H), 2.96 (d, J=5.0 Hz, 1H), 1.27 (t, J=7.0 Hz, 3H). MS (ESI): m/z 368 [M+H]$^+$.

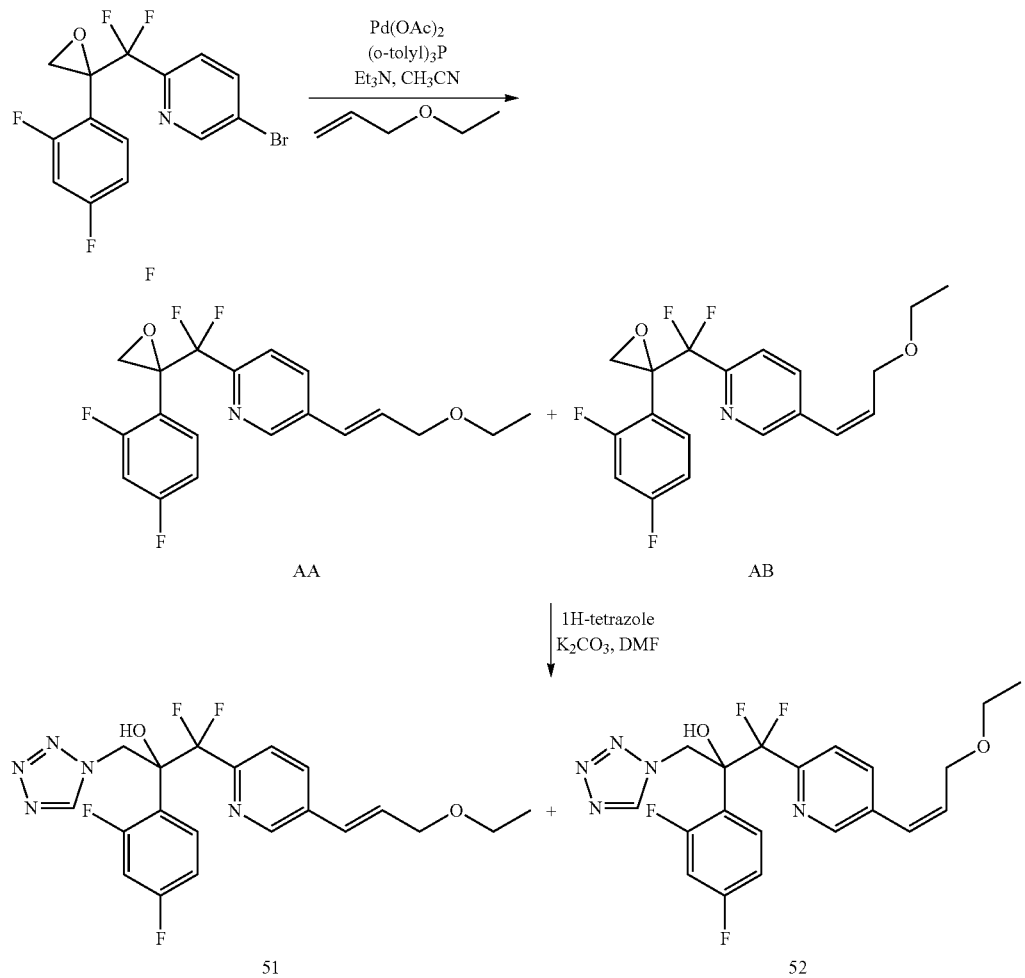

(E)-2-(2,4-Difluorophenyl)-1-(5-(3-ethoxyprop-1-en-1-yl)pyridin-2-yl)-1,1-difluoro-3-(1H-tetrazol-1-yl)propan-2-ol (51) and (Z)-2-(2,4-difluorophenyl)-1-(5-(3-ethoxyprop-1-en-1-yl)pyridin-2-yl)-1,1-difluoro-3-(1H-tetrazol-1-yl)propan-2-ol (52)

A mixture of compound F (500 mg, 1.38 mmol), Et$_3$N (0.53 mL, 3.7 mmol), tri-o-tolylphosphine (147 mg, 0.48 mmol), allyl ethyl ether (0.6 mL, 4.97 mmol), and Pd(OAc)$_2$ Compound AB: $^1$H NMR (200 MHz, CDCl$_3$): δ 8.52 (s, 1H), 7.57 (dd, J=8.0, 2.0 Hz, 1H), 7.40-7.35 (m, 2H), 6.84-6.80 (m, 1H), 6.76-6.71 (m, 1H), 6.12 (t, J=6.5 Hz, 1H), 4.53-4.49 (m, 1H), 3.84 (q, J=7.0 Hz, 2H), 3.46-3.42 (m, 3H), 2.95 (d, J=5.0 Hz, 1H), 1.27 (t, J=7.0 Hz, 3H). MS (ESI): m/z 368 [M+H]$^+$.

To a stirred solution of compound AA (0.32 g, 0.87 mmol) in DMF (10 mL) was added 1H-tetrazole (0.21 g, 3.04 mmol) followed by K$_2$CO$_3$ (0.21 g, 1.56 mmol) at RT under inert atmosphere; the resulting reaction mixture was gradually heated up to 65° C. and stirred for 20 h. After consumption of the starting material (by TLC), the reaction mixture was cooled to RT, diluted with water (50 mL) and extracted with EtOAc (2×50 mL). The combined organic extracts were washed with water (50 mL) and brine (50 mL), dried over anhydrous $Na_2SO_4$ and concentrated under reduced pressure to obtain the crude material. Purification by silica gel column chromatography (eluting with 35% EtOAc/hexanes) afforded 51 (0.24 g, 0.54 mmol, 63%) as a semi-solid. $^1$H NMR (500 MHz, $CDCl_3$): δ 8.74 (s, 1H), 8.50 (s, 1H), 7.77 (d, J=8.0 Hz, 1H), 7.66 (s, OH), 7.51 (d, J=8.0 Hz, 1H), 7.33-7.28 (m, 1H), 6.77-6.72 (m, 1H), 6.66-6.64 (m, 1H), 6.61 (d, J=15.5 Hz, 1H), 6.47-6.42 (m, 1H), 5.60 (d, J=14.0 Hz, 1H), 5.10 (d, J=14.0 Hz, 1H), 4.16 (d, J=5.0 Hz, 2H), 3.57 (q, J=7.0 Hz, 2H), 1.25 (t, J=7.0 Hz, 3H). MS (ESI): m/z 438 [M+H]$^+$. HPLC: 90%.

To a stirred solution of compound AB (130 mg, 0.35 mmol) in DMF (8 mL) was added 1H-tetrazole (87 mg, 1.23 mmol) followed by $K_2CO_3$ (88 mg, 0.63 mmol) at RT under inert atmosphere. The resulting reaction mixture was gradually heated up to 65° C. and stirred for 20 h. After consumption of the starting material (by TLC), the reaction mixture was cooled to RT, diluted with water (30 mL) and extracted with EtOAc (2×30 mL). The combined organic extracts were washed with water (30 mL) and brine (30 mL), dried over anhydrous $Na_2SO_4$ and concentrated under reduced pressure to obtain the crude material. Purification by silica gel column chromatography (eluting with 35% EtOAc/hexanes) afforded 52 (42 mg, 0.09 mmol, 27%) as a semi-solid. $^1$H NMR (500 MHz, $CDCl_3$): δ 8.74 (s, 1H), 8.39 (s, 1H), 8.00 (s, 1H), 7.65 (dd, J=8.5, 2.0 Hz, 1H), 7.48 (d, J=8.5 Hz, 1H), 7.37-7.32 (m, 1H), 6.77-6.72 (m, 1H), 6.66-6.63 (m, 1H), 6.13 (d, J=7.0 Hz, 1H), 5.59 (d, J=14.0 Hz, 1H), 5.04 (d, J=14.0 Hz, 1H), 4.48 (m, 1H), 3.84 (q, J=7.0 Hz, 2H), 3.43 (d, J=7.5 Hz, 2H), 1.26 (t, J=7.0 Hz, 3H). MS (ESI): m/z 438 [M+H]$^+$. HPLC: 90%.

Example 30

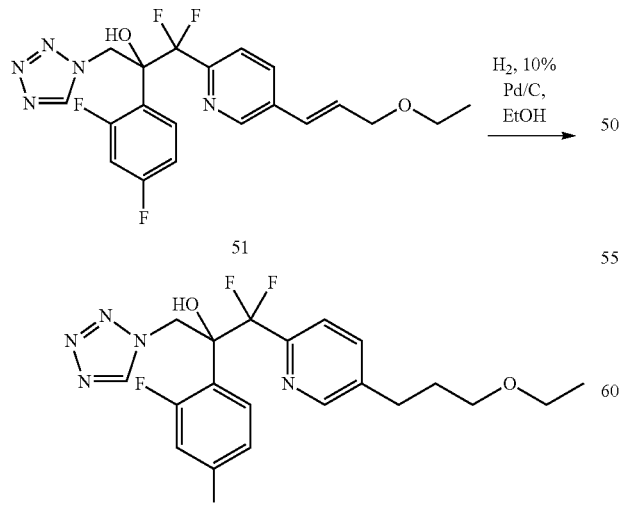

2-(2,4-Difluorophenyl)-1-(5-(3-ethoxypropyl)pyridin-2-yl)-1,1-difluoro-3-(1H-tetrazol-1-yl)propan-2-ol (53)

To a stirred solution of (E)-2-(2,4-difluorophenyl)-1-(5-(3-ethoxyprop-1-en-1-yl)pyridin-2-yl)-1,1-difluoro-3-(1H-tetrazol-1-yl)propan-2-ol (51; 80 mg, 0.21 mmol) in EtOH (10 mL) was added 10% Pd/C (8 mg), and the mixture was stirred under hydrogen atmosphere for 2 h. After consumption of the starting material (by TLC), the reaction mixture was filtered through a pad of Celite®, and the Celite® cake was washed thoroughly with EtOAc (3×10 mL). The filtrate was concentrated under reduced pressure to obtain the crude material. Purification by silica gel column chromatography (eluting with 30% EtOAc/hexanes) afforded 53 (65 mg, 0.14 mmol, 68%) as a semi-solid. $^1$H NMR (500 MHz, $CDCl_3$): δ 8.74 (s, 1H), 8.36 (s, 1H), 7.88 (s, OH), 7.64 (dd, J=8.0, 2.0 Hz, 1H), 7.50 (d, J=8.0 Hz, 1H), 7.37-7.32 (m, 1H), 6.77-6.73 (m, 1H), 6.67-6.63 (m, 1H), 5.56 (d, J=14.0 Hz, 1H), 5.09 (d, J=14.0 Hz, 1H), 3.46 (q, J=7.0 Hz, 2H), 3.39 (t, J=7.0 Hz, 2H), 2.76 (t, J=7.0 Hz, 2H), 1.90-1.85 (m, 2H), 1.20 (t, J=7.0 Hz, 3H). MS (ESI): m/z 440 (M+H)$^+$. HPLC: 95%.

Example 31

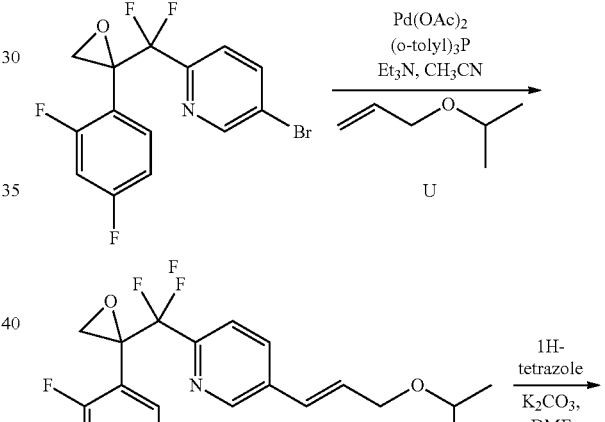

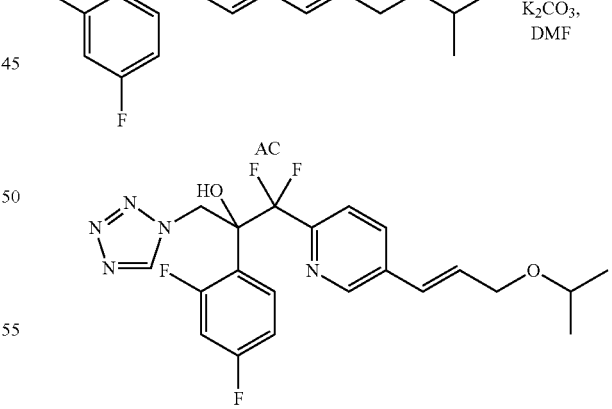

(E)-2-(2,4-Difluorophenyl)-1,1-difluoro-1-(5-(3-isopropoxyprop-1-en-1-yl)pyridin-2-yl)-3-(1H-tetrazol-1-yl)propan-2-ol (54)

A mixture of compound F (500 mg, 1.38 mmol), $Et_3N$ (0.5 mL, 3.7 mmol), tri-o-tolylphosphine (134 mg, 0.44 mmol), crude U (907 mg, 4.14 mmol), and Pd(OAc)₂ (68 mg, 0.30 mmol) in CH₃CN (50 mL) was degassed and backfilled with argon for 20 min. The reaction mixture was heated to 90° C. and stirred for 18 h. After consumption of the starting material (by TLC), the reaction mixture was allowed to cool to RT; the reaction mixture was filtered through a pad of Celite® and the Celite® cake was washed with EtOAc (3×50 mL). The filtrate was concentrated under reduced pressure to obtain the crude material. Purification by silica gel column chromatography (eluting with 12% EtOAc/hexane) afforded compound AC (110 mg, 0.28 mmol, 20%) as a thick syrup. ¹H NMR (500 MHz, CDCl₃): δ 8.50 (s, 1H), 7.56 (d, J=8.0 Hz, 1H), 7.40-7.36 (m, 2H), 6.84-6.80 (m, 1H), 6.75-6.71 (m, 1H), 6.21 (d, J=17 Hz, 1H), 4.99-4.93 (m, 1H), 4.00-3.97 (m, 1H), 3.42 (d, J=5.0 Hz, 1H), 3.29 (d, J=7.0 Hz, 2H), 2.98 (q, J=5.0 Hz, 1H), 1.24 (d, J=7.0 Hz, 6H). MS (ESI): m/z 382 [M+H]⁺.

To a stirred solution of compound AC (320 mg, 0.84 mmol) in DMF (10 mL) was added 1H-tetrazole (88 mg, 1.26 mmol) followed by K₂CO₃ (116 mg, 0.84 mmol) at RT under inert atmosphere. The resulting reaction mixture was gradually heated up to 65° C. and stirred for 20 h. After complete consumption of the starting material (by TLC), the reaction mixture was diluted with ice-cold water (50 mL) and extracted with EtOAc (2×50 mL). The combined organic extracts were washed with water (50 mL) and brine (50 mL), dried over anhydrous Na₂SO₄ and concentrated under reduced pressure to obtain the crude material. Purification by silica gel column chromatography (eluting with 35% EtOAc/hexanes) afforded 54 (240 mg, 0.53 mmol, 63%) as a colorless semi-solid. ¹H NMR (500 MHz, CDCl₃): δ 8.74 (s, 1H), 8.50 (s, 1H), 7.77 (t, J=8.0 Hz, 1H), 7.68 (br s, OH), 7.50 (d, J=8.0 Hz, 1H), 7.32-7.30 (m, 1H), 6.77-6.72 (m, 1H), 6.66-6.64 (m, 1H), 6.62-6.59 (d, J=16.0 Hz, 1H), 6.47-6.43 (m, 1H), 5.60 (d, J=14.0 Hz, 1H), 5.10 (d, J=14.0 Hz, 1H), 4.16 (d, J=6.0 Hz, 2H), 3.68 (q, J=6.0 Hz, 1H), 1.21 (d, J=6.0 Hz, 6H). MS (ESI): m/z 452 (M+H)⁺. HPLC: 94%.

Example 32

2-(2,4-Difluorophenyl)-1,1-difluoro-1-(5-(3-isopropoxypropyl)pyridin-2-yl)-3-(1H-tetrazol-1-yl) propan-2-ol (55)

To a stirred solution of (E)-2-(2,4-difluorophenyl)-1,1-difluoro-1-(5-(3-isopropoxyprop-1-en-1-yl)pyridin-2-yl)-3-(1H-tetrazol-1-yl)propan-2-ol (54; 24 mg, 0.05 mmol) in CH₃OH (2 mL) was added 10% Pd/C (2 mg), and the mixture was stirred under hydrogen atmosphere for 2 h. After consumption of the starting material (by TLC), the reaction mixture was filtered through a pad of Celite®, and the Celite® cake was washed thoroughly with EtOAc (3×10 mL). The filtrate was concentrated under reduced pressure to obtain the crude material. Purification by silica gel column chromatography (eluting with 30% EtOAc/hexane) afforded 55 (20 mg, 0.04 mmol, 80%) as a colorless semi-solid. ¹H NMR (500 MHz, CDCl₃): δ 8.74 (s, 1H), 8.36 (s, 1H), 7.89 (s, 1H), 7.64 (d, J=8.0 Hz, 1H), 7.50 (d, J=8.0 Hz, 1H), 7.36-7.31 (m, 1H), 6.77-6.73 (m, 1H), 6.67-6.63 (m, 1H), 5.56 (d, J=14.0 Hz, 1H), 5.09 (d, J=14.0 Hz, 1H), 3.53 (q, J=6.0 Hz, 1H), 3.38 (t, J=6.0 Hz, 2H), 2.75 (t, J=8.0 Hz, 2H), 1.86 (q, J=6.0 Hz, 2H), 1.14 (d, J=6.0 Hz, 6H). MS (ESI): m/z 454 (M+H)⁺. HPLC: 93%.

Example 33

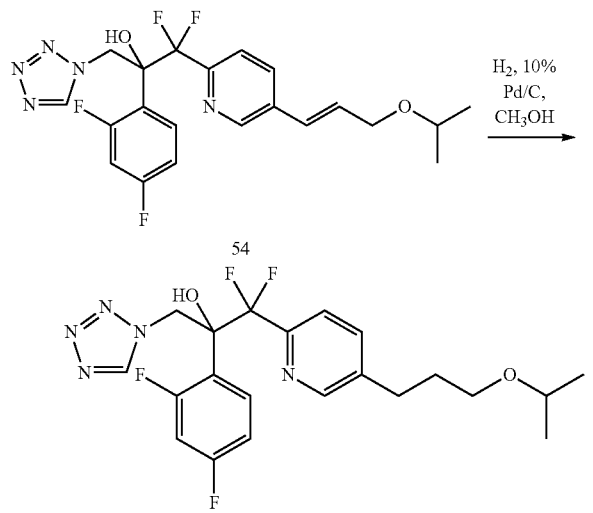

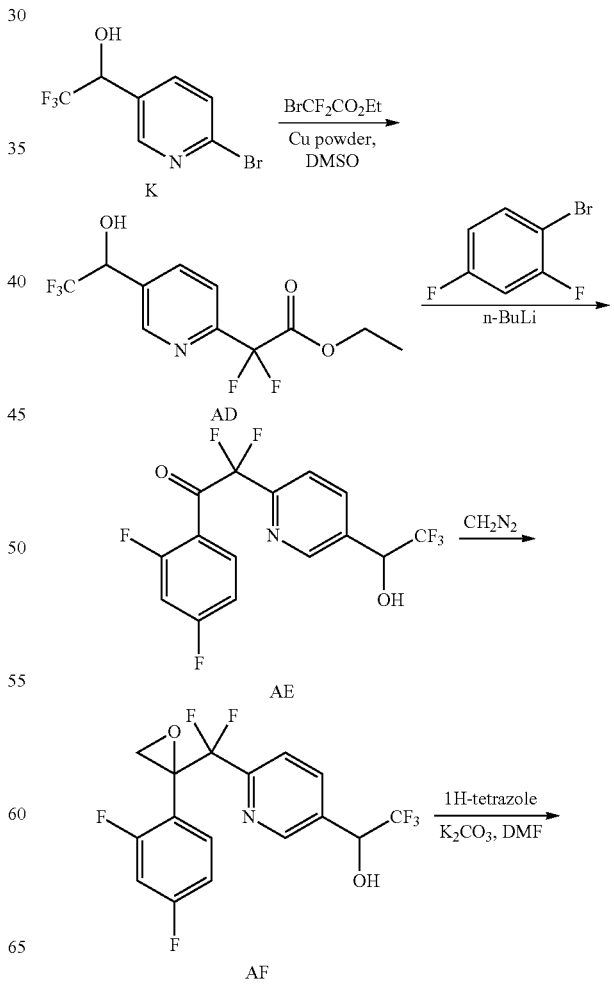

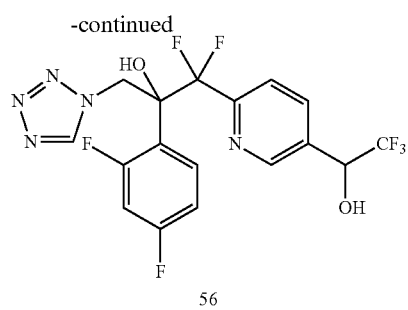

56

(2-(2,4-Difluorophenyl)-1,1-difluoro-3-(1H-tetrazol-1-yl)-1-(5-(2,2,2-trifluoro-1-hydroxyethyl)pyridin-2-yl)propan-2-ol) (56)

To a suspension of copper powder (50 mg, 0.78 mmol) in DMSO (5 mL) was added ethyl 2-bromo-2,2-difluoroacetate (0.05 mL, 0.39 mmol), and the mixture was stirred for 1 h at RT under inert atmosphere. To the resulting mixture, was added 1-(6-bromopyridin-3-yl)-2,2,2-trifluoroethanol (K; 50 mg, 0.19 mmol), and stirring was continued for 10 h at RT. Progress of the reaction was monitored by TLC. The reaction mixture was quenched with satd NH$_4$Cl solution (20 mL) and extracted with CH$_2$Cl$_2$ (3×10 mL). The combined organic extracts were washed with water (15 mL) and brine (15 mL), dried over anhydrous Na$_2$SO$_4$ and concentrated under reduced pressure to obtain the crude material. Purification by silica gel column chromatography (eluting with 10% EtOAc/hexanes) afforded the ester AD (20 mg, 0.06 mmol, 34%) as a colorless liquid. $^1$H NMR (500 MHz, CDCl$_3$): δ 8.71 (s, 1H), 8.04 (d, J=8.0 Hz, 1H), 7.80 (d, J=8.0 Hz, 1H), 5.18-5.16 (m, 1H), 4.37 (q, J=7.0 Hz, 2H), 1.23 (t, J=7.0 Hz, 3H). MS (ESI): m/z 300 [M+H]$^+$.

To a stirred solution of 1-bromo-2,4-difluorobenzene (0.05 mL, 0.33 mmol) in Et$_2$O (7 mL) was added n-BuLi (1.6 M in hexane; 0.2 mL, 0.33 mmol) at −78° C., and the mixture was stirred for 30 min under inert atmosphere. A solution of ester AD (100 mg, 0.33 mmol) in Et$_2$O (3 mL) was added to the reaction mixture at −78° C. and stirring was continued for another 2 h. Progress of the reaction was monitored by TLC. The reaction mixture was quenched with satd NH$_4$Cl solution (20 mL) and extracted with EtOAc (2×15 mL). The combined organic extracts were dried over anhydrous Na$_2$SO$_4$ and concentrated under reduced pressure to obtain crude AE (80 mg). The product was used in the next reaction without further purification. (All desired peaks were seen in the $^1$H NMR spectrum.)

To a stirred solution of crude AE (80 mg) in Et$_2$O (10 mL) was added freshly prepared diazomethane [prepared by dissolving NMU (112 mg, 1.08 mmol) in a 1:1 mixture of 10% KOH solution (15 mL) and ether (15 mL) at 0° C. followed by separation and drying of the organic layer using KOH pellets] at −5° C., and the mixture was stirred for 2 h. The resulting reaction mixture was allowed to warm to RT and stirring was continued for another 16 h. Progress of the reaction was monitored by TLC. The reaction mixture was concentrated under reduced pressure to obtain the crude material. Purification by silica gel column chromatography (eluting with 15% EtOAc/hexane) afforded the epoxide AF (50 mg, 0.13 mmol, 60% over two steps i.e., from AD to AF) as a pale yellow semi-solid. $^1$H NMR (500 MHz, CDCl$_3$): δ 8.73 (s, 1H), 7.93 (d, J=8.5 Hz, 1H), 7.54 (d, J=8.5 Hz, 1H), 7.38-7.35 (m, 1H), 6.84-6.81 (m, 1H), 6.75-6.71 (m, 1H), 5.16-5.14 (m, 1H), 3.44 (d, J=4.5 Hz, 1H), 3.07 (d, J=4.5 Hz, 1H), 2.97 (br s, OH). MS (ESI): m/z 380 [M−H]$^−$.

To a stirred solution of epoxide AF (100 mg, 0.26 mmol) in dry DMF (5 mL) was added 1H-tetrazole (27.5 mg, 0.39 mmol) followed by K$_2$CO$_3$ (36 mg, 0.26 mmol) at RT under inert atmosphere. The resulting reaction mixture was gradually heated up to 65° C. and stirred for 16 h; progress of the reaction was monitored by TLC. The reaction mixture was diluted with ice-cold water (20 mL) and extracted with EtOAc (2×20 mL). The combined organic extracts were washed with water (20 mL) and brine (20 mL), dried over anhydrous Na$_2$SO$_4$ and concentrated under reduced pressure. Purification by silica gel column chromatography (eluting with 45% EtOAc/hexane) afforded a diastereomeric mixture of 56 (26 mg, 0.05 mmol, 22%) as a pale yellow semi-solid. $^1$H NMR (500 MHz, CDCl$_3$; mixture of diastereomers): δ 8.75 (s, 2H), 8.62 (s, 1H), 8.54 (s, 1H), 8.03-8.00 (m, 1H), 7.96 (d, J=8.5 Hz, 1H), 7.68-7.64 (m, 2H), 7.47-7.37 (m, 4H), 6.81-6.76 (m, 2H), 6.74-6.68 (m, 2H), 5.47 (d, J=15.0 Hz, 1H), 5.41 (d, J=15.0 Hz, 1 Hz), 5.26-5.12 (m, 4H). MS (ESI): m/z 452 [M+H]$^+$. HPLC: 83.11%.

Example 34

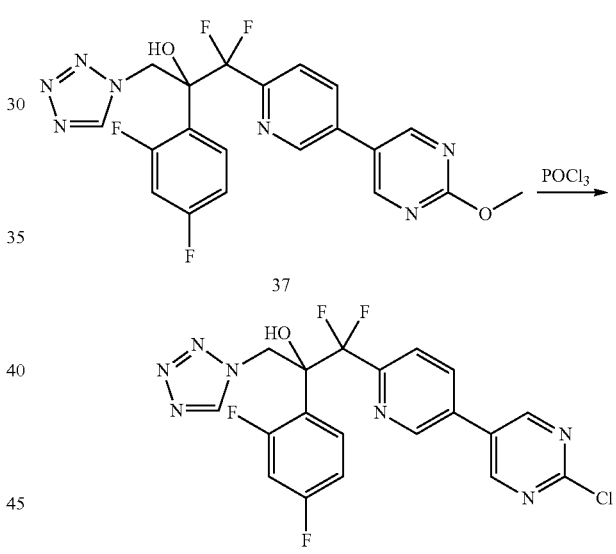

1-(5-(2-Chloropyrimidin-5-yl)pyridin-2-yl)-yl)-2-(2,4-difluorophenyl)-1,1-difluoro-3-(1H-tetrazol-1-yl)propan-2-ol (57)

To 2-(2,4-difluorophenyl)-1,1-difluoro-1-(5-(2-methoxypyrimidin-5-yl)pyridin-2-yl)-3-(1H-tetrazol-1-yl)propan-2-ol (37; 80 mg, 0.17 mmol) was added phosphorus oxychloride (POCl$_3$; 1.0 mL) followed by DMF (cat) at RT under inert atmosphere. The reaction mixture was gradually heated to 80° C. and stirred for 2 h. After complete consumption of the starting material (by TLC), the reaction mixture was cooled to RT, diluted with ice-cold water (30 mL), made basic (pH~8) using satd NaHCO$_3$ solution and extracted with EtOAc (2×50 mL). The combined organic extracts were washed with water (50 mL) and brine (50 mL), dried over anhydrous Na$_2$SO$_4$ and concentrated under reduced pressure to obtain the crude material. Purification by silica gel column chromatography (eluting with 38% EtOAc/hexane) afford 57 (25 mg, 0.05 mmol, 31%) as a semi-solid. ¹H NMR (500 MHz, CDCl₃): δ 8.84 (s, 2H), 8.74 (s, 1H), 8.71 (s, 1H), 8.01 (dd, J=8.0, 2.5 Hz, 1H), 7.77 (d, J=8.0 Hz, 1H), 7.42-7.39 (m, 1H), 7.05 (br s, OH), 6.82-6.77 (m, 1H), 6.73-6.69 (m, 1H), 5.52 (d, J=14.5 Hz, 1H), 5.23 (d, J=14.5 Hz, 1H). MS (ESI): m/z 466 (M+H)⁺. HPLC: 93%.

Example 35

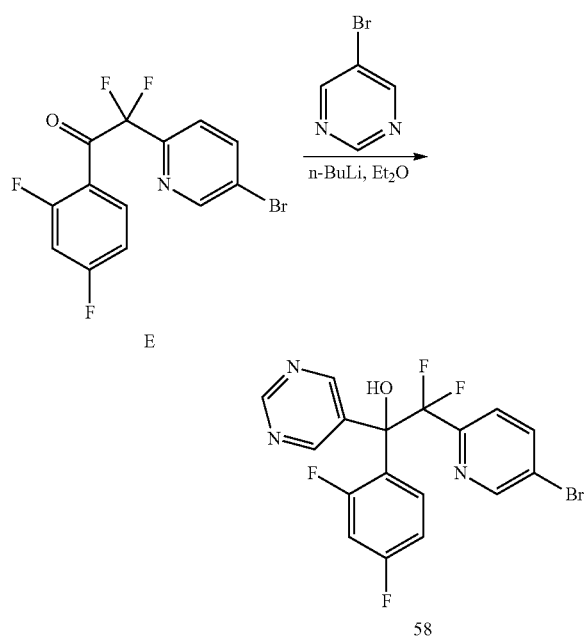

2-(5-Bromopyridin-2-yl)-1-(2,4-difluorophenyl)-2,2-difluoro-1-(pyrimidin-5-yl)ethanol (58)

To a stirred solution of 5-bromopyrimidine (0.45 g, 2.87 mmol) in Et₂O (30 mL) was added n-BuLi (1.6 M in hexane; 1.8 mL, 2.87 mmol) at −78° C., and the mixture was stirred for 1 h under inert atmosphere. A solution of compound E (1.0 g, 2.87 mmol) in Et₂O (10 mL) was added to the reaction mixture at −78° C., and stirring was continued for another 1 h. After complete consumption of the starting material (by TLC), the reaction mixture was quenched with satd NH₄Cl solution (20 mL) and extracted with EtOAc (2×100 mL). The combined organic extracts were washed with water (50 mL) and brine (50 mL), dried over anhydrous Na₂SO₄ and concentrated under reduced pressure to obtain the crude material. Purification by silica gel column chromatography (eluting with 40% EtOAc/hexanes) afforded 58 (0.16 g, 0.38 mmol, 13.3%) as a light yellow solid. ¹H NMR (500 MHz, CDCl₃): δ 9.10 (s, 1H), 8.80 (s, 2H), 8.55 (s, 1H), 8.06 (dd, J=8.5, 1.5 Hz, 1H), 7.74 (d, J=8.5 Hz, 1H), 7.71-7.67 (m, 1H), 7.00 (br s, OH), 6.88-6.86 (m, 1H), 6.74-6.70 (m, 1H). MS (ESI): m/z 429 [M+H]⁺. HPLC: 98%.

Example 36

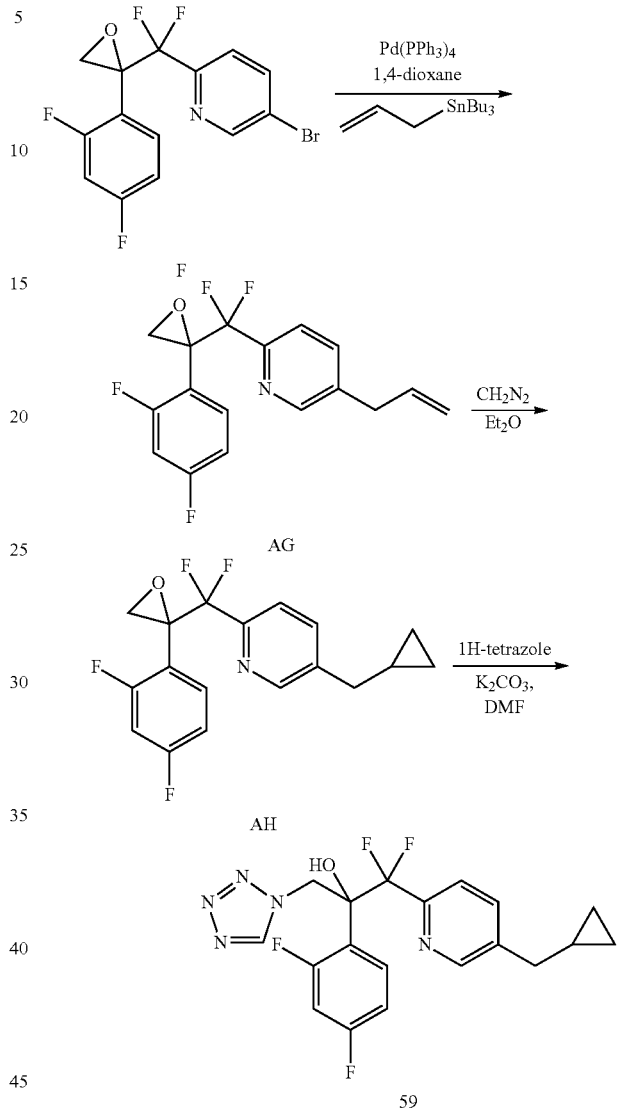

5-(Cyclopropylmethyl)pyridin-2-yl)-2-(2,4-difluorophenyl)-1,1-difluoro-3-(1H-tetrazol-1-yl)propan-2-ol (59)

A mixture of compound F (100 mg, 0.27 mmol), allyltributyltin (0.1 mL, 0.33 mmol), and Pd(PPh₃)₄ (32 mg, 0.027 mmol) in toluene (5 mL) was degassed with argon for 20 min. This mixture was heated to 90° C. and stirred for 12 h. After complete consumption of the starting material (by TLC), the reaction mixture was cooled to RT, filtered through a pad of Celite®, and the filtrate was concentrated under reduced pressure to obtain the crude material. Purification by silica gel column chromatography (eluting with 7% EtOAc/hexanes) afforded compound AG (30 mg, crude) as a colorless liquid. This material contains tin impurities and was used directly in the next step without further purification. ¹H NMR (500 MHz, CDCl₃): δ 8.49 (s, 1H), 7.55 (d, J=9.0 Hz, 1H), 7.41-7.36 (m, 2H), 6.84-6.80 (m, 1H), 6.75-6.71 (m, 1H), 5.94-5.91 (m, 1H), 5.16 (d, J=9.0 Hz, 1H), 5.08 (d, J=18.0 Hz, 1H), 3.43 (t, J=5.0 Hz, 3H), 2.96 (t, J=5.0 Hz, 1H).

To a stirred solution of compound AG (200 mg, crude) in Et$_2$O (5 mL) was added freshly prepared diazomethane [prepared by dissolving NMU (320 mg, 3.09 mmol) in a 1:1 mixture of 10% KOH solution (40 mL) and Et$_2$O (40 mL) at 0° C. followed by separation and drying of the organic layer using KOH pellets] at 0° C., and the mixture was stirred for 2 h. After complete consumption of the starting material (by TLC), the reaction mixture was filtered through a pad of Celite®, and the filtrate was concentrated under reduced pressure to obtain the crude AH (200 mg). The crude material was used in the next step without any further purification.

To a stirred solution of compound AH (200 mg, crude) in DMF (5 mL) was added K$_2$CO$_3$ (84 mg, 0.60 mmol) followed by 1H-tetrazole (64 mg, 0.90 mmol) at RT under an inert atmosphere. The resulting reaction mixture was gradually heated up to 65° C. and stirred for 18 h. After consumption of the starting material (by TLC), the reaction mixture was cooled to RT, diluted with water (50 mL) and extracted with EtOAc (2×50 mL). The combined organic extracts were washed with brine (50 mL), dried over anhydrous Na$_2$SO$_4$ and concentrated under reduced pressure to obtain the crude mixture. Purification by silica gel column chromatography (eluting with 40% EtOAc/hexanes) afforded 59 (65 mg, 0.16 mmol) as a colorless semi-solid. $^1$H NMR (500 MHz, CDCl$_3$): δ 8.74 (s, 1H), 8.42 (s, 1H), 7.93 (s, 1H), 7.72 (d, J=7.5 Hz, 1H), 7.52 (d, J=7.5 Hz, 1H), 7.39-7.34 (m, 1H), 6.78-6.73 (m, 1H), 6.68-6.64 (m, 1H), 5.58 (d, J=14.0 Hz, 1H), 5.07 (d, J=14.0 Hz, 1H), 2.58 (d, J=7.0 Hz, 2H), 0.95-0.92 (m, 1H), 0.61 (d, J=7.0 Hz, 2H), 0.22 (d, J=4.5 Hz, 2H). MS (ESI): m/z 408 [M+H]$^+$. HPLC: 94%.

Compounds 60 and 61 in Table 1 were prepared using the same conditions as compound 59. (See Table 1 for starting materials.)

Example 37

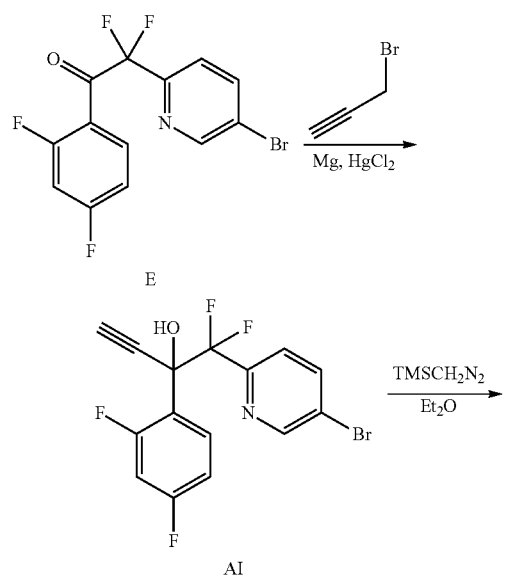

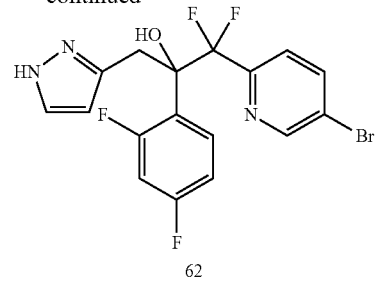

1-(5-Bromopyridin-2-yl)-2-(2,4-difluorophenyl)-1,1-difluoro-3-(1H-pyrazol-3-yl)propan-2-ol (62)

To a mixture of magnesium metal (Mg; 1.84 g, 75.7 mmol) and mercury(II) chloride (HgCl$_2$; 1.71 g, 6.29 mmol) in dry THF (15 mL) was added propargyl bromide (1.0 mL, 11.2 mmol) at RT, and the mixture was stirred for 30 min. The reaction mixture was cooled to −20° C., compound E (4.4 g, 12.6 mmol) and the remaining portion of propargyl bromide (1.3 mL, 14.5 mmol) in THF (10 mL) were added, and stirring was continued for 45 min at −20° C.

The progress of the reaction was monitored by TLC. The reaction was quenched with satd NH$_4$Cl solution and the mixture was extracted with EtOAc (2×150 mL). The combined organic extracts were washed with water (50 mL) and brine (50 mL), dried over anhydrous Na$_2$SO$_4$ and concentrated under reduced pressure to obtain the crude material. Purification by silica gel column chromatography (eluting with 45% EtOAc/hexanes) afforded compound AI (1.1 g, 2.83 mmol, 22%) as a brown solid. $^1$H NMR (200 MHz, CDCl$_3$): δ 8.68 (d, J=2.5 Hz, 1H), 7.94 (dd, J=8.5, 2.5 Hz, 1H), 7.65-7.53 (m, 1H), 7.43 (d, J=8.5 Hz, 1H), 6.88-6.73 (m, 2H), 5.60-5.42 (br s, OH), 3.46 (dd, J=16.8, 2.4 Hz, 1H), 2.96 (dt, J=16.8, 2.4 Hz, 1H), 1.85 (t, J=2.4 Hz, 1H). MS (ESI): m/z 388 [M$^+$].

A solution of compound AI (0.55 g, 1.41 mmol) in (trimethylsilyl)diazomethane (TMSCHN$_2$, 2 M in hexanes; 3.5 mL, 7.08 mmol) was heated to 120° C. and stirred for 20 h. Progress of the reaction was monitored by TLC. The volatiles were evaporated under reduced pressure to obtain the crude material. Purification by silica gel column chromatography (eluting with 20% EtOAc/hexanes) afforded 62 (0.23 g, 0.52 mmol, 41%). $^1$H NMR (500 MHz, CDCl$_3$): δ 8.64 (d, J=2.5 Hz, 1H), 8.01 (br s, 2H), 7.85 (dd, J=8.5, 2.5 Hz, 1H) 7.39-7.32 (m, 3H), 6.72-6.62 (m, 2H), 6.02 (br s, OH), 4.02 (d, J=14.5 Hz, 1H), 3.44 (dd, J=14.5, 7.0 Hz, 1H). MS (ESI): m/z 430 [M$^+$].

Chiral Preparative HPLC Separation of Enantiomers of 62

The enantiomers of 62 (60 mg, 0.16 mmol) were separated by normal-phase preparative HPLC using a CHIRALPAK® AD-H column (250×20 mm, 5 μm) with mobile phase (A) 0.1% TFA in n-hexane-(B) EtOH (A:B=80:20) and flow rate 15 mL/min to obtain 62-(−) (22 mg, 0.05 mmol) as an off-white solid.

Analytical Data:

Chiral HPLC: 98.5% ee, R$_t$=10.90 min (CHIRALPAK® IA column, 250×4.6 mm, 5μ; mobile phase (A) n-hexane-(B) EtOH (A:B=80:20); flow rate: 1.00 mL/min). Optical rotation [α]$_D^{25}$: −2.2° (c=0.1 in CH$_3$OH).

Example 38

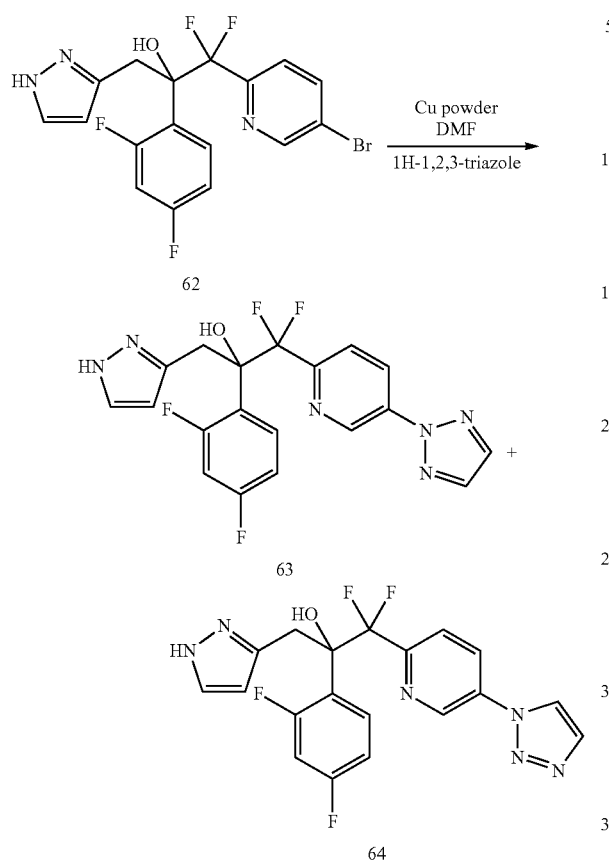

1-(5-(2H-1,2,3-Triazol-2-yl)pyridin-2-yl)-2-(2,4-difluorophenyl)-1,1-difluoro-3-(1H-pyrazol-3-yl)propan-2-ol (63) and 1-(5-(1H-1,2,3-triazol-1-yl)pyridin-2-yl)-2-(2,4-difluorophenyl)-1,1-difluoro-3-(1H-pyrazol-3-yl)propan-2-ol (64)

To a stirred solution of 1H-1,2,3-triazole (89.1 mg, 1.29 mmol) in dry DMF (5 mL) were added copper powder (19.1 mg, 0.3 mmol), $K_2CO_3$ (34.6 mg, 0.25 mmol) and 1-(5-bromopyridin-2-yl)-2-(2,4-difluorophenyl)-1,1-difluoro-3-(1H-pyrazol-3-yl)propan-2-ol (62; 65 mg, 0.15 mmol) at RT under $N_2$ atmosphere. The reaction mixture was gradually heated to 140° C. and stirred for 16 h. After consumption of the starting material (by TLC), the reaction mixture was cooled to RT, diluted with water (50 mL) and extracted with EtOAc (2×50 mL). The combined organic extracts were washed with water (50 mL) and brine (50 mL), dried over anhydrous $Na_2SO_4$ and evaporated under reduced pressure to obtain the crude material. Purification by silica gel column chromatography afforded 63 (60 mg, 0.14 mmol, 45%) (eluent: 25% EtOAc/hexanes) and 64 (55 mg, 0.13 mmol, 42%) (eluent: 45% EtOAc/hexanes) as off-white solids. Compound 63: $^1$H NMR (500 MHz, $CDCl_3$): δ 9.35 (s, 1H), 8.42 (dd, J=8.5, 2.5 Hz, 1H), 7.88 (s, 2H), 7.65 (d, J=8.5 Hz, 1H), 7.45-7.39 (m, 1H), 7.30 (s, 1H), 6.69-6.62 (m, 2H), 6.20 (br s, OH), 6.05 (s, 1H), 4.02 (d, J=16.0 Hz, 1H), 3.38 (d, J=16.0 Hz, 1H). MS (ESI): m/z 419 [M+H]$^+$. HPLC: 92%. Compound 64: $^1$H NMR (500 MHz, $CDCl_3$): δ 9.02 (s, 1H), 8.21 (d, J=8.5 Hz, 1H), 8.14 (s, 1H), 7.92 (s, 1H), 7.73 (d, J=8.5 Hz, 1H), 7.41-7.38 (m, 1H), 7.33 (s, 1H), 6.74-6.63 (m, 2H), 6.10 (s, 1H), 5.95 (br s, OH), 4.07 (d, J=16.0 Hz, 1H), 3.41 (d, J=16.0 Hz, 1H). MS (ESI): m/z 419 [M+H]$^+$. HPLC: 86%.

Example 39

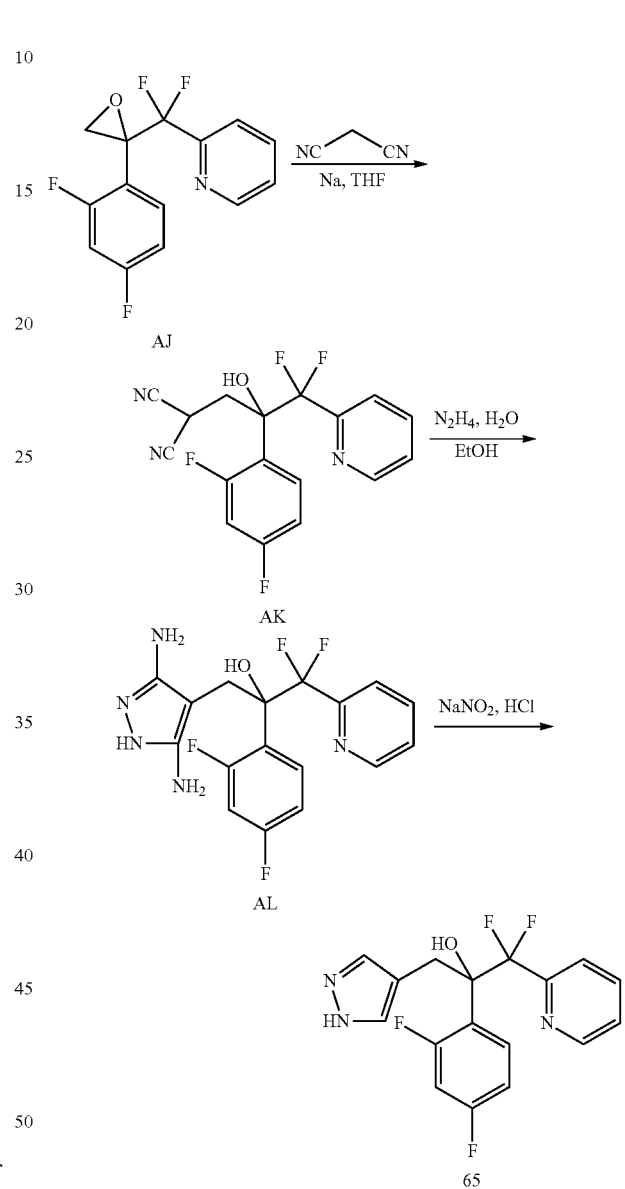

2-(2,4-Difluorophenyl)-1,1-difluoro-3-(1H-pyrazol-4-yl)-1-(pyridin-2-yl)propan-2-ol (65)

To a stirred solution of malononitrile (0.05 mL, 0.88 mmol) in THF (2 mL) was added portionwise NaH (20.7 mg, 0.86 mmol) at 0° C. under an inert atmosphere. After being stirred for 30 min at 0° C., a solution of compound AJ (50 mg, 0.17 mmol) in THF (2 mL) was added to the reaction mixture at 0° C., and stirring was continued for 16 h at RT. The progress of the reaction was monitored by TLC. The reaction was quenched with ice-cold water (20 mL) and extracted with EtOAc (2×20 mL). The combined organic layers were washed with water (20 mL) and brine (20 mL), dried over anhydrous Na₂SO₄ and concentrated under reduced pressure to obtain the crude material. Purification by silica gel column chromatography (eluting with 45% EtOAc/hexanes) afforded compound AK (40 mg, 0.11 mmol, 65%) as a colorless liquid. ¹H NMR (500 MHz, CDCl₃): δ 8.67 (d, J=4.5 Hz, 1H), 7.77 (t, J=7.5 Hz, 1H), 7.47 (d, J=7.5 Hz, 1H), 7.43-7.40 (m, 2H), 6.90-6.81 (m, 2H), 4.60 (s, 2H), 3.90 (d, J=13.5 Hz, 1H), 3.29 (d, J=13.5 Hz, 1H). MS (ESI): m/z 350 [M+H]⁺.

To a stirred solution of compound AK (0.9 g, 2.5 mmol) in EtOH (20 mL) was added hydrazine hydrate (0.18 mL, 3.8 mmol), and the reaction mixture was heated to reflux temperature for 16 h. The progress of the reaction was monitored by TLC. The volatiles were evaporated under reduced pressure to afford compound AL (0.58 g, crude) as a white solid. ¹H NMR (500 MHz, DMSO-d₆): δ 8.51 (d, J=4.0 Hz, 1H), 7.88-7.84 (m, 1H), 7.47-7.37 (m, 3H), 7.30 (br s, NH), 7.01-6.96 (m, 1H), 6.86-6.82 (m, 1H), 6.46 (s, 1H), 4.20 (br s, 4H), 3.43 (d, J=14.5 Hz, 1H), 2.84 (d, J=14.5 Hz, 1H). MS (ESI): m/z 382 [M+H]⁺.

To a stirred solution of compound AL (50 mg, crude) in AcOH (0.3 mL) was added concentrated HCl (0.3 mL) followed by dropwise addition of sodium nitrite (NaNO₂; 54 mg, 0.78 mmol) in water (1.5 mL) at 0° C. After being stirred for 30 min at 0° C., EtOH (5 mL) was added and the reaction mixture was stirred at reflux for 16 h. The volatiles were evaporated under reduced pressure; the residue was diluted with water (20 mL) and extracted with CH₂Cl₂ (2×20 mL). The combined organic extracts were washed with brine (20 mL), dried over anhydrous Na₂SO₄ and concentrated under reduced pressure to obtain the crude material. Purification by preparative TLC (eluent: 40% EtOAc:hexane) afforded 65 (7.0 mg, 0.019 mmol) as a pale yellow solid. ¹H NMR (500 MHz, CDCl₃): δ 8.61 (d, J=5.0 Hz, 1H), 7.82-7.78 (m, 1H), 7.58 (d, J=7.5 Hz, 1H), 7.48-7.39 (m, 3H), 7.34 (s, 2H), 6.70-6.63 (m, 3H), 3.74 (d, J=14.5 Hz, 1H), 3.08 (d, J=14.5 Hz, 1H). MS (ESI): m/z 352 [M+H]⁺. HPLC: 86%.

Example 40

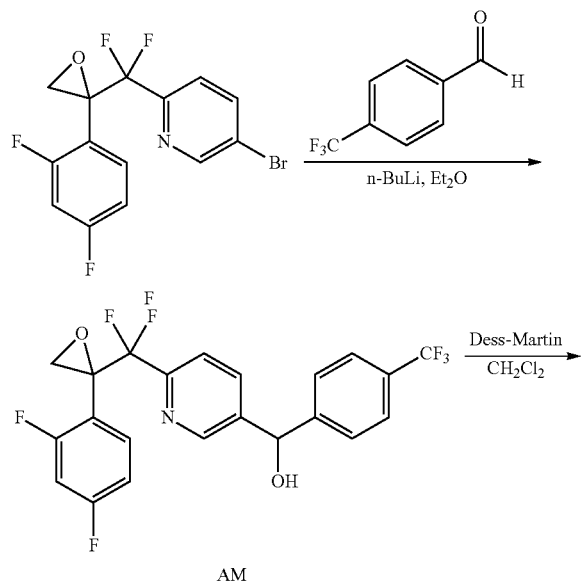

AM

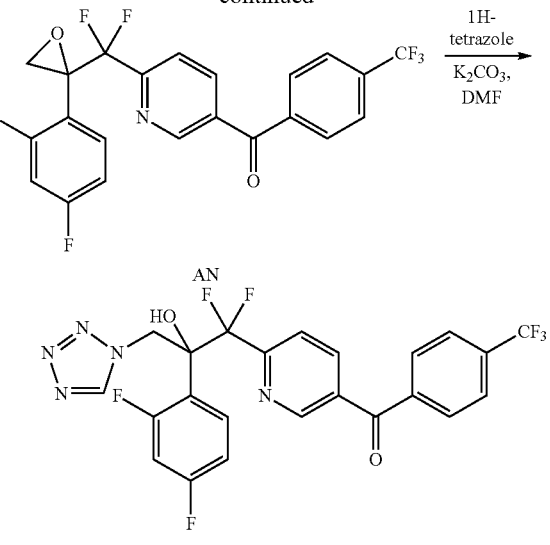

66

(6-(2-(2,4-Difluorophenyl)-1,1-difluoro-2-hydroxy-3-(1H-tetrazol-1-yl)propyl)pyridin-3-yl)(4-(trifluoromethyl)phenyl)methanone (66)

To a stirred solution of n-BuLi (1.6 M in hexane; 0.86 mL, 1.38 mmol) in Et₂O (10 mL) was added a solution of compound F (500 mg, 1.38 mmol) in Et₂O (10 mL) at −78° C. After being stirred for 1 h, 4-(trifluoromethyl)benzaldehyde (240 mg, 1.38 mmol) was added to the reaction mixture at −78° C. and the stirring was continued for 1 h. The reaction mixture was allowed to warm to RT and stirred for another 1 h progress of the reaction was monitored by TLC. The reaction mixture was quenched with satd NH₄Cl solution (30 mL) and extracted with EtOAc (2×30 mL). The combined organic extracts were washed with water (50 mL) and brine (50 mL), dried over anhydrous Na₂SO₄ and concentrated under reduced pressure to obtain the crude material. Purification by silica gel column chromatography (eluting with 25% EtOAc/hexanes) afforded compound AM (400 mg, 0.87 mmol, 63.4%) as a semi-solid. ¹H NMR (500 MHz, CDCl₃): δ 8.67 (s, 1H), 7.74 (dd, J=8.0, 2.5 Hz, 1H), 7.64 (d, J=8.5 Hz, 2H), 7.50-7.45 (m, 3H), 7.40-7.35 (m, 1H), 6.84-6.80 (m, 1H), 6.74-6.70 (m, 1H), 5.98 (s, 1H), 3.41 (d, J=3.0 Hz, 1H), 2.95 (d, J=3.0 Hz, 1H), 2.55 (s, 1H).

To a stirred solution of compound AM (100 mg, 0.22 mmol) in CH₂Cl₂ (10 mL) was added Dess-Martin periodinane (DMP; 139 mg, 0.32 mmol) at 0° C., and the reaction mixture was stirred at RT for 16 h; progress of the reaction was monitored by TLC. The reaction mixture was quenched with satd sodium thiosulfate (Na₂S₂O₃) solution (10 mL): NaHCO₃ solution (10 mL) and extracted with CH₂Cl₂ (2×20 mL). The combined organic extracts were washed with water (20 mL) and brine (20 mL), dried over anhydrous Na₂SO₄ and concentrated under reduced pressure to obtain the crude material. Purification by silica gel column chromatography (eluting with 10% EtOAc/hexanes) afforded ketone AN (70 mg, 0.15 mmol, 70%) as an off-white solid. ¹H NMR (500 MHz, CDCl₃): δ 8.57 (s, 1H), 8.20 (d, J=8.0 Hz, 2H), 7.74 (d, J=8.0 Hz, 2H), 7.50 (d, J=8.0 Hz, 1H), 7.42-7.39 (m, 1H), 7.34 (d, J=8.0 Hz, 1H), 6.88-6.82 (m, 1H), 6.74-6.68 (m, 1H), 3.43 (d, J=3.0 Hz, 1H), 2.98 (d, J=3.0 Hz, 1H). MS (ESI): m/z 456 [M+H]⁺.

To a stirred solution of ketone AN (150 mg, 0.32 mmol) in dry DMF (5 mL) was added 1H-tetrazole (35 mg, 0.48 mmol) followed by K₂CO₃ (45 mg, 0.32 mmol) at RT under inert atmosphere. The resulting reaction mixture was gradually heated up to 65° C. and stirred for 16 h; progress of the reaction was monitored by TLC. The reaction mixture was cooled to RT, diluted with ice-cold water (30 mL) and extracted with EtOAc (3×20 mL). The combined organic extracts were washed with brine (20 mL), dried over anhydrous Na₂SO₄ and concentrated under reduced pressure to obtain the crude material. Purification by silica gel column chromatography (eluting with 20% EtOAc/hexanes) afforded 66 (30 mg, 0.057 mmol, 17%) as an off-white solid. ¹H NMR (500 MHz, CDCl₃): δ 8.82 (s, 1H), 8.76 (s, 1H), 8.21 (dd, J=8.5, 1.5 Hz, 1H), 7.91 (d, J=8.5 Hz, 2H), 7.84-7.77 (m, 3H), 7.47-7.42 (m, 1H), 7.08 (s, 1H), 6.83-6.78 (m, 1H), 6.76-6.73 (m, 1H), 5.46 (d, J=14.0 Hz, 1H), 5.30 (d, J=14.0 Hz, 1H). MS (ESI): m/z 526 [M+H]⁺. HPLC: 98.2%.

Compounds 67-71 in Table 1 were prepared using the same conditions as compound 66. (See Table 1 for starting materials.)

Example 41

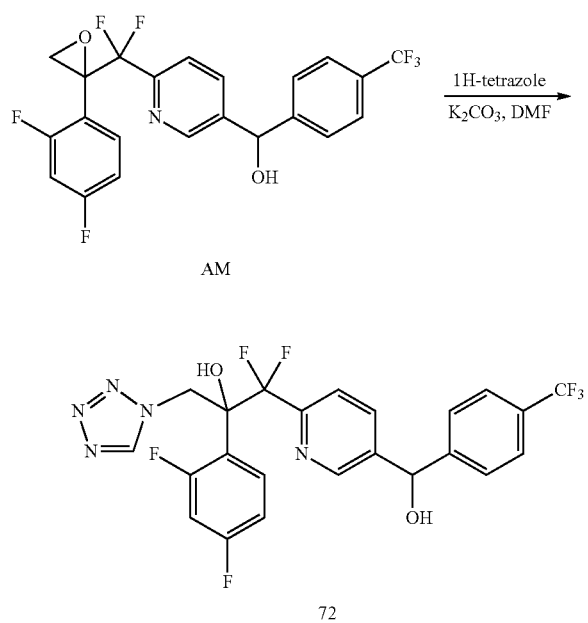

2-(2,4-Difluorophenyl)-1,1-difluoro-1-(5-(hydroxy(4-(trifluoromethyl)phenyl)methyl)pyridin-2-yl)-3-(1H-tetrazol-1-yl)propan-2-ol (72)

To a stirred solution of (6-((2-(2,4-difluorophenyl)oxiran-2-yl)difluoromethyl)pyridin-3-yl)(4-(trifluoromethyl)phenyl)methanol (AM; 600 mg, 0.32 mmol) in dry DMF (10 mL) was added 1H-tetrazole (138 mg, 1.97 mmol) followed by K₂CO₃ (181 mg, 1.31 mmol) at RT under inert atmosphere. The resulting reaction mixture was gradually heated up to 65° C. and stirred for 16 h; progress of the reaction was monitored by TLC. The reaction mixture was cooled to RT, diluted with ice-cold water (50 mL) and extracted with EtOAc (3×50 mL). The combined organic extracts were washed with water (50 mL) and brine (50 mL), dried over anhydrous Na₂SO₄ and concentrated under reduced pressure to obtain the crude material. Purification by silica gel column chromatography (eluting with 35-40% EtOAc/hexanes) afforded 72 (diastereomeric mixture; 300 mg, 0.57 mmol, 43%) as an off-white solid. ¹H NMR (500 MHz, CDCl₃; mixture of diastereomers): δ 8.73 (s, 2H), 8.54 (s, 1H), 8.48 (s, 1H), 7.83 (d, J=8.0 Hz, 1H), 7.79 (d, J=8.0 Hz, 1H), 7.64 (d, J=8.0 Hz, 4H), 7.62-7.58 (m, 4H), 7.50-7.44 (m, 4H), 7.42-7.39 (m, 2H), 6.81-6.74 (m, 2H), 6.72-6.64 (m, 2H), 5.99-5.93 (m, 2H), 5.48-5.40 (m, 2H), 5.20-5.12 (m, 2H), 2.78 (s, 1H), 2.70 (s, 1H). MS (ESI): m/z 528 [M+H]⁺.

Example 42

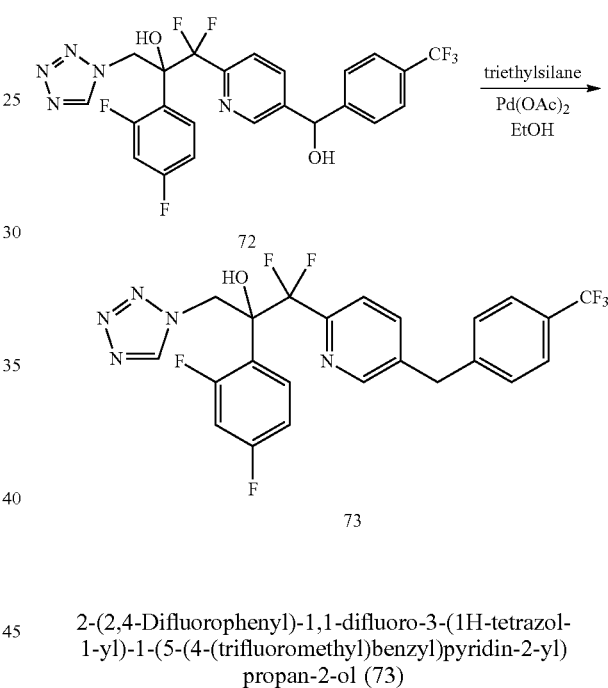

2-(2,4-Difluorophenyl)-1,1-difluoro-3-(1H-tetrazol-1-yl)-1-(5-(4-(trifluoromethyl)benzyl)pyridin-2-yl)propan-2-ol (73)

To a stirred solution of 2-(2,4-difluorophenyl)-1,1-difluoro-1-(5-(hydroxy(4-(trifluoromethyl)phenyl)methyl)pyridin-2-yl)-3-(1H-tetrazol-1-yl)propan-2-ol (72; 100 mg, 0.19 mmol) in EtOH (5 mL) was added triethylsilane (~0.18 mL, 1.13 mmol) and Pd(OAc)₂ (20 mg, 0.02 mmol) at RT under inert atmosphere. The reaction mixture was stirred under reflux conditions for 7-8 h; progress of the reaction was monitored by TLC. The reaction mixture was allowed to cool to RT, filtered through a pad of Celite®, and the Celite® cake was washed with EtOH (3×25 mL). The filtrate was concentrated under reduced pressure to obtain the crude material. Purification by silica gel column chromatography (eluting with 40% EtOAc/hexanes) afforded 73 (30 mg, 0.058 mmol, 31%) as an off-white solid. ¹H NMR (500 MHz, CDCl₃): δ 8.73 (s, 1H), 8.35 (s, 1H), 7.63-7.52 (m, 5H), 7.40-7.35 (m, 1H), 7.25-7.23 (m, 1H), 6.78-6.74 (m, 1H), 6.69-6.66 (m, 1H), 5.50 (d, J=14.5 Hz, 1H), 5.14 (d, J=14.5 Hz, 1H), 4.08 (s, 2H). MS (ESI): m/z 512 [M+H]⁺. HPLC: 91.7%.

Example 43

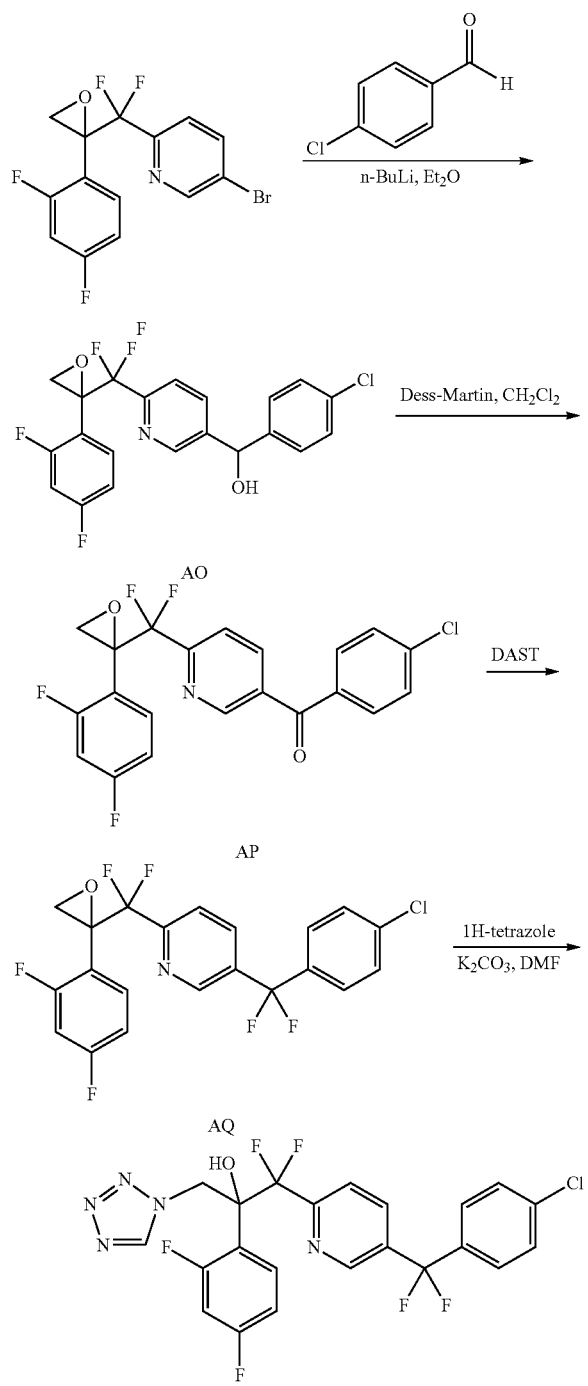

1-(5-((4-Chlorophenyl)difluoromethyl)pyridin-2-yl)-2-(2,4-difluorophenyl)-1,1-difluoro-3-(1H-tetrazol-1-yl)propan-2-ol (74)

To a stirred solution of n-BuLi (1.6 M in hexane; 1.70 mL, 2.76 mmol) in Et$_2$O (30 mL) was added a solution of compound F (1.0 g, 2.76 mmol) in Et$_2$O (30 mL) at −78° C. After being stirred for 1 h, 4-chlorobenzaldehyde (0.38 g, 2.76 mmol) was added to the reaction mixture at −78° C., and the stirring was continued for 1 h. The reaction mixture was allowed to warm to RT and stirred for another 1 h; progress of the reaction was monitored by TLC. The reaction mixture was quenched with satd NH$_4$Cl solution (100 mL) and the aqueous layer was extracted with EtOAc (2×100 mL). The combined organic extracts were washed with water (100 mL) and brine (100 mL), dried over anhydrous Na$_2$SO$_4$ and concentrated under reduced pressure to obtain the crude material. Purification by silica gel column chromatography (eluting with 25% EtOAc/hexanes) afforded compound AO (0.7 g, 0.94 mmol, 60.34%) as a semi-solid. $^1$H NMR (200 MHz, CDCl$_3$): δ 8.65 (s, 1H), 7.78-7.71 (m, 1H), 7.47-7.28 (m, 6H), 6.86-6.67 (m, 2H), 5.91 (d, J=3.0 Hz, 1H), 3.42 (d, J=5.2 Hz, 1H), 2.96 (d, J=5.2 Hz, 1H), 2.36 (d, J=3.0 Hz, 1H). MS (ESI): m/z 424 [M+H]$^+$.

To a stirred solution of compound AO (400 mg, 0.94 mmol) in CH$_2$Cl$_2$ (10 mL) was added Dess-Martin periodinane (601 mg, 1.41 mmol) at 0° C. under inert atmosphere. The reaction mixture was stirred at RT for 16 h; progress of the reaction was monitored by TLC. The reaction mixture was quenched with satd Na$_2$S$_2$O$_3$ solution (50 mL):NaHCO$_3$ solution (50 mL). The aqueous layer was extracted with CH$_2$C$_2$ (2×50 mL). The combined organic extracts were washed with water (50 mL), dried over anhydrous Na$_2$SO$_4$ and concentrated under reduced pressure to obtain the crude material. Purification by silica gel column chromatography (eluting with 10% EtOAc/hexanes) afforded ketone AP (300 mg, 0.71 mmol, 75%) as an off-white solid. $^1$H NMR (500 MHz, CDCl$_3$): δ 8.99 (s, 1H), 8.13 (dd, J=8.0, 1.5 Hz, 1H), 7.76 (d, J=9.0 Hz, 2H), 7.64 (d, J=8.0 Hz, 1H), 7.51 (d, J=9.0 Hz, 2H), 7.44-7.39 (m, 1H), 6.87-6.84 (m, 1H), 6.77-6.73 (m, 1H), 3.50 (d, J=4.5 Hz, 1H), 3.00 (d, J=4.5 Hz, 1H).

DAST (excess) was added to ketone AP (100 mg, 0.23 mmol) at 0° C., and the mixture was stirred at RT for 16 h. Progress of the reaction was monitored by TLC. The reaction mixture was quenched with ice-cold water (50 mL) and extracted with CH$_2$Cl$_2$ (2×30 mL). The combined organic extracts were washed with water (20 mL) and brine (20 mL), dried over anhydrous Na$_2$SO$_4$ and concentrated under reduced pressure to obtain the crude material. Purification by silica gel column chromatography (eluting with 3-4% EtOAc/hexanes) afforded compound AQ (80 mg, 0.19 mmol, 76%) as a thick syrup. $^1$H NMR (500 MHz, CDCl$_3$): δ 8.78 (s, 1H), 7.86 (d, J=7.5 Hz, 1H), 7.56 (d, J=7.5 Hz, 1H), 7.45-7.37 (m, 5H), 6.86-6.83 (m, 1H), 6.76-6.72 (m, 18), 3.44 (d, J=5.0 Hz, 1H), 2.97 (d, J=5.0 Hz, 1H). MS (ESI): m/z 444 [M+H]$^+$.

To a stirred solution of epoxide AQ (80 mg, 0.18 mmol) in dry DMF (3 mL) was added 1H-tetrazole (13 mg, 0.27 mmol) followed by K$_2$CO$_3$ (25 mg, 0.18 mmol) at RT under inert atmosphere. The resulting reaction mixture was gradually heated up to 65° C. and stirred for 16 h; progress of the reaction was monitored by TLC. The reaction mixture was cooled to RT, diluted with ice-cold water (30 mL) and extracted with EtOAc (3×20 mL). The combined organic extracts were washed with brine (20 mL), dried over anhydrous Na$_2$SO$_4$ and concentrated under reduced pressure. Purification by silica gel column chromatography (eluting with 35% EtOAc/hexanes) afforded 74 (25 mg, 0.051 mmol, 26.8%) as pale yellow solid. $^1$H NMR (500 MHz, CDCl$_3$): δ 8.72 (s, 1H), 8.64 (s, 1H), 7.92 (d, J=8.0 Hz, 1H), 7.66 (d, J=8.0 Hz, 1H), 7.46 (d, J=9.0 Hz, 2H), 7.40 (d, J=9.0 Hz, 2H), 7.37-7.32 (m, 1H), 7.06 (s, 1H), 6.79-6.75 (m, 1H), 6.71-6.67 (m, 1H), 5.53 (d, J=14.0 Hz, 1H), 5.16 (d, J=14.0 Hz, 1H). MS (ESI): m/z 514 [M+H]$^+$. HPLC: 99.2%.

Compounds 101-103 in Table 1 were prepared using the same conditions as compound 74. (See Table 1 for starting materials.)

Example 44

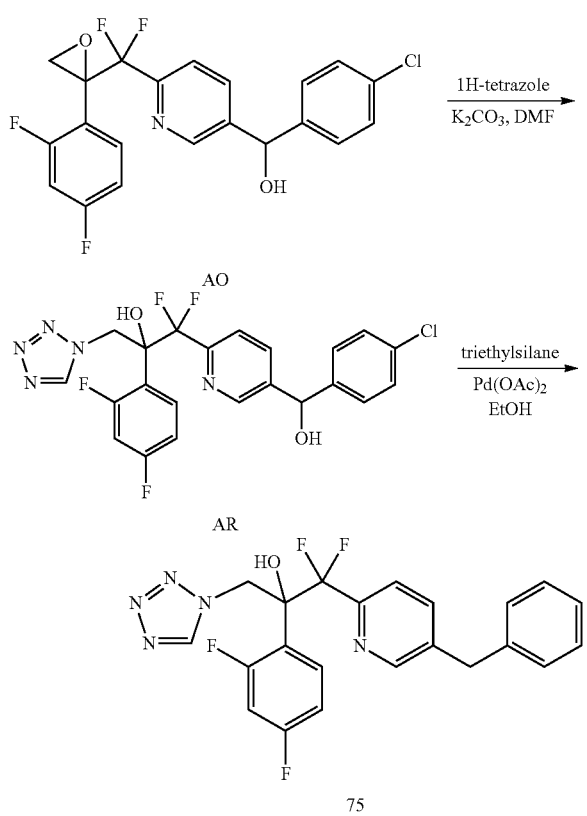

1-(5-Benzylpyridin-2-yl)-2-(2,4-difluorophenyl)-1,1-difluoro-3-(1H-tetrazol-1-yl)propan-2-ol (75)

To a stirred solution of epoxide AO (320 mg, 0.75 mmol) in dry DMF (5 mL) was added 1H-tetrazole (80 mg, 1.14 mmol) followed by $K_2CO_3$ (104 mg, 0.75 mmol) at RT under inert atmosphere. The resulting reaction mixture was gradually heated up to 65° C. and stirred for 16 h; progress of the reaction was monitored by TLC. The reaction mixture was cooled to RT, diluted with ice-cold water (30 mL) and extracted with EtOAc (3×20 mL). The combined organic extracts were washed with brine (30 mL), dried over anhydrous $Na_2SO_4$ and concentrated under reduced pressure to obtain the crude material. Purification by silica gel column chromatography (eluting with 30% EtOAc/hexanes) afforded the diastereomeric mixture of compound AR (140 mg, 0.28 mmol, 37.6%) as a pale yellow solid. MS (ESI): m/z 494 [M+H]$^+$.

To a stirred solution of compound AR (100 mg, 0.2 mmol) in EtOH (5 mL) were added triethylsilane (~0.2 mL, 1.23 mmol) and Pd(OAc)$_2$ (23 mg, 0.1 mmol) at RT under inert atmosphere. The reaction mixture was stirred under reflux conditions for 8 h; progress of the reaction was monitored by TLC. The reaction mixture was allowed to cool to RT, filtered through a pad of Celite®, and the Celite® cake was washed with EtOH (3×15 mL). The filtrate was concentrated under reduced pressure to obtain the crude material. Purification by silica gel column chromatography (eluting with 25% EtOAc/hexanes) afforded 75 (35 mg, 0.08 mmol, 39%) as an off-white solid. $^1$H NMR (500 MHz, CDCl$_3$): δ 9.12 (s, 1H), 8.53 (s, 1H), 7.75 (d, J=8.0 Hz, 1H), 7.39 (d, J=8.0 Hz, 1H), 7.33-7.30 (m, 2H), 7.24-7.21 (m, 5H), 7.19-7.12 (m, 1H), 6.88-6.84 (m, 1H), 5.62 (d, J=14.5 Hz, 1H), 5.06 (d, J=14.5 Hz, 1H), 4.03 (s, 2H). MS (ESI): m/z 444 [M+H]$^+$. HPLC: 97.9%.

Example 45

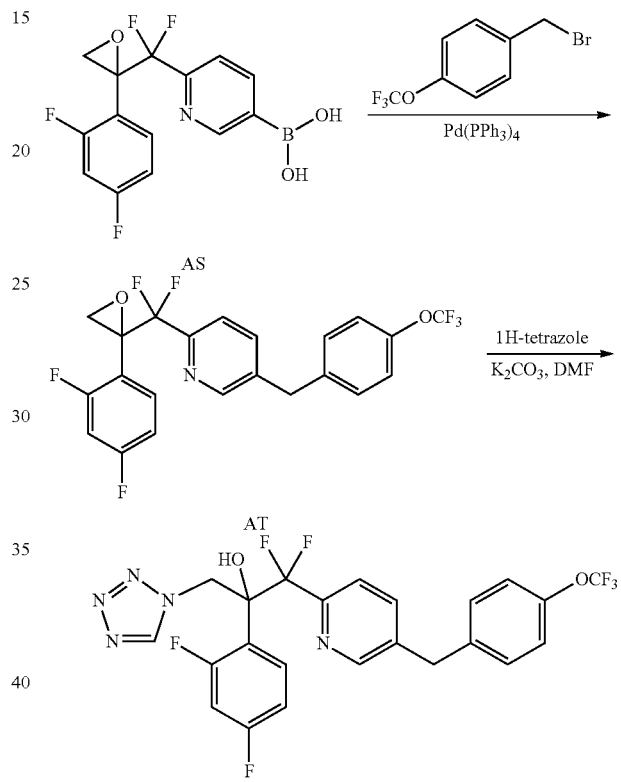

2-(2,4-Difluorophenyl)-1,1-difluoro-3-(1H-tetrazol-1-yl)-1-(4-(trifluoromethoxy)benzyl)pyridin-2-yl) propan-2-ol (76)

To a stirred solution of boronic acid AS (prepared as in the first step of Example 15; 200 mg, 0.60 mmol) in a mixture of toluene-EtOH (4:1, 10 mL) were added 2 N Na$_2$CO$_3$ (2.0 mL, 1.20 mmol) and 1-(bromomethyl)-4-(trifluoromethoxy)benzene (0.09 mL, 0.60 mmol), and the mixture was purged with inert gas for 20 min. Pd(PPh$_3$)$_4$ (34 mg, 0.03 mmol) was added and the reaction mixture was purged for another 20 min. The resultant reaction mixture was gradually heated up to 80° C. and stirred for 16 h; the progress of the reaction was monitored by TLC. The reaction mixture was quenched with ice-cold water (30 mL) and extracted with EtOAc (2×20 mL); the combined organic extracts were washed with water (20 mL) and brine (20 mL), dried over anhydrous Na$_2$SO$_4$ and concentrated under reduced pressure to obtain the crude material. Purification by column chromatography (eluting with 8% EtOAc/hexanes) afforded compound AT (150 mg, 0.32 mmol, 53%) as a thick syrup. $^1$H NMR (200 MHz, CDCl$_3$): δ 8.52 (s, 1H), 7.53-7.38 (m, 3H), 7.23-7.16 (m, 4H), 6.87-6.67 (m, 2H), 4.03 (s, 2H), 3.43 (d, J=4.8 Hz, 1H), 2.96 (d, J=4.8 Hz, 1H).

To a stirred solution of compound AT (150 mg, 0.32 mmol) in DMF (5 mL) was added 1H-tetrazole (34 mg, 0.49 mmol) followed by K$_2$CO$_3$ (44 mg, 0.32 mmol) at RT under inert atmosphere. The resulting reaction mixture was gradually heated up to 65° C. and stirred for 16 h; the progress of the reaction was monitored by TLC. The reaction mixture was cooled to RT, then quenched with ice-cold water (40 mL) and extracted with EtOAc (2×20 mL). The combined organic extracts were washed with water (30 mL) and brine (30 mL), dried over anhydrous Na$_2$SO$_4$ and concentrated under reduced pressure to obtain the crude material. Purification by silica gel column chromatography (eluting with 30-35% EtOAc/hexanes) afforded 76 (25 mg, 0.04 mmol, 14.5%) as an off-white solid. $^1$H NMR (500 MHz, CDCl$_3$): δ 8.73 (s, 1H), 8.35 (s, 1H), 7.67 (s, 1H), 7.58 (d, J=8.0 Hz, 1H), 7.52 (d, J=8.0 Hz, 2H), 7.39-7.34 (m, 1H), 7.19-7.05 (m, 3H), 6.78-6.74 (m, 1H), 6.69-6.65 (m, 1H), 5.52 (d, J=14.0 Hz, 1H), 5.12 (d, J=14.0 Hz, 1H), 4.02 (s, 2H). MS (ESI): m/z 528 [M+H]$^+$. HPLC: 98.0%.

Compound 77 in Table 1 was prepared using the same conditions as compound 76. (See Table 1 for starting material.)

Example 46

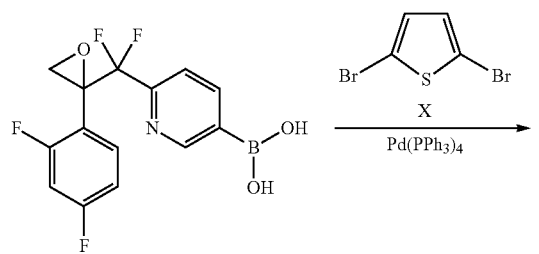

AS

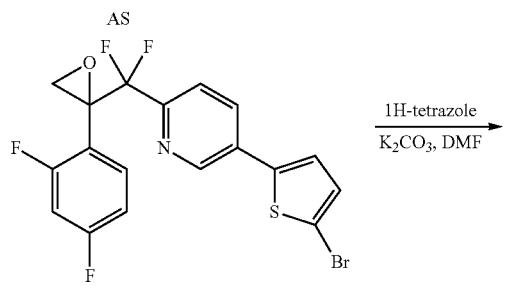

AU

78

1-(5-(5-Bromothiophen-2-yl)pyridin-2-yl)-2-(2,4-difluorophenyl)-1,1-difluoro-3-(1H-tetrazol-1-yl)propan-2-ol (78)

To a stirred solution of AS (prepared as in the first step of Example 15; 500 mg, 2.06 mmol) in THF—H$_2$O (4:1, 20 mL) were added compound X (675 mg, 2.06 mmol) and Na$_2$CO$_3$ (240 mg, 2.20 mmol), and the reaction mixture was purged with inert gas for 20 min. Pd(PPh$_3$)$_4$ (118 mg, 0.10 mmol) was added at RT and the reaction mixture was purged for another 20 min. The resulting reaction mixture was gradually heated up to 65° C. and stirred for 6 h; progress of the reaction was monitored by TLC. The reaction mixture was then filtered through a pad of Celite®, and the Celite® cake was washed with EtOAc (3×20 mL). The filtrate was washed with water (100 mL), dried over anhydrous Na$_2$SO$_4$ and concentrated under reduced pressure to obtain the crude material. Purification by column chromatography (eluting with 5% EtOAc/hexanes) afforded compound AU (220 mg, 0.49 mmol, 24%) as a thick syrup. $^1$H NMR (500 MHz, CDCl$_3$): δ 8.82 (d, J=1.5 Hz, 1H), 7.82 (dd, J=8.0, 1.5 Hz, 1H), 7.48 (d, J=8.0 Hz, 1H), 7.42-7.38 (m, 1H), 7.18 (d, J=4.0 Hz, 1H), 7.11 (d, J=4.0 Hz, 1H), 6.86-6.82 (m, 1H), 6.77-6.73 (m, 1H), 3.47 (d, J=5.0 Hz, 1H), 2.98 (d, J=5.0 Hz, 1H).

To a stirred solution of epoxide AU (220 mg, 0.49 mmol) in dry DMF (5 mL) was added 1H-tetrazole (52 mg, 0.74 mmol) followed by K$_2$CO$_3$ (67 mg, 0.49 mmol) at RT under inert atmosphere. The resulting reaction mixture was gradually heated up to 65° C. and stirred for 16 h; progress of the reaction was monitored by TLC. The reaction mixture was cooled to RT, then quenched with ice-cold water (30 mL) and extracted with EtOAc (2×30 mL). The combined organic extracts were washed with water (30 mL) and brine (30 mL), dried over anhydrous Na$_2$SO$_4$ and concentrated under reduced pressure to obtain the crude material. Purification by silica gel column chromatography (eluting with 30-35% EtOAc/hexanes) afforded 78 (120 mg, 0.23 mmol, 47%) as an off-white solid. $^1$H NMR (500 MHz, CDCl$_3$): δ 8.75 (s, 1H), 8.68 (s, 1H), 7.87 (dd, J=8.0, 2.0 Hz, 1H), 7.58 (d, J=8.0 Hz, 1H), 7.38 (s, 1H), 7.37-7.32 (m, 1H), 7.18 (d, J=4.0 Hz, 1H), 7.12 (d, J=4.0 Hz, 1H), 6.79-6.74 (m, 1H), 6.69-6.65 (m, 1H), 5.59 (d, J=14.5 Hz, 1H), 5.11 (d, J=14.5 Hz, 1H). MS (ESI): m/z 516 [M+2]$^+$. HPLC: 98.6%.

Chiral Preparative HPLC Separation of Enantiomers of 78

The enantiomers of 78 (460 mg) were separated by normal-phase preparative HPLC using a CHIRALPAK® IC column (25×20 mm, 5μ; mobile phase (A) n-hexane-(B) EtOH (A:B=80:20) and flow rate 15 mL/min) to obtain 78-(+) (75 mg) as an off-white solid.

Example 47

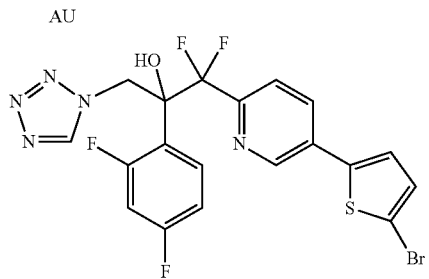

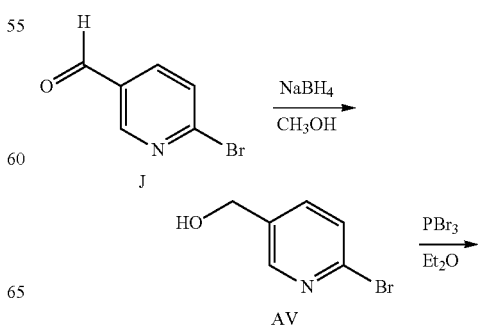

J

AV

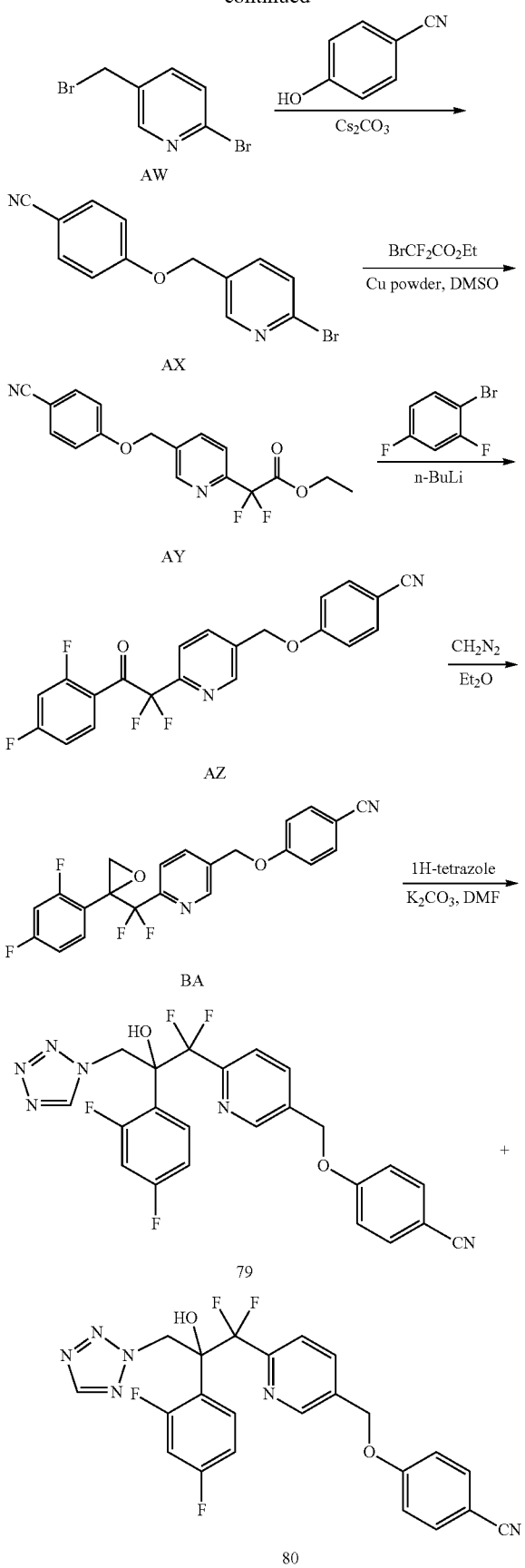

4-((6-(2-(2,4-Difluorophenyl)-1,1-difluoro-2-hydroxy-3-(1H-tetrazol-1-yl)propyl)pyridin-3-yl)methoxy)benzonitrile (79) and 4-((6-(2-(2,4-difluorophenyl)-1,1-difluoro-2-hydroxy-3-(2H-tetrazol-2-yl)propyl)pyridin-3-yl)methoxy)benzonitrile (80)

To a stirred solution of compound J (prepared as in the first step of Example 17; 2.0 g, 10.75 mmol) in $CH_3OH$ (30 mL) was added $NaBH_4$ (0.53 g, 13.97 mmol) portionwise at 0° C. and the reaction mixture was stirred at 0° C. for 1 h. After completion of the reaction (by TLC), $CH_3OH$ was removed under reduced pressure, and the reaction mixture was diluted with ice-cold water (75 mL) and extracted with EtOAc (2×75 mL). The combined organic layers were washed with water (75 mL) and brine (75 mL), dried over anhydrous $Na_2SO_4$ and concentrated under reduced pressure to obtain the crude material. Purification by silica gel column chromatography (eluting with 40% EtOAc/hexanes) afforded compound AV (1.4 g, 7.44 mmol, 69%) as a yellow solid. $^1$H NMR (400 MHz, $CDCl_3$): δ 8.35 (s, 1H), 7.59 (dd, J=8.0, 2.4 Hz, 1H), 7.48 (d, J=8.0 Hz, 1H), 4.71 (d, J=6.0 Hz, 2H), 2.03 (t, J=6.0 Hz, OH). MS (ESI): m/z 188 [M$^+$].

To a stirred solution of compound AV (1.0 g, 5.31 mmol) in $Et_2O$ (20 mL) was added phosphorus tribromide ($PBr_3$; 1.5 mL, 15.95 mmol) at 0° C., and the mixture was stirred for 1 h at RT. After complete consumption of the starting material (by TLC), the reaction mixture was quenched with ice-cold water (30 mL), adjusted to pH-8 using satd $NaHCO_3$ and extracted with EtOAc (2×100 mL). The combined organic extracts were washed with water (100 mL) and brine (100 mL), dried over anhydrous $Na_2SO_4$ and concentrated under reduced pressure to obtain the crude material. Purification by silica gel column chromatography (10% EtOAc/hexanes) afforded compound AW (0.83 g, 3.30 mmol, 62%) as a colorless liquid. $^1$H NMR (400 MHz, $CDCl_3$): δ 8.38 (d, J=2.4 Hz, 1H), 7.59 (dd, J=8.0, 2.4 Hz, 1H), 7.48 (d, J=8.0 Hz, 1H), 4.41 (s, 2H).

To a stirred suspension of 4-hydroxybenzonitrile (0.39 g, 3.30 mmol) and $Cs_2CO_3$ (1.62 g, 4.96 mmol) in DMF (10 mL) was added compound AW (0.83 g, 3.30 mmol) at RT, and the mixture was stirred for 4 h. After completion of the reaction (by TLC), the reaction mixture was quenched with ice-cold water (25 mL) and extracted with EtOAc (4×50 mL). The combined organic extracts were washed with water (50 mL) and brine (50 mL), dried over anhydrous $Na_2SO_4$ and concentrated under reduced pressure to obtain the crude material. Purification by silica gel column chromatography (eluting with 10% EtOAc/hexanes) afforded compound AX (0.90 g, 3.11 mmol, 94%) as a pale yellow solid. $^1$H NMR (500 MHz, $CDCl_3$): δ 8.44 (d, J=2.0 Hz, 1H), 7.64-7.61 (m, 3H), 7.54 (d, J=8.5 Hz, 1H), 7.01 (d, J=8.5 Hz, 2H), 5.08 (s, 2H). MS (ESI): m/z 291 [M+2]$^+$.

To a stirred suspension of copper powder (1.55 g, 6.22 mmol) in DMSO (10 mL) was added ethyl 2-bromo-2,2-difluoroacetate (0.63 g, 3.11 mmol) at RT and the mixture was stirred for 1 h. A solution of compound AX (0.9 g, 3.11 mmol) in DMSO (5 mL) was added to the reaction mixture and stirring was continued for another 16 h at RT. After complete consumption of the starting material (by TLC), the reaction mixture was quenched with satd $NH_4Cl$ solution (100 mL) and extracted with EtOAc (2×100 mL). The combined organic extracts were washed with water (100 mL) and brine (100 mL), dried over anhydrous $Na_2SO_4$ and concentrated under reduced pressure to obtain the crude material. Purification by silica gel column chromatography (eluting with 25% EtOAc/hexane) afforded compound AY (0.5 g, 1.5 mmol, 49%) as a pale yellow solid. $^1$H NMR (500

MHz, CDCl₃): δ 8.71 (s, 1H), 7.94 (d, J=8.0 Hz, 1H), 7.80 (d, J=8.0 Hz, 1H), 7.63 (d, J=9.0 Hz, 2H), 7.03 (d, J=9.0 Hz, 2H), 5.18 (s, 2H), 4.38 (q, J=7.0 Hz, 2H), 1.34 (t, J=7.0 Hz, 3H). MS (ESI): m/z 334 [M+2]⁺.

To a stirred solution of 1-bromo-2,4-difluorobenzene (348 mg, 1.80 mmol) in Et₂O (10 mL) was added n-BuLi (1.6 M in hexane; 0.7 mL, 1.80 mmol) at −78° C., and the mixture was stirred for 30 min under inert atmosphere. A solution of compound AY (500 mg, 1.50 mmol) in Et₂O (30 mL) was added to the reaction mixture at −78° C. and stirring was continued for another 2 h. After completion of the reaction (by TLC), the reaction mixture was quenched with satd NH₄Cl solution (100 mL) and extracted with EtOAc (2×100 mL). The combined organic extracts were washed with water (100 mL) and brine (100 mL), dried over anhydrous Na₂SO₄ and concentrated under reduced pressure to afford the crude AZ (1.5 g) as a brownish liquid. This crude material was used in the next step without any further purification. MS (ESI): m/z 401 [M+H]⁺.

To a stirred solution of crude AZ (650 mg, crude) in Et₂O (100 mL) was added freshly prepared diazomethane [prepared by dissolving NMU (1.67 g, 16.25 mmol) in a 1:1 mixture of 10% KOH solution (100 mL) and Et₂O (100 mL) at 0° C. followed by separation and drying of the organic layer using KOH pellets] at −5° C. and the mixture was stirred for 2 h. The resulting reaction mixture was allowed to warm to RT and stirring was continued for another 16 h; progress of the reaction was monitored by TLC. The reaction mixture was concentrated under reduced pressure to obtain the crude material. Purification by silica gel column chromatography (eluting with 25% EtOAc/hexanes) afforded compound BA (250 mg, 0.60 mmol, 37%) as a yellow liquid. ¹H NMR (400 MHz, CDCl₃): δ 8.73 (s, 1H), 7.84 (d, J=8.0 Hz, 1H), 7.65-7.53 (m, 3H), 7.38-7.36 (m, 1H), 7.03 (d, J=8.0 Hz, 2H), 6.86-6.71 (m, 2H), 5.18 (s, 2H), 3.45 (d, J=5.2 Hz, 1H), 2.98 (t, J=5.2 Hz, 1H). MS (ESI): m/z 415 [M+H]⁺.

To a stirred solution of compound BA (250 mg, 0.60 mmol) in dry DMF (8 mL) was added 1H-tetrazole (62.5 mg, 0.90 mmol) followed by K₂CO₃ (83.3 mg, 0.60 mmol) at RT under inert atmosphere. The reaction mixture was heated to 65° C. and stirred for 16 h. After completion of the reaction (by TLC), the reaction mixture was quenched with ice-cold water and extracted with EtOAc (2×50 mL). The combined organic extracts were washed with water (50 mL) and brine (50 mL), dried over Na₂SO₄ and concentrated under reduced pressure to obtain the crude material. Purification by silica gel column chromatography afforded 80 (40 mg, 0.15 mmol, 13%; eluent: 35% EtOAc/hexanes) as a yellow liquid and 79 (75 mg, 0.28 mmol, 25%; eluent: 60% EtOAc/hexanes) as a thick yellow solid. Compound 79: ¹H NMR (400 MHz, CDCl₃): δ 8.74 (s, 1H), 8.58 (s, 1H), 7.90 (dd, J=8.0, 2.0 Hz, 1H), 7.66-7.62 (m, 3H), 7.45 (br s, OH), 7.40-7.34 (m, 1H), 7.02 (d, J=8.0 Hz, 2H), 6.80-6.65 (m, 2H), 5.52 (d, J=14.0 Hz, 1H), 5.18 (d, J=14.0 Hz, 1H), 5.16 (s, 2H). MS (ESI): m/z 485 [M+H]⁺. HPLC: 97%. Compound 80: ¹H NMR (400 MHz, CDCl₃): δ 8.63 (s, 1H), 8.31 (s, 1H), 7.90 (dd, J=8.4, 1.6 Hz, 1H), 7.66-7.62 (m, 3H), 7.44-7.38 (m, 1H), 7.03 (d, J=8.4 Hz, 2H), 6.83-6.67 (m, 2H), 6.63 (br s, OH), 5.82 (d, J=14.0 Hz, 1H), 5.40 (d, J=14.0 Hz, 1H), 5.16 (s, 2H). MS (ESI): m/z 485 [M+H]⁺. HPLC: 97%.

Example 48

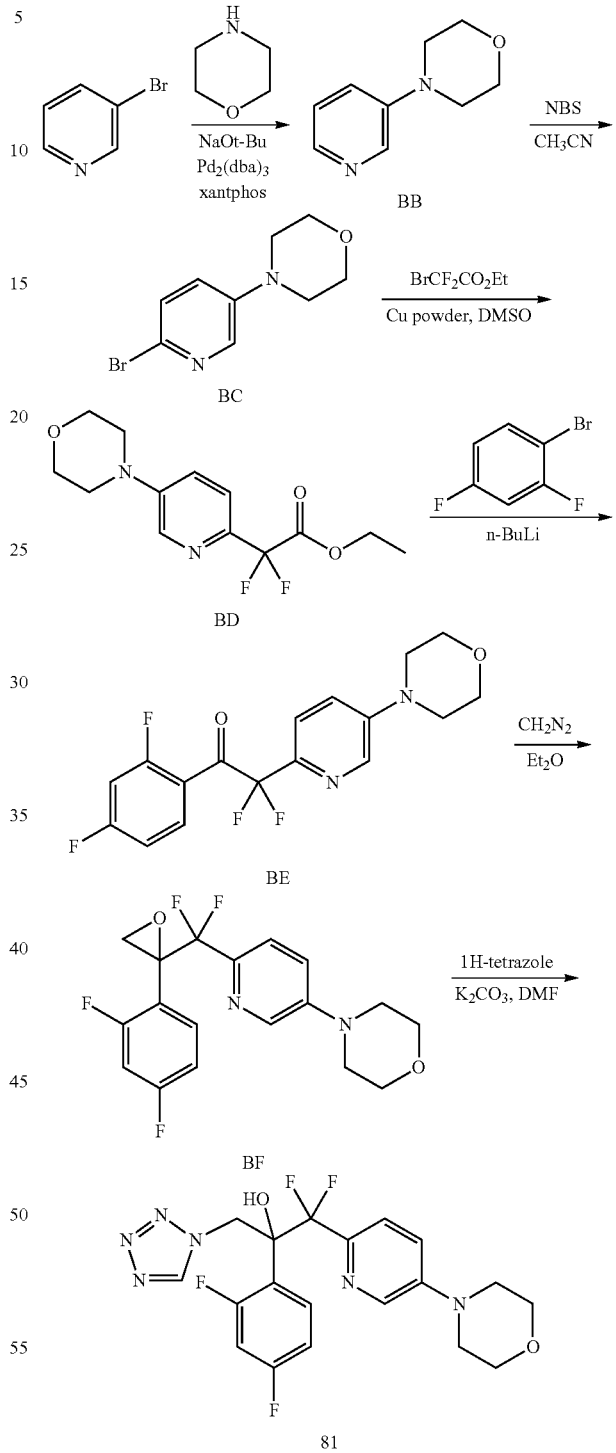

2-(2,4-Difluorophenyl)-1,1-difluoro-1-(5-morpholinopyridin-2-yl)-3-(1H-tetrazol-1-yl)propan-2-ol (81)

To a mixture of morpholine (1.08 g, 12.4 mmol) and 3-bromopyridine (1.5 g, 9.61 mmol) in toluene (50 mL) were added tris(dibenzylideneacetone)dipalladium(0) (Pd₂

(dba)₃; 0.2 g, 0.22 mmol), xantphos (0.18 g, 0.31 mmol), sodium tert-butoxide (NaO$^t$Bu; 1.39 g, 14.4 mmol). The reaction mixture was stirred at RT for 16 h under inert atmosphere. After completion of the reaction (by TLC), the reaction mixture was diluted with water (50 mL) and extracted with EtOAc (2×50 mL). The combined organic extracts were washed with water (50 mL) and brine (50 mL), dried over anhydrous Na₂SO₄ and concentrated under reduced pressure to obtain the crude material. Purification by silica gel column chromatography (eluting with 5% CH₃OH/CH₂Cl₂) afforded compound BB (0.97 g, 5.95 mmol, 62%) as an off-white solid. ¹H NMR (500 MHz, CDCl₃): δ 8.30 (s, 1H), 8.13 (s, 1H), 7.17 (d, J=2.0 Hz, 2H), 3.87 (t, J=5.0 Hz, 4H), 3.19 (t, J=5.0 Hz, 4H). MS (ESI): m/z 165 [M+H]⁺.

To a stirred solution of compound BB (0.98 g, 5.95 mmol) in CH₃CN (60 mL) was added dropwise NBS (1.15 g, 6.5 mmol) in CH₃CN (10 mL) at 0° C., and the mixture was stirred for 30 min. The resultant reaction mixture was allowed to warm to RT and stirring was continued for another 1 h. After complete consumption of the starting material (by TLC); the reaction mixture was diluted with water (20 mL) and extracted with CH₂Cl₂ (2×20 mL). The combined organic extracts were washed with water (20 mL) and brine (20 mL), dried over anhydrous Na₂SO₄ and concentrated under reduced pressure to obtain the crude material. Purification by silica gel column chromatography (eluting with 3% CH₃OH/CH₂Cl₂) afforded compound BC (1.1 g, 4.52 mmol, 74%) as a pale yellow solid. ¹H NMR (500 MHz, CDCl₃): δ 8.01 (s, 1H), 7.32 (d, J=8.5 Hz, 1H), 7.07 (dd, J=8.5, 3.0 Hz, 1H), 3.86 (t, J=5.0 Hz, 4H), 3.15 (t, J=5.0 Hz, 4H). MS (ESI): m/z 244 [M+H]⁺.

To a stirred suspension of copper powder (104 mg, 3.29 mmol) in DMSO (5 mL) was added ethyl 2-bromo-2,2-difluoroacetate (167 mg, 1.64 mmol) at RT, and the mixture was stirred for 1 h. To the resulting reaction mixture compound BC (200 mg, 0.82 mmol) was added and stirring was continued for another 16 h at RT. After completion of reaction (by TLC), the reaction mixture was quenched with satd NH₄Cl solution and extracted with CH₂Cl₂ (2×100 mL). The combined organic extracts were washed with water (100 mL) and brine (100 mL), dried over anhydrous Na₂SO₄ and concentrated under reduced pressure to obtain the crude material. Purification by silica gel column chromatography (eluting with 35% EtOAc/hexanes) afforded crude BD (110 mg) which was used without further purification. ¹H NMR (500 MHz, CDCl₃): δ 8.27 (s, 1H), 7.59 (d, J=8.5 Hz, 1H), 7.22 (dd, J=8.5 Hz, 1H), 4.37 (q, J=7.0 Hz, 2H), 3.88 (t, J=5.0 Hz, 4H), 3.25 (t, J=5.0 Hz, 4H), 1.33 (t, J=7.0 Hz, 3H). MS (ESI): m/z 287 [M+H]⁺.

To a stirred solution of 1-bromo-2,4-difluorobenzene (408 mg, 2.11 mmol) in Et₂O (15 mL) was added n-BuLi (1.6 M in hexane; 1.32 mL, 2.11 mmol) at −78° C., and the mixture was stirred for 1 h under inert atmosphere. A solution of compound BD (550 mg, crude) in Et₂O (5 mL) was added to the reaction mixture at −78° C. and stirring was continued for another 2 h. The progress of the reaction was monitored by TLC. The reaction mixture was quenched with satd NH₄Cl solution and extracted with CH₂Cl₂ (2×100 mL). The combined organic extracts were washed with water (100 mL) and brine (100 mL), dried over anhydrous Na₂SO₄ and concentrated under reduced pressure to afford compound BE (700 mg, crude). The crude material was used in the next step without any further purification. ¹H NMR (500 MHz, CDCl₃): δ 8.19 (s, 1H), 8.03 (d, J=8.5 Hz, 1H), 7.67 (d, J=8.5 Hz, 1H), 7.58-7.56 (m, 1H), 6.97-6.94 (m, 1H), 6.84-6.79 (m, 1H), 3.86 (t, J=5.0 Hz, 4H), 3.25 (t, J=5.0 Hz, 4H). MS (ESI): m/z 355 [M+H]⁺.

To a stirred solution of compound BE (0.7 g, crude) in Et₂O (100 mL) was added freshly prepared diazomethane [prepared by using dissolving NMU (2.0 g, 19.75 mmol) in a 1:1 mixture of 10% KOH solution (100 mL) and Et₂O (100 mL) at 0° C. followed by separation and drying of the organic layer using KOH pellets at 0° C., and the mixture was stirred for 2 h. The resulting reaction mixture was allowed to warm to RT and stirring was continued for another 16 h; progress of the reaction was monitored by TLC. The reaction mixture was concentrated under reduced pressure to obtain the crude material. Purification by silica gel column chromatography (eluting with 30% EtOAc/hexanes) afforded compound BF (0.2 g, 0.54 mmol) as a yellow syrup. ¹H NMR (500 MHz, CDCl₃): δ 8.30 (s, 1H), 7.67-7.57 (m, 1H), 7.41-7.33 (m, 1H), 7.12 (d, J=3.5 Hz, 1H), 6.84-6.81 (m, 1H), 6.76-6.72 (m, 1H), 3.88 (d, J=5.0 Hz, 4H), 3.77 (d, J=5.0 Hz, 1H), 3.25-3.21 (m, 4H), 2.96-2.85 (m, 1H). MS (ESI): m/z 369 [M+H]⁺.

To a stirred solution of compound BF (200 mg, 0.54 mmol) in dry DMF (8 mL) was added 1H-tetrazole (75 mg, 1.08 mmol) followed by K₂CO₃ (75 mg, 0.54 mmol) at RT under inert atmosphere. The resulting reaction mixture was gradually heated up to 65° C. and stirred for 16 h. After consumption of the starting material (by TLC), the reaction mixture was cooled to RT, diluted with water (30 mL) and extracted with EtOAc (2×75 mL). The combined organic extracts were washed with water (50 mL) and brine (50 mL), dried over anhydrous Na₂SO₄ and concentrated under reduced pressure to give the crude material. Purification by silica gel column chromatography (eluting with 45-60% EtOAc/hexanes) afforded 81 (70 mg, 0.16 mmol, 29%). ¹H NMR (500 MHz, CDCl₃): δ 8.73 (s, 1H), 8.11 (s, 1H), 7.93 (br s, OH), 7.44 (d, J=8.0 Hz, 1H), 7.38 (d, J=7.0 Hz, 1H), 7.16 (d, J=8.0 Hz, 1H), 6.78-6.74 (m, 1H), 6.70-6.67 (m, 1H), 5.55 (d, J=14.0 Hz, 1H), 5.06 (d, J=14.0 Hz, 1H), 3.86 (s, 4H), 3.25 (s, 4H). MS (ESI): m/z 440.4 [M+2]⁺. HPLC: 97%.

Compound 82 in Table 1 was prepared using the same conditions as compound 81. (See Table 1 for starting material.)

Example 49

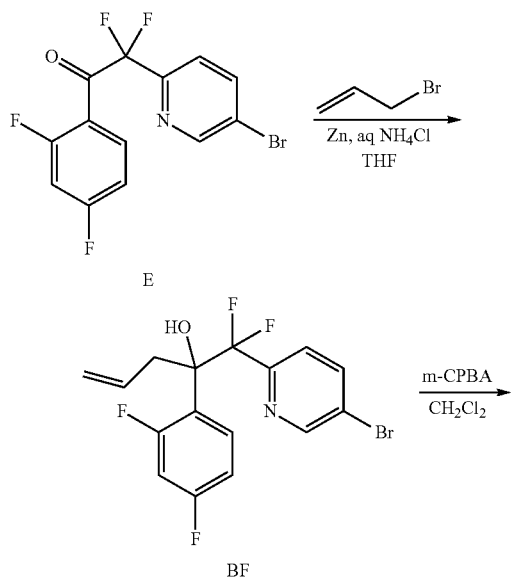

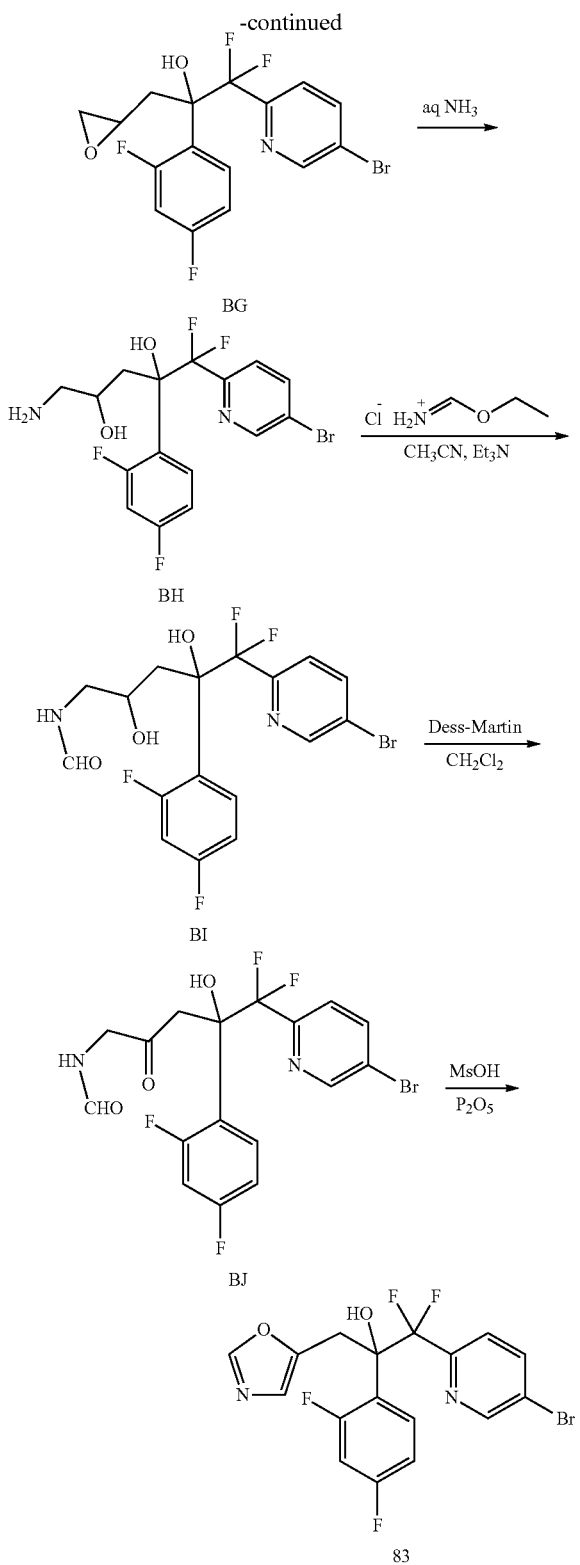

1-(5-Bromopyridin-2-yl)-2-(2,4-difluorophenyl)-1,1-difluoro-3-(oxazol-5-yl)propan-2-ol (83)

To a stirred solution of ketone E (4.8 g, 13.90 mmol) in THF (40 mL) was added zinc dust (Zn; 2.71 g, 41.72 mmol) followed by allyl bromide (3.5 mL, 41.72 mmol) at RT, and the mixture was stirred for 30 min. The reaction mixture was cooled to 0° C., and satd NH$_4$Cl solution (50 mL) was added dropwise over a period of 30 min. The resulting mixture was stirred for 2 h at RT; progress of the reaction was monitored by TLC. The reaction mixture was filtered through a pad of Celite® and the Celite® cake was washed with EtOAc (2×100 mL). The two layers were separated and the aqueous layer was extracted with EtOAc (2×100 mL). The combined organic extracts were washed with water (150 mL) and brine (150 mL), dried over anhydrous Na$_2$SO$_4$ and concentrated under reduced pressure to obtain the crude material. Purification by silica gel column chromatography (eluting with 5-6% EtOAc/hexanes) afforded compound BF (4.5 g, 11.53 mmol, 85%) as a colorless oil. $^1$H NMR (200 MHz, CDCl$_3$): δ 8.65 (d, J=1.6 Hz, 1H), 7.92 (dd, J=7.6, 1.6 Hz, 1H), 7.61-7.50 (m, 1H), 7.43 (d, J=7.6 Hz, 1H), 6.88-6.63 (m, 2H), 5.76-5.52 (m, 1H), 5.38 (s, 1H), 5.20-5.00 (m, 2H), 3.30 (dd, J=8.0, 2.0 Hz, 1H), 2.61 (dd, J=8.0, 2.0 Hz, 1H). MS (EI): m/z 390 [M]$^+$.

To a stirred solution of compound BF (4.0 g, 10.25 mmol) in CH$_2$Cl$_2$ (100 mL) was added m-chloroperoxybenzoic acid (m-CPBA; 8.8 g, 51.28 mmol) in portions at 0° C., and the mixture was stirred at RT for 5 h. Progress of the reaction was monitored by TLC. The reaction mixture was quenched with satd sodium thiosulfite solution and extracted with CH$_2$Cl$_2$ (2×100 mL). The combined organic extracts were washed with satd NaHCO$_3$ solution (2×150 mL) and brine (150 mL), dried over anhydrous Na$_2$SO$_4$ and concentrated under reduced pressure to obtain the crude material. Purification by silica gel column chromatography (eluting with 6-7% EtOAc/hexanes) afforded the epoxide BG (1.6 g, 3.94 mmol, 39%) as a colorless viscous liquid. $^1$H NMR (500 MHz, CDCl$_3$): δ 8.64 (d, J=2.0 Hz, 1H), 7.89 (dd, J=8.5, 2.0 Hz, 1H), 7.65-7.60 (m, 1H), 7.39 (d, J=8.5 Hz, 1H), 6.86-6.77 (m, 2H), 5.07 (s, 1H), 3.04 (dt, J=14.5, 4.5 Hz, 1H), 2.93-2.91 (m, 1H), 2.65 (t, J=4.5 Hz, 1H), 2.50-2.48 (m, 1H), 1.95 (dd, J=14.5, 7.0 Hz, 1H). MS (EI): m/z 406 [M]$^+$.

To a stirred solution of epoxide BG (1.25 g, 3.07 mmol) in DMF (3 mL) was added aq ammonia (NH$_3$; excess), and the resulting mixture was gradually heated up to 60° C. and stirred for 3 h. Progress of the reaction was monitored by TLC. The reaction mixture was cooled to RT, diluted with water (20 mL) and extracted with EtOAc (2×20 mL). The combined organic extracts were washed with water (20 mL) and brine (20 mL), dried over anhydrous Na$_2$SO$_4$ and concentrated under reduced pressure to obtain BH (500 mg, crude), which was taken on to the next step without further purification.

To a stirred solution of BH (500 mg, crude) in EtOH (10 mL) was added ethyl farmamidite hydrochloride (259 mg, 2.36 mmol) at RT and the mixture was gradually heated up to 80° C. and stirred for 16 h. Progress of the reaction was monitored by TLC. The reaction mixture was cooled to RT, the volatiles were evaporated under reduced pressure, and the residue was diluted with water (100 mL) and extracted with EtOAc (2×100 mL). The combined organic extracts were washed with water (50 mL) and brine (50 mL), dried over anhydrous Na$_2$SO$_4$ and concentrated under reduced pressure to obtain the crude material. Purification by silica gel column chromatography (35% EtOAc/CH$_2$Cl$_2$) afforded compound BI (110 mg, 0.24 mmol) as a thick syrup. $^1$H NMR (500 MHz, CDCl$_3$): δ 8.64 (s, 1H), 8.16 (s, 1H), 7.91 (dd, J=8.0, 2.0 Hz, 1H), 7.60-7.55 (m, 1H), 7.48-7.44 (m, 1H), 7.42 (d, J=8.0 Hz, 1H), 6.86-6.75 (m, 2H), 6.34 (br s, 1H), 5.99 (br s, 1H), 3.76-3.74 (m, 1H), 3.45-3.40 (m, 1H), 3.33-3.27 (m, 1H), 2.73 (d, J=14.5 Hz, 1H), 2.07-2.02 (m, 1H).

To a stirred solution of compound BI (110 mg, 0.24 mmol) in CH$_2$Cl$_2$ (5 mL) was added Dess-Martin periodinane (129 mg, 0.30 mmol) at 0° C., and the mixture was stirred at RT for 16 h. Progress of the reaction was monitored by TLC. The reaction mixture was quenched with satd NaHCO$_3$ (10 mL) and satd Na$_2$S$_2$O$_3$ (10 mL) and extracted with CH$_2$Cl$_2$ (2×30 mL). The combined organic extracts were washed with water (50 mL) and brine (30 mL), dried over anhydrous Na$_2$SO$_4$ and concentrated under reduced pressure to obtain the crude material. Purification by silica gel column chromatography (eluting with 30% EtOAc/CH$_2$Cl$_2$) afforded compound BJ (40 mg, 0.09 mmol, 36%) as a pale yellow thick syrup. $^1$H NMR (500 MHz, CDCl$_3$): δ 8.65 (s, 1H), 8.17 (s, 1H), 7.89 (dd, J=8.0, 2.0 Hz, 1H), 7.49-7.43 (m, 1H), 7.35 (d, J=8.0 Hz, 1H), 6.81-6.73 (m, 2H), 6.14 (br s, 1H), 5.78 (s, 1H), 4.34 (dd, J=20.0, 4.5 Hz, 1H), 4.20 (dd, J=20.0, 4.5 Hz, 1H), 3.75 (d, J=16.0 Hz, 1H), 3.33 (dd, J=16.0, 2.5 Hz, 1H). MS (EI): m/z 449 [M]$^+$.

Methanesulfonic acid (MsOH; 0.4 mL) was added to compound BJ (35 mg, 0.07 mmol). The mixture was gradually heated up to 100° C. and stirred for 1 h, then diphosphorus pentaoxide (P$_2$O$_5$; 70 mg, 0.24 mmol) was added and stirring was continued at same temperature for 2.5 h. Progress of the reaction was monitored by TLC. The reaction mixture was allowed to cool to RT, poured into ice-cold water, the pH was adjusted to 14 using 15% aq NaOH solution and the mixture was extracted with EtOAc (2×15 mL). The combined organic extracts were washed with water (10 mL) and brine (10 mL), dried over anhydrous Na$_2$SO$_4$ and concentrated under reduced pressure to obtain the crude material. Purification by preparative HPLC afforded 83 (5 mg, 0.01 mmol, 15%) as a pale yellow solid. $^1$H NMR (500 MHz, CDCl$_3$): δ 8.66 (s, 1H), 8.18 (s, 1H), 7.93 (d, J=8.0 Hz, 1H), 7.63 (s, 1H), 7.49-7.41 (m, 1H), 7.35 (d, J=8.0 Hz, 1H), 6.88-6.70 (m, 2H), 6.01 (s, 1H), 3.97 (d, J=15.5 Hz, 1H), 3.75 (d, J=15.5 Hz, 1H). MS (EI): m/z 432 [M+H]$^+$. HPLC: 45.6%.

Preparative HPLC Specifications:
Column: Sunfire C-18 (25×30 mm, 10µ)
Mobile Phase: A) CH$_3$CN; B) 0.1% aq TFA
Flow Rate: 30 mL/min
Time (min)/% B: 0.01/80, 5/80, 25/10

Example 50

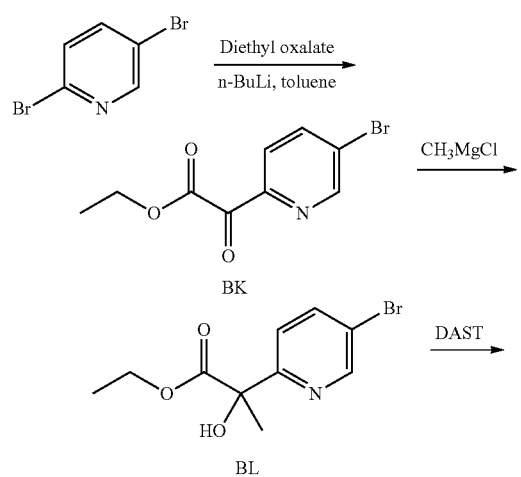

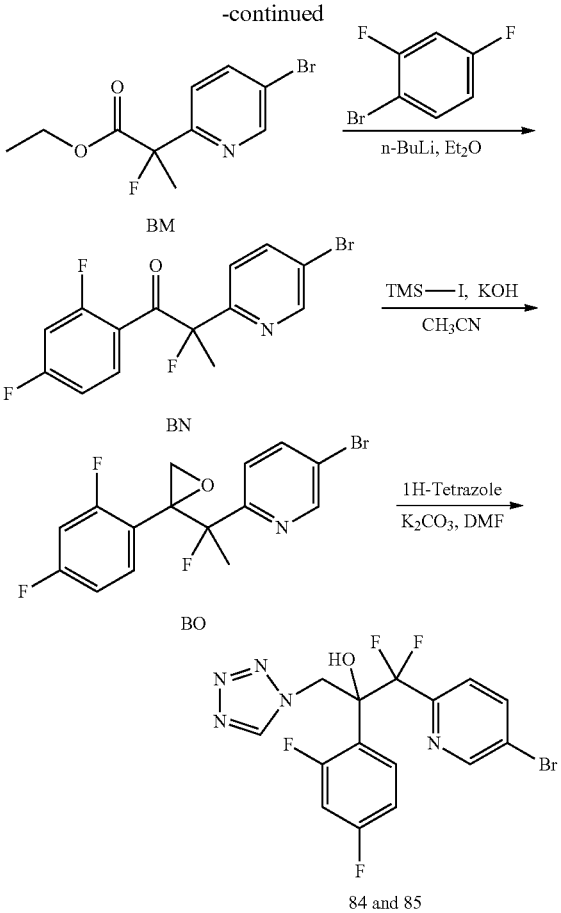

To a stirred solution of 2,5-dibromopyridine (30 g, 126.5 mmol) in toluene (1.5 L) was added n-BuLi (1.6 M solution in hexane; 79 mL, 126 mmol) dropwise at −78° C. under an inert atmosphere. After being stirred for 40 min at −78° C., diethyl oxalate (20.6 mL, 126.5 mmol) was added to the reaction mixture at −78° C. and stirring was continued for another 20 min. After completion of the reaction (by TLC), the reaction mixture was quenched with satd NH$_4$Cl solution and extracted with EtOAc (2×1.0 L). The combined organic extracts were washed with water and brine, dried over anhydrous Na$_2$SO$_4$ and concentrated under reduced pressure to obtain the crude product. The crude material was purified by silica gel column chromatography (eluting with EtOAc/hexane) to afford BK (13 g, 50.37 mmol, 38%). $^1$H NMR (200 MHz, CDCl$_3$): δ 8.81 (d, J=1.4 Hz, 1H), 8.17-7.98 (m, 2H), 4.48 (q, J=7.4 Hz, 2H), 1.41 (t, J=7.4 Hz, 3H). MS (ESI): m/z 259 [M+1]$^+$.

To a stirred solution of BK (13 g, 50.3 mmol) in THF (150 mL) was added methyl magnesium chloride (CH$_3$MgCl, 3 M solution in THF; 15 mL, 50.3 mmol) at −5° C. under an inert atmosphere. Stirring was continued for another 2 h. Progress of the reaction was monitored by TLC. The reaction mixture was then quenched with satd NH$_4$Cl solution and extracted with EtOAc (2×200 mL). The combined organic extracts were washed with water and brine, dried over anhydrous Na$_2$SO$_4$ and concentrated under reduced pressure to obtain the crude product. The crude material was purified by silica gel column chromatography (eluting with EtOAc/hexane) to afford BL (2.8 g, 10.76 mmol, 21%). $^1$H NMR (200 MHz, CDCl$_3$): δ 8.61 (d, J=1.4 Hz, 1H), 7.84

(dd, J=8.0, 1.4 Hz, 1H), 7.49 (d, J=8.0 Hz, 1H), 4.92 (br s, 1H), 4.20 (q, J=7.4 Hz, 2H), 1.80 (s, 3H), 1.22 (t, J=7.4 Hz, 3H).

To a stirred solution of BL (2.8 g, 10.7 mmol) in $CH_2Cl_2$ (50 mL) was added DAST (3.5 mL, 26.5 mmol) at 0° C. under an inert atmosphere, and the reaction mixture was stirred for 16 h at RT. Progress of the reaction was monitored by TLC. The reaction mixture was then quenched with ice-cold water and extracted with $CH_2Cl_2$ (2×100 mL). The combined organic extracts were washed with water and brine, dried over anhydrous $Na_2SO_4$ and concentrated under reduced pressure. The crude material was purified by silica gel column chromatography (eluting with EtOAc/hexane) to afford BM (2.1 g, 7.6 mmol, 75%). $^1$H NMR (200 MHz, $CDCl_3$): δ 8.62 (d, J=1.4 Hz, 1H), 7.85 (dd, J=8.0, 1.4 Hz, 1H), 7.50 (d, J=8.0 Hz, 1H), 4.23 (q, J=7.4 Hz, 2H), 1.95 (d, $J_{F-H}$=24.0 Hz, 3H), 1.24 (t, J=7.4 Hz, 3H). MS (ESI): m/z 276 $[M]^+$.

To a stirred solution of 1-bromo-2,4-difluorobenzene (0.9 mL, 8.01 mmol) in $Et_2O$ (50 mL) was added dropwise n-BuLi (1.6 M solution; 5 mL, 8.01 mmol) at −78° C. under an inert atmosphere. After being stirred for 40 min at −78° C., a solution of BM (2.1 g, 8.01 mmol) in $Et_2O$ (50 mL) was added dropwise to the reaction mixture at −78° C. Stirring was continued for another 20 min. After completion of the reaction (by TLC), the reaction mixture was quenched with satd $NH_4Cl$ solution and extracted with EtOAc. The combined organic extracts were washed with water and brine, dried over anhydrous $Na_2SO_4$ and concentrated under reduced pressure to obtain the crude product. The crude material was purified by silica gel column chromatography (eluting with EtOAc/hexane) to afford ketone BN (2.15 g, 6.24 mmol, 77.9%). $^1$H NMR (200 MHz, $CDCl_3$): δ 8.61 (d, J=1.6 Hz, 1H), 7.96 (dd, J=8.0, 1.6 Hz, 1H), 7.67-7.62 (m, 1H), 7.48 (d, J=8.0 Hz, 1H), 6.98-6.67 (m, 2H), 1.98 (d, $J_{F-H}$=24.0 Hz, 3H). MS (ESI): m/z 343.9 $[M+1]^+$.

To a stirred solution of ketone BN (2.1 g, 6.10 mmol) in $CH_3CN$ (30 mL) were added iodotrimethylsilane (TMS-I; 1.47 g, 6.71 mmol) and KOH (683 mg, 12.20 mmol) at RT under an inert atmosphere. The resulting reaction mixture was heated to 70° C. and stirred for 1.5 h; progress of the reaction was monitored by TLC. The reaction mixture was then diluted with EtOAc, stirred for 5 min and filtered; the filtrate was concentrated under reduced pressure to obtain the crude product. The crude material was purified by silica gel column chromatography (eluting with EtOAc/hexane) to afford epoxide BO (1.92 g, 5.36 mmol, 88%) as a mixture of diastereomers. The product was confirmed by $^1$H-NMR spectral analysis and was taken forward to the next step without any further purification.

To a stirred solution of compound BO (250 mg, 0.7 mmol) in DMF (10 mL) was added 1H-tetrazole (73 mg, 1.05 mmol) followed by $K_2CO_3$ (96 mg, 0.7 mmol) at RT under inert atmosphere. The resulting reaction mixture was heated to 65° C. and stirred for 48 h. After consumption of the starting material (by TLC), the reaction mixture was cooled to RT, diluted with water (50 mL) and extracted with EtOAc (2×50 mL). The combined organic layers were washed with water (50 mL) and brine (50 mL), dried over anhydrous $Na_2SO_4$ and concentrated under reduced pressure to obtain the crude material. Purification by silica gel column chromatography afforded 84 (40 mg, 0.09 mmol, 13%; eluent: 32-35% EtOAc/hexanes) and 85 (40 mg, 0.09 mmol, 13%; eluent: 38-40% EtOAc/hexanes) as white solids. Compound 84: $^1$H NMR (500 MHz, $CDCl_3$): δ 8.62 (s, 1H), 8.58 (s, 1H), 8.05 (dd, J=8.0, 2.0 Hz, 1H), 7.76-7.71 (m, 1H), 7.66 (d, J=8.0 Hz, 1H), 7.18 (br s, OH), 6.88-6.78 (m, 2H), 5.49 (d, J=14.0 Hz, 1H), 4.26 (d, J=14.0 Hz, 1H), 1.49 (t, $J_{F-H}$=23.0 Hz, 3H). MS (ESI): m/z 427 $[M+H]^+$. HPLC: 99%. Compound 85: $^1$H NMR (500 MHz, $CDCl_3$): δ 8.70 (s, 1H), 8.53 (s, 1H), 7.72 (d, J=8.5 Hz, 1H), 7.13 (d, J=8.5 Hz, 1H), 6.83-6.81 (m, 2H), 6.64-6.60 (m, 1H), 6.48-6.44 (m, 1H), 5.72 (d, J=14.0 Hz, 1H), 4.97 (d, J=14.0 Hz, 1H), 1.93 (d, $J_{F-H}$=22.5 Hz, 3H). MS (ESI): m/z 427 $[M+H]^+$. HPLC: 92%.

Example 51

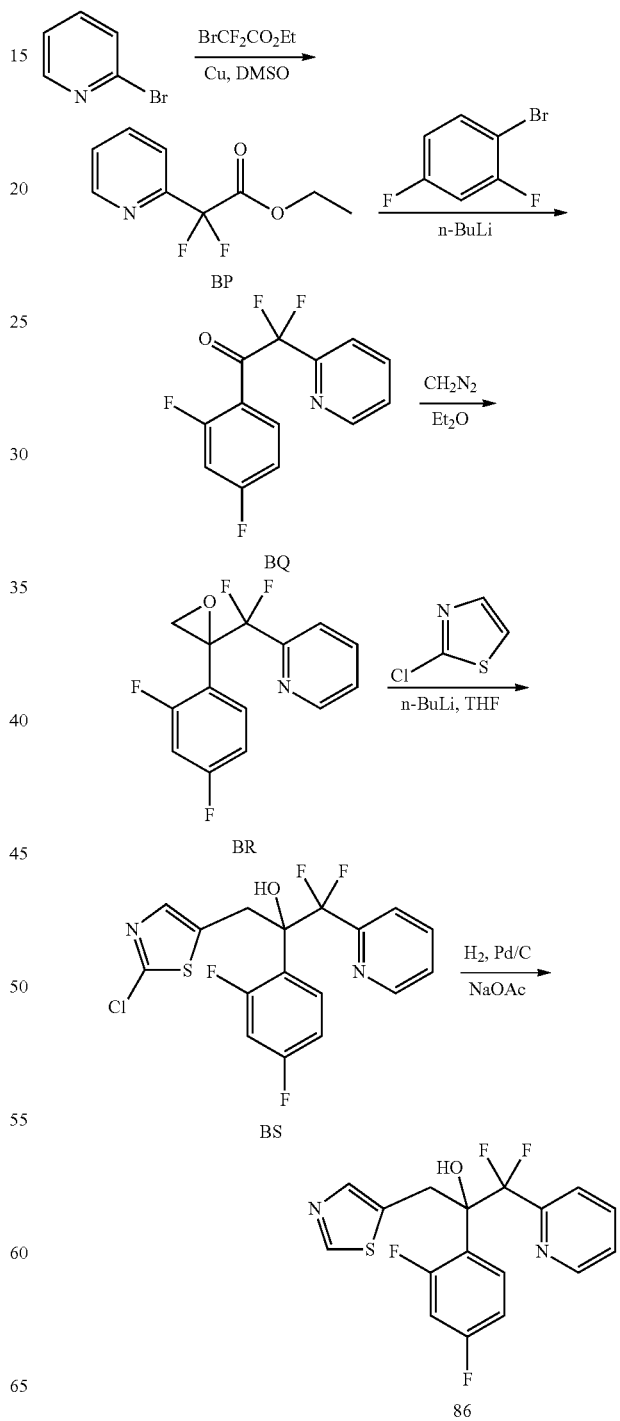

2-(2,4-Difluorophenyl)-1,1-difluoro-1-(pyridin-2-yl)-3-(thiazol-5-yl)propan-2-ol (86)

To a suspension of copper powder (804 mg, 12.6 mmol) in DMSO (5 mL) was added ethyl 2-bromo-2,2-difluoroacetate (1.0 mL, 6.30 mmol) and the mixture was stirred for 1 h at RT. 2-Bromopyridine (498 mg, 3.15 mmol) was then added and the reaction mixture was stirred for another 15 h at RT. The progress of the reaction was monitored by TLC. The reaction was quenched with satd NH$_4$Cl solution and extracted with CH$_2$Cl$_2$ (3×25 mL). The combined organic extracts were washed with water (50 mL) and brine (50 mL), dried over anhydrous Na$_2$SO$_4$ and concentrated under reduced pressure to afford the crude material. Purification by silica gel column chromatography (eluting with 1% EtOAc/hexanes) afforded compound BP (255 mg, 1.27 mmol, 40%) as a light yellow liquid. $^1$H NMR (500 MHz, CDCl$_3$): δ 8.66 (d, J=4.0 Hz, 1H), 7.86 (t, J=7.5 Hz, 1H), 7.74 (d, J=7.5 Hz, 1H), 7.44-7.41 (m, 1H), 4.38 (q, J=7.0 Hz, 2H), 1.33 (t, J=7.0 Hz, 3H). MS (ESI): m/z 202 [M+H]$^+$.

To a stirred solution of 1-bromo-2,4-difluorobenzene (225 mg, 1.11 mmol) in Et$_2$O (5 mL) was added n-BuLi (1.6 M in hexane; 0.5 mL, 1.30 mmol) at −78° C. and the mixture was stirred for 30 min. Compound BP (216 mg, 1.11 mol) in Et$_2$O (5 mL) was added dropwise and the mixture was stirred for 1 h at −78° C. The temperature was gradually raised to ambient temperature and the stirring was continued for another 1 h. The reaction mixture was quenched with satd NH$_4$Cl solution and extracted with EtOAc (3×10 mL). The combined organic layers were washed with water (30 mL) and brine (30 mL), dried over anhydrous Na$_2$SO$_4$ and concentrated under reduced pressure to obtain the crude material. Purification by silica gel column chromatography (eluting with 3% EtOAc/hexanes) afforded compound BQ (115 mg, 0.43 mmol, 38%) as a yellow liquid. $^1$H NMR (500 MHz, CDCl$_3$): δ 8.58 (d, J=4.0 Hz, 1H), 8.10-8.04 (m, 1H), 7.92-7.82 (m, 2H), 7.43-7.41 (m, 1H), 7.00-6.98 (m, 1H), 6.83-6.80 (m, 1H). MS (ESI): m/z 270 [M+H]$^+$.

To a stirred solution of compound BQ (100 mg, 0.37 mmol) in Et$_2$O (20 mL) was added freshly prepared diazomethane [prepared by dissolving NMU (250 mg, 2.43 mmol) in a 1:1 mixture of 100/KOH solution (25 mL) and Et$_2$O (25 mL) at 0° C. followed by separation and drying of the organic layer using KOH pellets] at −5° C. and the mixture was stirred for 2 h. The resulting reaction mixture was allowed to warm to RT and stirring was continued for another 16 h. The progress of the reaction was monitored by TLC. The reaction mixture was concentrated under reduced pressure to obtain the crude material. Purification by silica gel column chromatography (eluting with 3-5% EtOAc/hexanes) afforded compound BR (60 mg, 0.21 mmol, 57%) as a light-yellow solid. $^1$H NMR (500 MHz, CDCl$_3$): δ 8.67 (d, J=4.0 Hz, 1H), 7.77-7.74 (m, 1H), 7.48 (d, J=7.5 Hz, 1H), 7.40-7.35 (m, 2H), 6.84-6.81 (m, 1H), 6.75-6.71 (m, 1H), 3.46 (d, J=5.0 Hz, 1H), 2.97 (d, J=5.0 Hz, 1H). MS (ESI): m/z 284 [M+H]$^+$.

To a stirred solution of 2-chlorothiazole (213 mg, 1.76 mmol) in THF (7 mL) was added n-BuLi (2.5 M solution in hexane; 2 mL, 5.30 mmol) at −78° C. and the mixture was stirred for 10 min. A solution of compound BR (500 mg, 1.76 mmol) in dry THF (3 mL) was added at −78° C.; then the reaction mixture was slowly warmed to RT and stirred for 3 h. The reaction was quenched with satd NH$_4$Cl solution and extracted with EtOAc (2×20 mL). The organic layer was washed with water (20 mL) and brine (20 mL), dried over anhydrous Na$_2$SO$_4$ and concentrated under reduced pressure to obtain the crude material. Purification by silica gel column chromatography (eluting with 2% CH$_3$OH/CH$_2$Cl$_2$) afforded BS (115 mg, 0.28 mmol, 16%) as a semi-solid. $^1$H NMR (500 MHz, CDCl$_3$): δ 8.62 (d, J=5.0 Hz, 1H), 7.84-7.81 (m, 1H), 7.55 (d, J=7.5 Hz, 1H), 7.49-7.43 (m, 2H), 7.38 (s, 1H), 7.26-7.24 (m, 1H), 6.71-6.67 (m, 2H), 4.06 (d, J=14.5 Hz, 1H), 3.29 (d, J=14.5 Hz, 1H). MS (ESI): m/z 403 [M+H]$^+$. HPLC: 94%.

To a stirred solution of BS (115 mg, 0.28 mmol) in EtOH (10 ml) was added sodium acetate (NaOAc; 5 mg, 0.05 mmol) and 10% Pd/C (10 mg) and the mixture was stirred under hydrogen atmosphere for 2 h. After consumption of the starting material (by TLC), the reaction mixture was filtered through a pad of Celite® and the Celite® cake was washed thoroughly with CH$_3$OH (20 mL). The filtrate was concentrated under reduced pressure to afford 86 (75 mg, 0.20 mmol, 72%) as a viscous liquid. $^1$H NMR (500 MHz, CDCl$_3$): δ 8.61 (d, J=4.0 Hz, 1H), 8.53 (s, 1H), 7.84-7.81 (m, 1H), 7.62-7.60 (m, 2H), 7.47-7.42 (m, 2H), 7.27-7.24 (m, 1H), 6.70-6.64 (m, 2H), 4.17 (d, J=14.5 Hz, 1H), 3.38 (d, J=14.5 Hz, 1H). MS (ESI): m/z 369 [M+H]$^+$. HPLC: 96%.

Chiral Preparative HPLC Separation of Enantiomers of 86

The enantiomers of 86 (60 mg, 0.16 mmol) were separated by normal-phase preparative HPLC using a CHIRALPAK® AD-H column (250×20 mm, 5 µm; mobile phase (A) 0.1% TFA in n-hexane-(B) EtOH (A:B=80:20) and flow rate 15 mL/min) to obtain 86-(−) (22 mg, 0.05 mmol) as an off-white solid.

Analytical Data:

Chiral HPLC: 98.5% ee, R$_4$=10.90 min (CHIRALPAK® IA column, 250×4.6 mm, 5µ; mobile phase (A) n-hexane-(B) EtOH (A:B=80:20); flow rate 1.00 mL/min). Optical rotation [α]$_D^{25}$: −2.2° (c=0.1% in CH$_3$OH).

Example 52

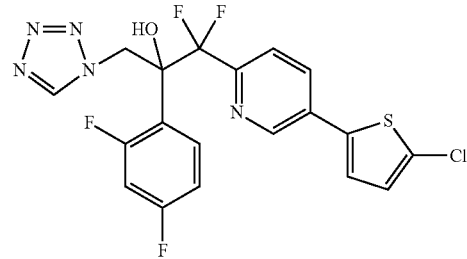 [SMILES: OC(Cn1cnnn1)(c1ccc(F)cc1F)C(F)(F)c1ccc(-c2ccc(Cl)s2)cn1]

1-(5-(5-Chlorothiophen-2-yl) pyridin-2-yl)-2-(2,4-difluorophenyl)-1,1-difluoro-3-(1H-tetrazol-1-yl)propan-2-ol (87)

To a stirred solution of epoxide F (0.25 g, 0.69 mmol) in THF/H$_2$O (30 mL, 2:1) was added Na$_2$CO$_3$ (0.36 g, 0.34 mmol) followed by 5-chloro-thiophene-2-boronic acid (0.13 g, 0.80 mmol) at RT under inert atmosphere. After purging with nitrogen for a period of 30 min, Pd (PPh$_3$)$_4$ (79 mg, 0.69 mmol) was added to the reaction mixture under an inert atmosphere. The resulting reaction mixture was gradually heated to reflux for 16 h. After consumption of the starting material (by TLC), the reaction mixture was cooled to room temperature and the aqueous layer was extracted with EtOAc (2×50 mL). The combined organic layers were washed with water, brine, dried over $Na_2SO_4$ and concentrated in vacuo. The crude material was purified by column chromatography ($SiO_2$, 100-200 mesh; eluting with EtOAc/Hexane) to afford coupled product (50 mg, 0.12 mmol, 18%) as a syrup. $^1$H NMR (500 MHz, $CDCl_3$): δ 8.81 (s, 1H), 7.81 (d, J=8.5 Hz, 1H), 7.48 (d, J=8.5 Hz, 1H), 7.41 (q, J=8.5 Hz, 1H), 7.20 (d, J=4.5 Hz, 1H), 6.96 (d, J=3.5 Hz, 1H), 6.84 (t, J=8.0 Hz, 1H), 6.75 (t, J=9.0 Hz, 1H), 3.47 (d, J=4.5 Hz, 1H), 2.99 (d, J=4.5 Hz, 1H). MS (ESI): m/z 400 [M$^+$+1].

To a stirred solution of coupled product (0.12 g, 0.30 mmol) in dry DMF (3 mL) was added 1H-tetrazole (25 mg, 0.36 mmol) followed by $K_2CO_3$ (41 mg, 0.30 mmol) at RT under an inert atmosphere. The reaction mixture was gradually heated to 65° C. and stirred for 16 h. The reaction mixture was diluted with water and extracted with EtOAc (2×25 mL). The combined organic layers were dried over $Na_2SO_4$ and concentrated under reduced pressure. The obtained crude material was purified by column chromatography ($SiO_2$, 100-200 mesh; eluting with EtOAc/Hexane) to afford 87 (50 mg, 0.10 mmol, 35%) as a pale yellow semi solid. $^1$H NMR (500 MHz, $CDCl_3$): δ 8.75 (s, 1H), 8.68 (d, J=6.0 Hz, 1H), 7.86 (dd, J=8.5, 2.5 Hz, 1H), 7.58 (d, J=8.0 Hz, 1H), 7.37-7.32 (m, 1H), 7.35 (d, J=9.0 Hz, 1H), 7.20 (d, J=3.5 Hz, 1H), 6.98 (d, J=4.5 Hz, 1H), 6.78-6.74 (m, 1H), 6.69-6.65 (m, 1H), 5.60 (d, J=14.5 Hz, 1H), 5.12 (d, J=14.5 Hz, 1H). MS (ESI): m/z 470 [M$^+$+1]. HPLC: 96.22%.

Example 53

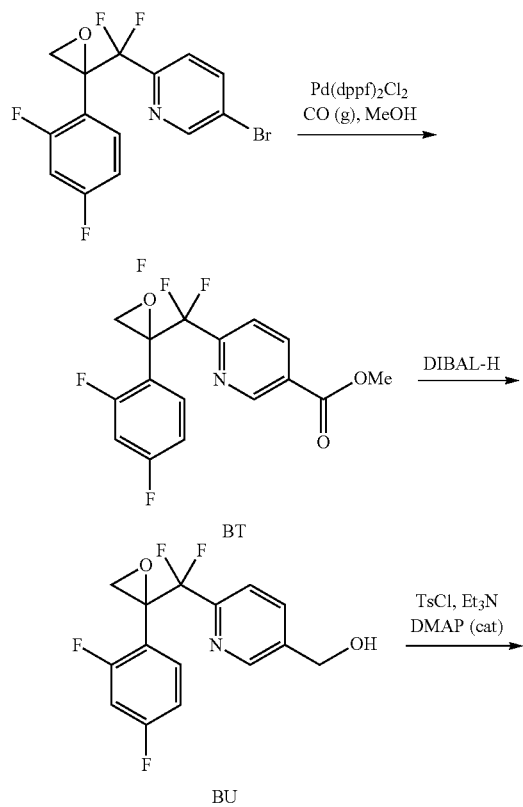

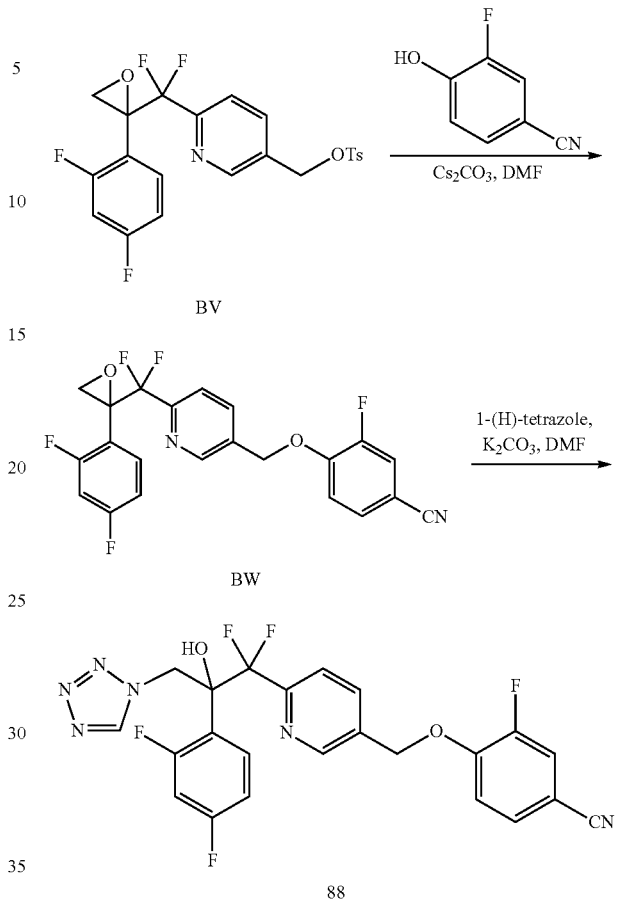

4-((6-(2-(2,4-difluorophenyl)-1,1-difluoro-2-hydroxy-3-(1H-tetrazol-1-yl)propyl)pyridin-3-yl)methoxy)-3-fluorobenzonitrile (88)

A mixture of compound F (5.0 g, 13.8 mmol), $Et_3N$ (3.48 g, 34.5 mmol), Pd(dppf)$_2$Cl$_2$ (2.0 g, 2.73 mmol) in MeOH—$CH_3CN$ (4:1, 100 mL) was stirred at RT in a pressure reaction vessel under argon atmosphere for 15 min. To this solution, carbon monoxide (CO) gas was filled up to 80 psi and maintained the reaction at 70° C. for 16 h. After complete consumption of the starting material (by TLC), the reaction mixture was filtered through a pad of Celite® and washed with EtOAc (3×50 mL). The filtrate was concentrated under reduced pressure to obtain the crude material. The crude material was purified by silica gel column chromatography (eluent: 10% EtOAc/Hexanes) to afford compound BT (4.0 g, 11.7 mmol, 85%) as a yellow solid. $^1$HNMR (400 MHz, $CDCl_3$): δ 9.24 (d, J=2.0 Hz, 1H), 8.35 (dd, J=8.2, 2.0 Hz, 1H), 7.57 (d, J=8.2, 1H) 7.39-7.33 (m, 1H), 6.86-6.80 (m, 1H), 6.75-6.70 (m, 1H), 3.98 (s, 3H), 3.48 (d, J=5.0 Hz, 1H), 2.98 (d, J=5.0 Hz, 1H). MS (ESI): m/z 342 [M+H]$^+$.

To a stirred solution of BT (3.5 g, 10.26 mmol) in DCM (80 mL) was added DIBAL-H (18 mL, 30.6 mmol; 1.7M in toluene) at −78° C. under inert atmosphere and then the reaction mixture was stirred at RT for 6 h. After complete consumption of the starting material (by TLC), the reaction mixture was quenched with saturated $NH_4Cl$ solution (100 ml) and extracted with DCM (3×100 mL). The combined organic extracts were washed with water (100 mL), brine (100 mL), dried over anhydrous Na$_2$SO$_4$ and concentrated under reduced pressure to obtain the crude BU (3.5 g) which was taken for the next step without purification.

To a stirred solution of compound BU (1.0 g, crude) in DCM (20 mL) was added tosyl chloride (TsCl; 0.91 g, 4.79 mmol), Et$_3$N (0.64 g, 6.38 mmol) and DMAP (cat) at 0° C. under inert atmosphere and maintained for 1 h at same temperature. After complete consumption of the starting material (by TLC), the reaction mixture was diluted with ice-cold water (40 mL) and extracted with DCM (2×50 mL). The combined organic extracts were washed with saturated NaHCO$_3$ solution (50 mL), water (50 mL), brine (50 mL), dried over anhydrous Na$_2$SO$_4$ and concentrated under reduced pressure to obtain the crude material. The crude material was purified by silica gel column chromatography (eluent: 15% EtOAc/Hexanes) to afford compound BV (0.85 g, 1.82 mmol) as a red solid. $^1$HNMR (400 MHz, CDCl$_3$): δ 8.51 (d, J=2.0 Hz, 1H), 7.79 (d, J=8.0 Hz, 2H), 7.68 (dd, J=8.4, 2.0 Hz, 1H), 7.45 (d, J=8.4 Hz, 1H), 7.37-7.32 (m, 3H), 6.85-6.80 (m, 1H), 6.76-6.71 (m, 1H), 5.12 (s, 2H), 3.39 (d, J=5.0 Hz, 1H), 2.95 (d, J=5.0 Hz, 1H), 2.44 (s, 3H).

To a stirred suspension of 3-fluoro-4-hydroxybenzonitrile (73.3 mg, 0.53 mmol) and Cs$_2$CO$_3$ (261 mg, 0.80 mmol) in DMF (8 mL) was added compound BV (250 mg, 0.53 mmol) at RT and stirred for 4 h. After completion of the reaction (by TLC), the reaction mixture was quenched with ice-cold water (25 mL) and extracted with EtOAc (4×50 mL). The combined organic extracts were washed with water (50 mL), brine (50 mL), dried over anhydrous Na$_2$SO$_4$ and concentrated under reduced pressure to obtain the crude. The crude material was purified by silica gel column chromatography (eluent: 30% EtOAc/hexanes) to afford the compound BW (200 mg, 0.463 mmol, 87%) as a pale yellow solid. $^1$HNMR (400 MHz, CDCl$_3$): δ 8.73 (d, J=2.0 Hz, 1H), 7.86 (dd, J=8.0, 2.0 Hz, 1H) 7.54 (d, J=8.0 Hz, 1H), 7.45-7.38 (m, 3H), 7.07 (t, J=8.4 Hz, 1H), 6.84-6.79 (m, 1H), 6.76-6.71 (m, 1H), 5.25 (s, 2H), 3.45 (d, J=5.0 Hz, 1H), 2.98 (d, J=5.0 Hz, 1H).

To a stirred solution of compound BW (250 mg, 0.57 mmol) in dry DMF (8 mL) was added 1H-tetrazole (60 mg, 0.87 mmol) followed by K$_2$CO$_3$ (80 mg, 0.57 mmol) at RT under inert atmosphere. The reaction mixture was heated to 65° C. and stirred for 16 h. After completion of the reaction (by TLC), the reaction mixture was quenched with ice-cold water and extracted with EtOAc (2×50 mL). The combined organic extracts were washed with water (50 mL), brine (50 mL), dried over Na$_2$SO$_4$ and concentrated under reduced pressure to obtain the crude. The crude material was purified by silica gel column chromatography (eluent: 60% EtOAc/Hexanes) to afford 88 (40 mg, 0.079 mmol, 13.9%) as an off-white solid. $^1$HNMR (500 MHz, CDCl$_3$): δ 8.74 (s, 1H), 8.59 (s, 1H), 7.92 (d, J=8.0 Hz, 1H), 7.66 (d, J=8.0 Hz, 1H), 7.46-7.36 (m, 4H), 7.09-7.05 (m, 1H), 6.79-6.75 (m, 1H), 6.70-6.67 (m, 1H), 5.51 (d, J=14.5 Hz, 1H), 5.23 (s, 2H), 5.18 (d, J=14.5 Hz, 1H). MS(ESI): m/z 503 [M+H]$^+$.

Compounds 89-91 in Table 1 were prepared using the same conditions as compound 88 (See Table 1 for starting material).

Example 54

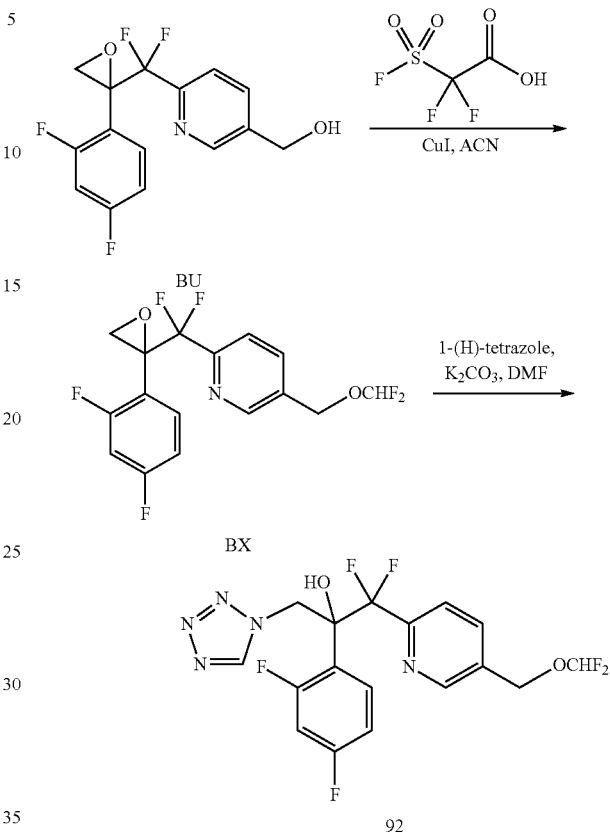

S-(5-((difluoromethoxy)methyl)pyridin-2-yl)-2-(2,4-difluorophenyl)-1,1-difluoro-3-(1H-tetrazol-1-yl)propan-2-ol (92)

To a stirred solution of compound BU (400 mg, 1.27 mmol) in CH$_3$CN (12 mL) was added copper(I) iodide (CuI; 24 mg, 0.12 mmol) at RT under inert atmosphere and then heated to 60° C. for 10 min. 2,2-difluoro-2-(fluorosulfonyl) acetic acid (0.26 mL, 2.5 mmol) was added drop wise to the above reaction mixture and 60° C. temperature was maintained for another 4 h. After complete consumption of the starting material (by TLC), the reaction mixture was diluted with ice-cold water (30 mL) and extracted with DCM (2×50 mL). The combined organic extracts were washed with water (50 mL) and brine (50 mL), dried over anhydrous Na$_2$SO$_4$ and concentrated under reduced pressure to obtain the crude. The crude material was purified by silica gel column chromatography (eluent: 15% EtOAc/Hexanes) to afford compound BX (200 mg, 0.55 mmol, 43%) as a reddish liquid. $^1$H NMR (400 MHz, CDCl$_3$): δ 8.64 (d, J=2.0 Hz, 1H), 7.77 (dd, J=8.0, 2.0 Hz, 1H), 7.75 (d, J=8.0 Hz, 1H), 7.40-7.34 (m, 1H), 6.85-6.76 (m, 1H), 6.74-6.71 (m, 1H), 6.35 (t, J=73.2 Hz, 1H), 4.97 (s, 2H), 3.44 (d, J=5.2 Hz, 1H), 2.97 (d, J=5.2 Hz, 1H). MS (ESI): m/z 364 [M+H]$^+$.

To a stirred solution of epoxide BX (200 mg, 0.55 mmol) in dry DMF (6 mL) was added K$_2$CO$_3$ (75 mg, 0.55 mmol) followed by 1H-tetrazole (57 mg, 0.82 mmol) at RT under inert atmosphere. The resulting reaction mixture was heated to 65° C. and maintained for 16 h. The progress of the reaction was monitored by TLC. The reaction was diluted with ice-cold water (30 mL) and extracted with EtOAc (3×50 mL). The combined organic layers were washed with water (50 mL), brine (50 mL), dried over anhydrous $Na_2SO_4$ and concentrated under reduced pressure to obtain the crude. The crude was purified by silica gel column chromatography (eluent: 40% EtOAc/Hexane) to afford 92 (45 mg, 0.103 mmol, 19%) as an off-white solid. $^1$H NMR (500 MHz, $CDCl_3$): δ 8.74 (s, 1H), 8.53 (s, 1H), 7.82 (d, J=7.5 Hz, 1H), 7.60 (d, J=7.5 Hz, 1H), 7.47 (s, 1H, OH), 7.34-7.29 (m, 1H), 6.78-6.73 (m, 1H), 6.67-6.64 (m, 1H), 6.35 (t, J=73.0 Hz, 1H), 5.57 (d, J=15.0 Hz, 1H), 5.12, (d, J=15.0 Hz, 1H), 4.96 (s, 2H). MS (ESI): m/z 434 [M+H]$^+$.

Example 55

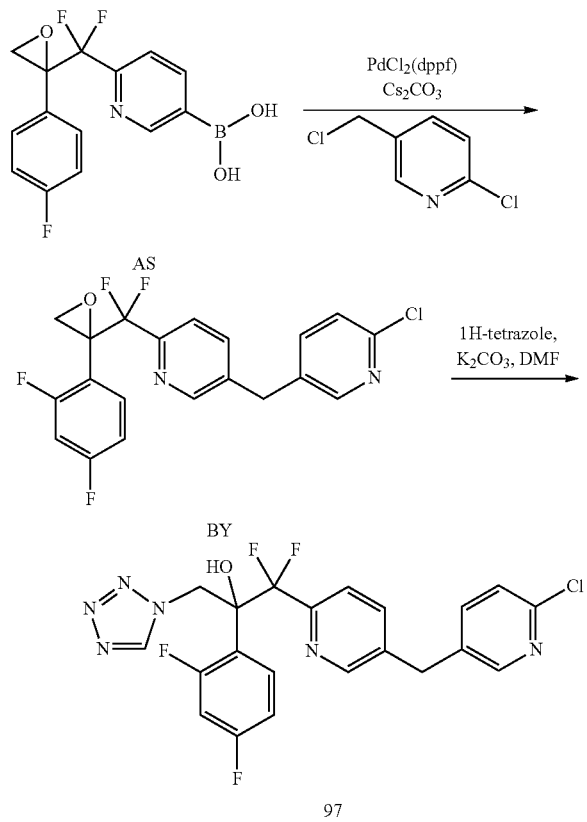

1-(((6-chloropyridin-3-yl)methyl)pyridin-2-yl)-2-(2,4-difluorophenyl)-1,1-difluoro-3-(1H-tetrazol-1-yl)propan-2-ol (97)

To a stirred solution of boronic acid AS (prepared as in the first step of Example 15; 532 mg, 1.63 mmol) and 2-chloro-5-(chloromethyl)pyridine (220 mg, 1.36 mmol) in toluene:ethanol (2:1) (0.1M) was added cesium carbonate (1.10 g, 3.39 mmol), purged with argon gas for 5 min then $PdCl_2$(dppf) (100 mg, 0.136 mmol) was added, again purged with argon gas for 5 min. The reaction mixture was then heated at 100° C. for 1 hr. The reaction mixture was then diluted with ethyl acetate and washed with $H_2O$. The organic layer was concentrated under reduced pressure. The obtained residue was purified by silica gel chromatography to afford 250 mg of BY (44% yield). $^1$H NMR (400 MHz, DMSOd$_6$) δ 8.625 (s 1H), δ 8.374-8.380 (d, J=2.4 Hz, 1H) δ 7.765-7.790 (dd, J=6.0, 2.0 Hz, 1H), δ 7.704-7.731 (dd, J=6.4, 2.8 Hz, 1H), δ 7.358-7.483 (m, 3H), δ 7.193-7.249 (m, 1H), δ 7.046-7.088 (m, 1H), δ 3.38 (s, 1H), δ 3.13 (s, 1H), δ 4.078 (s, 2H). LCMS m/z 408.08 [M−H]$^+$.

To a stirred solution of compound BY (250 mg, 0.61 mmol) in DMF (5 mL) was added 1H-tetrazole (64 mg, 0.92 m.mol) followed by $K_2CO_3$ (127 mg, 0.92 mmol) at RT under an inert atmosphere. The reaction mixture was heated to 60° C. for 16 h. The reaction mixture was diluted with ice cold water (20 mL) and extracted with EtOAc (2×50 mL). The combined organic layers were dried over $Na_2SO_4$ and concentrated under reduced pressure. The obtained crude material was purified by column chromatography ($SiO_2$, 100-200 mesh) to afford 115 mg (39% yield) of the title compound 97 as a brown sticky liquid. $^1$H NMR (400 MHz, d$_6$-DMSO) δ 9.12 (s, 1H), 8.56 (s, 1H), 8.38 (d, J=2.4 Hz, 1H), 7.79 (dd, J=8.2, 1.8 Hz, 1H), 7.71 (dd, J=8.3, 2.4 Hz, 1H), 7.48 (d, J=8.3 Hz, 1H), 7.40 (d, J=8.1 Hz, 1H), 7.24 (s, 1H), 7.23-7.12 (m, 2H), 6.87 (td, J=8.5, 2.4 Hz, 1H), 5.62 (d, J=14.7 Hz, 1H), 5.06 (d, J=14.9 Hz, 1H), 4.08 (s, 2H). $^{19}$F NMR (282 MHz, $CDCl_3$) δ −103.65, −104.14 (m), −104.84 (d, J=17.6 Hz), −105.77 (d, J=17.6 Hz), −108.09 (dt, J=16.1, 8.0 Hz), −109.63 (d, J=38.6 Hz), −110.56 (d, J=39.2 Hz). MS (ESI): m/z 479.1 (M+H)$^+$.

Example 56

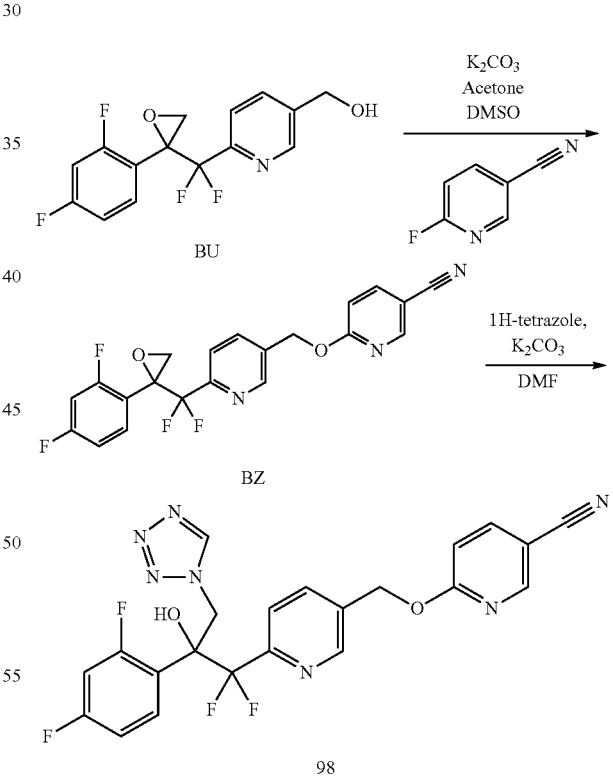

6-((6-(2-(2,4-difluorophenyl)-1,1-difluoro-2-hydroxy-3-(1H-tetrazol-1-yl)propyl)pyridin-3-yl)methoxy)nicotinonitrile (98)

To a magnetically stirred mixture of (6-((2-(2,4-difluorophenyl)oxiran-2-yl)difluoromethyl)pyridin-3-yl)methanol (BU from Example 53; 156 mg, 0.498 mmol) in Acetone (2.490 mL) was added $K_2CO_3$ (138 mg, 0.996 mmol) in a dry 25 mL vial under $N_2$ atmosphere. 6-fluoronicotinonitrile (73.0 mg, 0.598 mmol) was added and the reaction mixture was stirred at RT for 2 hours, but no reaction progress was noted. DMSO (1 mL) was added, and the reaction mixture was stirred at RT overnight HPLC-MS indicated the reaction was ~50% complete. The reaction mixture was heated to 55° C. for 6 hours, at which point, TLC and HPLC-MS indicated the reaction was mostly complete. The crude material was diluted with ice-water and ether and the layers were separated. The aq. layer was extracted again with ether, and the combined ether extracts were dried over sodium sulfate, filtered, and evaporated. The crude residue was purified on silica (40 gram column, gradient to 20% EA/Hex over 15 minutes, hold for 20 minutes) to afford compound BZ. Yield=200 mg (92%) of a white waxy solid. 1H NMR (400 MHz, $CDCl_3$) δ 8.75 (s, 1H), 8.49 (dd, J=2.4, 0.6 Hz, 1H), 7.84 (dd, J=8.7, 2.4 Hz, 2H), 7.51 (d, J=8.0 Hz, 1H), 7.39 (dd, J=14.7, 8.2 Hz, 1H), 6.91 (dd, J=8.7, 0.6 Hz, 1H), 6.84 (ddd, J=7.8, 2.4, 1.3 Hz, 1H), 6.78-6.70 (m, 1H), 5.51 (s, 2H), 3.44 (d, J=5.0 Hz, 1H), 3.01-2.94 (m, 1H). 1H-decoupled $^{19}F$ NMR (376 MHz, $CDCl_3$) δ −107.07 (d, J=9.5 Hz), −107.54 (d, J=9.5 Hz), −107.75 (d, J=8.2 Hz), −107.98 (d, J=8.2 Hz), −108.67 (d, J=8.2 Hz), −109.35 (dd, J=17.7, 9.5 Hz). MS (ESI): m/z 416.9 $(M+H)^+$.

To a magnetically stirred mixture of 6-((6-((2-(2,4-difluorophenyl)oxiran-2-yl)difluoromethyl)pyridin-3-yl)methoxy)nicotinonitrile (BZ; 200 mg, 0.482 mmol) and 1H-tetrazole (67.5 mg, 0.963 mmol) in dry DMF (4.815 mL) was added $K_2CO_3$ (133 mg, 0.963 mmol) in a dry 25 mL vial under $N_2$ atmosphere. The reaction mixture was stirred at 55° C. for 36 hours, then cooled to RT, and diluted with ice-water and ether. The layers were separated and the aq. layer was extracted again with ether (2×). The combined ether extracts were dried over sodium sulfate, filtered, and evaporated. The crude residue was purified on silica (40 gram column, gradient over 15 min to 40% EA/Hex, hold 10 min then 10 min at 80% EA/hex, monitor 240 and 254 nm). The respective product fractions were evaporated to afford the title compound contaminated with DMF. The material was diluted with water and extracted 3× with ether, the combined ether extracts were diluted with pet. ether and washed with sat'd $NH_4Cl$ (2×) and brine (1×), dried over $MgSO_4$, filtered, and evaporated to afford 98. Yield=62 mg (25.2%) of a white foam. $^1H$ NMR (400 MHz, $CDCl_3$) δ 8.75 (s, 1H), 8.63 (d, J=1.3 Hz, 1H), 8.48 (dd, J=2.3, 0.8 Hz, 1H), 7.91 (dd, J=8.2, 2.1 Hz, 1H), 7.85 (dd, J=8.7, 2.4 Hz, 1H), 7.62 (d, J=8.0 Hz, 1H), 7.56 (s, 1H), 7.35 (td, J=9.0, 6.5 Hz, 1H), 6.92 (dd, J=8.5, 0.8 Hz, 1H), 6.76 (ddd, J=12.0, 8.5, 2.5 Hz, 1H), 6.71-6.61 (m, 1H), 5.56 (d, J=14.3 Hz, 1H), 5.50 (s, 2H), 5.13 (dd, J=14.2, 1.1 Hz, 1H). $^1H$-decoupled $^{19}F$ NMR (376 MHz, $CDCl_3$) δ −103.83 (ddd, J=42.2, 17.0, 10.2 Hz), −104.20 (d, J=16.3 Hz), −104.89 (d, J=16.3 Hz), −107.90-108.07 (m), −110.92 (dd, J=262.9, 42.2 Hz). MS (ESI): m/z 486.1 $(M+H)^+$.

Compounds 99 and 100 in Table 1 were prepared using the same conditions as compound 98. (See Table 1 for starting materials.)

Analytical HPLC Methods (Included in Table 2)

Method A Specifications
 Column: Aquity BEH C-18 (50×2.1 mm, 1.7μ)
 Mobile Phase: A) $CH_3CN$; B) 0.025% aq TFA
 Flow Rate: 0.50 mL/min
 Time (min)/% B: 0.01/90, 0.5/90, 3/10, 6/10

Method B Specifications:
 Column: Eclipse XDB C-18 (150×4.6 mm, 5.0μ)
 Mobile Phase: A) $CH_3CN$; B) 5 millimolar (mM) acetic acid
 Flow Rate: 1.0 mL/min
 Time (min)/% B: 0.01/80, 2/80, 15/10, 15.01/stop Method C Specifications:
 Column: Eclipse XDB C-18 (150×4.6 mm, 5.0μ)
 Mobile Phase: A) $CH_3CN$; B) 5 mM ammonium acetate ($NH_4OAc$)
 Flow Rate: 1.0 mL/min
 Time (min)/% B: 0.01/80, 3/80, 10/10, 20/10

Method D Specifications:
 Column: Develosil ODS-HG-3 (5×4.6 mm)
 Mobile Phase: A) $CH_3CN$; B) 10 mM $NH_4OAc$
 Flow Rate: 1.0 mL/min
 Time (min)/% B: 0.01/90, 1/90, 4/10, 10/10

Method E Specifications:
 Column: Kromasil C-18 (250×4.6 mm, 5μ)
 Mobile Phase: n-Hexane:IPA (90:10)
 Flow Rate: 1.00 mL/min
 Time: 35 min Method F Specifications:
 Column: Kromasil C-18 (250×4.6 mm, 5μ)
 Mobile Phase: $CH_3CN$ −0.1% TFA in water (40:60)
 Flow Rate: 1.00 mL/min
 Time: 40 min Method G Specifications:
 Column: Zorbax SB-C18 (150×4.6 mm, 5μ)
 Mobile Phase: A) $CH_3CN$; B) 50 mM $NH_4OAc$
 Flow Rate: 1.00 mL/min
 Time (min)/% B: 0.01/90, 3/90, 10/10, 25/10

Method H Specifications:
 Column: Zorbax SB-C18 (150×4.6 mm, 5μ)
 Mobile Phase: A) $CH_3CN$; B) 0.1% TFA in water
 Flow Rate: 1.00 mL/min
 Time (min)/% B: 0.01/90, 3/90, 10/10, 25/10

Method I Specifications:
 Column: Atlantis d-C18 (250×4.6 mm, 5μ)
 Mobile Phase: A) $CH_3CN$; B) 0.1% TFA in water
 Flow Rate: 1.00 mL/min
 Time (min)/% B: 0.01/90, 2/90, 6/50, 10/20, 15/20

Method J Specifications:
 Column: Aquity UPLC BEH C-18 (50×2.1 mm, 1.7μ)
 Mobile Phase: A) $CH_3CN$; B) 5 mM $NH_4OAc$
 Flow Rate: 0.30 mL/min
 Time (min)/B: 0.01/90, 1/90, 4/50, 6/10, 10/10

Method K Specifications:
 Column: Aquity BEH Phenyl (100×2.1 mm, 1.7μ)
 Mobile Phase: A) $CH_3CN$ −10 mM $NH_4OAc$ (90:10); B) 10 mM $NH_4OAc$—$CH_3CN$ (90:10)
 Flow Rate: 0.30 mL/min
 Time (min)/% B: 0.01/90, 1/90, 6/10, 10/10

Method L Specifications:
 Column: Aquity BEH Phenyl (100×2.1 mm, 1.7μ)
 Mobile Phase: A) $CH_3CN$; B) 5 mM $NH_4OAc$
 Flow Rate: 0.30 mL/min
 Time (min)/% B: 0.01/90, 1/90, 4/50, 6/10, 10/10

Method M Specifications:
 Column: Aquity UPLC BEH C-18 (50×2.1 mm, 1.7μ)
 Mobile Phase: A) $CH_3CN$; B) 0.025% aq TFA
 Flow Rate: 0.30 mL/min
 Time (min)/% B: 0.01/90, 1/90, 6/10, 10/10

Method N Specifications:
 Column: Zorbax C18 (150×4.6 mm, 5μ)
 Mobile Phase: A) $CH_3CN$; B) 0.1% TFA in water
 Flow Rate: 1.00 mL/min
 Time (min)/% B: 0.01/95, 3/95, 10/10, 24/10

Method O Specifications:
  Column: X-Bridge, $C_{18}$, 3.5 nm, 4.6×75 mm
  Mobile Phase: A) Acetonitrile; B) 5 mM $NH_4OAc$
  Flow Rate: 0.8 mL/min
  Time (min)/% B: 0/98, 1.5/98, 3/10, 7/10, 8.01/98
Method P Specifications:
  Column: Acquity UPLC™ BEH, $C_{18}$, 1.7 nm, 2.1×50 mm
  Mobile Phase: A) 0.1% TFA in Acetonitrile; B) 0.1% TFA in $H_2O$
  Flow Rate: 0.4 mL/min
  Time (min)/% B: 0/100, 1.8/100, 3.8/25, 4.5/5, 6/5, 6.01/100
Method Q Specifications:
  Column: X-Bridge, $C_{18}$, 3.5 μm, 4.6×75 mm
  Mobile Phase: A) Acetonitrile; B) 5 mM $NH_4OAc$
  Flow Rate: 0.8 mL/min
  Time (min)/% B: 0/100, 2/55, 2.8/5, 6.8/5, 7.5/100
Method R Specifications:
  Column: Symmetry, $C_{18}$, 3.5 μm, 4.6×50 mm
  Mobile Phase: A) Acetonitrile; B) 0.1% TFA in $H_2O$
  Flow Rate: 0.8 mL/min
  Time (min)/% B: 0/98, 2/98, 4/10, 6/10, 6.5/2, 8/2, 8.01/98
Method S Specifications:
  Column: X-Select, $C_{18}$, 3.5 m, 4.6×50 mm
  Mobile Phase: A) 0.1% TFA in Acetonitrile; B) 0.1% aq. TFA
  Flow Rate: 0.8 mL/min
  Time (min)/% B: 0/90, 2/90, 5/35, 8.0/35, 8.5/5, 10/5, 10.01/90
Method T Specifications:
  Column: Acquity UPLC™ BEH, $C_{18}$, 1.7 μm, 2.1×30 mm
  Mobile Phase: A) 0.03% aq. AcOH; B) 0.03% AcOH in Acetontrile
  Flow Rate: 1.3 mL/min
  Time (min)/% B: gradient from 0/5 to 0.8/95 hold to 1.5/95
Method U Specifications:
  Column: Acquity UPLC™ BEH, $C_{18}$, 1.7 μm, 2.1×50 mm
  Mobile Phase: A) 0.1% TFA in Acetonitrile; B) 0.1% aq. TFA
  Flow Rate: 0.5 mL/min
  Time (min)/% B: 0/90, 0.7/90, 2/15, 4/15, 4.01/90
Method V Specifications:
  Column: X-Bridge, $C_{18}$, 3.5 μm, 4.6×75 mm
  Mobile Phase: A) Acetonitrile; B) 0.1% aq. TFA
  Flow Rate: 0.8 mL/min
  Time (min)/% B: 0/95, 1.5/95, 3.2/15, 4.5/5, 7.5/5, 7.51/95
Method W Specifications:
  Column: Acquity UPLC™ BEH, $C_{18}$, 1.7 μm, 2.1×50 mm
  Mobile Phase: A) 0.1% TFA in Acetonitrile; B) 0.1% aq. TFA
  Flow Rate: 0.4 mL/min
  Time (min)/% B: 0/100, 1.8/100, 3.8/25, 4.5/5, 6/5, 6.01/100

TABLE 1

Structures for Example Compounds

| Compound Number | Structure | Starting Material or Example |
|---|---|---|
| 1 | (structure shown) | Example 1 |
| 2 | (structure shown) | Example 2 |
| 3 | (structure shown) | Example 3 |

TABLE 1-continued

Structures for Example Compounds

| Compound Number | Structure | Starting Material or Example |
|---|---|---|
| 4 | (structure) | Example 4 |
| 5 | (structure) | Example 5 |
| 6 | (structure) | Example 6 |
| 7 | (structure) | Example 7 |
| 8 | (structure) | Example 8 |
| 9 | (structure) | Example 9 |

TABLE 1-continued

Structures for Example Compounds

| Compound Number | Structure | Starting Material or Example |
|---|---|---|
| 10 | 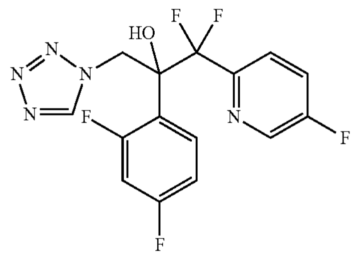 [SMILES: OC(Cn1cnnn1)(c1ccc(F)cc1F)C(F)(F)c1ccc(F)cn1] | Example 10 |
| 11 | 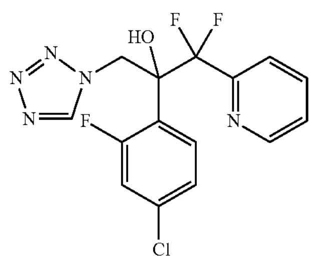 [SMILES: OC(Cn1cnnn1)(c1ccc(Cl)cc1F)C(F)(F)c1ccccn1] | Example 11 |
| 12 | 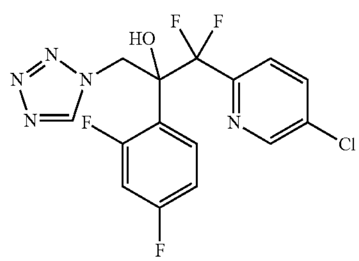 [SMILES: OC(Cn1cnnn1)(c1ccc(F)cc1F)C(F)(F)c1ccc(Cl)cn1] | Example 12 |
| 13 | 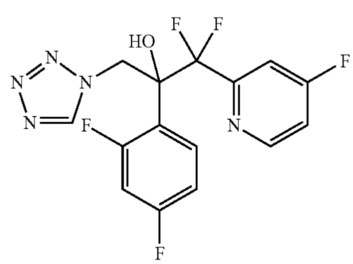 [SMILES: OC(Cn1cnnn1)(c1ccc(F)cc1F)C(F)(F)c1cc(F)ccn1] | Example 13 |
| 14 | 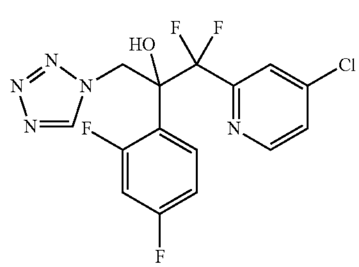 [SMILES: OC(Cn1cnnn1)(c1ccc(F)cc1F)C(F)(F)c1cc(Cl)ccn1] | Example 14 |

TABLE 1-continued

Structures for Example Compounds

| Compound Number | Structure | Starting Material or Example |
|---|---|---|
| 15 | 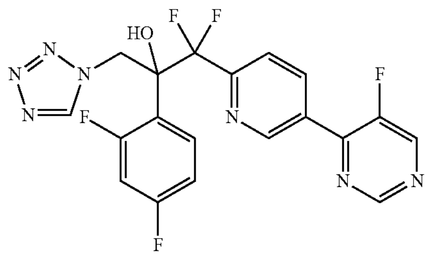 [SMILES: OC(Cn1cnnn1)(c1ccc(F)cc1F)C(F)(F)c1ccc(-c2ncncc2F)cn1] | Example 15 |
| 16 | 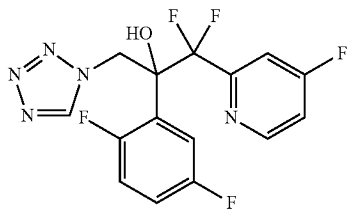 [SMILES: OC(Cn1cnnn1)(c1cc(F)ccc1F)C(F)(F)c1cc(F)ccn1] | Example 16 |
| 17 | 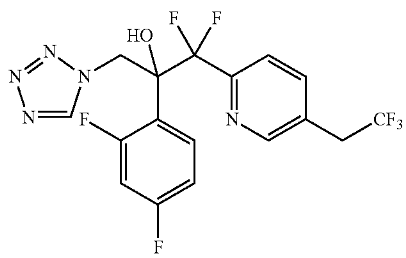 [SMILES: OC(Cn1cnnn1)(c1ccc(F)cc1F)C(F)(F)c1ccc(CC(F)(F)F)cn1] | Example 17 |
| 18 | 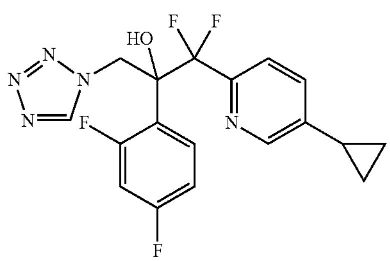 [SMILES: OC(Cn1cnnn1)(c1ccc(F)cc1F)C(F)(F)c1ccc(C2CC2)cn1] | Example 18 |
| 19 | 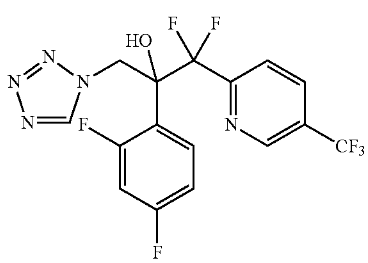 [SMILES: OC(Cn1cnnn1)(c1ccc(F)cc1F)C(F)(F)c1ccc(C(F)(F)F)cn1] | 2-bromo-5-(trifluoromethyl)pyridine |
| 20 | 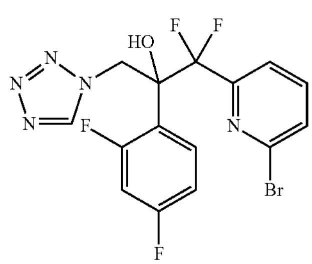 [SMILES: OC(Cn1cnnn1)(c1ccc(F)cc1F)C(F)(F)c1cccc(Br)n1] | 2,6-dibromopyridine |

TABLE 1-continued

Structures for Example Compounds

| Compound Number | Structure | Starting Material or Example |
|---|---|---|
| 21 | 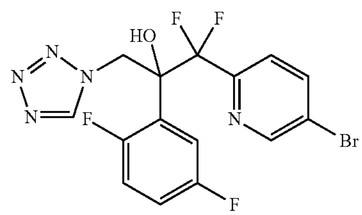 [SMILES: OC(Cn1cnnn1)(c1cc(F)ccc1F)C(F)(F)c1ccc(Br)cn1] | 2-bromo-1,4-dibromopyridine |
| 22 | 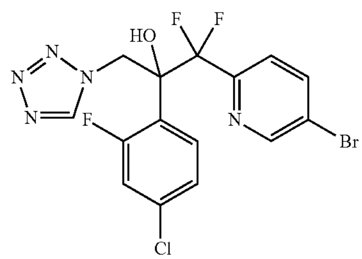 | 1-bromo-4-chloro-2-fluorobenzene |
| 23 | 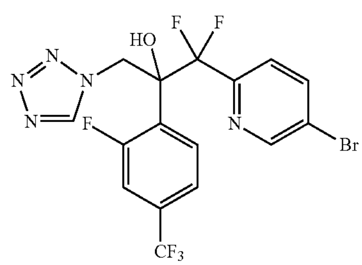 [SMILES: OC(Cn1cnnn1)(c1ccc(C(F)(F)F)cc1F)C(F)(F)c1ccc(Br)cn1] | 1-bromo-2-fluoro-4-(trifluoromethyl)benzene |
| 24 | 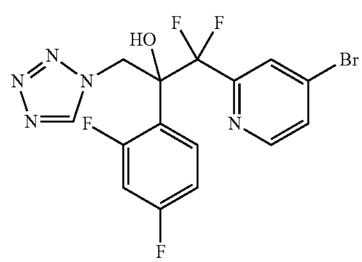 [SMILES: OC(Cn1cnnn1)(c1ccc(F)cc1F)C(F)(F)c1cc(Br)ccn1] | 2,4-dibromopyridine |
| 25 | 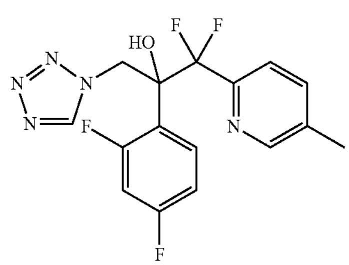 [SMILES: Cc1ccc(C(F)(F)C(O)(Cn2cnnn2)c2ccc(F)cc2F)nc1] | 2-bromo-5-methylpyridine |
| 26 | 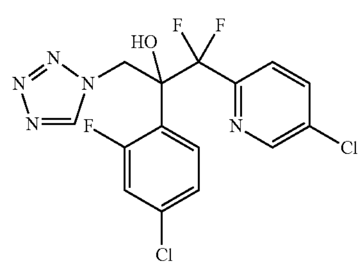 [SMILES: OC(Cn1cnnn1)(c1ccc(Cl)cc1F)C(F)(F)c1ccc(Cl)cn1] | 2-bromo-5-chloropyridine |

TABLE 1-continued

Structures for Example Compounds

| Compound Number | Structure | Starting Material or Example |
|---|---|---|
| 27 | 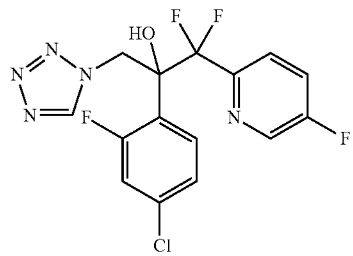 [SMILES: OC(Cn1cnnn1)(c1ccc(Cl)cc1F)C(F)(F)c1ccc(F)cn1] | 2-bromo-5-fluoropyridine |
| 28 | 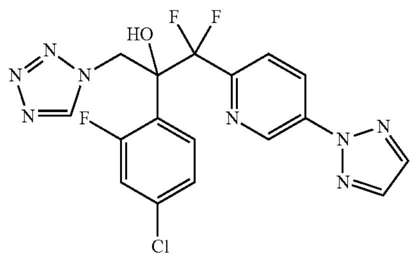 [SMILES: OC(Cn1cnnn1)(c1ccc(Cl)cc1F)C(F)(F)c1ccc(-n2nccn2)cn1] | 1-bromo-4-chloro-2-fluorobenzene |
| 29 | 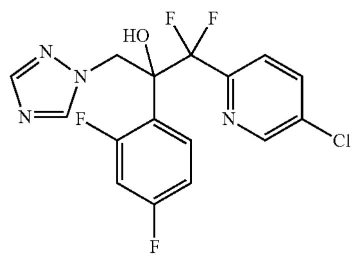 [SMILES: OC(Cn1cncn1)(c1ccc(F)cc1F)C(F)(F)c1ccc(Cl)cn1] | 1H-1,2,4-triazole |
| 30 | 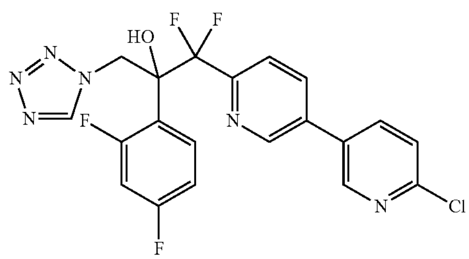 | 5-bromo-2-chloropyridine |
| 31 | 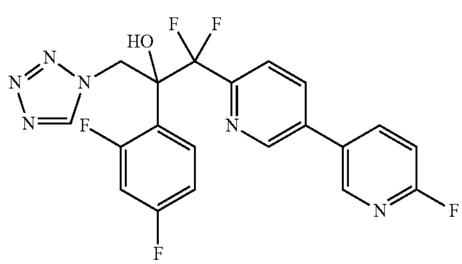 [SMILES: OC(Cn1cnnn1)(c1ccc(F)cc1F)C(F)(F)c1ccc(-c2ccc(F)nc2)cn1] | 5-bromo-2-fluoropyridine |
| 32 | 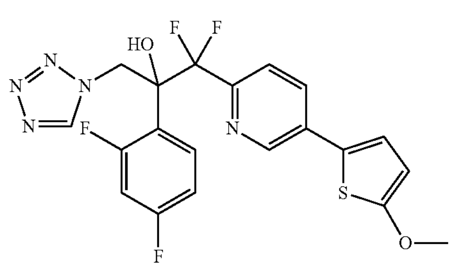 [SMILES: COc1ccc(-c2ccc(C(F)(F)C(O)(Cn3cnnn3)c3ccc(F)cc3F)nc2)s1] | 2-bromo-5-methoxythiophene |

TABLE 1-continued

Structures for Example Compounds

| Compound Number | Structure | Starting Material or Example |
|---|---|---|
| 33 | 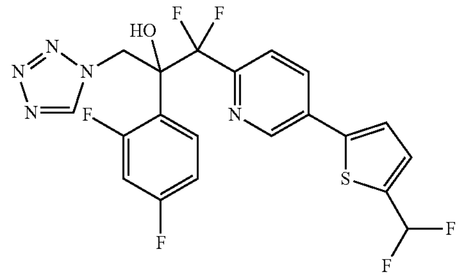 [SMILES: OC(Cn1cnnn1)(c1ccc(F)cc1F)C(F)(F)c1ccc(-c2ccc(C(F)F)s2)cn1] | 2-bromo-5-(difluoromethyl)thiophene (R) |
| 34 | 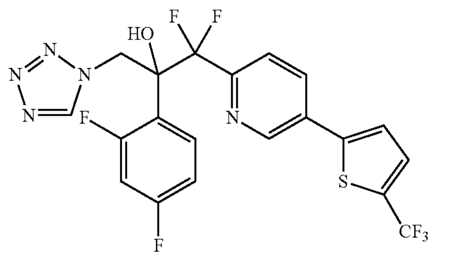 [SMILES: OC(Cn1cnnn1)(c1ccc(F)cc1F)C(F)(F)c1ccc(-c2ccc(C(F)(F)F)s2)cn1] | 2-bromo-5-(trifluoromethyl)thiophene |
| 35 | 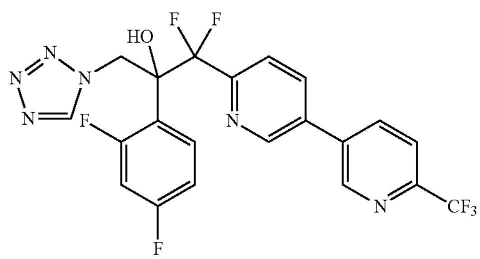 [SMILES: OC(Cn1cnnn1)(c1ccc(F)cc1F)C(F)(F)c1ccc(-c2ccc(C(F)(F)F)nc2)cn1] | 5-bromo-2-(trifluoromethyl)pyridine |
| 36 | 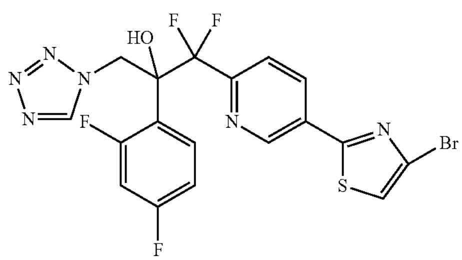 [SMILES: OC(Cn1cnnn1)(c1ccc(F)cc1F)C(F)(F)c1ccc(-c2nc(Br)cs2)cn1] | 2,4-dibromothiazole |
| 37 | 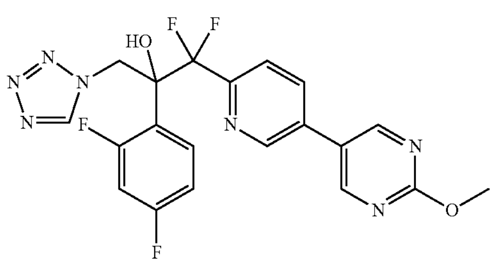 [SMILES: COc1ncc(-c2ccc(C(F)(F)C(O)(Cn3cnnn3)c3ccc(F)cc3F)nc2)cn1] | 5-bromo-2-methoxypyrimidine (S) |

TABLE 1-continued

Structures for Example Compounds

| Compound Number | Structure | Starting Material or Example |
|---|---|---|
| 38 | 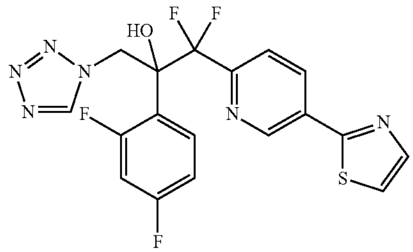 [SMILES: OC(Cn1cnnn1)(c1ccc(F)cc1F)C(F)(F)c1ccc(-c2nccs2)cn1] | 2-bromothiazole |
| 39 | 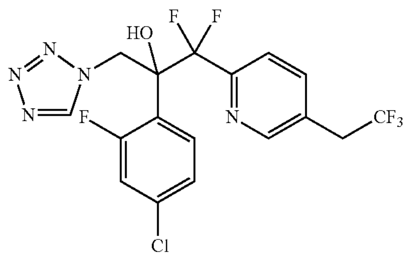 [SMILES: OC(Cn1cnnn1)(c1ccc(Cl)cc1F)C(F)(F)c1ccc(CC(F)(F)F)cn1] | 1-bromo-4-chloro-2-fluorobenzene |
| 40 | 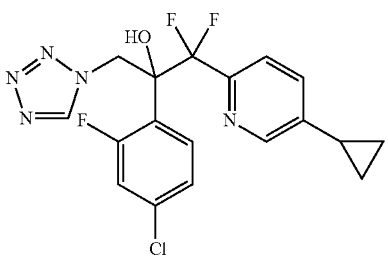 [SMILES: OC(Cn1cnnn1)(c1ccc(Cl)cc1F)C(F)(F)c1ccc(C2CC2)cn1] | 1-bromo-4-chloro-2-fluorobenzene |
| 41 | 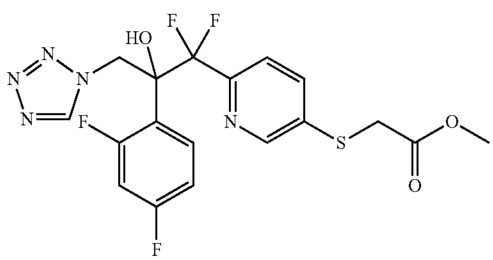 [SMILES: COC(=O)CSc1ccc(C(F)(F)C(O)(Cn2cnnn2)c2ccc(F)cc2F)nc1] | Example 20 |
| 42 | 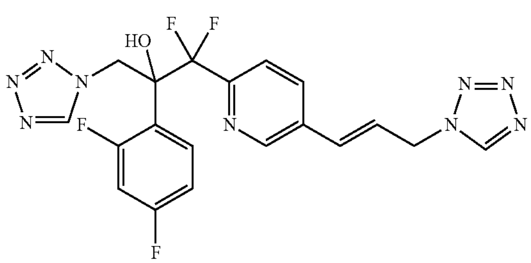 [SMILES: OC(Cn1cnnn1)(c1ccc(F)cc1F)C(F)(F)c1ccc(/C=C/Cn2cnnn2)cn1] | Example 21 |
| 43 | 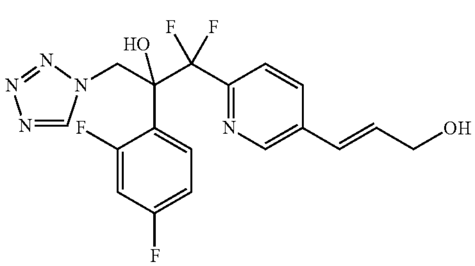 [SMILES: OC/C=C/c1ccc(C(F)(F)C(O)(Cn2cnnn2)c2ccc(F)cc2F)nc1] | Example 22 |

TABLE 1-continued

Structures for Example Compounds

| Compound Number | Structure | Starting Material or Example |
|---|---|---|
| 44 | 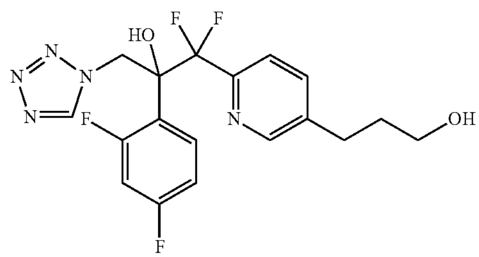 [SMILES: OCCCc1ccc(C(F)(F)C(O)(Cn2cnnn2)c2ccc(F)cc2F)nc1] | Example 23 |
| 45 | 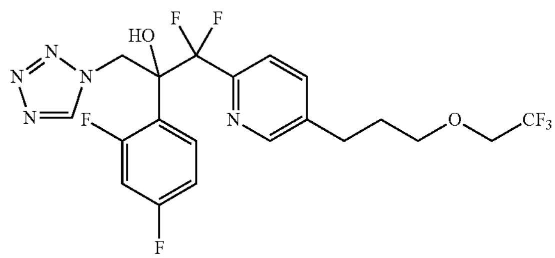 [SMILES: OC(Cn1cnnn1)(c1ccc(F)cc1F)C(F)(F)c1ccc(CCCOCC(F)(F)F)cn1] | Example 24 |
| 46 | 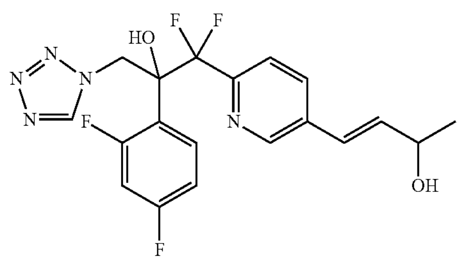 [SMILES: CC(O)/C=C/c1ccc(C(F)(F)C(O)(Cn2cnnn2)c2ccc(F)cc2F)nc1] | Example 25 |
| 47 | 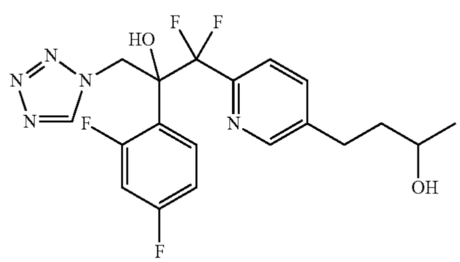 [SMILES: CC(O)CCc1ccc(C(F)(F)C(O)(Cn2cnnn2)c2ccc(F)cc2F)nc1] | Example 26 |
| 48 | 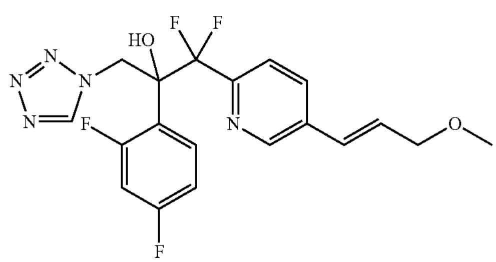 [SMILES: COC/C=C/c1ccc(C(F)(F)C(O)(Cn2cnnn2)c2ccc(F)cc2F)nc1] | Example 27 |

TABLE 1-continued

Structures for Example Compounds

| Compound Number | Structure | Starting Material or Example |
|---|---|---|
| 49 | 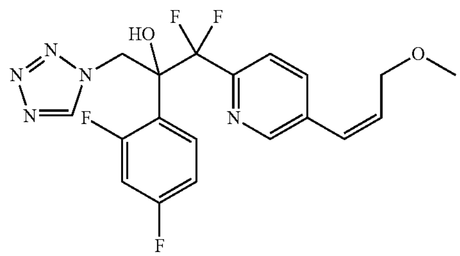 [SMILES: COC/C=C\c1ccc(C(F)(F)C(O)(Cn2cnnn2)c2ccc(F)cc2F)nc1] | Example 27 |
| 50 | 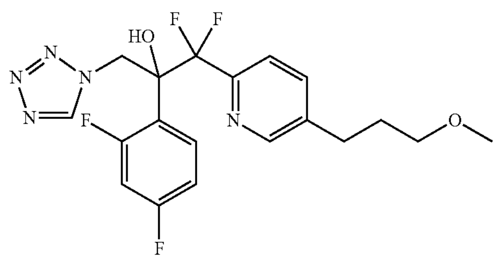 [SMILES: COCCCc1ccc(C(F)(F)C(O)(Cn2cnnn2)c2ccc(F)cc2F)nc1] | Example 28 |
| 51 | 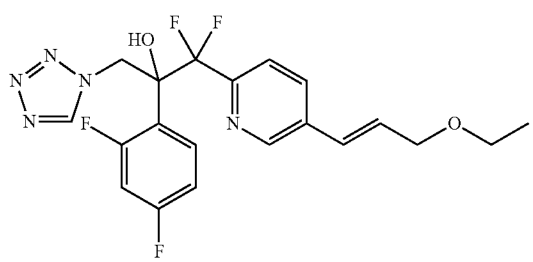 [SMILES: CCOC/C=C/c1ccc(C(F)(F)C(O)(Cn2cnnn2)c2ccc(F)cc2F)nc1] | Example 29 |
| 52 | 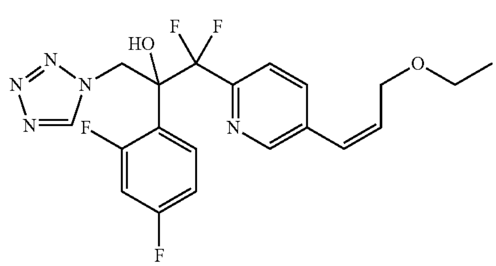 [SMILES: CCOC/C=C\c1ccc(C(F)(F)C(O)(Cn2cnnn2)c2ccc(F)cc2F)nc1] | Example 29 |
| 53 | 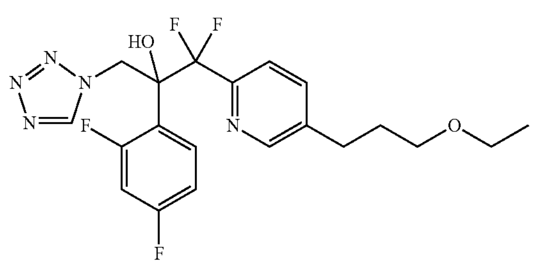 [SMILES: CCOCCCc1ccc(C(F)(F)C(O)(Cn2cnnn2)c2ccc(F)cc2F)nc1] | Example 30 |

TABLE 1-continued

Structures for Example Compounds

| Compound Number | Structure | Starting Material or Example |
|---|---|---|
| 54 | 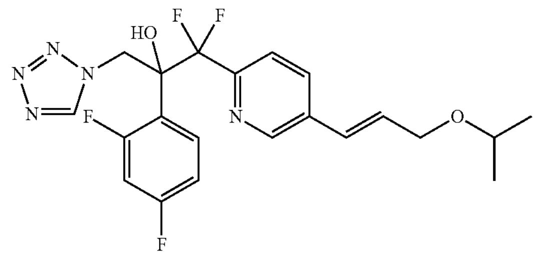 [SMILES: CC(C)OC/C=C/c1ccc(C(F)(F)C(O)(Cn2cnnn2)c2ccc(F)cc2F)nc1] | Example 31 |
| 55 | 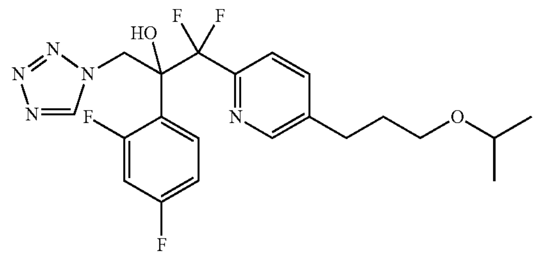 [SMILES: CC(C)OCCCc1ccc(C(F)(F)C(O)(Cn2cnnn2)c2ccc(F)cc2F)nc1] | Example 32 |
| 56 | 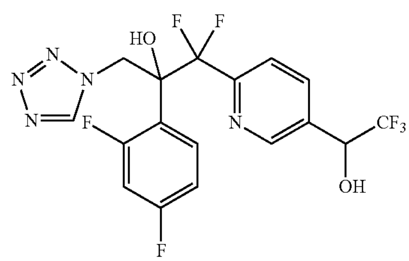 [SMILES: OC(c1ccc(C(F)(F)C(O)(Cn2cnnn2)c2ccc(F)cc2F)nc1)C(F)(F)F] | Example 33 |
| 57 | 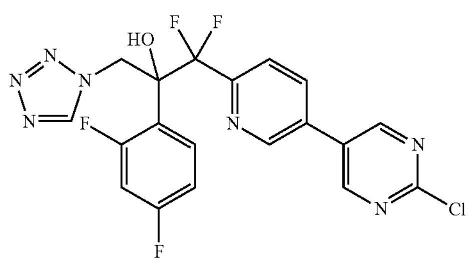 | Example 34 |
| 58 | 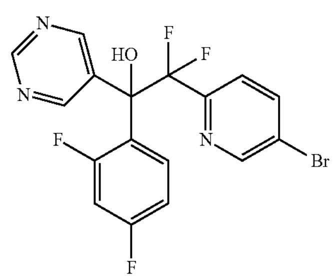 [SMILES: OC(c1cncnc1)(c1ccc(F)cc1F)C(F)(F)c1ccc(Br)cn1] | Example 35 |

TABLE 1-continued

Structures for Example Compounds

| Compound Number | Structure | Starting Material or Example |
|---|---|---|
| 59 | 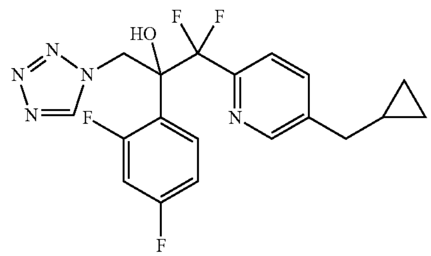 [SMILES: OC(Cn1cnnn1)(c1ccc(Cl)cc1F)C(F)(F)c1ccc(CC2CC2)cn1] | Example 36 |
| 60 | 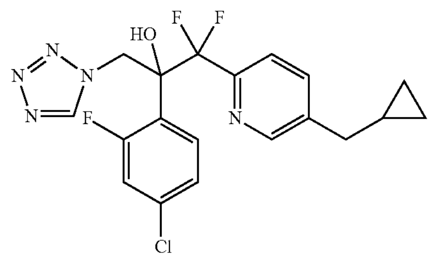 | 1-bromo-4-chloro-2-fluorobenzene |
| 61 | 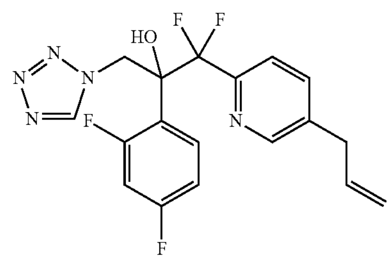 [SMILES: C=CCc1ccc(C(F)(F)C(O)(Cn2cnnn2)c2ccc(F)cc2F)nc1] | Example 36, AG |
| 62 | 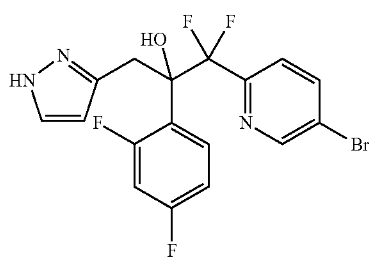 [SMILES: OC(Cc1cc[nH]n1)(c1ccc(F)cc1F)C(F)(F)c1ccc(Br)cn1] | Example 37 |
| 63 | 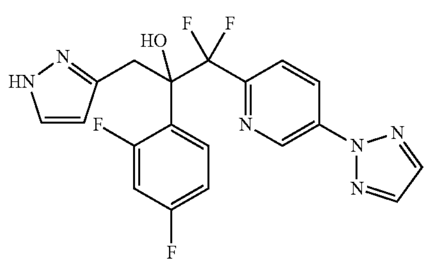 [SMILES: OC(Cc1cc[nH]n1)(c1ccc(F)cc1F)C(F)(F)c1ccc(-n2nccn2)cn1] | Example 38 |
| 64 | 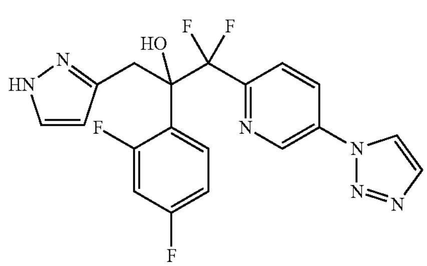 [SMILES: OC(Cc1cc[nH]n1)(c1ccc(F)cc1F)C(F)(F)c1ccc(-n2ccnn2)cn1] | Example 38 |

TABLE 1-continued

Structures for Example Compounds

| Compound Number | Structure | Starting Material or Example |
|---|---|---|
| 65 | 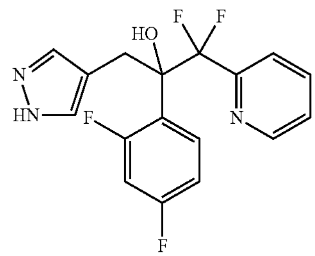 [SMILES: OC(Cc1cn[nH]c1)(c1ccc(F)cc1F)C(F)(F)c1ccccn1] | Example 39 |
| 66 | 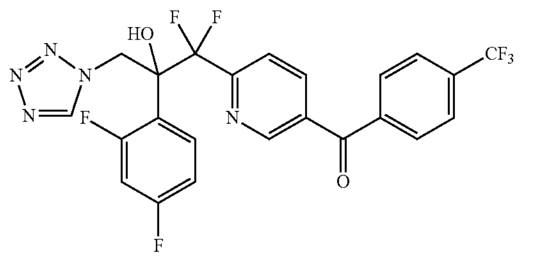 [SMILES: O=C(c1ccc(C(F)(F)F)cc1)c1ccc(C(F)(F)C(O)(Cn2cnnn2)c2ccc(F)cc2F)nc1] | Example 40 |
| 67 | 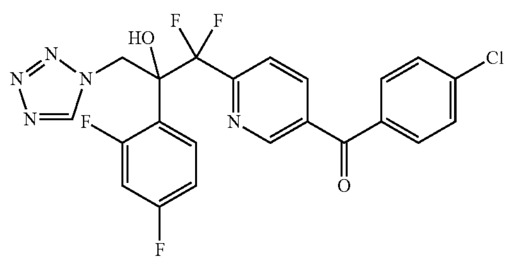 [SMILES: O=C(c1ccc(Cl)cc1)c1ccc(C(F)(F)C(O)(Cn2cnnn2)c2ccc(F)cc2F)nc1] | 4-chlorobenzaldehyde |
| 68 | 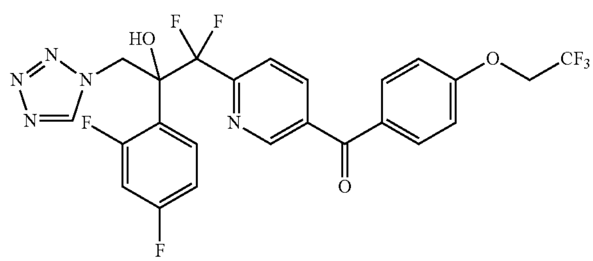 [SMILES: O=C(c1ccc(OCC(F)(F)F)cc1)c1ccc(C(F)(F)C(O)(Cn2cnnn2)c2ccc(F)cc2F)nc1] | 4-(2,2,2-trifluoroethoxy)benzaldehyde (W) |
| 69 | 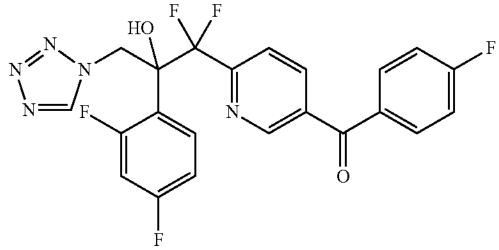 [SMILES: O=C(c1ccc(F)cc1)c1ccc(C(F)(F)C(O)(Cn2cnnn2)c2ccc(F)cc2F)nc1] | 4-fluorobenzaldehyde |

TABLE 1-continued

Structures for Example Compounds

| Compound Number | Structure | Starting Material or Example |
|---|---|---|
| 70 | 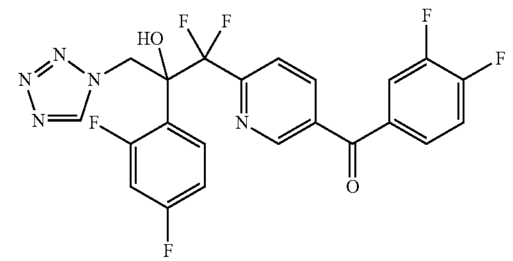 [SMILES: O=C(c1ccc(C(F)(F)C(O)(Cn2cnnn2)c2ccc(F)cc2F)nc1)c1ccc(F)c(F)c1] | 3,4-difluorobenzaldehyde |
| 71 | 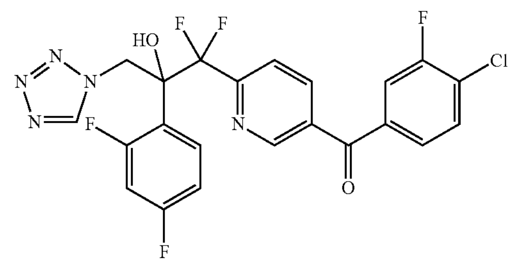 [SMILES: O=C(c1ccc(C(F)(F)C(O)(Cn2cnnn2)c2ccc(F)cc2F)nc1)c1ccc(Cl)c(F)c1] | 4-chloro-3-fluorobenzaldehyde |
| 72 | 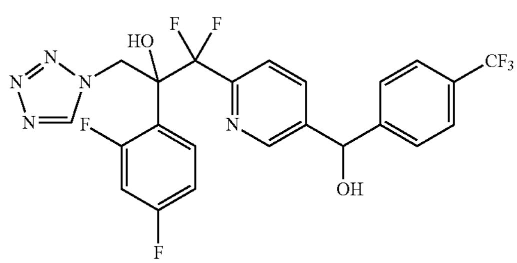 [SMILES: OC(c1ccc(C(F)(F)F)cc1)c1ccc(C(F)(F)C(O)(Cn2cnnn2)c2ccc(F)cc2F)nc1] | Example 41 |
| 73 | 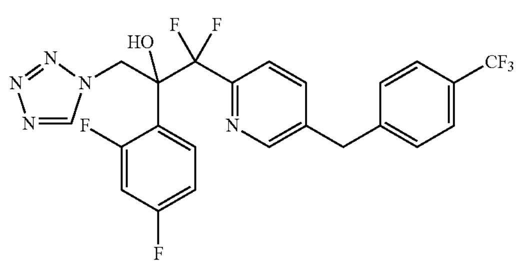 [SMILES: OC(Cn1cnnn1)(c1ccc(F)cc1F)C(F)(F)c1ccc(Cc2ccc(C(F)(F)F)cc2)cn1] | Example 42 |
| 74 | 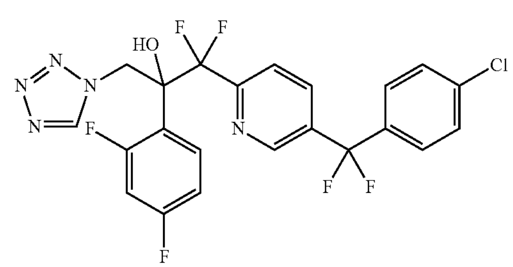 [SMILES: OC(Cn1cnnn1)(c1ccc(F)cc1F)C(F)(F)c1ccc(C(F)(F)c2ccc(Cl)cc2)cn1] | Example 43 |

TABLE 1-continued

Structures for Example Compounds

| Compound Number | Structure | Starting Material or Example |
|---|---|---|
| 75 | 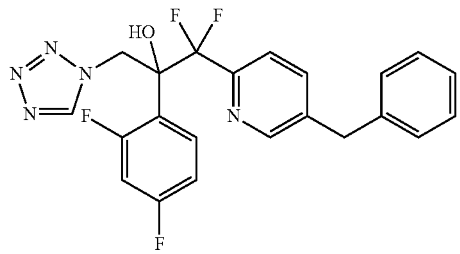 [SMILES: OC(Cn1cnnn1)(c1ccc(F)cc1F)C(F)(F)c1ccc(Cc2ccccc2)cn1] | Example 44 |
| 76 | 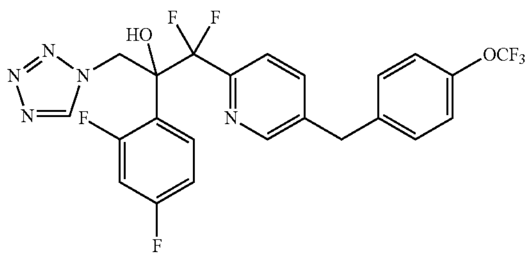 [SMILES: OC(Cn1cnnn1)(c1ccc(F)cc1F)C(F)(F)c1ccc(Cc2ccc(OC(F)(F)F)cc2)cn1] | Example 45 |
| 77 | 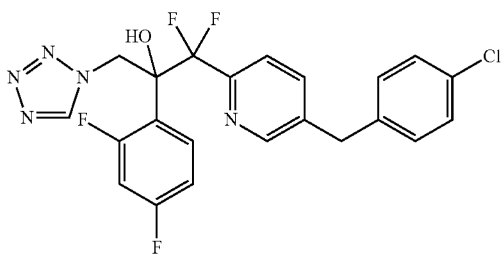 [SMILES: OC(Cn1cnnn1)(c1ccc(F)cc1F)C(F)(F)c1ccc(Cc2ccc(Cl)cc2)cn1] | 1-(bromomethyl)-4-chlorobenzene |
| 78 | 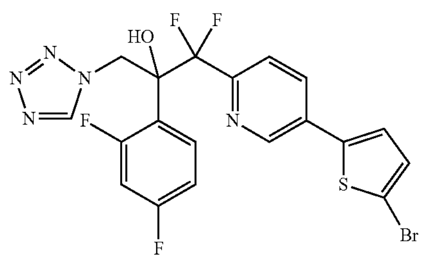 [SMILES: OC(Cn1cnnn1)(c1ccc(F)cc1F)C(F)(F)c1ccc(-c2ccc(Br)s2)cn1] | Example 46 |
| 79 | 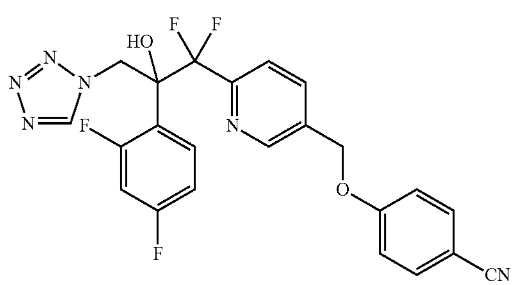 [SMILES: N#Cc1ccc(OCc2ccc(C(F)(F)C(O)(Cn3cnnn3)c3ccc(F)cc3F)nc2)cc1] | Example 47 |

TABLE 1-continued

Structures for Example Compounds

| Compound Number | Structure | Starting Material or Example |
|---|---|---|
| 80 | 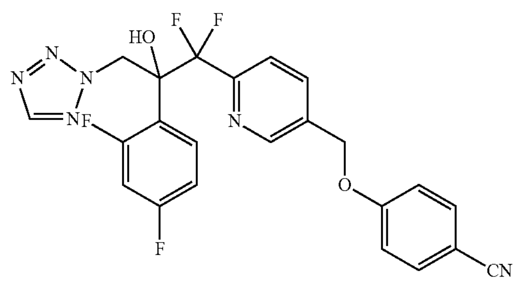 [SMILES: N#Cc1ccc(OCc2ccc(C(F)(F)C(O)(Cn3ncnn3)c3ccc(F)cc3F)nc2)cc1] | Example 47 |
| 81 | 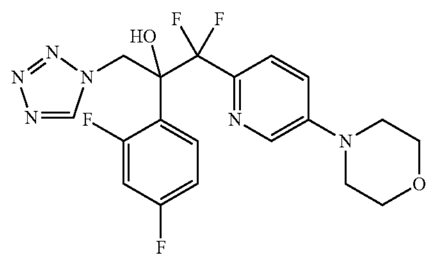 [SMILES: OC(Cn1cnnn1)(c1ccc(F)cc1F)C(F)(F)c1ccc(N2CCOCC2)cn1] | Example 48 |
| 82 | 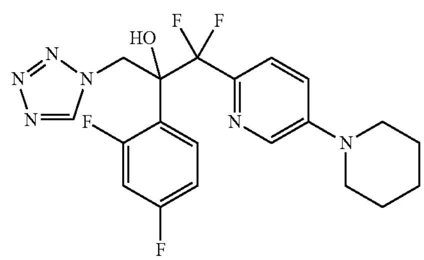 [SMILES: OC(Cn1cnnn1)(c1ccc(F)cc1F)C(F)(F)c1ccc(N2CCCCC2)cn1] | piperidine |
| 83 | 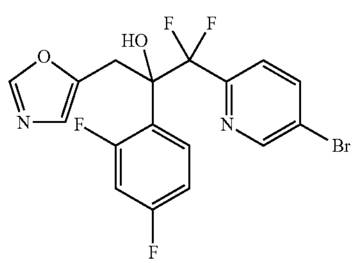 [SMILES: OC(Cc1cnco1)(c1ccc(F)cc1F)C(F)(F)c1ccc(Br)cn1] | Example 49 |
| 84 | 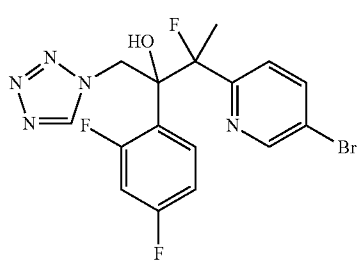 [SMILES: CC(F)(c1ccc(Br)cn1)C(O)(Cn1cnnn1)c1ccc(F)cc1F] | Example 50 |

TABLE 1-continued

Structures for Example Compounds

| Compound Number | Structure | Starting Material or Example |
|---|---|---|
| 85 | 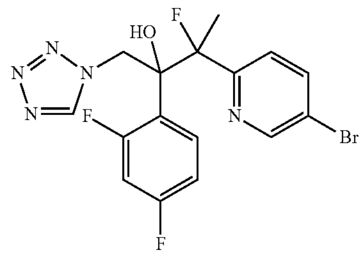 [SMILES: CC(F)(c1ccc(Br)cn1)C(O)(Cn1cnnn1)c1ccc(F)cc1F] | Example 50 |
| 86 | 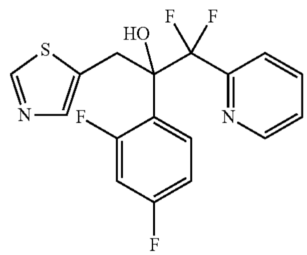 [SMILES: OC(Cc1cncs1)(c1ccc(F)cc1F)C(F)(F)c1ccccn1] | Example 51 |
| 87 | 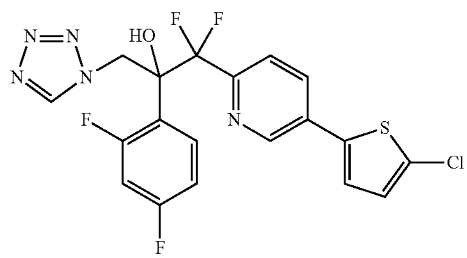 [SMILES: OC(Cn1cnnn1)(c1ccc(F)cc1F)C(F)(F)c1ccc(-c2ccc(Cl)s2)cn1] | Example 52 |
| 88 | 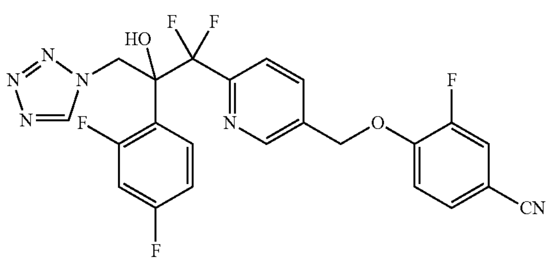 | Example 53 |
| 89 | 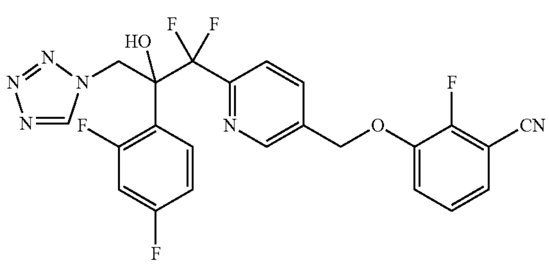 | 2-fluoro-3-hydroxybenzonitrile |
| 90 | 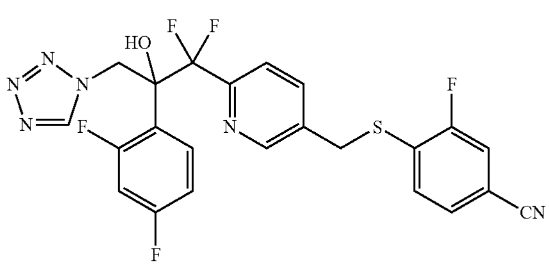 [SMILES: N#Cc1ccc(OCc2ccc(C(F)(F)C(O)(Cn3cnnn3)c3ccc(F)cc3F)nc2)c(F)c1] | 3-fluoro-4-mercaptobenzonitrile |

TABLE 1-continued
Structures for Example Compounds
| Compound Number | Structure | Starting Material or Example |
|---|---|---|
| 91 | 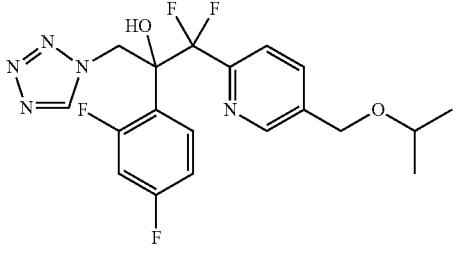 [SMILES: CC(C)OCc1ccc(C(F)(F)C(O)(Cn2cnnn2)c2ccc(F)cc2F)nc1] | propan-2-ol |
| 92 | 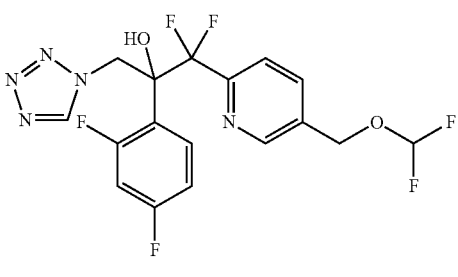 [SMILES: OC(Cn1cnnn1)(c1ccc(F)cc1F)C(F)(F)c1ccc(COC(F)F)cn1] | Example 54 |
| 93 | 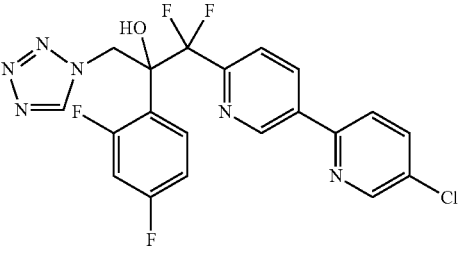 [SMILES: OC(Cn1cnnn1)(c1ccc(F)cc1F)C(F)(F)c1ccc(-c2ccc(Cl)cn2)cn1] | 2-bromo-5-chloropyridine |
| 94 | 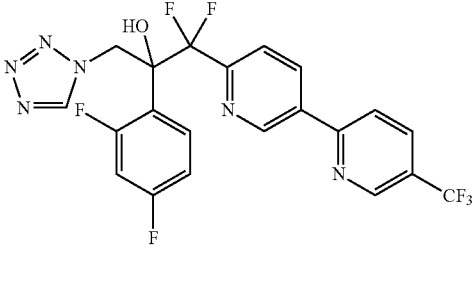 [SMILES: OC(Cn1cnnn1)(c1ccc(F)cc1F)C(F)(F)c1ccc(-c2ccc(C(F)(F)F)cn2)cn1] | 5-chloro-2-(trifluoromethyl)pyridine |
| 95 | 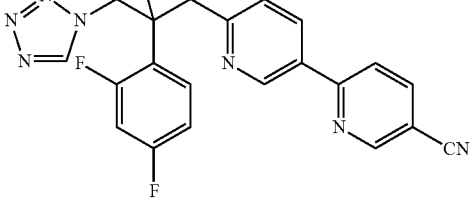 | 5-chloropicolinonitrile |

TABLE 1-continued

Structures for Example Compounds

| Compound Number | Structure | Starting Material or Example |
|---|---|---|
| 96 | 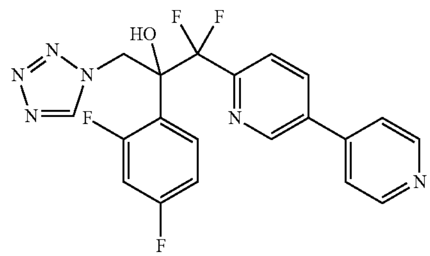 [SMILES: OC(Cn1cnnn1)(c1ccc(F)cc1F)C(F)(F)c1ccc(-c2ccncc2)cn1] | 4-bromopyridine |
| 97 | 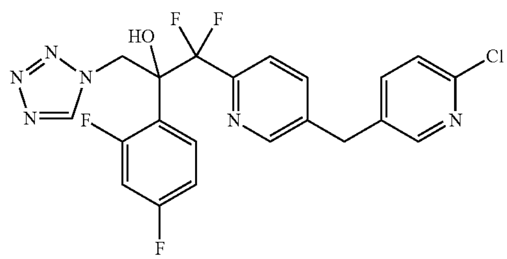 [SMILES: OC(Cn1cnnn1)(c1ccc(F)cc1F)C(F)(F)c1ccc(Cc2ccc(Cl)nc2)cn1] | Example 55 |
| 98 | 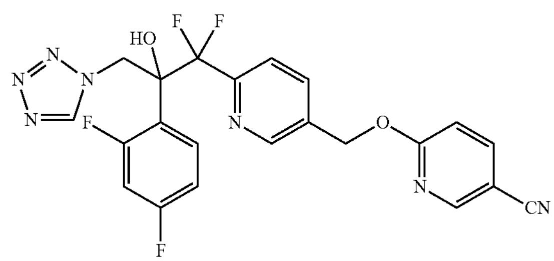 [SMILES: N#Cc1ccc(OCc2ccc(C(F)(F)C(O)(Cn3cnnn3)c3ccc(F)cc3F)nc2)nc1] | Example 56 |
| 99 | 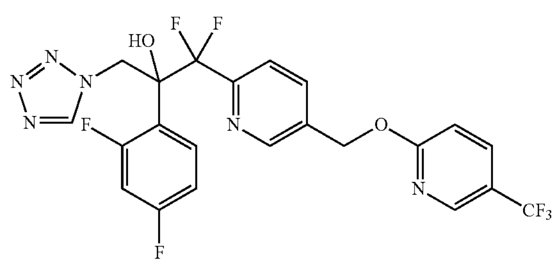 [SMILES: OC(Cn1cnnn1)(c1ccc(F)cc1F)C(F)(F)c1ccc(COc2ccc(C(F)(F)F)cn2)cn1] | 2-fluoro-5-(trifluoromethyl)pyridine |
| 100 | 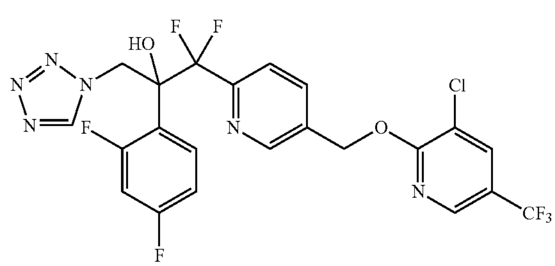 [SMILES: OC(Cn1cnnn1)(c1ccc(F)cc1F)C(F)(F)c1ccc(COc2ncc(C(F)(F)F)cc2Cl)cn1] | 3-chloro-2-fluoro-5-(trifluoromethyl)pyridine |

TABLE 1-continued

Structures for Example Compounds

| Compound Number | Structure | Starting Material or Example |
|---|---|---|
| 101 | 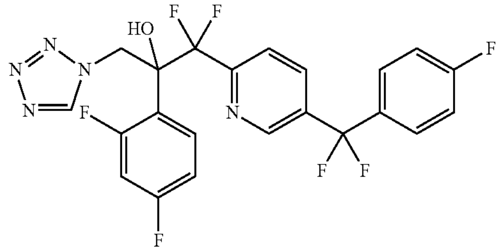 [SMILES: OC(Cn1cnnn1)(c1ccc(F)cc1F)C(F)(F)c1ccc(C(F)(F)c2ccc(F)cc2)cn1] | 4-fluorobenzaldehyde |
| 102 | 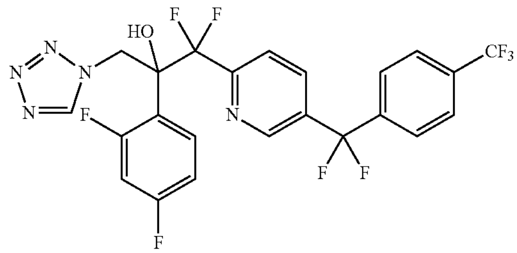 [SMILES: OC(Cn1cnnn1)(c1ccc(F)cc1F)C(F)(F)c1ccc(C(F)(F)c2ccc(C(F)(F)F)cc2)cn1] | 4-(trifluoromethyl)benzaldehyde |
| 103 | 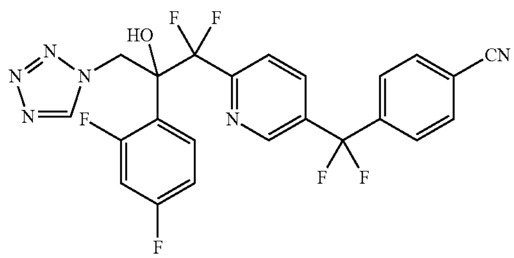 [SMILES: N#Cc1ccc(C(F)(F)c2ccc(C(F)(F)C(O)(Cn3cnnn3)c3ccc(F)cc3F)nc2)cc1] | 4-formylbenzonitrile |

TABLE 2

Analytical Data for Example Compounds in TABLE 1

| Compound Number | HPLC Method | HPLC RT | MS(ESI) (M + H) |
|---|---|---|---|
| 1 | G | 10.56 | 434.0 |
| 2 | N | 9.93 | 354.0 |
| 2(−) | A | 2.07 | 354.0 |
| 3 | D | 4.86 | 405.0 |
| 4 | H | 10.56 | 452.0 |
| 5 | D | 4.44 | 454.0 |
| 6 | A | 2.57 | 492.0 |
| 7 | D | 5.10 | 422.1 |
| 8 | D | 4.18 | 424.1 |
| 9 | D | 4.43 | 420.9 |
| 10 | A | 2.21 | 372.0 |
| 11 | A | 2.22 | 369.9 |
| 12 | A | 2.30 | 388.0 |
| 13 | A | 2.16 | 372.2 |
| ent-13 | A | 2.17 | 372.2 |
| 14 | A | 2.31 | 388.0 |
| 15 | A | 2.14 | 450.0 |
| 16 | A | 2.13 | 372.0 |
| 17 | A | 2.33 | 436.3 |
| 18 | A | 2.41 | 394.7 |
| 19 | A | 2.42 | 422.0 |
| 20 | A | 2.33 | 433.6 |
| 21 | A | 2.33 | 433.6 |
| 22 | A | 2.49 | 449.9 |
| 23 | A | 2.58 | 483.8 |
| 24 | K | 4.04 | 434.0 |
| 25 | A | 2.2 | 368.4 |
| 26 | A | 2.46 | 404.6 |
| 27 | A | 2.3 | 386 (M − 1) |
| 28 | A | 2.43 | 437.0 |
| 29 | A | 2.21 | 387.0 |
| 30 | A | 2.36 | 464.9 |
| 30(+) | A | 2.37 | 465.5 |
| 31 | A | 2.27 | 448.9 |
| 31(+) | A | 2.27 | 449.3 |
| 32 | A | 2.62 | 466.1 |
| 33 | A | 2.59 | 486.0 |
| 34 | A | 2.82 | 504.0 |
| 35 | A | 2.50 | 499.0 |
| 36 | A | 2.52 | 517.0 |
| 37 | A | 2.11 | 462.2 |
| 38 | A | 2.24 | 437.1 |
| 39 | A | 2.51 | 452.0 |
| 40 | C | 10.71 | 410.5 |
| 41 | D | 4.30 | 458.0 |
| 42 | M | 4.08 | 462.1 |
| 43 | D | 3.94 | 410.1 |
| 44 | D | 4.08 | 412.1 |
| 45 | A | 2.58 | 492.1 |
| 46 | I | 11.37 | 424.0 |
| 47 | D | 4.08 | 426.2 |
| 48 | L | 5.47 | 424.2 |
| 49 | A | 2.44 | 424.0 |
| 50 | A | 2.27 | 426.1 |

TABLE 2-continued

Analytical Data for Example Compounds in TABLE 1

| Compound Number | HPLC Method | HPLC RT | MS(ESI) (M + H) |
|---|---|---|---|
| 51 | A | 2.42 | 438.1 |
| 52 | A | 2.60 | 438.1 |
| 53 | J | 4.98 | 440.1 |
| 54 | A | 2.54 | 452.1 |
| 55 | A | 2.58 | 454.3 |
| 56 | C | 9.29 | 452.0 |
| 57 | A | 2.22 | 466.1 |
| 58 | A | 2.34 | 430.0 |
| 59 | A | 2.54 | 408.0 |
| 60 | A | 2.72 | 422 (M − 1) |
| 61 | A | 2.49 | 394.0 |
| 62 | J | 4.89 | 430.0 |
| 63 | F | 19.83 | 419.1 |
| 64 | B | 8.25 | 419.0 |
| 65 | ND | ND | 351.3 |
| 66 | A | 2.74 | 526.1 |
| 67 | A | 2.65 | 492.1 |
| 68 | A | 2.70 | 556.1 |
| 69 | A | 2.51 | 476.0 |
| 70 | A | 2.55 | 494.0 |
| 71 | A | 2.70 | 510.0 |
| 72 | E | 18.8 | 528.1 |
| 73 | A | 2.80 | 512.1 |
| 74 | A | 2.86 | 514.0 |
| 75 | A | 2.64 | 444.0 |
| 76 | A | 2.85 | 528.0 |
| 77 | A | 2.79 | 478.0 |
| 78 | A | 2.78 | 516.0 |
| 78(+) | A | 2.79 | 514.0 |
| 79 | B | 8.14 | 485.4 |
| 80 | B | 8.39 | 485.3 |
| 81 | A | 2.14 | 440.4 |
| 82 | A | 2.57 | 437.5 |
| 83 | A | 2.43 | 432.8 |
| 84 | A | 2.64 | 427.9 |
| 85 | A | 2.51 | 428.0 |
| 86 | C | 9.62 | 368.9 |
| 87 | A | 2.68 | 470 |
| 88 | A | 2.51 | 502 |
| 89 | A | 2.54 | 503 |
| 90 | A | 2.61 | 519 |
| 91 | A | 2.51 | 426 |
| 92 | A | 2.37 | 434.5 |
| 93 | O | 4.75 | 465.1 |
| 94 | P | 4.01 | 499.2 |
| 95 | Q | 4.48 | ND |
| 96 | R | 4.55 | 430.7 |
| 97 | S | 6.37 | 479.1 |
| 98 | T | 0.58 | 486.1 |
| 99 | T | 0.72 | 529.1 |
| 100 | T | 0.75 | 563.0 |
| 101 | U | 3.65 | 497.8 |
| 102 | V | 5.59 | 548.0 |
| 103 | W | 4.01 | 504.9 |

ND—Not detected

Example 57

Metalloenzyme Activity

A. Minimum Inhibitory Concentration (MIC) (*C. albicans*)

Compounds of the present disclosure were assessed for their ability to inhibit the growth of common strains of fungus, *C. albicans* using a standardized procedure (CLSI M27-A2).

Stock solutions of the test compounds and standards were prepared in DMSO at 1,600 µg/mL (*C. albicans*). Eleven, serial, one-half dilutions of compounds were prepared in 96-well plates in RPMI+MOPS. The assay concentration ranges were 8-0.001 µg/mL (*C. albicans*). Cell suspensions of *C. albicans* were prepared and added to each well at concentrations of approximately $3.7 \times 10^3$ colony-forming-units per milliliter (cfu/mL). All testing was in duplicate. The inoculated plates were incubated for approximately 48 h at 35±1° C. At the completion of incubation the wells of each plate were evaluated visually for the presence of fungal growth.

For fluconazole and the test compounds, the MIC was the concentration at which growth was significantly reduced (about 50% reduction). For voriconazole the MIC was the concentration which reduced *C. albicans* growth by 50% (per CLSI, M27-A2). For QC purposes *C. krusei* isolate ATCC 6258 ($4.0 \times 10^3$ cfu/mL) was included in the VOR assay. This isolate did not exhibit trailing growth against voriconazole, therefore the MIC was the concentration at which growth was completely inhibited.

B. Inhibition of Liver Cytochrome P450 Enzymes

Solutions of each test compound were separately prepared at concentrations of 20000, 6000, 2000, 600, 200, and 60 µM by serial dilution with DMSO:MeCN (50:50 v/v). The individual test compound solutions were then diluted 20-fold with DMSO:MeCN:deionized water (5:5:180 v/v/v) to concentrations of 1000, 300, 100, 30, 10, and 3 µM. Mixtures of isozyme inhibitors (sulfaphenazole, tranylcypromine, and ketoconazole as specific inhibitors of isozymes 2C9, 2C19, and 3A4, respectively) were prepared containing each inhibitor at concentrations of 6000, 2000, 600, 200, 60, 20, 6, and 2 µM by serial dilution with DMSO:CH$_3$CN (50:50 v/v). The mixed inhibitor solutions were then diluted 20-fold with DMSO: CH$_3$CN:deionized water (5:5:180 v/v/v) to concentrations of 300, 100, 30, 10, 3, 1, 0.3, and 0.1 µM. The percent of organic solvent attributable to the test compound or inhibitor mixture in the final reaction mixture was 2% v/v.

Pooled human liver microsome suspension (20 mg/mL) was diluted with phosphate buffer to obtain a 5 mg/mL suspension. A solution of NADPH was prepared in phosphate buffer at a concentration of 5 mM. Separate stock solutions of each substrate were prepared in DMSO:MeCN (50:50 v/v), mixed, and diluted in phosphate buffer to obtain a single solution containing each substrate at five times its experimentally determined $K_m$ concentration. The percent of organic solvent attributable to substrate mixture in the final reaction mixture was 1% v/v.

Substrate solution and microsome suspension were combined in a 1:1 volume ratio, mixed, and distributed to reaction wells of a PCR plate. Individual test compound or combined inhibitor solutions at each concentration were added to the wells and mixed by repetitive aspirate-dispense cycles. For active controls, blank phosphate buffer solution was added in place of test compound solution. Reaction mixtures were allowed to equilibrate at 37° C. for approximately two minutes before adding NADPH solution to initiate reaction, followed by pipette mixing of reaction mixture. Ten minutes after addition of NADPH, the reaction mixtures were quenched with cold acetonitrile. The samples were mixed by orbital shaking for approximately one minute and centrifuged at 2900 RCF for ten minutes. A portion of the supernatant was analyzed by gradient reverse-phase HPLC with detection by electrospray ionization triple quadrupole mass spectrometry in the positive ion mode.

Data was fitted to sigmoid dose-response curves and the inhibitory potency of each test compound was determined as its IC$_{50}$ value.

Results

Note: conversion of *Candida* MIC (median inhibitory concentration) results expressed as µg/mL provides:

| Example | Candida MIC* | CYP2C9 IC50 | CYP2C19 IC50 | CYP3A4 IC50 |
|---|---|---|---|---|
| 4 | ≤0.016 | 75 | 166 | 83 |
| 6 | ≤0.016 | 145 | 91 | 81 |
| 30 | 0.062 | 42 | 53 | 17 |
| 31 | 0.062 | 81 | 61 | 33 |
| Fluconazole | 0.5 | 29 | 8.2 | 8.0 |
| Voriconazole | 0.016 | 14 | 15 | 13 |

*Candida albicans* MICs are in μg/mL; CYP IC50s are in μM.

C. Minimum Inhibitory Concentration (MIC) (*Septoria tritici*)

Compounds of the present disclosure were assessed for their ability to inhibit the growth of a common strain of the fungal plant pathogen *Septoria tritici* (ATCC 26517) using a procedure based on a Clinical and Laboratory Standards Institute (CLSI) microdilution assay protocol for filamentous fungi.

Stock solutions of the test compounds and standards were prepared in DMSO at 6400 μg/mL. Each stock solution was used to prepare a 2-fold dilution series ranging from 16 to 0.016 μg/mL (total of 11 compound concentrations) in RPMI-1640 (Roswell Park Memorial Institute) medium containing 3-(N-morpholino)propanesulfonic acid (MOPS) buffer and 2% DMSO. A 100 μL aliquot of the dilutions was added to columns 1 (16 μg/mL compound) through 11 (0.016 μg/mL compound) of a 96-well microtiter plate. This format was replicated in a second row of the microtiter plate. Thus, each microtiter plate could include 11 concentrations of four test or control compounds replicated twice. A 100 μL aliquot of RPMI-1640/MOPS/2% DMSO medium was added to column 12 (no compound control) of the microtiter plate.

A fresh culture of *S. tritici* was used to prepare a solution of approximately $5 \times 10^4$ colony-forming units per milliliter (cfu/mL) in RPMI/MOPS medium without DMSO. A 100 μL aliquot of this solution was added to all 96 wells in the microtiter plate. This results in final concentrations of each test or control compound of 8 μg/mL to 0.008 μg/mL in 200 μL of RPMI/MOPS media containing 1% DMSO and approximately $2.5 \times 10^4$ cfu/mL of *S. tritici*. The assay plates were incubated at 22° C. for seven days in the dark without shaking. The MIC for each compound was visually determined as the concentration which resulted in 50% reduction in the growth of *S. tritici* in comparison to the control (column 12).

In each case of Table 3 the *Septoria* rating scale is as follows:

| MIC (μg/mL) | Rating |
|---|---|
| ≤0.5 | A |
| >0.5-1.5 | B |
| >1.5-4 | C |
| >4 | D |
| Not tested | E |

D. Evaluation of Fungicidal Activity Vs. Leaf Rust (Causal Agent *Puccinia recondita tritici*=*Puccinia triticina*; Bayer code PUCCRT).

Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compounds. The compounds were formulated at 50 ppm in 10 vol. % acetone plus 90 vol. % Triton X water (deionized water 99.99 wt %+0.01 wt % Triton X100), giving a "formulated test compound." Formulated test compounds were applied to plants using a turn table sprayer fitted with two opposing air atomization nozzles which delivered approximately 1500 L/ha of spray volume. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants. Disease severity was evaluated 7-9 days later, depending on the speed of disease development.

In each case of Table 3, the *Puccinia* rating scale is as follows:

| % Disease Control @ 50 ppm | Rating |
|---|---|
| 80-100 | A |
| 60-79 | B |
| 40-59 | C |
| <40 | D |
| Not tested | E |

TABLE 3

Biological Data for Compounds in TABLE 1

| Compound Number | *Septoria* Rating | *Puccinia* Rating |
|---|---|---|
| 1 | A | A |
| 2 | E | E |
| 2(−) | A | A |
| 3 | B | E |
| 4 | A | E |
| 5 | A | E |
| 6 | A | D |
| 7 | C | E |
| 8 | B | E |
| 9 | C | E |
| 10 | B | A |
| 11 | C | E |
| 12 | B | E |
| 13 | E | E |
| ent-13 | B | E |
| 14 | C | E |
| 15 | E | E |
| 16 | E | E |
| 17 | A | A |
| 18 | A | A |
| 19 | C | E |
| 20 | C | E |
| 21 | D | E |
| 22 | A | A |
| 23 | C | E |
| 24 | C | E |
| 25 | B | A |
| 26 | A | A |
| 27 | B | A |
| 28 | A | A |
| 29 | A | A |
| 30 | A | A |
| 30(+) | B | E |
| 31 | C | E |
| 31(+) | A | E |
| 32 | A | C |
| 33 | A | A |
| 34 | B | A |
| 35 | C | E |
| 36 | B | E |
| 37 | C | E |
| 38 | A | E |
| 39 | A | A |
| 40 | A | A |

TABLE 3-continued

Biological Data for Compounds in TABLE 1

| Compound Number | Septoria Rating | Puccinia Rating |
|---|---|---|
| 41 | D | E |
| 42 | D | E |
| 43 | C | E |
| 44 | C | E |
| 45 | A | A |
| 46 | C | E |
| 47 | C | E |
| 48 | B | E |
| 49 | A | E |
| 50 | B | E |
| 51 | A | D |
| 52 | A | D |
| 53 | A | A |
| 54 | B | D |
| 55 | A | E |
| 56 | D | E |
| 57 | D | E |
| 58 | B | E |
| 59 | A | A |
| 60 | A | A |
| 61 | C | E |
| 62 | A | E |
| 63 | B | E |
| 64 | D | E |
| 65 | C | E |
| 66 | A | A |
| 67 | A | A |
| 68 | A | A |
| 69 | A | A |
| 70 | A | E |
| 71 | A | A |
| 72 | C | E |
| 73 | A | A |
| 74 | C | E |
| 75 | A | A |
| 76 | A | A |
| 77 | A | A |
| 78 | A | E |
| 78(+) | A | E |
| 79 | A | A |
| 80 | D | E |
| 81 | C | E |
| 82 | C | E |
| 83 | A | A |
| 84 | B | E |
| 85 | C | E |
| 86 | A | E |
| 87 | E | E |
| 88 | A | A |
| 89 | A | A |
| 90 | B | C |
| 91 | B | E |
| 92 | A | A |
| 93 | A | A |
| 94 | A | A |
| 95 | C | A |
| 96 | C | B |
| 97 | A | E |
| 98 | A | A |
| 99 | A | A |
| 100 | A | A |
| 101 | C | A |
| 102 | C | A |
| 103 | C | A |

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method of inhibiting metalloenzyme activity comprising contacting a compound of Formula I, or salt thereof, with a metalloenzyme:

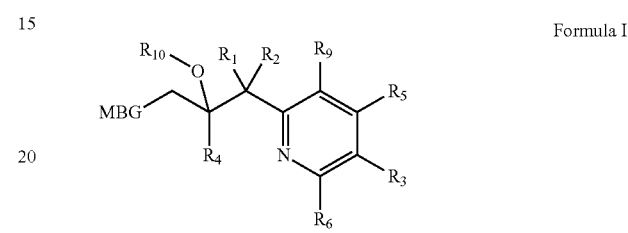

Formula I

MBG is optionally substituted tetrazolyl, optionally substituted oxazolyl, optionally substituted pyrimidinyl, optionally substituted thiazolyl, or optionally substituted pyrazolyl;

$R_1$ is halo or haloalkyl;

$R_2$ is H, halo, alkyl, or haloalkyl;

$R_3$ is independently H, alkyl, alkenyl, cycloalkyl, heteroaryl, hydroxyalkyl, cyano, haloalkyl, halo, —C(O)phenyl, —CH(OH)(aryl), —CH$_2$(aryl), —CH$_2$(heteroaryl), —CF$_2$(aryl), —CF$_2$(heteroaryl), —CH$_2$O(aryl), —CH$_2$O(heteroaryl), —CH$_2$S(O)$_x$(aryl), and cyclic amino, wherein each of the alkyl, alkenyl, cycloalkyl, heteroaryl, hydroxyalkyl, haloalkyl, —C(O)phenyl, —CH(OH)(aryl), —CH$_2$(aryl), —CH$_2$(heteroaryl), —CF$_2$(aryl), CF$_2$(heteroaryl), —CH$_2$O(aryl), —CH$_2$O(heteroaryl), —CH$_2$S(O)$_x$(aryl), and cyclic amino may be optionally substituted with 1, 2 or 3 independent $R_7$;

$R_4$ is aryl, heteroaryl, or cycloalkyl, each optionally substituted with 0, 1, 2 or 3 independent $R_8$;

$R_5$ is independently H, halo, alkyl, alkoxy, cyano, haloalkyl, haloalkoxy, halothioalkyl, thioalkyl, SF$_3$, SF$_6$, SCN, SO$_2$R$_{11}$, cycloalkyl, —C(O)alkyl, —C(O)OH, —C(O)Oalkyl;

$R_6$ is independently H, halo, alkyl, alkoxy, cyano, haloalkyl, haloalkoxy, halothioalkyl, thioalkyl, SF$_3$, SF$_6$, SCN, SO$_2$R$_{11}$, cycloalkyl, —C(O)alkyl, —C(O)OH, —C(O)Oalkyl;

each $R_7$ is independently cyano, cycloalkyl, haloalkyl, hydroxy, alkoxy, aryl, aryloxy, heteroaryloxy, halo, haloalkoxy, —C(O)alkyl, —C(O)OH, —C(O)Oalkyl;

each $R_8$ is independently cyano, haloalkyl, hydroxy, alkoxy, halo, or haloalkoxy;

$R_9$ is H, halo, or haloalkyl;

$R_{10}$ is H, alkyl, —Si(R$_{12}$)$_3$, —P(O)(OH)$_2$, —CH$_2$—O—P(O)(OH)$_2$, or C(O)alkyl optionally substituted with amino;

$R_{11}$ is independently alkyl, aryl, substituted aryl, heteroaryl or substituted heteroaryl;

$R_{12}$ is independently alkyl or aryl; and x is independently 0, 1, or 2.

2. The method of claim 1, wherein the metalloenzyme is lanosterol demethylase (CYP51).

3. A method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound of Formula I, or salt thereof, such that said subject is treated for said disorder:

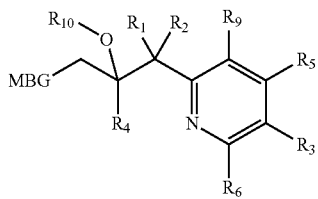

Formula I

MBG is optionally substituted tetrazolyl, optionally substituted oxazolyl, optionally substituted pyrimidinyl, optionally substituted thiazolyl, or optionally substituted pyrazolyl;

$R_1$ is halo or haloalkyl;

$R_2$ is H, halo, alkyl, or haloalkyl;

$R_3$ is independently H, alkyl, alkenyl, cycloalkyl, heteroaryl, hydroxyalkyl, cyano, haloalkyl, halo, —C(O)phenyl, —CH(OH)(aryl), —CH$_2$(aryl), —CH$_2$(heteroaryl), —CF$_2$(aryl), —CF$_2$(heteroaryl), —CH$_2$O(aryl), —CH$_2$O(heteroaryl), —CH$_2$S(O)$_x$(aryl), and cyclic amino, wherein each of the alkyl, alkenyl, cycloalkyl, heteroaryl, hydroxyalkyl, haloalkyl, —C(O)phenyl, —CH(OH)(aryl), —CH$_2$(aryl), —CH$_2$(heteroaryl), —CF$_2$(aryl), CF$_2$(heteroaryl), —CH$_2$O(aryl), —CH$_2$O(heteroaryl), —CH$_2$S(O)$_x$(aryl), and cyclic amino may be optionally substituted with 1, 2 or 3 independent $R_7$;

$R_4$ is aryl, heteroaryl, or cycloalkyl, each optionally substituted with 0, 1, 2 or 3 independent $R_8$;

$R_5$ is independently H, halo, alkyl, alkoxy, cyano, haloalkyl, haloalkoxy, halothioalkyl, thioalkyl, SF$_3$, SF$_6$, SCN, SO$_2$R$_{11}$, cycloalkyl, —C(O)alkyl, —C(O)OH, —C(O)Oalkyl;

$R_6$ is independently H, halo, alkyl, alkoxy, cyano, haloalkyl, haloalkoxy, halothioalkyl, thioalkyl, SF$_3$, SF$_6$, SCN, SO$_2$R$_{ii}$, cycloalkyl, —C(O)alkyl, —C(O)OH, —C(O)Oalkyl;

each $R_7$ is independently cyano, cycloalkyl, haloalkyl, hydroxy, alkoxy, aryl, aryloxy, heteroaryloxy, halo, haloalkoxy, —C(O)alkyl, —C(O)OH, —C(O)Oalkyl;

each $R_8$ is independently cyano, haloalkyl, hydroxy, alkoxy, halo, or haloalkoxy;

$R_9$ is H, halo, or haloalkyl;

$R_{10}$ is H, alkyl, —Si(R$_{12}$)$_3$, —P(O)(OH)$_2$, —CH$_2$—O—P(O)(OH)$_2$, or —C(O)alkyl optionally substituted with amino;

$R_{11}$ is independently alkyl, aryl, substituted aryl, heteroaryl or substituted heteroaryl;

$R_{12}$ is independently alkyl or aryl; and x is independently 0, 1, or 2.

4. The method of claim 3, wherein the disease or disorder is mediated by any of 4-hydroxyphenyl pyruvate dioxygenase, 5-lipoxygenase, adenosine deaminase, alcohol dehydrogenase, aminopeptidase N, angiotensin converting enzyme, aromatase (CYP19), calcineurin, carbamoyl phosphate synthetase, carbonic anhydrase family, catechol-O-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, or xanthine oxidase.

5. The method of claim 3, wherein the disease or disorder is cancer, cardiovascular disease, endocrinologic disease, inflammatory disease, infectious disease, gynecologic disease, metabolic disease, ophthalmologic disease, central nervous system (CNS) disease, urologic disease, or gastrointestinal disease.

6. The method of claim 3, wherein the disease or disorder is systemic fungal infection, or onychomycosis.

7. The method of claim 3, wherein $R_1$ is fluoro.

8. The method of claim 3, wherein $R_2$ is fluoro.

9. The method of claim 3, wherein $R_1$ and $R_2$ are fluoro.

10. The method of claim 3, wherein $R_4$ is phenyl optionally substituted with 0, 1, 2 or 3 independent $R_8$.

11. The method of claim 3, wherein $R_4$ is phenyl optionally substituted with 0, 1, 2 or 3 independent halo.

12. The method of claim 3, wherein $R_4$ is phenyl optionally substituted with 0, 1, 2 or 3 independent fluoro.

13. The method of claim 3, wherein $R_4$ is 2,4-difluorophenyl.

14. The method of claim 3, wherein $R_5$ is halo.

15. The method of claim 3, wherein $R_3$ is heteroaryl optionally substituted with 1, 2 or 3 independent $R_7$.

16. The method of claim 3, wherein:
$R_1$ is fluoro;
$R_2$ is fluoro;
$R_4$ is 2,4-difluorophenyl; and
$R_3$ is alkyl substituted with 1, 2 or 3 independent $R_7$.

17. The method of claim 3, wherein:
$R_1$ is fluoro;
$R_2$ is fluoro;
$R_4$ is 2,4-difluorophenyl; and
$R_3$ is alkenyl substituted with 1, 2 or 3 independent $R_7$.

18. The method of claim 3, wherein:
$R_3$ is halo.

19. The method of claim 3, wherein the compound is one of:
1-(5-Bromopyridin-2-yl)-2-(2,4-difluorophenyl)-1,1-difluoro-3-(1H-tetrazol-1-yl) propan-2-ol (1);
2-(2,4-Difluorophenyl)-1,1-difluoro-1-(pyridin-2-yl)-3-(1H-tetrazol-1-yl)propan-2-ol (2);
(E)-3-(6-(2-(2,4-Difluorophenyl)-1,1-difluoro-2-hydroxy-3-(1H-tetrazol-1-yl)propyl)pyridin-3-yl)acrylonitrile (3);
(E)-Ethyl 3-(6-(2-(2,4-difluorophenyl)-1,1-difluoro-2-hydroxy-3-(1H-tetrazol-1-yl)propyl)pyridin-3-yl)acrylate (4);
Ethyl 3-(6-(2-(2,4-difluorophenyl)-1,1-difluoro-2-hydroxy-3-(1H-tetrazol-1-yl)propyl)pyridin-3-yl)propanoate (5);
(E)-2-(2,4-Difluorophenyl)-1,1-difluoro-3-(1H-tetrazol-1-yl)-1-(5-(3-(2,2,2-trifluoroethoxy)prop-1-enyl)pyridin-2-yl)propan-2-ol (6);
(E)-4-(6-(2-(2,4-Difluorophenyl)-1,1-difluoro-2-hydroxy-3-(1H-tetrazol-1-yl)propyl)pyridin-3-yl)but-3-en-2-one (7);

4-(6-(2-(2,4-Difluorophenyl)-1,1-difluoro-2-hydroxy-3-(1H-tetrazol-1-yl)propyl)pyridin-3-yl)butan-2-one (8);

1-(5-(2H-1,2,3-Triazol-2-yl)pyridin-2-yl)-2-(2,4-difluorophenyl)-1,1-difluoro-3-(1H-tetrazol-1-yl)propan-2-ol (9);

2-(2,4-Difluorophenyl)-1,1-difluoro-1-(5-fluoropyridin-2-yl)-3-(1H-tetrazol-1-yl)propan-2-ol (10);

2-(4-Chloro-2-fluorophenyl)-1,1-difluoro-1-(pyridin-2-yl)-3-(1H-tetrazol-1-yl)propan-2-ol (11);

1-(5-Chloropyridin-2-yl)-2-(2,4-difluorophenyl)-1,1-difluoro-3-(1H-tetrazol-1-yl)propan-2-ol (12);

2-(2,4-Difluorophenyl)-1,1-difluoro-1-(4-fluoropyridin-2-yl)-3-(1H-tetrazol-1-yl)propan-2-ol (13);

1-(4-Chloropyridin-2-yl)-2-(2,4-difluorophenyl)-1,1-difluoro-3-(1H-tetrazol-1-yl)propan-2-ol (14);

2-(2,4-Difluorophenyl)-1,1-difluoro-1-(5-(5-fluoropyrimidin-4-yl)pyridin-2-yl)-3-(1H-tetrazol-1-yl)propan-2-ol (15);

2-(2,5-Difluorophenyl)-1,1-difluoro-1-(4-fluoropyridin-2-yl)-3-(1H-tetrazol-1-yl)propan-2-ol (16);

2-(2,4-Difluorophenyl)-1,1-difluoro-3-(1H-tetrazol-1-yl)-1-(5-(2,2,2-trifluoroethyl)pyridin-2-yl)propan-2-ol (17);

1-(5-Cyclopropylpyridin-2-yl)-2-(2,4-difluorophenyl)-1,1-difluoro-3-(1H-tetrazol-1-yl)propan-2-ol (18);

2-(2,4-Difluorophenyl)-1,1-difluoro-3-(1H-tetrazol-1-yl)-1-(5-(trifluoromethyl)pyridin-2-yl)propan-2-ol (19);

1-(6-Bromopyridin-2-yl)-2-(2,4-difluorophenyl)-1,1-difluoro-3-(1H-tetrazol-1-yl)propan-2-ol (20);

1-(5-Bromopyridin-2-yl)-2-(2,5-difluorophenyl)-1,1-difluoro-3-(1H-tetrazol-1-yl)propan-2-ol (21);

1-(5-Bromopyridin-2-yl)-2-(4-chloro-2-fluorophenyl)-1,1-difluoro-3-(1H-tetrazol-1-yl)propan-2-ol (22);

1-(5-Bromopyridin-2-yl)-1,1-difluoro-2-(2-fluoro-4-(trifluoromethyl)phenyl)-3-(1H-tetrazol-1-yl)propan-2-ol (23);

1-(4-Bromopyridin-2-yl)-2-(2,4-difluorophenyl)-1,1-difluoro-3-(1H-tetrazol-1-yl)propan-2-ol (24);

2-(2,4-Difluorophenyl)-1,1-difluoro-1-(5-methylpyridin-2-yl)-3-(1H-tetrazol-1-yl)propan-2-ol (25);

2-(4-Chloro-2-fluorophenyl)-1-(5-chloropyridin-2-yl)-1,1-difluoro-3-(1H-tetrazol-1-yl)propan-2-ol (26);

2-(4-Chloro-2-fluorophenyl)-1,1-difluoro-1-(5-fluoropyridin-2-yl)-3-(1H-tetrazol-1-yl)propan-2-ol (27);

1-(5-(2H-1,2,3-Triazol-2-yl)pyridin-2-yl)-2-(4-chloro-2-fluorophenyl)-1,1-difluoro-3-(1H-tetrazol-1-yl)propan-2-ol (28);

1-(6'-Chloro-[3,3'-bipyridin]-6-yl)-2-(2,4-difluorophenyl)-1,1-difluoro-3-(1H-tetrazol-1-yl)propan-2-ol (30);

2-(2,4-Difluorophenyl)-1,1-difluoro-1-(6'-fluoro-[3,3'-bipyridin]-6-yl)-3-(1H-tetrazol-1-yl)propan-2-ol (31);

2-(2,4-Difluorophenyl)-1,1-difluoro-1-(5-(5-methoxythiophen-2-yl)pyridin-2-yl)-3-(1H-tetrazol-1-yl)propan-2-ol (32);

1-(5-(5-(Difluoromethyl)thiophen-2-yl)pyridin-2-yl)-2-(2,4-difluorophenyl)-1,1-difluoro-3-(1H-tetrazol-1-yl)propan-2-ol (33);

2-(2,4-Difluorophenyl)-1,1-difluoro-3-(1H-tetrazol-1-yl)-1-(5-(5-(trifluoromethyl)thiophen-2-yl)pyridin-2-yl)propan-2-ol (34);

2-(2,4-Difluorophenyl)-1,1-difluoro-3-(1H-tetrazol-1-yl)-1-(6'-(trifluoromethyl)-[3,3'-bipyridin]-6-yl)propan-2-ol (35);

1-(5-(5-Bromothiazol-2-yl)pyridin-2-yl)-2-(2,4-difluorophenyl)-1,1-difluoro-3-(1H-tetrazol-1-yl)propan-2-ol (36);

2-(2,4-Difluorophenyl)-1,1-difluoro-1-(5-(2-methoxypyrimidin-5-yl)pyridin-2-yl)-3-(1H-tetrazol-1-yl)propan-2-ol (37);

2-(2,4-Difluorophenyl)-1,1-difluoro-3-(1H-tetrazol-1-yl)-1-(5-(thiazol-2-yl)pyridin-2-yl)propan-2-ol (38);

2-(4-Chloro-2-fluorophenyl)-1,1-difluoro-3-(1H-tetrazol-1-yl)-1-(5-(2,2,2-trifluoroethyl)pyridin-2-yl)propan-2-ol (39);

2-(4-Chloro-2-fluorophenyl)-1-(5-cyclopropylpyridin-2-yl)-1,1-difluoro-3-(1H-tetrazol-1-yl)propan-2-ol (40);

Methyl 2-((6-(2-(2,4-difluorophenyl)-1,1-difluoro-2-hydroxy-3-(1H-tetrazol-1-yl)propyl)pyridin-3-yl)thio)acetate (41);

(E)-1-(5-(3-(1H-Tetrazol-1-yl)prop-1-en-1-yl)pyridin-2-yl)-2-(2,4-difluorophenyl)-1,1-difluoro-3-(1H-tetrazol-1-yl)propan-2-ol (42);

(E)-3-(6-(2-(2,4-Difluorophenyl)-1,1-difluoro-2-hydroxy-3-(1H-tetrazol-1-yl)propyl)pyridin-3-yl)prop-2-en-1-ol (43);

3-(6-(2-(2,4-Difluorophenyl)-1,1-difluoro-2-hydroxy-3-(1H-tetrazol-1-yl)propyl)pyridin-3-yl)propan-1-ol (44);

2-(2,4-Difluorophenyl)-1,1-difluoro-3-(1H-tetrazol-1-yl)-1-(5-(3-(2,2,2-trifluoroethoxy)propyl)pyridin-2-yl)propan-2-ol (45);

(E)-4-(6-(2-(2,4-Difluorophenyl)-1,1-difluoro-2-hydroxy-3-(1H-tetrazol-1-yl)propyl)pyridin-3-yl)but-3-en-2-ol (46);

4-(6-(2-(2,4-Difluorophenyl)-1,1-difluoro-2-hydroxy-3-(1H-tetrazol-1-yl)propyl)pyridin-3-yl)butan-2-ol (47);

(E)-2-(2,4-Difluorophenyl)-1,1-difluoro-1-(5-(3-methoxyprop-1-en-1-yl)pyridin-2-yl)-3-(1H-tetrazol-1-yl)propan-2-ol (48);

(Z)-2-(2,4-Difluorophenyl)-1,1-difluoro-1-(5-(3-methoxyprop-1-en-1-yl)pyridin-2-yl)-3-(1H-tetrazol-1-yl)propan-2-ol (49);

2-(2,4-Difluorophenyl)-1,1-difluoro-1-(5-(3-methoxypropyl)pyridin-2-yl)-3-(1H-tetrazol-1-yl)propan-2-ol (50);

(E)-2-(2,4-Difluorophenyl)-1-(5-(3-ethoxyprop-1-en-1-yl)pyridin-2-yl)-1,1-difluoro-3-(1H-tetrazol-1-yl)propan-2-ol (51);

(Z)-2-(2,4-Difluorophenyl)-1-(5-(3-ethoxyprop-1-en-1-yl)pyridin-2-yl)-1,1-difluoro-3-(1H-tetrazol-1-yl)propan-2-ol (52);

2-(2,4-Difluorophenyl)-1-(5-(3-ethoxypropyl)pyridin-2-yl)-1,1-difluoro-3-(1H-tetrazol-1-yl)propan-2-ol (53);

(E)-2-(2,4-Difluorophenyl)-1,1-difluoro-1-(5-(3-isopropoxyprop-1-en-1-yl)pyridin-2-yl)-3-(1H-tetrazol-1-yl)propan-2-ol (54);

2-(2,4-Difluorophenyl)-1,1-difluoro-1-(5-(3-isopropoxypropyl)pyridin-2-yl)-3-(1H-tetrazol-1-yl)propan-2-ol (55);

1-(5-(2-Chloropyrimidin-5-yl)pyridin-2-yl)-2-(2,4-difluorophenyl)-1,1-difluoro-3-(1H-tetrazol-1-yl)propan-2-ol (56);

2-(2,4-Difluorophenyl)-1,1-difluoro-3-(1H-tetrazol-1-yl)-1-(5-(2,2,2-trifluoro-1-hydroxyethyl)pyridin-2-yl)propan-2-ol (57);

2-(5-Bromopyridin-2-yl)-1-(2,4-difluorophenyl)-2,2-difluoro-1-(pyrimidin-5-yl)ethanol (58);

1-(5-(Cyclopropylmethyl)pyridin-2-yl)-2-(2,4-difluorophenyl)-1,1-difluoro-3-(1H-tetrazol-1-yl)propan-2-ol (59);

2-(4-Chloro-2-fluorophenyl)-1-(5-(cyclopropylmethyl)pyridin-2-yl)-1,1-difluoro-3-(1H-tetrazol-1-yl)propan-2-ol (60);

1-(5-Allylpyridin-2-yl)-2-(2,4-difluorophenyl)-1,1-difluoro-3-(1H-tetrazol-1-yl)propan-2-ol (61);
1-(5-Bromopyridin-2-yl)-2-(2,4-difluorophenyl)-1,1-difluoro-3-(1H-pyrazol-3-yl)propan-2-ol (62);
1-(5-(2H-1,2,3-Triazol-2-yl)pyridin-2-yl)-2-(2,4-difluorophenyl)-1,1-difluoro-3-(1H-pyrazol-3-yl)propan-2-ol (63);
1-(5-(1H-1,2,3-Triazol-1-yl)pyridin-2-yl)-2-(2,4-difluorophenyl)-1,1-difluoro-3-(1H-pyrazol-3-yl)propan-2-ol (64);
2-(2,4-Difluorophenyl)-1,1-difluoro-3-(1H-pyrazol-4-yl)-1-(pyridin-2-yl)propan-2-ol (65);
(6-(2-(2,4-Difluorophenyl)-1,1-difluoro-2-hydroxy-3-(1H-tetrazol-1-yl)propyl)pyridin-3-yl)(4-(trifluoromethyl)phenyl)methanone (66);
(4-Chlorophenyl)(6-(2-(2,4-difluorophenyl)-1,1-difluoro-2-hydroxy-3-(1H-tetrazol-1-yl)propyl)pyridin-3-yl)methanone (67);
(6-(2-(2,4-Difluorophenyl)-1,1-difluoro-2-hydroxy-3-(1H-tetrazol-1-yl)propyl)pyridin-3-yl)(4-(2,2,2-trifluoroethoxy)phenyl)methanone (68);
(6-(2-(2,4-Difluorophenyl)-1,1-difluoro-2-hydroxy-3-(1H-tetrazol-1-yl)propyl)pyridin-3-yl)(4-fluorophenyl)methanone (69);
(3,4-Difluorophenyl)(6-(2-(2,4-difluorophenyl)-1,1-difluoro-2-hydroxy-3-(1H-tetrazol-1-yl)propyl)pyridin-3-yl)methanone (70);
(4-Chloro-3-fluorophenyl)(6-(2-(2,4-difluorophenyl)-1,1-difluoro-2-hydroxy-3-(1H-tetrazol-1-yl)propyl)pyridin-3-yl)methanone (71);
2-(2,4-Difluorophenyl)-1,1-difluoro-1-(5-(hydroxy(4-(trifluoromethyl)phenyl)methyl)pyridin-2-yl)-3-(1H-tetrazol-1-yl)propan-2-ol (72);
2-(2,4-Difluorophenyl)-1,1-difluoro-3-(1H-tetrazol-1-yl)-1-(5-(4-(trifluoromethyl)benzyl)pyridin-2-yl)propan-2-ol (73);
1-(5-((4-Chlorophenyl)difluoromethyl)pyridin-2-yl)-2-(2,4-difluorophenyl)-1,1-difluoro-3-(1H-tetrazol-1-yl)propan-2-ol (74);
1-(5-Benzylpyridin-2-yl)-2-(2,4-difluorophenyl)-1,1-difluoro-3-(1H-tetrazol-1-yl)propan-2-ol (75);
2-(2,4-Difluorophenyl)-1,1-difluoro-3-(1H-tetrazol-1-yl)-1-(5-(4-(trifluoromethoxy)benzyl)pyridin-2-yl)propan-2-ol (76);
1-(5-(4-Chlorobenzyl)pyridin-2-yl)-2-(2,4-difluorophenyl)-1,1-difluoro-3-(1H-tetrazol-1-yl)propan-2-ol (77);
1-(5-(5-Bromothiophen-2-yl)pyridin-2-yl)-2-(2,4-difluorophenyl)-1,1-difluoro-3-(1H-tetrazol-1-yl)propan-2-ol (78);
4-((6-(2-(2,4-Difluorophenyl)-1,1-difluoro-2-hydroxy-3-(1H-tetrazol-1-yl)propyl)pyridin-3-yl)methoxy)benzonitrile (79);
4-((6-(2-(2,4-Difluorophenyl)-1,1-difluoro-2-hydroxy-3-(2H-tetrazol-2-yl)propyl)pyridin-3-yl)methoxy)benzonitrile (80);
2-(2,4-Difluorophenyl)-1,1-difluoro-1-(5-morpholinopyridin-2-yl)-3-(1H-tetrazol-1-yl)propan-2-ol (81);
2-(2,4-Difluorophenyl)-1,1-difluoro-1-(5-(piperidin-1-yl)pyridin-2-yl)-3-(1H-tetrazol-1-yl)propan-2-ol (82);
1-(5-Bromopyridin-2-yl)-2-(2,4-difluorophenyl)-1,1-difluoro-3-(oxazol-5-yl)propan-2-ol (83);
3-(5-Bromopyridin-2-yl)-2-(2,4-difluorophenyl)-3-fluoro-1-(1H-tetrazol-1-yl)butan-2-ol (84);
3-(5-Bromopyridin-2-yl)-2-(2,4-difluorophenyl)-3-fluoro-1-(1H-tetrazol-1-yl)butan-2-ol (85);
2-(2,4-Difluorophenyl)-1,1-difluoro-1-(pyridin-2-yl)-3-(thiazol-5-yl)propan-2-ol (86);
1-(5-(5-Chlorothiophen-2-yl) pyridin-2-yl)-2-(2, 4-difluorophenyl)-1, 1-difluoro-3-(1H-tetrazol-1-yl) propan-2-ol (87);
4-((6-(2-(2,4-Difluorophenyl)-1,1-difluoro-2-hydroxy-3-(1H-tetrazol-1-yl)propyl)pyridin-3-yl)methoxy)-3-fluorobenzonitrile (88);
3-((6-(2-(2,4-Difluorophenyl)-1,1-difluoro-2-hydroxy-3-(1H-tetrazol-1-yl)propyl)pyridin-3-yl)methoxy)-2-fluorobenzonitrile (89);
4-(((6-(2-(2,4-Difluorophenyl)-1,1-difluoro-2-hydroxy-3-(1H-tetrazol-1-yl)propyl)pyridin-3-yl)methyl)thio)-3-fluorobenzonitrile (90);
2-(2,4-difluorophenyl)-1,1-difluoro-1-(5-(isopropoxymethyl)pyridin-2-yl)-3-(1H-tetrazol-1-yl)propan-2-ol (91);
1-(5-((difluoromethoxy)methyl)pyridin-2-yl)-2-(2,4-difluorophenyl)-1,1-difluoro-3-(1H-tetrazol-1-yl)propan-2-ol (92);
1-(5-chloro-[2,3'-bipyridin]-6'-yl)-2-(2,4-difluorophenyl)-1,1-difluoro-3-(1H-tetrazol-1-yl)propan-2-ol (93);
2-(2,4-Difluorophenyl)-1,1-difluoro-3-(1H-tetrazol-1-yl)-1-(5-(trifluoromethyl)-[2,3'-bipyridin]-6'-yl)propan-2-ol (94);
6'-(2-(2,4-Difluorophenyl)-1,1-difluoro-2-hydroxy-3-(1H-tetrazol-1-yl)propyl)-[2,3'-bipyridine]-5-carbonitrile (95);
1-([3,4'-bipyridin]-6-yl)-2-(2,4-difluorophenyl)-1,1-difluoro-3-(1H-tetrazol-1-yl)propan-2-ol (96);
1-(5-((6-chloropyridin-3-yl)methyl)pyridin-2-yl)-2-(2,4-difluorophenyl)-1,1-difluoro-3-(1H-tetrazol-1-yl)propan-2-ol (97);
6-((6-(2-(2,4-difluorophenyl)-1,1-difluoro-2-hydroxy-3-(1H-tetrazol-1-yl)propyl)pyridin-3-yl)methoxy)nicotinonitrile (98);
2-(2,4-difluorophenyl)-1,1-difluoro-3-(1H-tetrazol-1-yl)-1-(5-(((5-(trifluoromethyl)pyridin-2-yl)oxy)methyl)pyridin-2-yl)propan-2-ol (99);
1-(5-(((3-chloro-5-(trifluoromethyl)pyridin-2-yl)oxy)methyl)pyridin-2-yl)-2-(2,4-difluorophenyl)-1,1-difluoro-3-(1H-tetrazol-1-yl)propan-2-ol (100);
1-(5-(difluoro(4-fluorophenyl)methyl)pyridin-2-yl)-2-(2,4-difluorophenyl)-1,1-difluoro-3-(1H-tetrazol-1-yl)propan-2-ol (101);
1-(5-(difluoro(4-(trifluoromethyl)phenyl)methyl)pyridin-2-yl)-2-(2,4-difluorophenyl)-1,1-difluoro-3-(1H-tetrazol-1-yl)propan-2-ol (102); or
4-((6-(2-(2,4-difluorophenyl)-1,1-difluoro-2-hydroxy-3-(1H-tetrazol-1-yl)propyl)pyridin-3-yl)difluoromethyl)benzonitrile (103).

20. The method of claim 3, wherein the disease or disorder is systemic fungal infection, skin structure fungal infection, mucosal fungal infection, or onychomycosis.

* * * * *